(12) United States Patent
Jeon et al.

(10) Patent No.: US 10,043,983 B2
(45) Date of Patent: Aug. 7, 2018

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Soonok Jeon, Seoul (KR); Sangmo Kim, Hwaseong-si (KR); Hyunjung Kim, Suwon-si (KR); Yeonsook Chung, Seoul (KR); Yongsik Jung, Yongin-si (KR); Miyoung Chae, Suwon-si (KR); Dalho Huh, Suwon-si (KR); Jongsoo Kim, Suwon-si (KR); Myungsun Sim, Seoul (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 294 days.

(21) Appl. No.: 14/963,862

(22) Filed: Dec. 9, 2015

(65) Prior Publication Data
US 2017/0025620 A1  Jan. 26, 2017

(30) Foreign Application Priority Data
Jul. 24, 2015 (KR) .................. 10-2015-0105302

(51) Int. Cl.
*H01L 51/00* (2006.01)
*C09K 11/02* (2006.01)
(Continued)

(52) U.S. Cl.
CPC ........ *H01L 51/0072* (2013.01); *C07D 401/10* (2013.01); *C09K 11/025* (2013.01);
(Continued)

(58) Field of Classification Search
CPC ............ H01L 51/0072; H01L 51/5016; H01L 51/005; C07D 401/10; C09K 11/025;
(Continued)

(56) References Cited

U.S. PATENT DOCUMENTS

| | | | |
|---|---|---|---|
| 2012/0032115 A1* | 2/2012 | Harada | ............... H01L 51/0072 252/301.16 |
| 2012/0035217 A1* | 2/2012 | Nilsson | ............... C07D 213/74 514/333 |

(Continued)

FOREIGN PATENT DOCUMENTS

| | | |
|---|---|---|
| KR | 1020120125286 A | 11/2012 |
| KR | 1020140010875 A | 1/2014 |

(Continued)

*Primary Examiner* — Golam Mowla
(74) *Attorney, Agent, or Firm* — Cantor Colburn LLP

(57) ABSTRACT

A condensed cyclic compound represented by Formula 1:

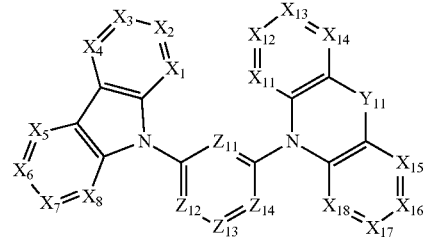

Formula 1 wherein, in Formula 1, $X_1$ to $X_8$, $X_{11}$ to $X_{18}$, $Y_{11}$, and $Z_{11}$ to $Z_{14}$ are the same as described in the specification.

20 Claims, 2 Drawing Sheets

(51) Int. Cl.
*C09K 11/06* (2006.01)
*C07D 401/10* (2006.01)
*H01L 51/50* (2006.01)

(52) U.S. Cl.
CPC ............ *C09K 11/06* (2013.01); *H01L 51/005* (2013.01); *C09K 2211/1007* (2013.01); *C09K 2211/1022* (2013.01); *C09K 2211/1044* (2013.01); *C09K 2211/185* (2013.01); *H01L 51/5016* (2013.01)

(58) Field of Classification Search
CPC .............. C09K 11/06; C09K 2211/185; C09K 2211/1007; C09K 2211/1022; C09K 2211/1044
See application file for complete search history.

(56) References Cited

U.S. PATENT DOCUMENTS

| | | | | |
|---|---|---|---|---|
| 2012/0037898 A1* | 2/2012 | Wu | ........................ | C07C 211/61 257/40 |
| 2012/0040936 A1* | 2/2012 | Kanno | ................. | C07D 217/14 514/82 |
| 2012/0298846 A1 | 11/2012 | Nomura et al. | | |

FOREIGN PATENT DOCUMENTS

| | | |
|---|---|---|
| KR | 1020140076520 A | 6/2014 |
| WO | 2013108589 A | 7/2013 |

* cited by examiner

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2015-0105302, filed on Jul. 24, 2015, in the Korean Intellectual Property Office, the content of which is incorporated herein in its entirety by reference.

BACKGROUND

1. Field

The present disclosure relates to condensed cyclic compounds and organic light-emitting devices including the same.

2. Description of the Related Art

Organic light-emitting devices (OLEDs) are self-emission devices that have wide viewing angles, high contrast ratios, short response times. In addition, OLEDs display excellent luminance, driving voltage, and response speed characteristics, and produce full-color images.

In an example, an organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons change from an excited state to a ground state, thereby generating light.

Different types of organic light emitting devices are known. However, there still remains a need in OLEDs having low driving voltage, high efficiency, high brightness, and long lifespan.

SUMMARY

One or more embodiments relate to a novel condensed cyclic compound and an organic light-emitting device including the same.

Additional aspects will be set forth in part in the description which follows and, in part, will be apparent from the description, or may be learned by practice of the presented exemplary embodiments.

Provided is condensed cyclic compounds represented by Formula 1:

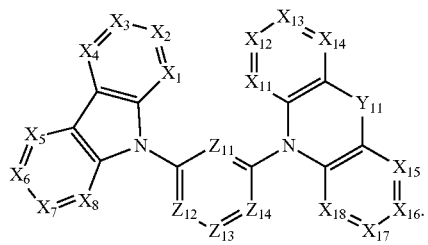

Formula 1

In Formula 1, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{15}$ is N or $C(R_{16})$, $X_{17}$ is N or $C(R_{17})$, and $X_{18}$ is N or $C(R_{18})$, $Y_{11}$ is O, S, $C(R_{101})(R_{102})$, or $Si(R_{101})(R_{102})$;

$Z_{11}$ to $Z_{14}$ are each independently selected from N, $C(A_{11})$, and $C(A_{12})$; and at least one selected from $Z_{11}$ to $Z_{14}$ is $C(A_{11})$;

$A_{11}$ includes at least one cyano group (CN); and may be a cyano group (CN) or a group represented by one of Formulae 2-1 to 2-10;

$A_{12}$ is selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —$Si(Q_{21})(Q_{22})(Q_{23})$; and —$Si(Q_{31})(Q_{32})(Q_{33})$;

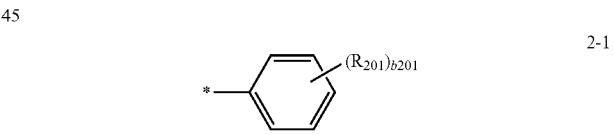

2-1

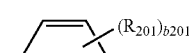

2-2

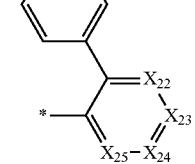

2-3

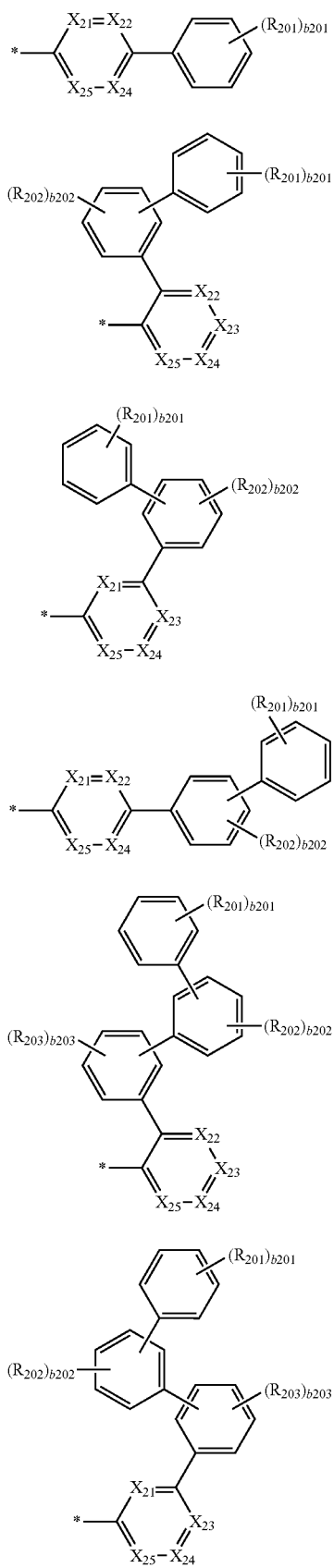

In Formulae 2-1 to 2-10, $X_{21}$ is N or $C(R_{21})$, $X_{22}$ is N or $C(R_{22})$, $X_{23}$ is N or $C(R_{23})$, $X_{24}$ is N or $C(R_{24})$, and $X_{25}$ is N or $C(R_{25})$, $R_1$ to $R_8$, $R_{11}$ to $R_{18}$, $R_{101}$, $R_{102}$, $R_{21}$ to $R_{25}$, and $R_{201}$ to $R_{203}$ are each independently selected from a hydrogen, a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group and —$Si(Q_1)(Q_2)(Q_3)$; and —$Si(Q_{11})(Q_{12})(Q_{13})$, $R_{101}$ and $R_{102}$ may be optionally linked to each other to form a saturated ring or an unsaturated ring;

b201 is selected from 1, 2, 3, 4, and 5;

b202 and b203 are each independently selected from 1, 2, 3, and 4; and

* indicates a carbon atom in Formula 1, wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

Provided is an organic light-emitting device including: a first electrode; a second electrode; and an organic layer between the first electrode and the second electrode, the organic layer including an emission layer and at least one of condensed cyclic compounds represented by Formula 1.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION

Figure 1:
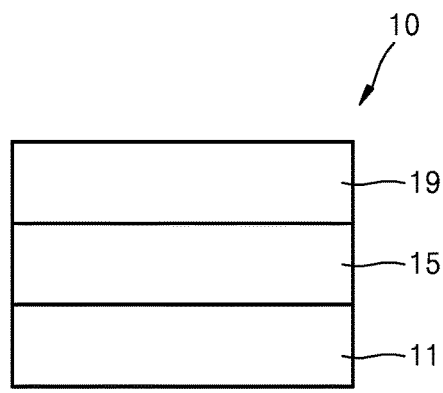
FIG. 1 is a schematic view of an organic light-emitting device according to an embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims. In the drawings, like reference numerals denote like elements throughout, and thus redundant description thereof will be omitted.

It will be understood that, although the terms first, second, third etc, may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." As used herein, the terms such as "comprising", "including", "having", or the like are intended to indicate the existence of the features regions, integers, steps, operations, components, and/or elements disclosed in the specification, and are not intended to preclude the possibility that one or more other features or elements may exist or may be added.

It will also be understood that when an element such as a layer, a region or a component is referred to as being "on" another layer or element, it can be directly on the other layer or element, or intervening layers, regions, or components may also be present. In contrast, when an element is referred to as being "directly on" another element, there are no intervening elements present.

In the drawings, the sizes of elements are exaggerated or reduced for ease of description. The size or thickness of each element shown in the drawings are arbitrarily illustrated for better understanding or ease of description, and thus the present disclosure is not limited thereto.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A condensed cyclic compound according to an embodiment is represented by Formula 1:

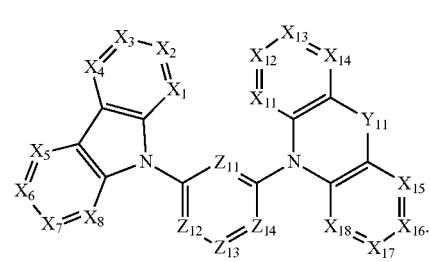

Formula 1

In Formula 1, $X_1$ may be N or $C(R_1)$, $X_2$ may be N or $C(R_2)$, $X_3$ may be N or $C(R_3)$, $X_4$ may be N or $C(R_4)$, $X_5$ may be N or $C(R_5)$, $X_6$ may be N or $C(R_6)$, $X_7$ may be N or $C(R_7)$, $X_8$ may be N or $C(R_8)$, $X_{11}$ may be N or $C(R_{11})$, $X_{12}$ may be N or $C(R_{12})$, $X_{13}$ may be N or $C(R_{13})$, $X_{14}$ may be N or $C(R_{14})$, $X_{15}$ may be N or $C(R_{15})$, $X_{16}$ may be N or $C(R_{16})$, $X_{17}$ may be N or $C(R_{17})$, and $X_{18}$ may be N or $C(R_{18})$.

For example, in Formula 1, $X_1$ may be N, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be N, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be N, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be $C(R_3)$, $X_4$ may be N, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be $C(R_3)$, $X_4$ may be $C(R_4)$, $X_5$ may be N, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be N, $X_7$ may be $C(R_7)$, $X_8$ may be $C(R_6)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be N, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be N, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

For example, in Formula 1, $X_1$ may be $C(R_1)$, $X_2$ may be $C(R_2)$, $X_3$ may be $C(R_3)$, $X_4$ may be $C(R_4)$, $X_5$ may be $C(R_5)$, $X_6$ may be $C(R_6)$, $X_7$ may be $C(R_7)$, $X_8$ may be $C(R_8)$, $X_{11}$ may be $C(R_{11})$, $X_{12}$ may be $C(R_{12})$, $X_{13}$ may be $C(R_{13})$, $X_{14}$ may be $C(R_{14})$, $X_{15}$ may be $C(R_{15})$, $X_{16}$ may be $C(R_{16})$, $X_{17}$ may be $C(R_{17})$, and $X_{18}$ may be $C(R_{18})$, but they are not limited thereto.

In Formula 1, $Y_{11}$ may be O, S, $C(R_{101})(R_{102})$, or $Si(R_{101})(R_{102})$. $R_{101}$ and $R_{102}$ will be explained in detail below.

For example, in Formula 1, $Y_{11}$ may be $C(R_{101})(R_{102})$, but is not limited thereto.

In Formula 1, $Z_{11}$ to $Z_{14}$ may be each independently selected from N, $C(A_{11})$, and $C(A_{12})$; and at least one of $Z_{11}$ to $Z_{14}$ may be $C(A_{11})$, $A_{11}$ and $A_{12}$ will be explained in detail below.

For example, in Formula 1, $Z_{11}$ may be N, $Z_{12}$ may be $C(A_{12})$, $Z_{13}$ may be $C(A_{11})$, and $Z_{14}$ may be $C(A_{12})$, but they are not limited thereto.

For example, in Formula 1, $Z_{11}$ may be $C(A_{12})$, $Z_{12}$ may be N, $Z_{13}$ may be $C(A_{11})$, and $Z_{14}$ may be $C(A_{12})$, but they are not limited thereto.

For example, in Formula 1, may be $C(A_{12})$, $Z_{12}$ may be $C(A_{12})$, $Z_{13}$ may be $C(A_{11})$, and $Z_{14}$ may be N, but they are not limited thereto.

For example, in Formula 1, $Z_{11}$ may be $C(A_{12})$, $Z_{12}$ may be $C(A_{12})$, $Z_{13}$ may be $C(A_{11})$, and $Z_{14}$ may be $C(A_{12})$, but they are not limited thereto.

In some embodiments, in Formula 1, $Z_{11}$ may be N, $Z_{12}$ may be CH, $Z_{13}$ may be $C(A_{11})$, and $Z_{14}$ may be CH, but they are not limited thereto.

In some embodiments, in Formula 1, $Z_{11}$ may be CH, $Z_{12}$ may be N, $Z_{13}$ may be $C(A_{11})$, and $Z_{14}$ may be CH, but they are not limited thereto.

In some embodiments, in Formula 1, $Z_{11}$ may be CH, $Z_{12}$ may be CH, $Z_{13}$ may be $C(A_{11})$, and $Z_{14}$ may be N, but they are not limited thereto.

In some embodiments, in Formula 1, $Z_{11}$ may be CH, $Z_{12}$ may be CH, $Z_{13}$ may be $C(A_{11})$, and $Z_{14}$ may be CH, but they are not limited thereto.

In Formula 1, $A_{11}$ includes at least one cyano group (CN); and may be a cyano group (CN) or a group represented by one of Formulae 2-1 to 2-10:

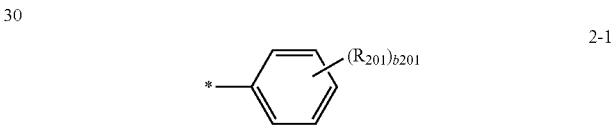

2-1

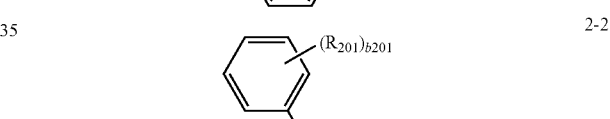

2-2


2-3

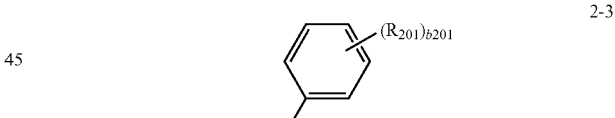

2-4

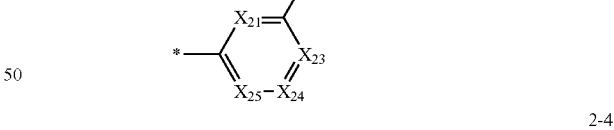

2-5

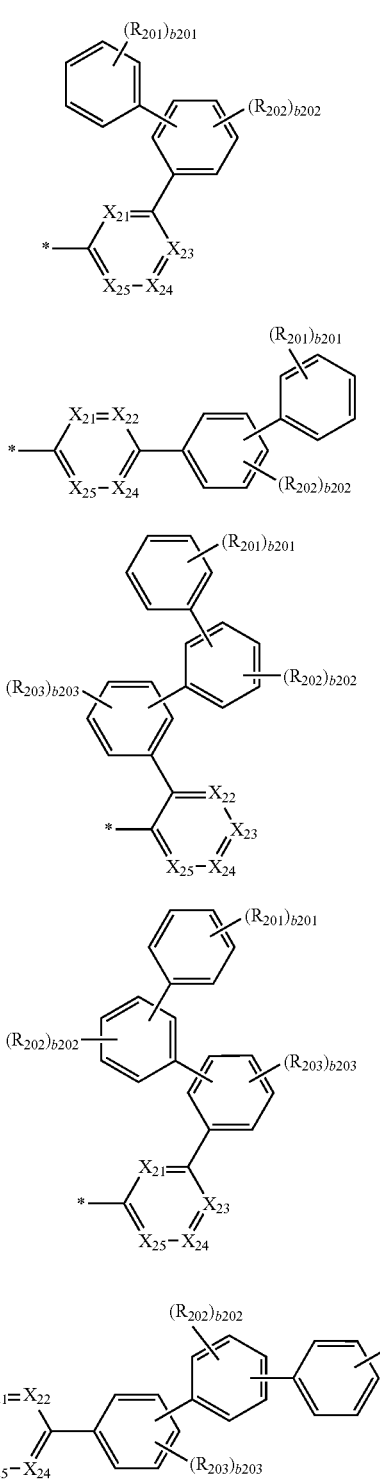

In Formulae 2-1 to 2-10,

* indicates a carbon atom in Formula 1;

$X_{21}$ may be N or $C(R_{21})$, $X_{22}$ may be N or $C(R_{22})$, $X_{23}$ may be N or $C(R_{23})$, $X_{24}$ may be N or $C(R_{74})$, and $X_{25}$ may be N or $C(R_{25})$, and $R_{21}$ to $R_{25}$, $R_{201}$ to $R_{203}$, and $b201$ to $b203$ will be explained in detail below.

For example, $A_{11}$ in Formula 1 may be a cyano group (CN), or may be represented by one of Formulae 2-1 to 2-7, but is not limited thereto.

In some embodiments, $A_{11}$ in Formula 1 may be represented by one of Formulae 2-2, 2-5, and 2-8; and
in Formulae 2-2, 2-5, and 2-8,
$X_{22}$ may be N, $X_{23}$ may be $C(R_{23})$, $X_{24}$ may be $C(R_{24})$, and $X_{25}$ may be $C(R_{25})$;
$X_{22}$ may be $C(R_{22})$, $X_{23}$ may be N, $X_{24}$ may be $C(R_{24})$, and $X_{25}$ may be $C(R_{25})$;
$X_{22}$ may be $C(R_{22})$, $X_{23}$ may be $C(R_{23})$, $X_{24}$ may be N, and $X_{25}$ may be $C(R_{25})$; or
$X_{22}$ may be $C(R_{22})$, $X_{23}$ may be $C(R_{23})$, $X_{24}$ may be $C(R_{24})$, and $X_{25}$ may be N, but they are not limited thereto.

In some embodiments, $A_{11}$ in Formula 1 may be represented by one of Formulae 2-3, 2-6 and 2-9; and
in Formulae 2-3, 2-6, and 2-9,
$X_{21}$ may be N, $X_{23}$ may be $C(R_{23})$, $X_{24}$ may be $C(R_{24})$, and $X_{25}$ may be $C(R_{25})$;
$X_{21}$ may be $C(R_{21})$, $X_{23}$ may be N, $X_{24}$ may be $C(R_{24})$, and $X_{25}$ may be $C(R_{25})$;
$X_{21}$ may be $C(R_{21})$, $X_{23}$ may be $C(R_{23})$, $X_{24}$ may be N, and $X_{25}$ may be $C(R_{25})$; or
$X_{21}$ may be $C(R_{21})$, $X_{23}$ may be $C(R_{23})$, $X_{24}$ may be $C(R_{24})$, and $X_{25}$ may be N, but they are not limited thereto.

In some embodiments, $A_{11}$ in Formula 1 may be represented by one of Formulae 2-4, 2-7, and 2-10; and
in Formulae 2-4, 2-7 and 2-10,
$X_{21}$ may be N, $X_{22}$ may be $C(R_{22})$, $X_{24}$ may be $C(R_{24})$, and $X_{25}$ may be $C(R_{25})$;
$X_{21}$ may be $C(R_{21})$, $X_{22}$ may be N, $X_{24}$ may be $C(R_{24})$, and $X_{25}$ may be $C(R_{25})$;
$X_{21}$ may be $C(R_{21})$, $X_{22}$ may be $C(R_{22})$, $X_{24}$ may be N, and $X_{25}$ may be $C(R_{25})$; or
$X_{21}$ may be $C(R_{21})$, $X_{22}$ may be $C(R_{22})$, $X_{24}$ may be $C(R_{24})$, and $X_{25}$ may be N, but they are not limited thereto.

In some embodiments, $A_{11}$ in Formula 1 may be a cyano group (CN) or a group represented by one of Formulae 3-1 to 3-110, but is not limited thereto:

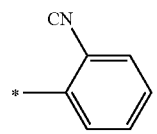

3-1

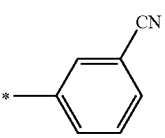

3-2

3-3

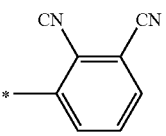

3-4

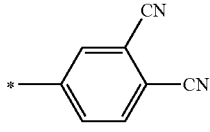

3-5

3-6
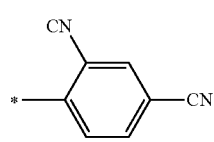
3-7
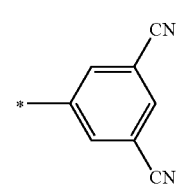
3-8
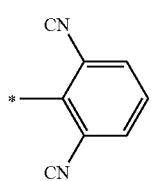
3-9
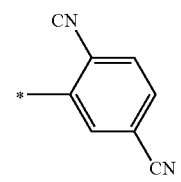
3-10
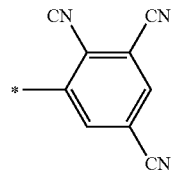
3-11
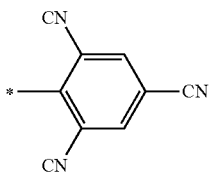
3-12
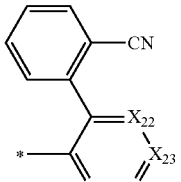
3-13
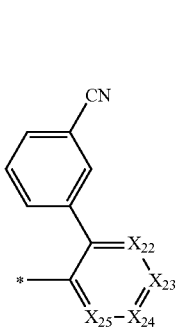
3-14
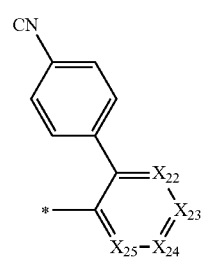
3-15
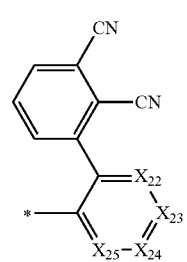
3-16
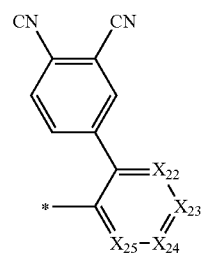
3-17
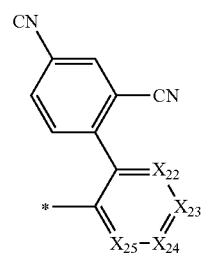
3-18
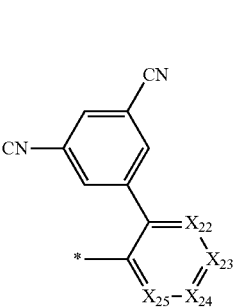
3-19
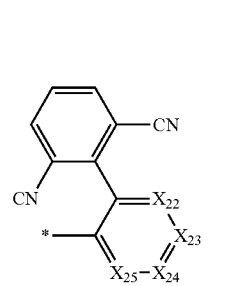

-continued
3-20
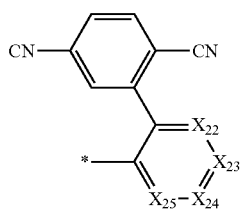
3-21
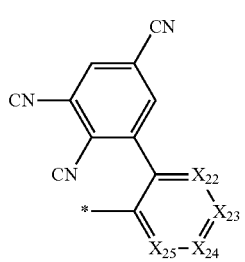
3-22
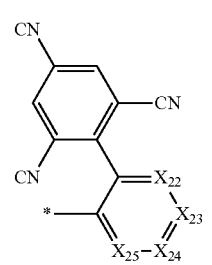
3-23
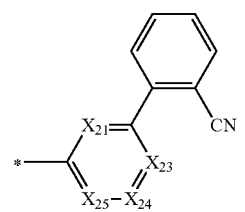
3-24
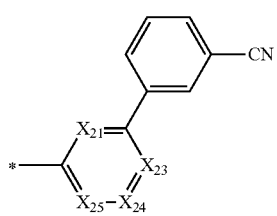
3-25
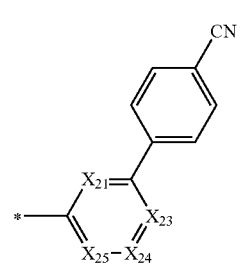
3-26
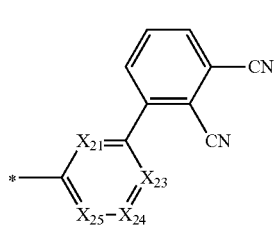
-continued
3-27
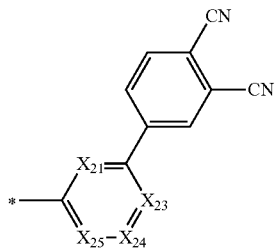
3-28
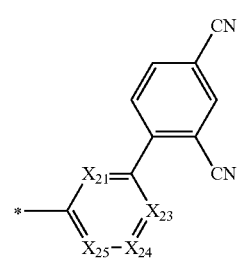
3-29
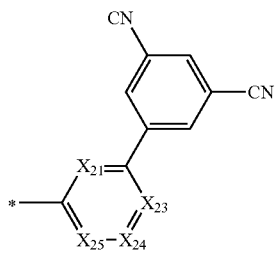
3-30
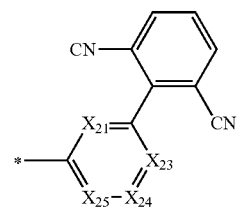
3-31
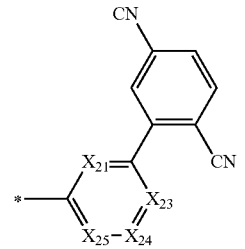
3-32
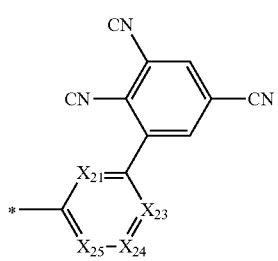

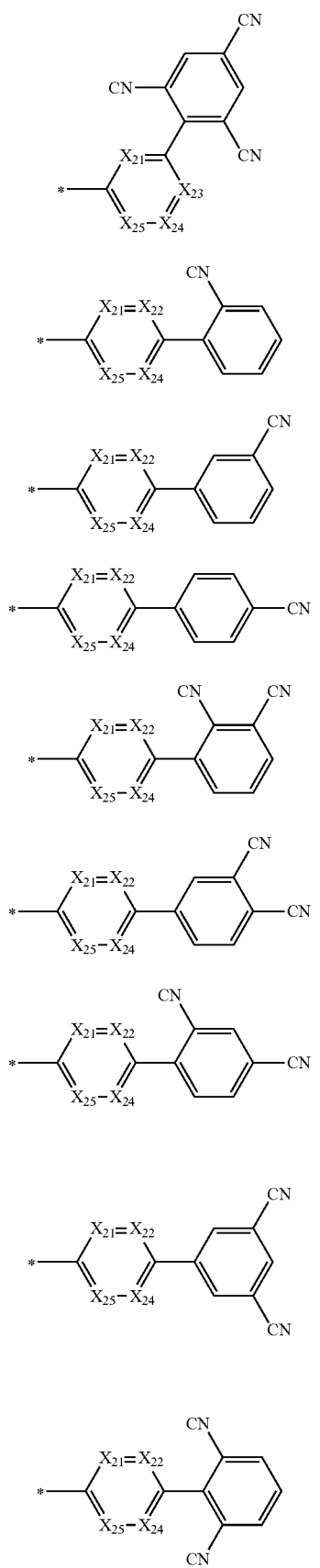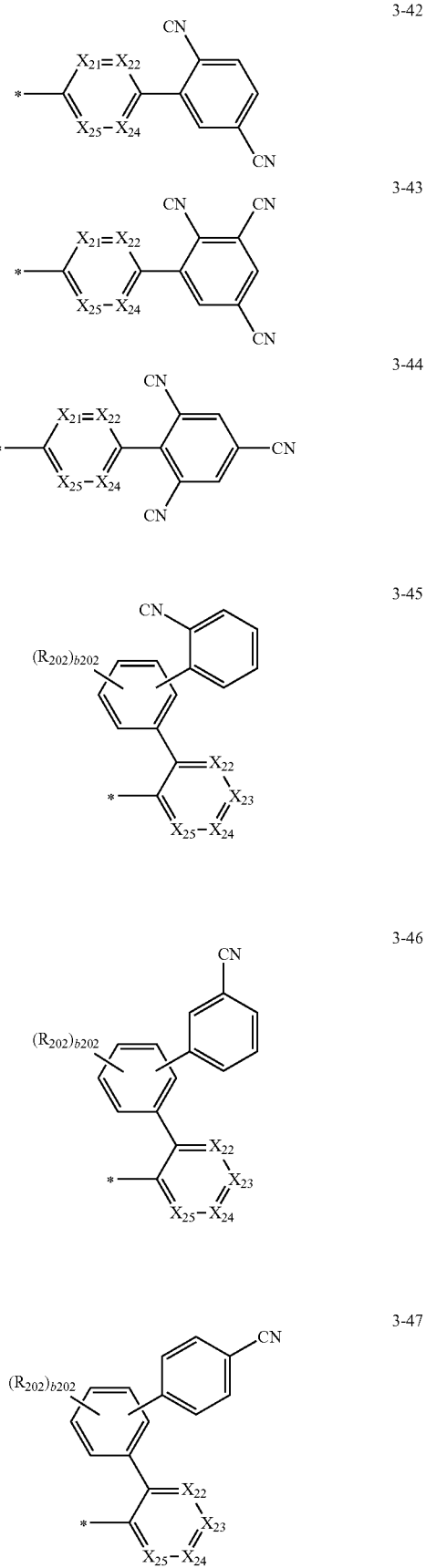

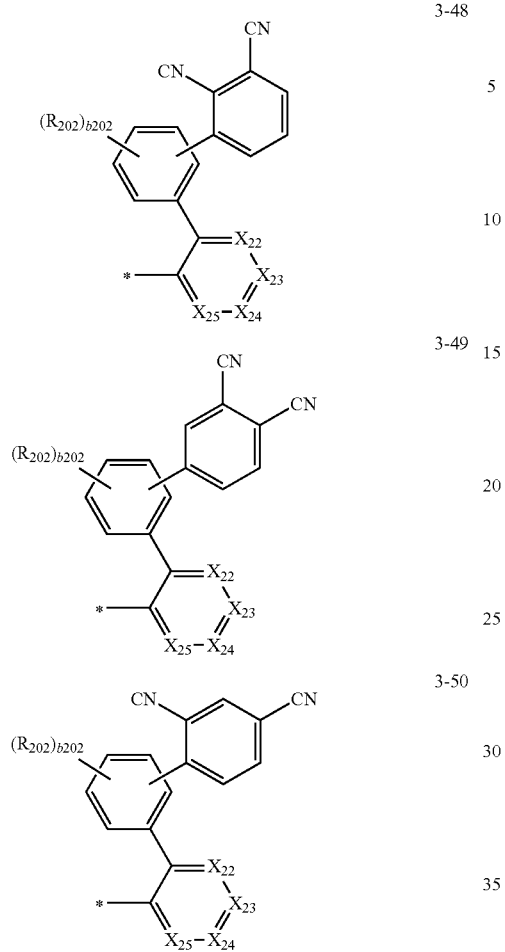
3-48
3-49
3-50
3-51
3-52
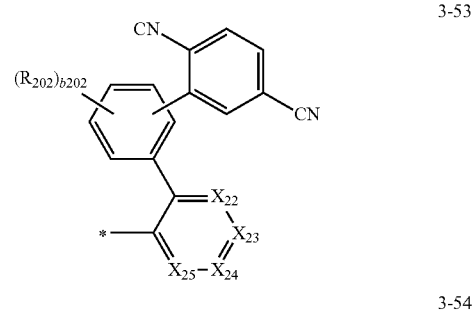
3-53
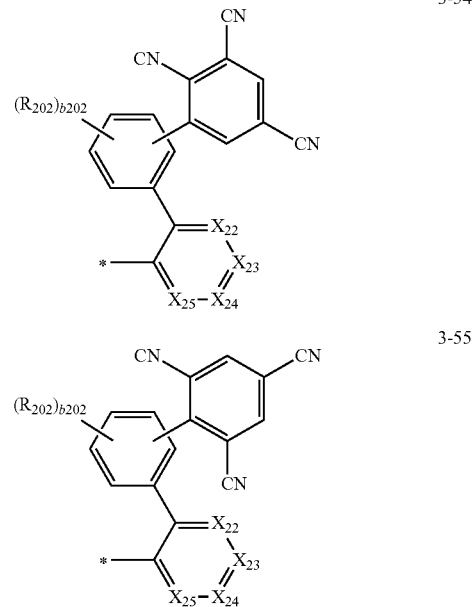
3-54
3-55
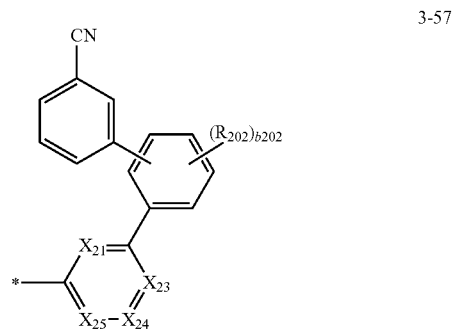
3-56
3-57

3-58
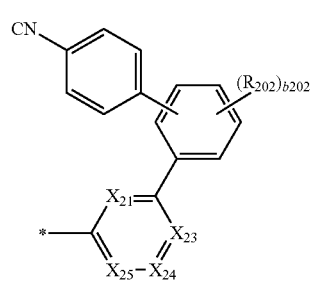
3-59
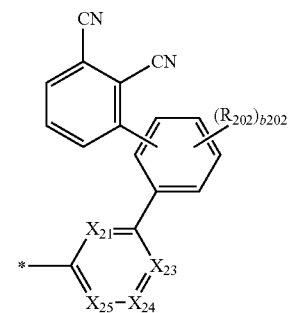
3-60
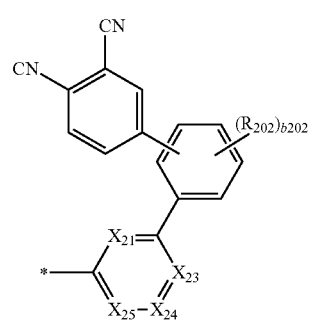
3-61
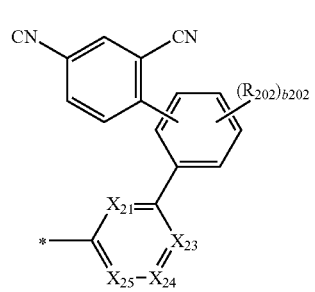
3-62
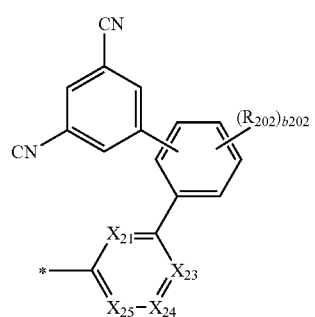
3-63
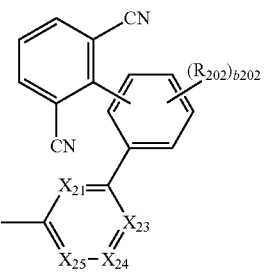
3-64
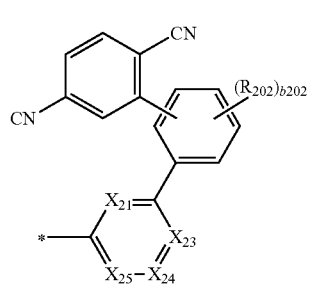
3-65
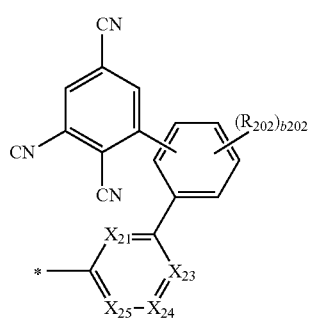
3-66
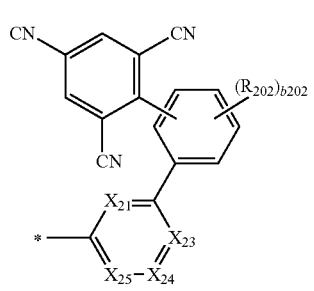
3-67
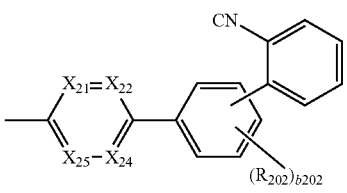
3-68
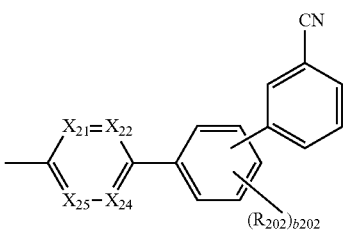

3-69
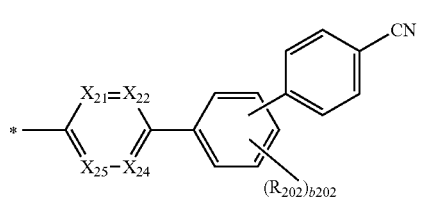
3-70
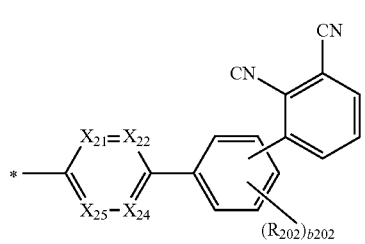
3-71
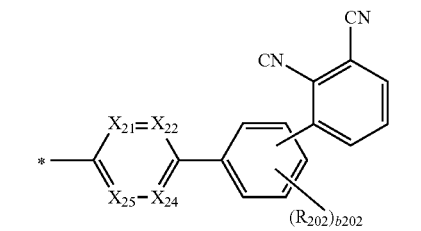
3-72
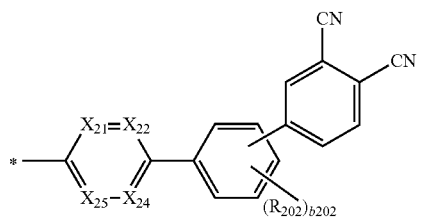
3-73
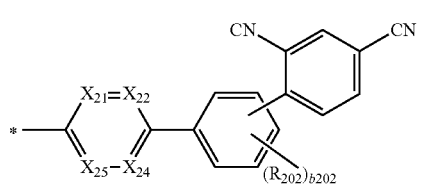
3-74
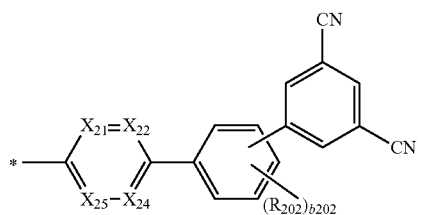
3-75
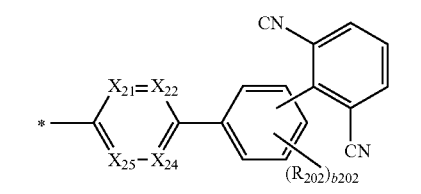
3-76
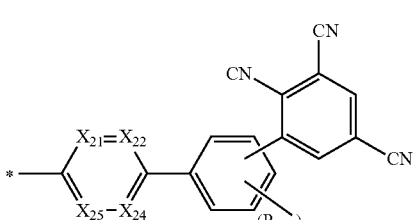
3-77
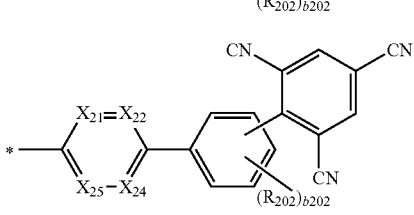
3-78
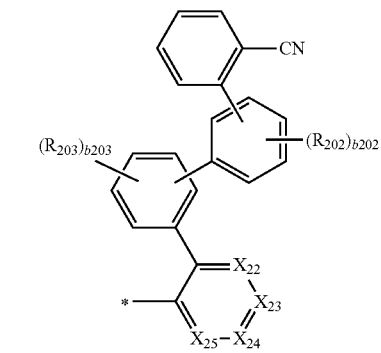
3-79
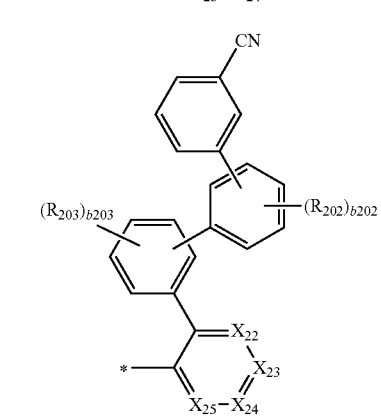
3-80
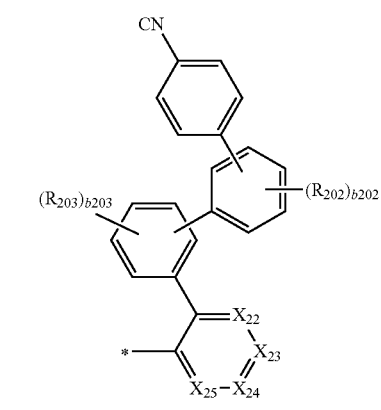

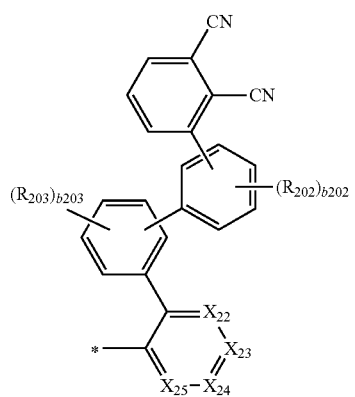
3-81

3-82
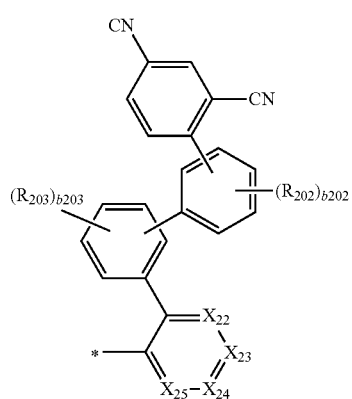
3-83
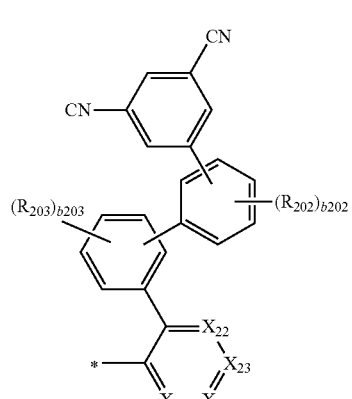
3-84
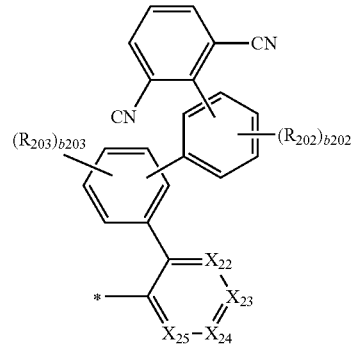
3-85
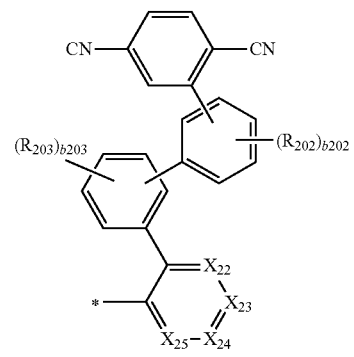
3-86
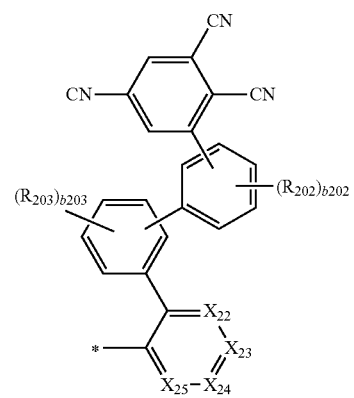
3-87
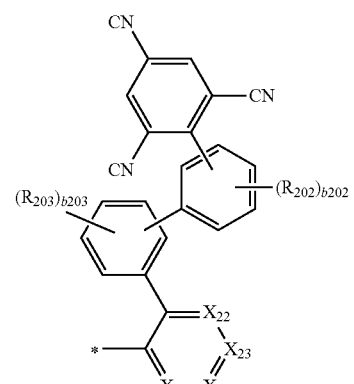
3-88

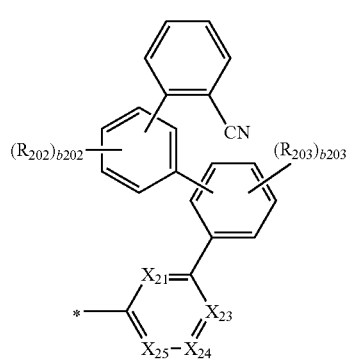
3-89
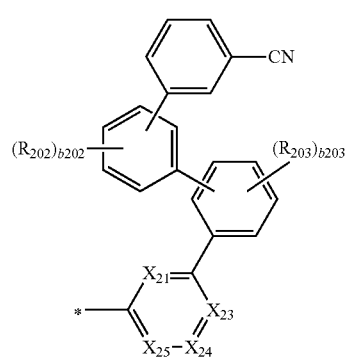
3-90
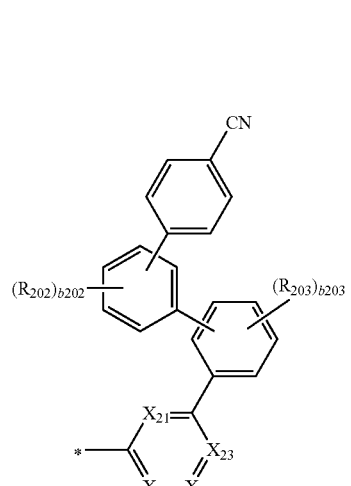
3-91
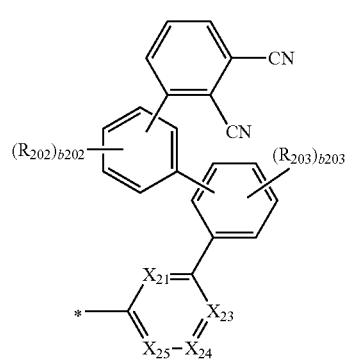
3-92
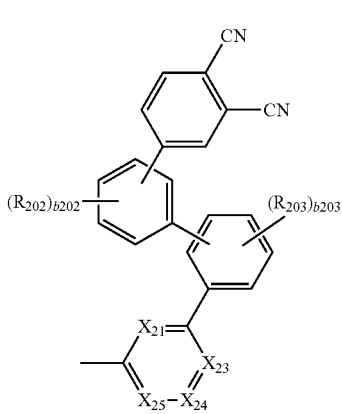
3-93
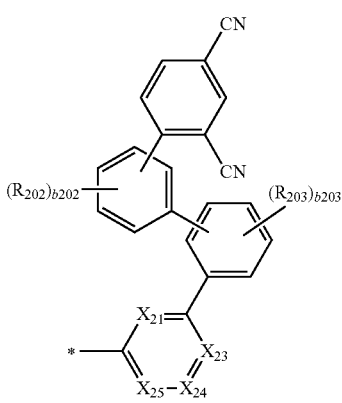
3-94
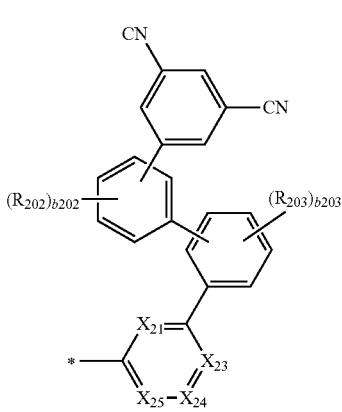
3-95
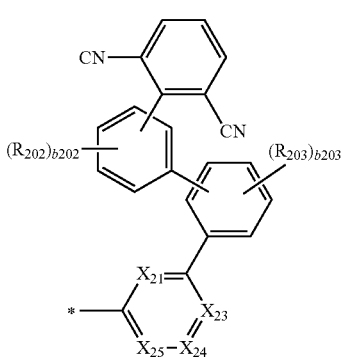
3-96

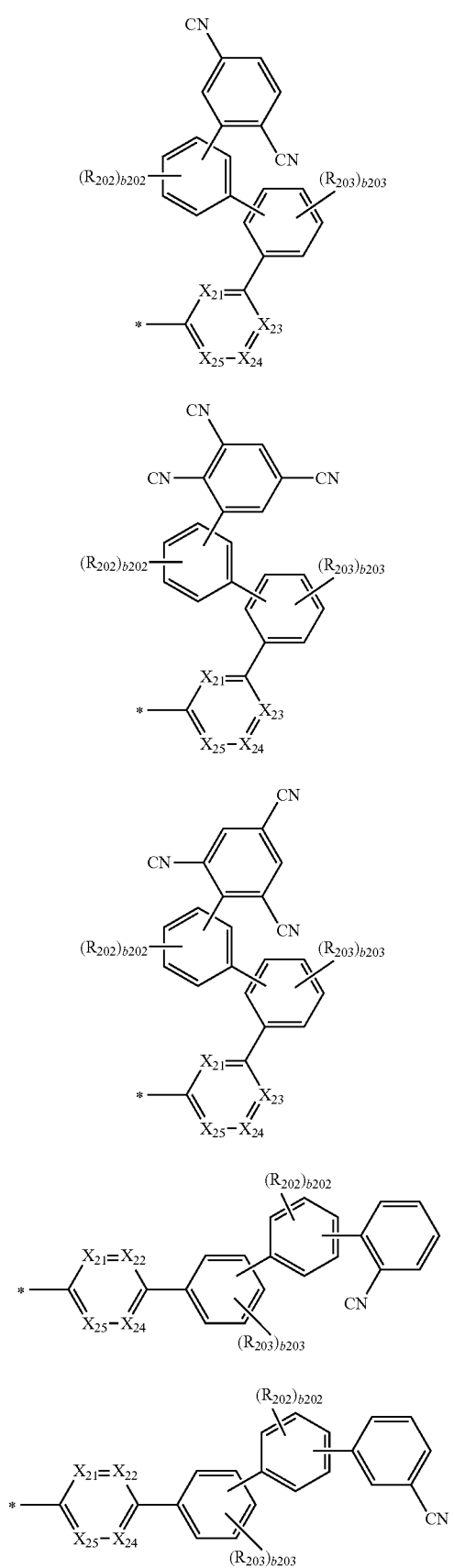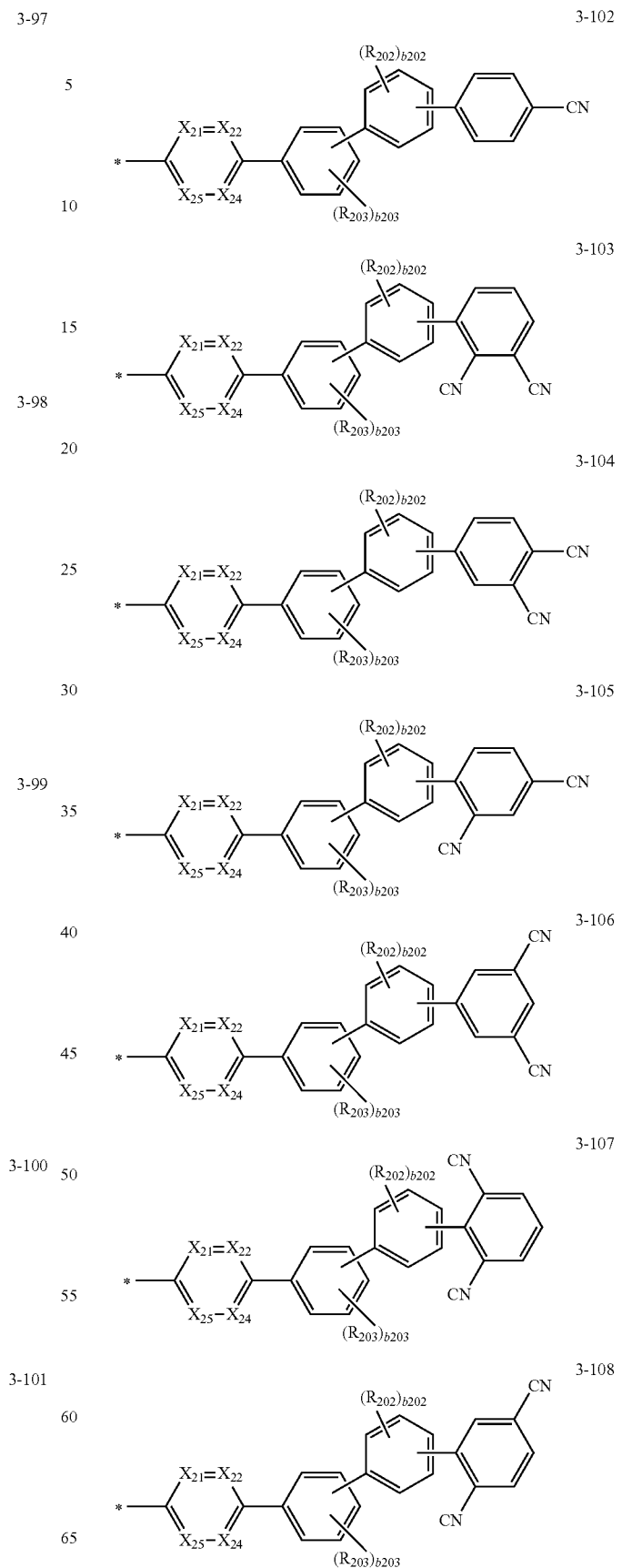

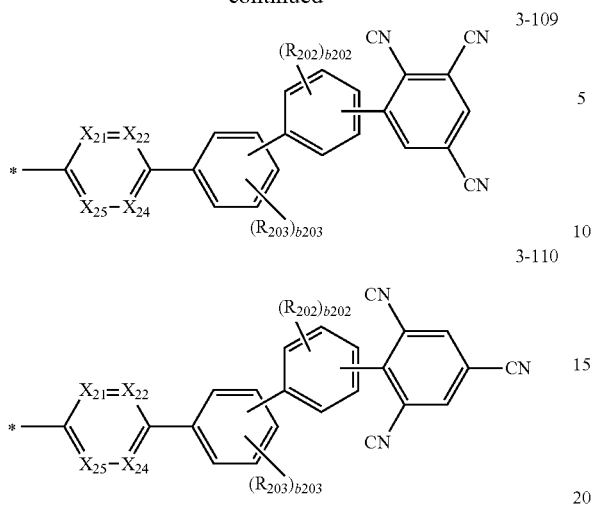

3-109

3-110

In Formulae 3-1 to 3-110,

* indicates a carbon atom in Formula 1;

$X_{21}$ may be N or $C(R_{21})$, $X_{22}$ may be N or $C(R_{22})$, $X_{23}$ may be N or $C(R_{23})$, $X_{24}$ may be N or $C(R_{24})$, and $X_{25}$ may be N or $C(R_{25})$, and $R_{21}$ to $R_{25}$, $R_{202}$, $R_{203}$, b202, and b203 will be explained in detail below.

In some embodiments, in Formulae 3-12 to 3-22, 3-45 to 3-55, and 3-78 to 3-88, $X_{22}$ may be N, $X_{23}$ may be $C(R_{23})$, $X_{24}$ may be $C(R_{24})$, and $X_{25}$ may be $C(R_{25})$;

$X_{22}$ may be $C(R_{22})$, $X_{23}$ may be N, $X_{24}$ may be $C(R_{24})$, and $X_{25}$ may be $C(R_{25})$;

$X_{22}$ may be $C(R_{22})$, $X_{23}$ may be $C(R_{23})$, $X_{24}$ may be N, and $X_{25}$ may be $C(R_{25})$; or $X_{22}$ may be $C(R_{22})$, $X_{23}$ may be $C(R_{23})$, $X_{24}$ may be $C(R_{24})$, and $X_{25}$ may be N, but they are not limited thereto.

In some embodiments, in Formulae 3-23 to 3-33, 3-56 to 3-66, and 3-89 to 3-99, $X_{21}$ may be N, $X_{23}$ may be $C(R_{23})$, $X_{24}$ may be $C(R_{24})$, and $X_{25}$ may be $C(R_{25})$;

$X_{21}$ may be $C(R_{21})$, $X_{23}$ may be N, $X_{24}$ may be $C(R_{24})$, and $X_{25}$ may be $C(R_{25})$;

$X_{21}$ may be $C(R_{21})$, $X_{23}$ may be $C(R_{23})$, $X_{24}$ may be N, and $X_{25}$ may be $C(R_{25})$; or $X_{21}$ may be $C(R_{21})$, $X_{23}$ may be $C(R_{23})$, $X_{24}$ may be $C(R_{24})$, and $X_{25}$ may be N, but they are not limited thereto.

In some embodiments, in Formulae 3-34 to 3-44, 3-67 to 3-77, and 3-100 to 3-110, $X_{21}$ may be N, $X_{22}$ may be $C(R_{22})$, $X_{24}$ may be $C(R_{24})$, and $X_{25}$ may be $C(R_{25})$;

$X_{21}$ may be $C(R_{21})$, $X_{22}$ may be N, $X_{24}$ may be $C(R_{24})$, and $X_{25}$ may be $C(R_{25})$;

$X_{21}$ may be $C(R_{21})$, $X_{22}$ may be $C(R_{22})$, $X_{24}$ may be N, and $X_{25}$ may be $C(R_{25})$; or $X_{21}$ may be $C(R_{21})$, $X_{22}$ may be $C(R_{22})$, $X_{24}$ may be $C(R_{24})$, and $X_{25}$ may be N, but they are not limited thereto.

In some embodiments, $A_{11}$ in Formula 1 may be a cyano group (CN) or a group represented by one of Formulae 4-1 to 4-110, but the structure thereof is not limited thereto:

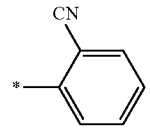
4-1

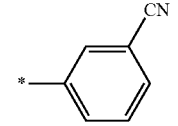
4-2

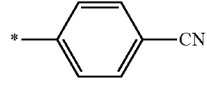
4-3

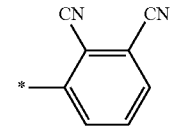
4-4

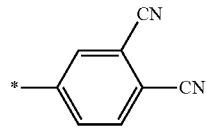
4-5

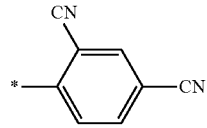
4-6

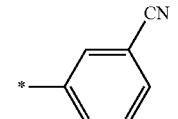
4-7

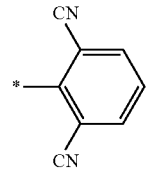
4-8

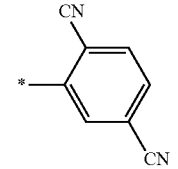
4-9

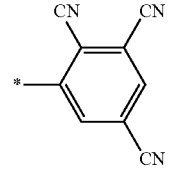
4-10

-continued
4-11 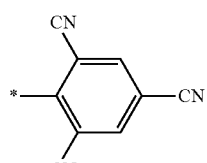
4-12 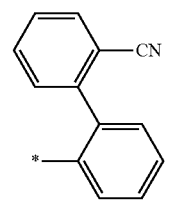
4-13 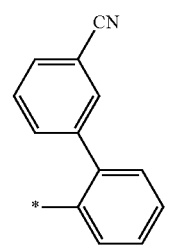
4-14 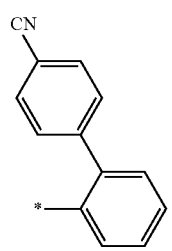
4-15 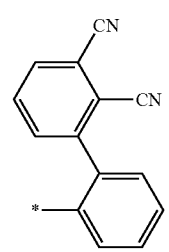
4-16 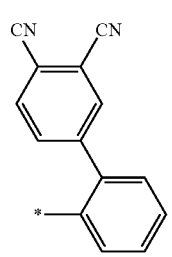
4-17 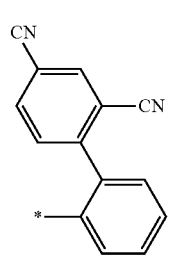
-continued
4-18 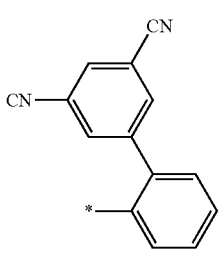
4-19 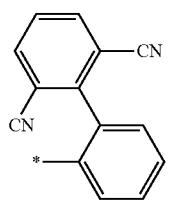
4-20 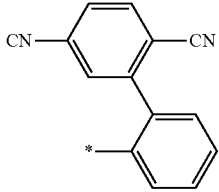
4-21 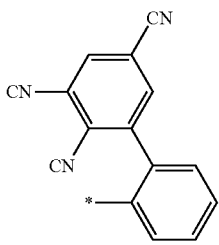
4-22 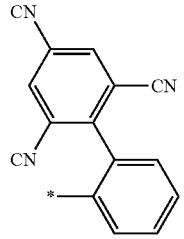
4-23 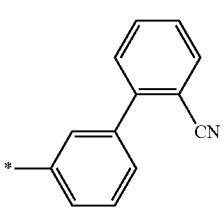
4-24 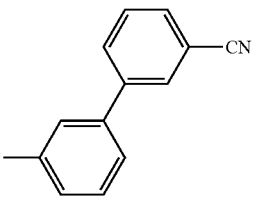

-continued
4-25 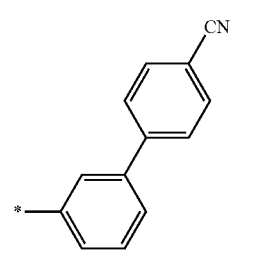
4-26 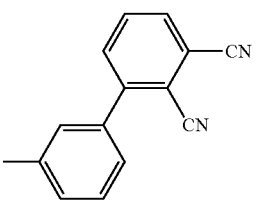
4-27 
4-28 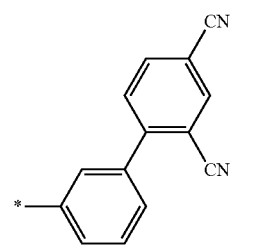
4-29 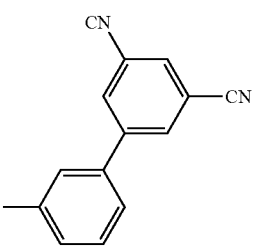
4-30 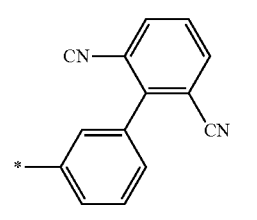
4-31 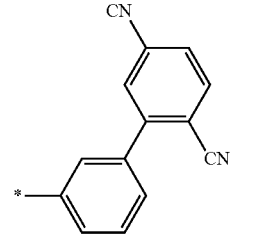
-continued
4-32 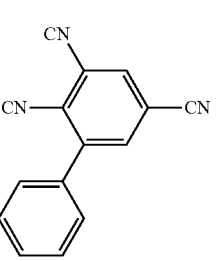
4-33 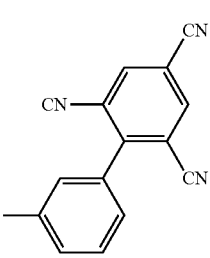
4-34 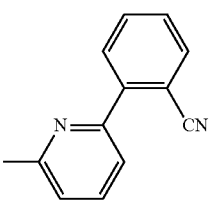
4-35 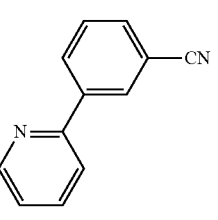
4-36 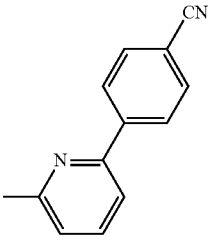
4-37 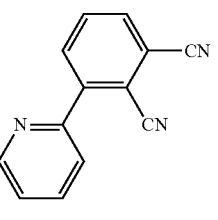
4-38 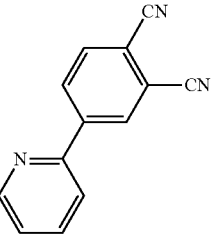

4-39 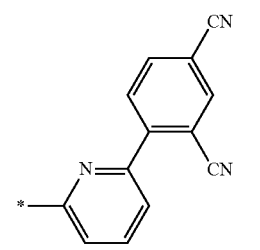
4-40 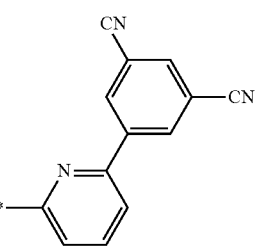
4-41 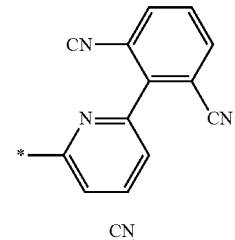
4-42 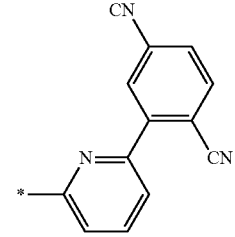
4-43 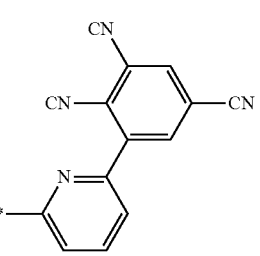
4-44 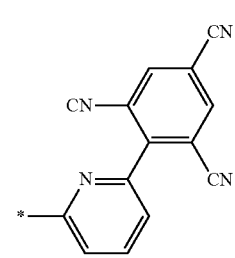
4-45 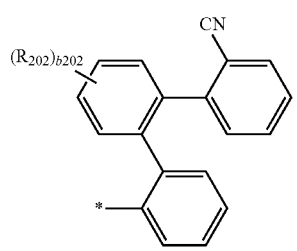
4-46 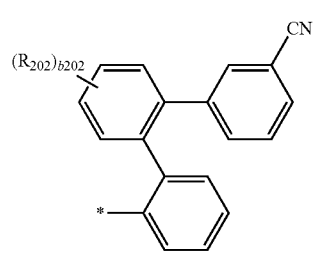
4-47 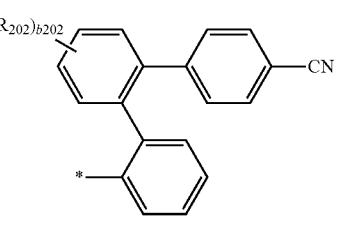
4-48 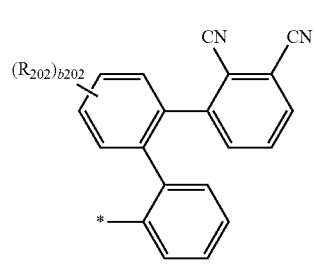
4-49 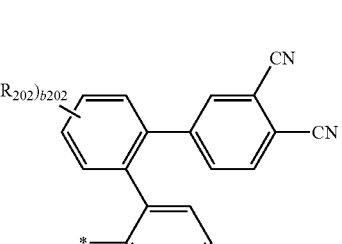
4-50 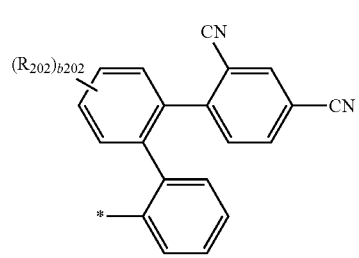

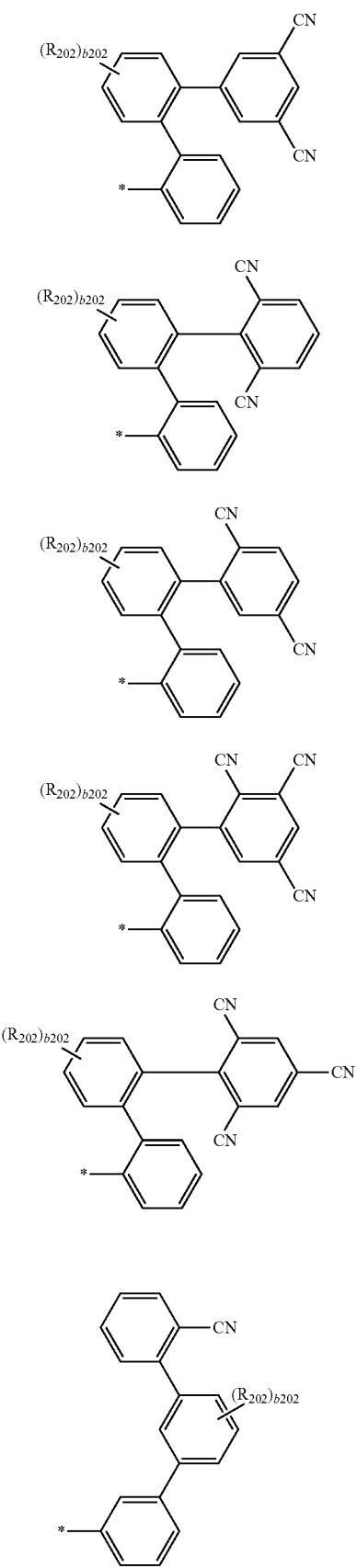
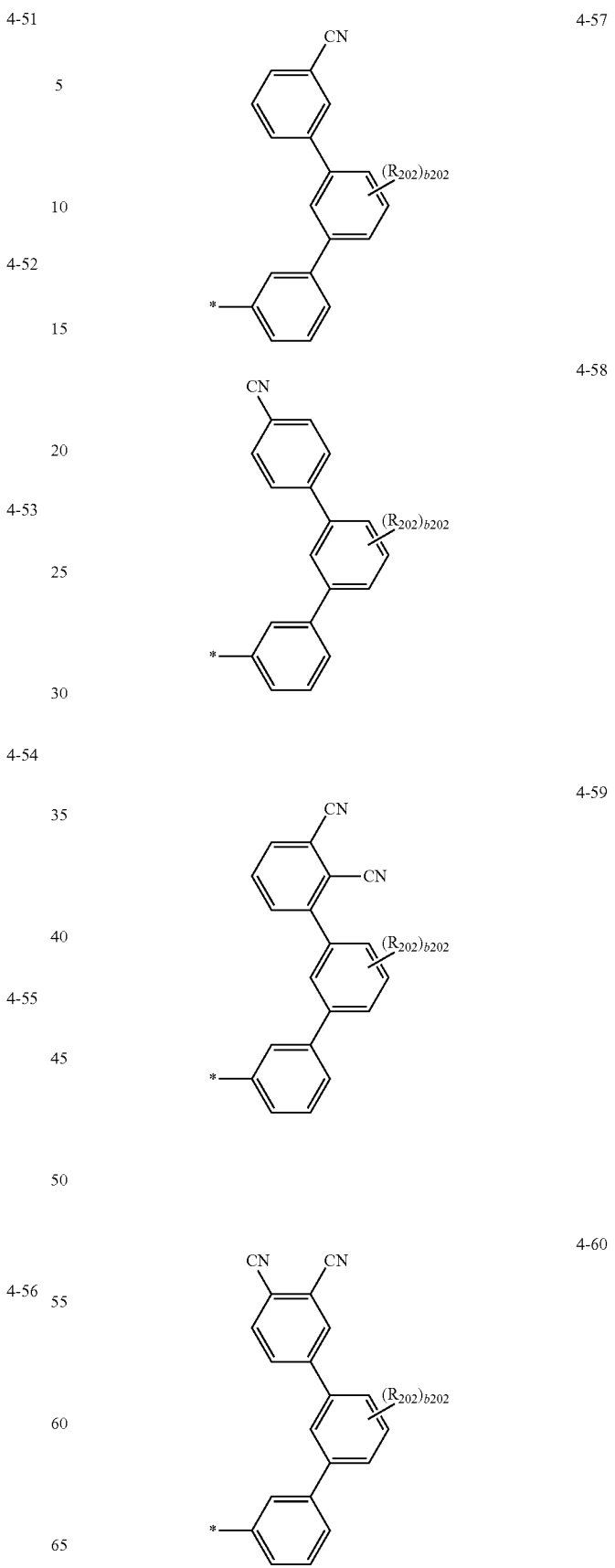

-continued
4-61
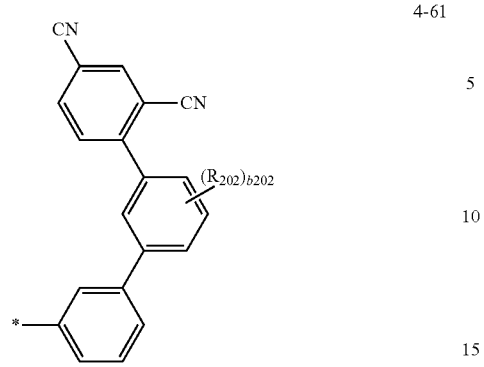
4-62
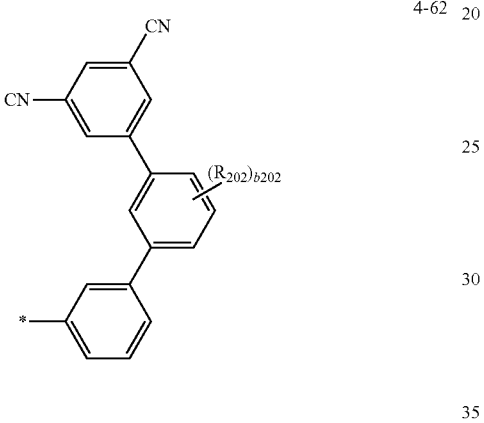
4-63
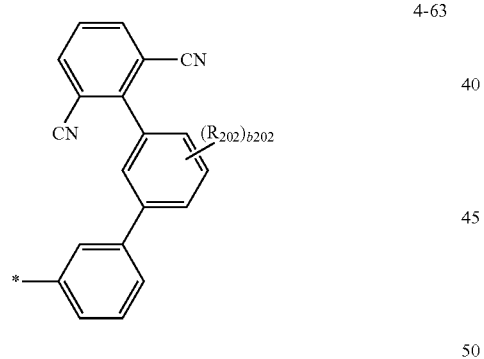
4-64
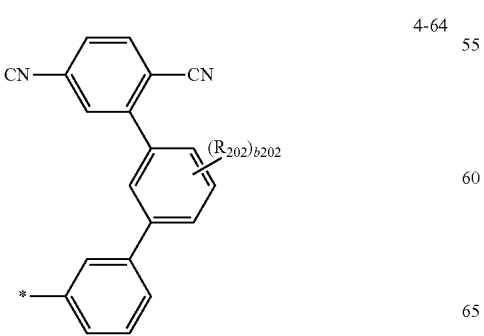
-continued
4-65
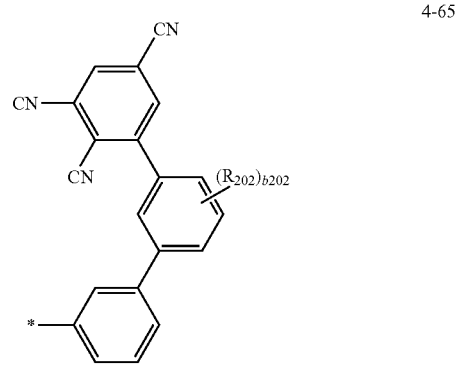
4-66
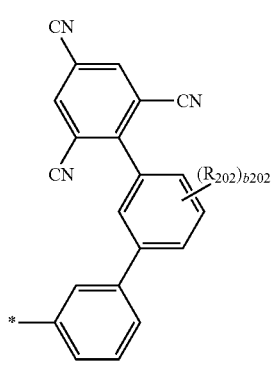
4-67
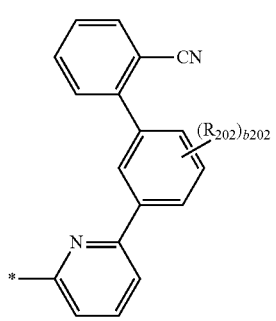
4-68
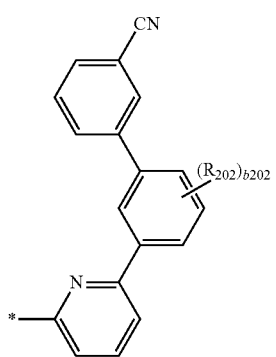

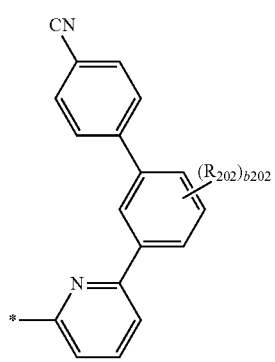
4-69
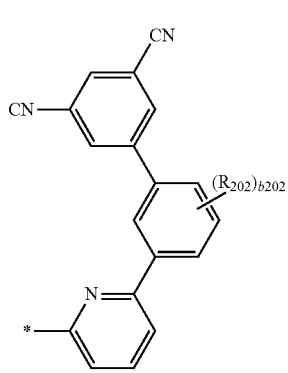
4-73
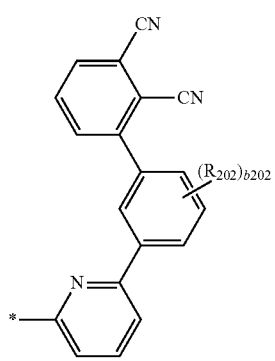
4-70
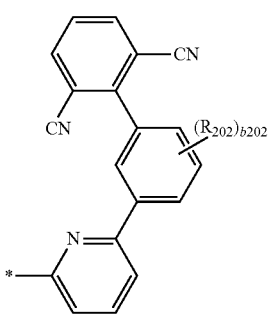
4-74
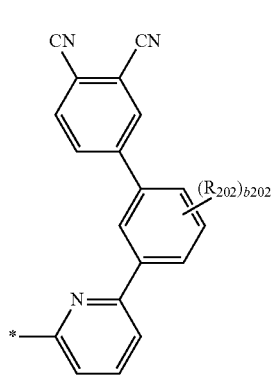
4-71
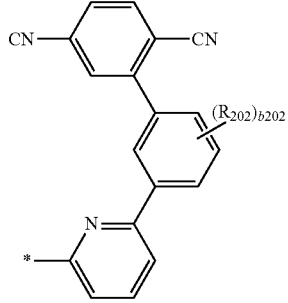
4-75
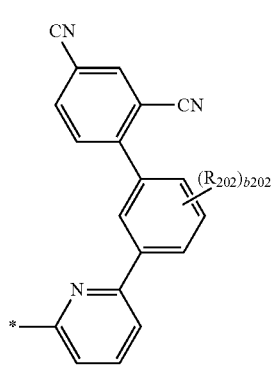
4-72
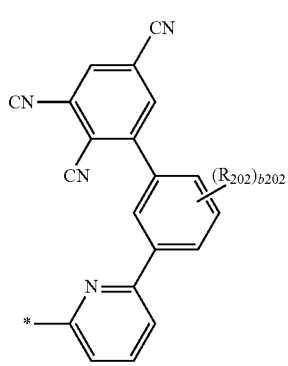
4-76

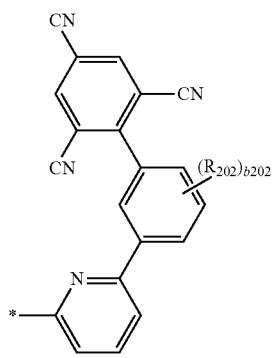
4-77
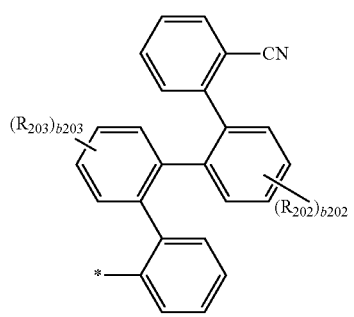
4-78
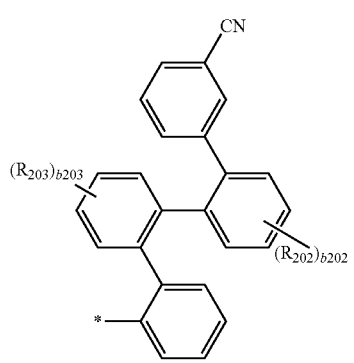
4-79
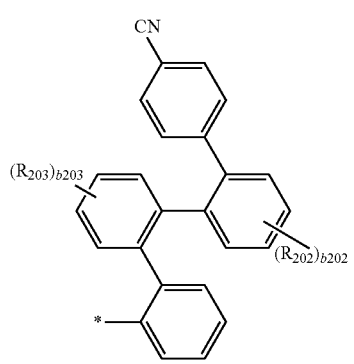
4-80
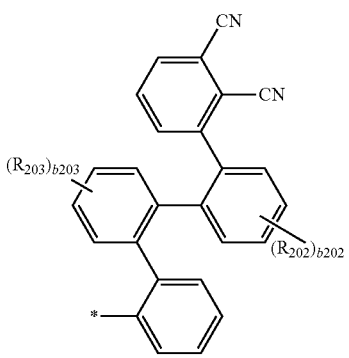
4-81
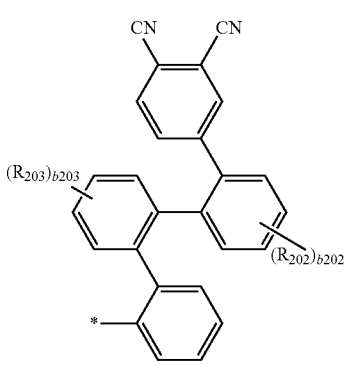
4-82
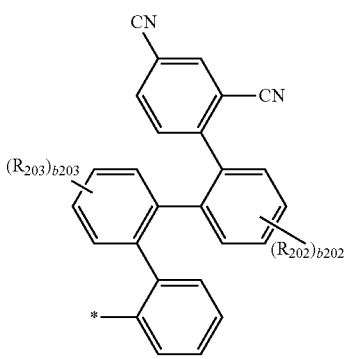
4-83
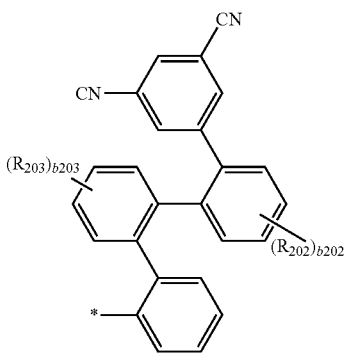
4-84

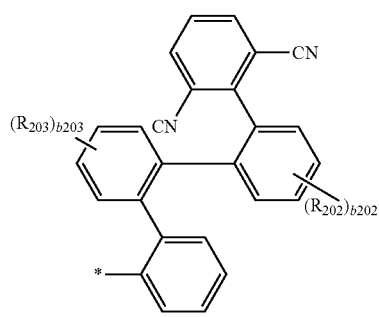
4-85
4-86
4-87
4-88
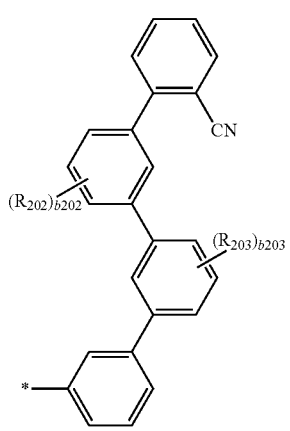
4-89
4-90
4-91

4-92
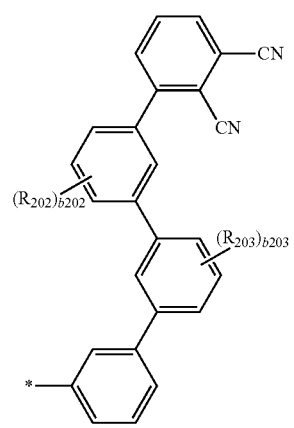
4-93
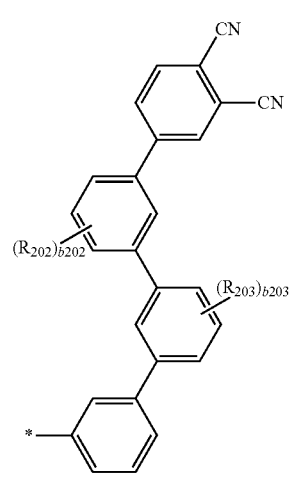
4-94
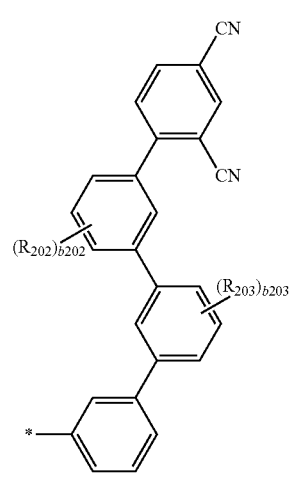
4-95
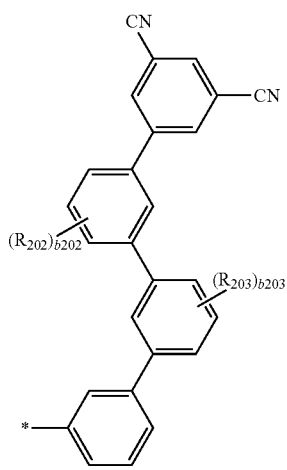
4-96
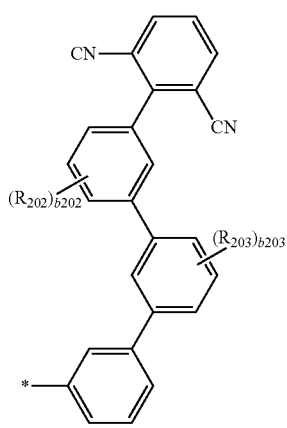
4-97
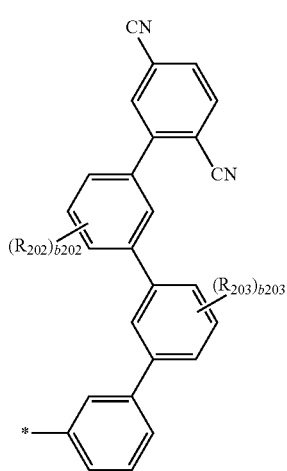

4-98
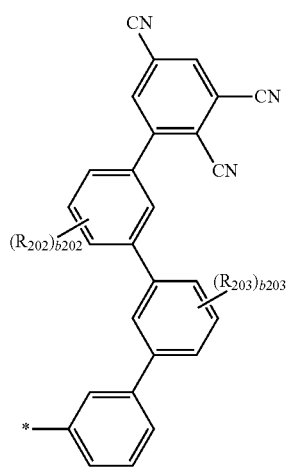
4-99
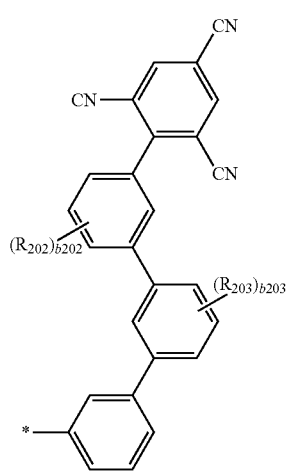
4-100
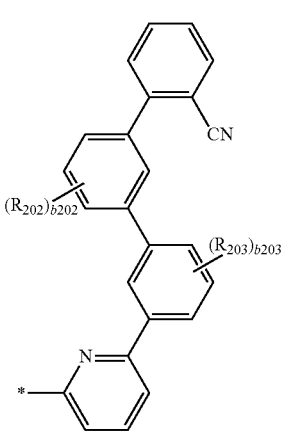
4-101
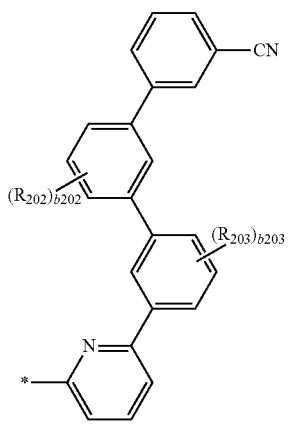
4-102
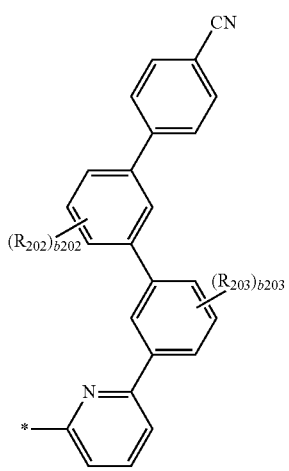
4-103
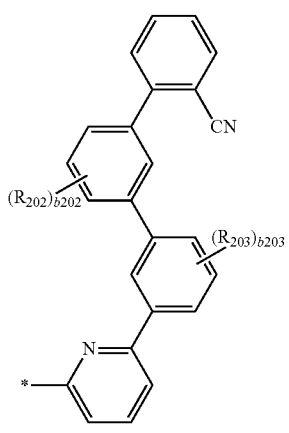

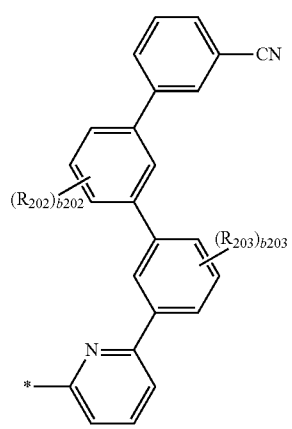
4-104
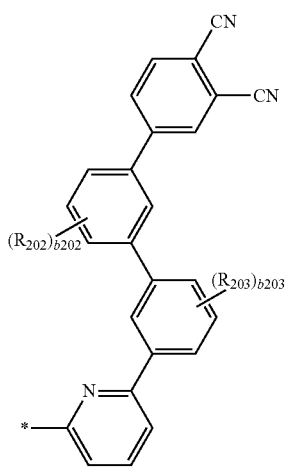
4-107
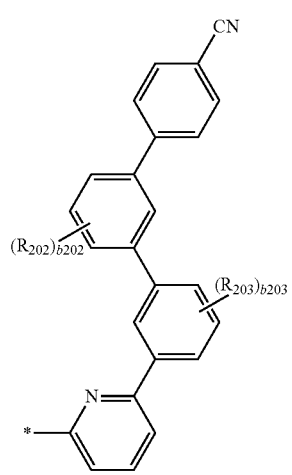
4-105
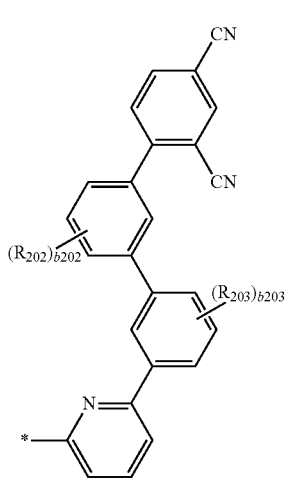
4-108
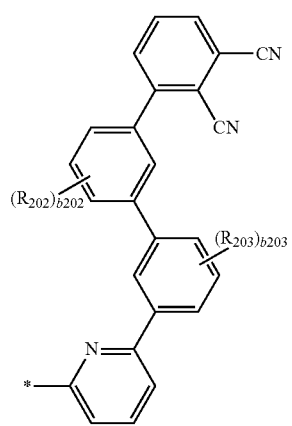
4-106
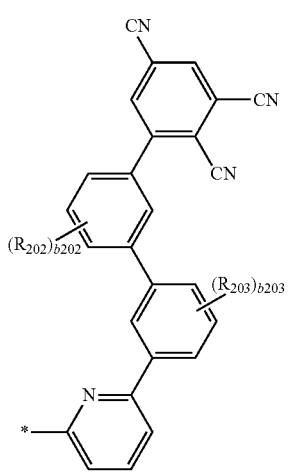
4-109

4-110

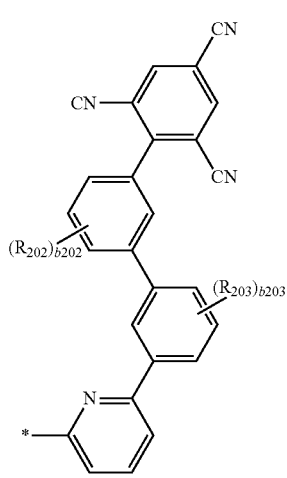

In Formulae 4-1 to 4-110,
* indicates a carbon atom in Formula 1; and
$R_{202}$, $R_{203}$, b201, and b202 will be explained in detail below.

In Formula 1, $A_{12}$ may be selected from hydrogen, deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_{21}$)($Q_{22}$)($Q_{23}$); and
—Si($Q_{31}$)($Q_{32}$)($Q_{33}$), wherein $Q_{21}$ to $Q_{23}$ and $Q_{31}$ to $Q_{33}$ may be each independently selected from hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

For example, $A_{12}$ in Formula 1 may be selected from hydrogen, deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a phenyl group, a pyridinyl group, a fluorenyl group, a dibenzofuranyl group, and a dibenzothiophenyl group; and
—Si($Q_{31}$)($Q_{32}$)($Q_{33}$), wherein $Q_{31}$ to $Q_{33}$ may be each independently selected from a $C_1$-$C_{10}$ alkyl group, a $C_1$-$C_{10}$ alkoxy group, a phenyl group, a naphthyl group, and a pyridinyl group, but $A_{12}$ is not limited thereto.

$R_1$ to $R_8$, $R_{11}$ to $R_{18}$, $R_{101}$, $R_{102}$, $R_{21}$ to $R_{25}$, $R_{201}$ to $R_{203}$ in Formulae 1 and 2-1 to 2-10 may be each independently selected from hydrogen, deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$);
—Si($Q_{11}$)($Q_{12}$)($Q_{13}$); and $R_{101}$ and $R_{102}$ may be optionally linked to each other to form a saturated ring or an unsaturated ring, wherein $Q_1$ to $Q_3$ and $Q_{11}$ to $Q_{13}$ may be each independently selected from hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

For example, $R_1$ to $R_8$, $R_{11}$ to $R_{18}$, $R_{101}$, $R_{102}$, $R_{21}$ to $R_{25}$, and $R_{201}$ to $R_{203}$ in Formulae 1 and 2-1 to 2-10 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group;

a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_{11}$)($Q_{12}$)($Q_{13}$), wherein $Q_{11}$ to $Q_{13}$ may be each independently selected from hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group, but they are not limited thereto.

In some embodiments, $R_1$ to $R_8$, $R_{11}$ to $R_{18}$, $R_{21}$ to $R_{25}$, and $R_{201}$ to $R_{203}$ in Formulae 1 and 2-1 to 2-10 may be each independently selected from hydrogen, deuterium, a cyano group, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, and —Si($Q_{11}$)($Q_{12}$)($Q_{13}$), wherein $Q_{11}$ to $Q_{13}$ may be each independently selected from hydrogen, a $C_1$-$C_{20}$ alkyl group, a $C_1$-$C_{20}$ alkoxy group, and a phenyl group, but they are not limited thereto.

In some embodiments, $R_{101}$ and $R_{102}$ in Formula 1 may be linked to each other to form the structure represented by Formula 8, but they are not limited thereto:

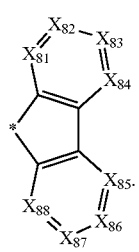

Formula 8

In Formula 8,

* indicates a carbon atom that belongs to $Y_{11}$ in Formula 1;

$X_{81}$ may be N or C($R_{81}$), $X_{82}$ may be N or C($R_{82}$), $X_{83}$ may be N or C($R_{83}$), $X_{84}$ may be N or C($R_{84}$), $X_{85}$ may be N or C($R_{85}$), $X_{86}$ may be N or C($R_{86}$), $X_{87}$ may be N or C($R_{87}$), and $X_{88}$ may be N or C($R_{88}$), and $R_{81}$ to $R_{88}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In some embodiments, $R_{101}$ and $R_{102}$ in Formula 1 may be linked to each other to form the structure represented by Formula 9, but they are not limited thereto:

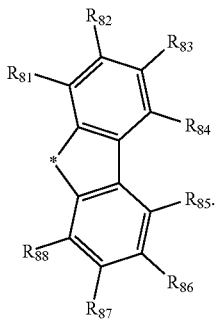

Formula 9

In Formula 9,

* indicates a carbon atom that belongs to $Y_{11}$ in Formula 1; and $R_{81}$ to $R_{88}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In some embodiments, $R_{101}$ and $R_{102}$ in Formula 1 may be linked to each other to form the structure represented by one of Formulae 10-1 and 10-2, but they are not limited thereto:

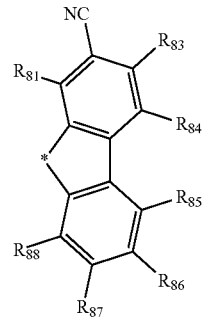

10-1

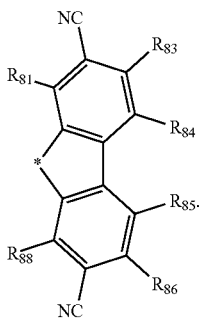

10-2

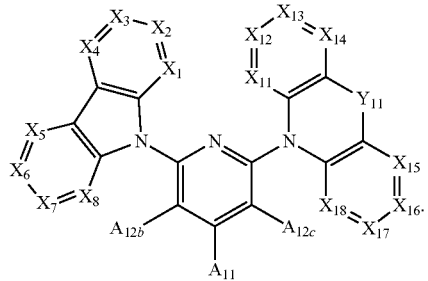

1-2

In Formula 10-1 and 10-2,

* indicates a carbon atom that belongs to $Y_{11}$ in Formula 1; and $R_{81}$ to $R_{88}$ may be each independently selected from hydrogen; deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ are each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

In Formulae 2-1 to 2-10, b201 indicates the number of groups $R_{201}$, and b201 may be selected from 1, 2, 3, 4, and 5. When b201 is 2 or more, groups $R_{301}$ may be identical to or different from each other.

In Formulae 2-1 to 2-10, b202 indicates the number of groups $R_{202}$, and b202 may be selected from 1, 2, 3, and 4. When b202 is 2 or more, groups $R_{202}$ may be identical to or different from each other.

In Formulae 2-1 to 2-10, b203 indicates the number of groups $R_{203}$, and b203 may be selected from 1, 2, 3, and 4. When b203 is 2 or more, groups $R_{203}$ may be identical to or different from each other.

For example, at least one selected from $X_3$, $X_6$, $X_{13}$, and $X_{16}$ in Formula 1 may be C(CN), but embodiments are not limited thereto.

In some embodiments, $R_1$, $R_2$, $R_4$, $R_5$, $R_7$, $R_8$, $R_{11}$, $R_{12}$, $R_{14}$, $R_{15}$, $R_{17}$, and $R_{18}$ in Formula 1 may not be a cyano group, but they are not limited thereto.

The condensed cyclic compound represented by Formula 1 may be represented by one of Formulae 1-1 and 1-2, but they are not limited thereto;

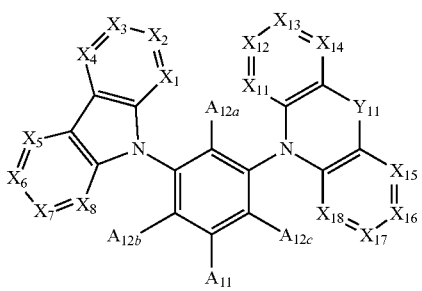

1-1

In Formulae 1-1 and 1-2, $X_1$ to $X_8$, $X_{11}$ to $X_{18}$, $Y_{11}$, and $A_{11}$ may be understood by referring to descriptions thereof made in connection with Formula 1;

$A_{12a}$, $A_{12b}$, and $A_{12c}$ may be understood by referring to descriptions thereof made in connection with $A_{12}$ in Formula 1.

For example, $A_{11}$ in Formulae 1-1 and 1-2 may be a cyano group (CN), or a group represented by one of Formulae 4-1 to 4-110, but $A_{11}$ is not limited thereto.

In some embodiments, at least one selected from $X_3$, $X_8$, $X_{13}$, and $X_{16}$ in Formulae 1-1 and 1-2 may be C(CN), but embodiments are not limited thereto.

The condensed cyclic compound represented by Formula 1 may be represented by one of Formulae 1-3 to 1-6, but they are not limited thereto:

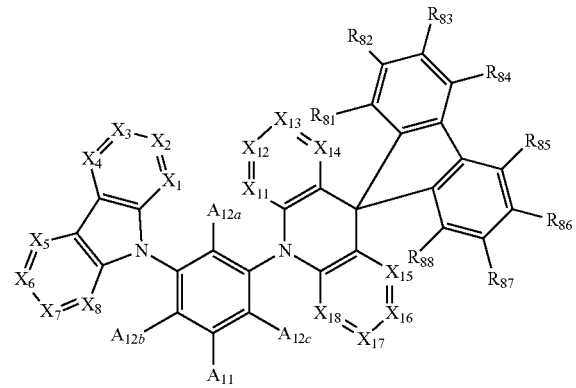

1-3

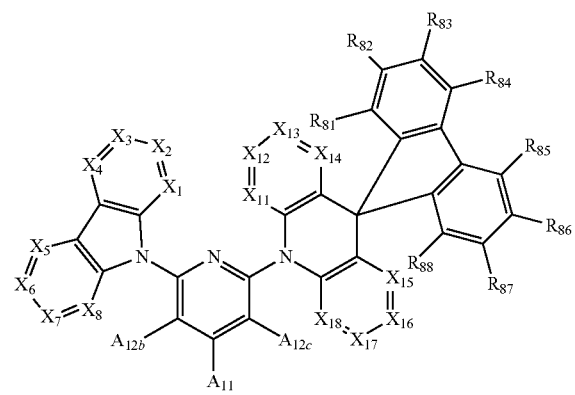

1-4

1-5

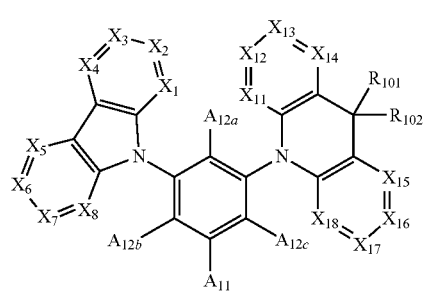

1-6

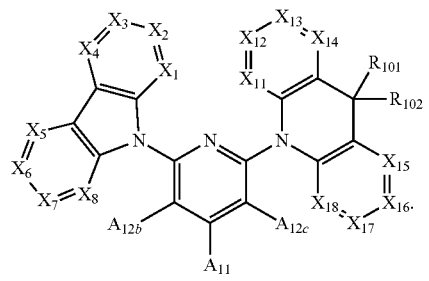

In Formulae 1-3 to 1-6, $X_1$ to $X_8$, $X_{11}$ to $X_{18}$, $Y_{11}$, $R_{101}$, $R_{102}$, and $A_{11}$ may be understood by referring to descriptions thereof made in connection with Formula 1;

$A_{12a}$, $A_{12b}$, and $A_{12c}$ may be understood by referring to descriptions thereof made in connection with $A_{12}$ in Formula 1;

$R_{81}$ to $R_{88}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$);

$Q_{31}$ to $Q_{33}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

For example, $A_{11}$ in Formulae 1-3 to 1-6 may be a cyano group (CN) or a group represented by any one of Formulae 4-1 to 4-110, but is not limited thereto.

In some embodiments, at least one of $X_3$, $X_6$, $X_{13}$, and $X_{16}$ in Formulae 1-3 to 1-6 may be C(CN), but embodiments are not limited thereto.

The condensed cyclic compound represented by Formula 1 may be selected from one of Formulae 1-11 to 1-25, but embodiments are not limited thereto:

1-11

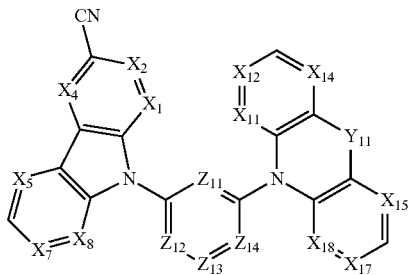

1-12

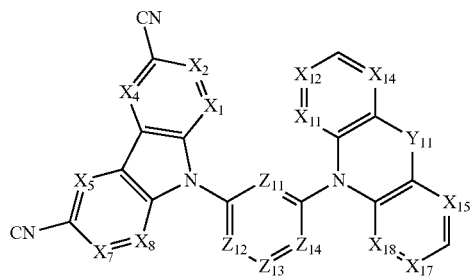

1-13

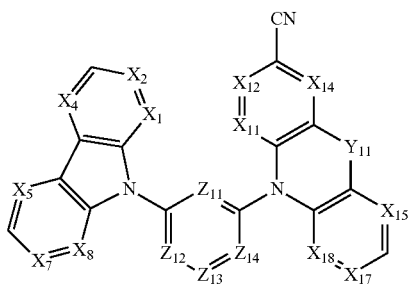

1-14

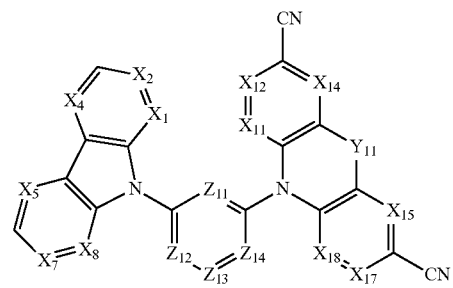

1-15

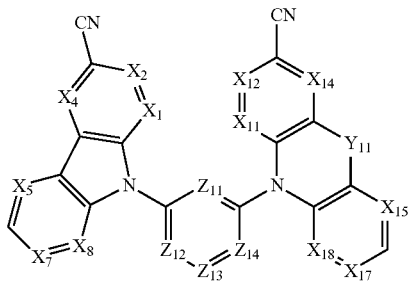

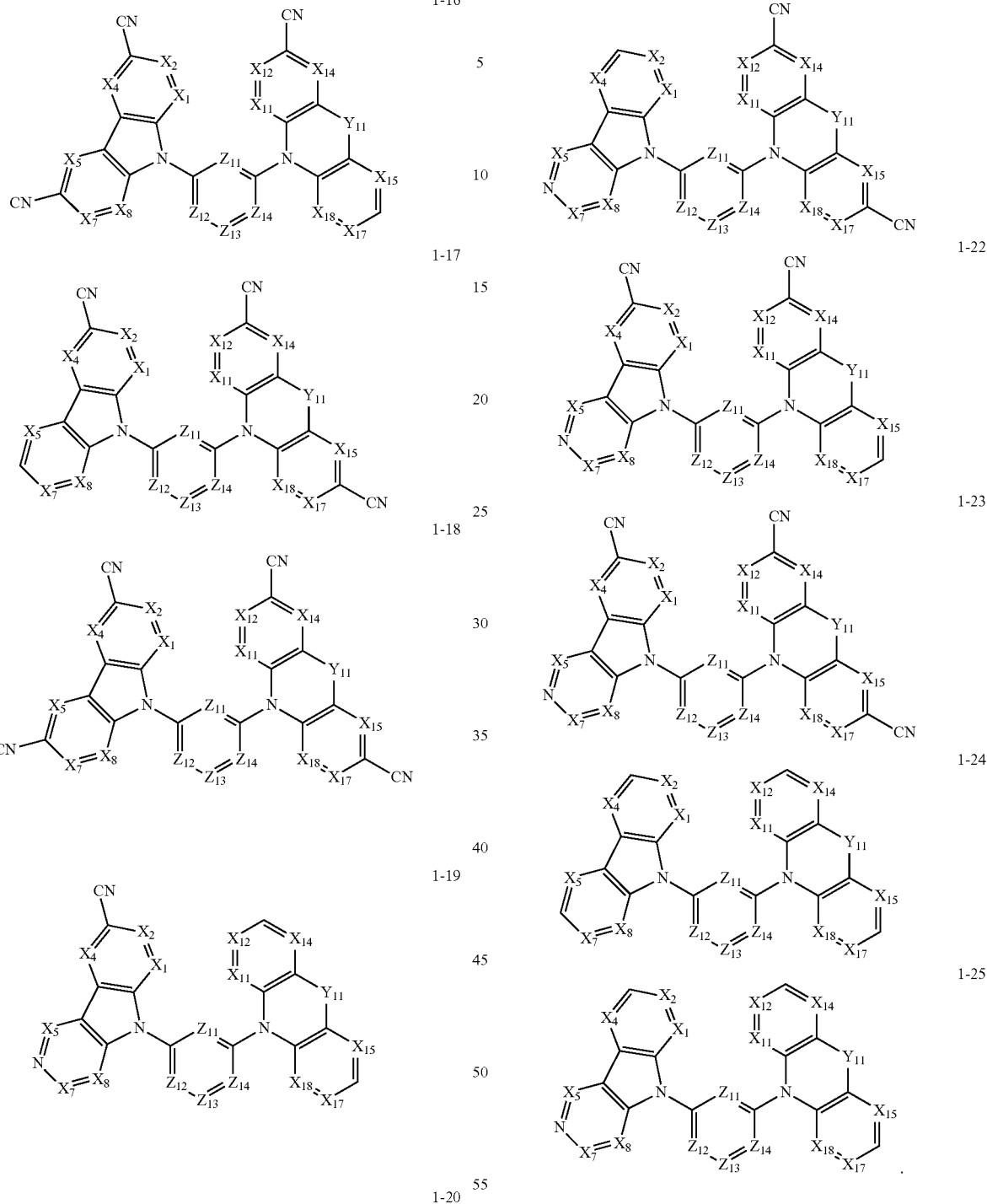

In Formulae 1-11 to 1-25, $X_1$, $X_2$, $X_4$, $X_5$, $X_7$, $X_8$, $X_{11}$, $X_{12}$, $X_{14}$, $X_{15}$, $X_{17}$, $X_{18}$, $Y_{11}$, and $Z_{11}$ to $Z_{14}$ may be understood by referring to descriptions thereof made in connection with Formula 1.

For example, in Formulae 1-11 to 1-25, $X_1$ may be N, $X_2$ may be $C(R_2)$, $X_4$ may be $C(R_4)$, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$;

$X_1$ may be $C(R_1)$, $X_2$ may be N, $X_4$ may be $C(R_4)$, $X_5$ may be $C(R_5)$, $X_7$ may be $C(R_7)$, $X_8$ may be $C(R_8)$, $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$);

$X_1$ may be C($R_1$), $X_2$ may be C($R_2$), $X_4$ may be N, $X_5$ may be C($R_5$), $X_7$ may be C($R_7$), $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$);

$X_1$ may be C($R_1$), $X_2$ may be C($R_2$), $X_4$ may be C($R_4$), $X_5$ may be N, $X_7$ may be C($R_7$), $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$);

$X_1$ may be C($R_1$), $X_2$ may be C($R_2$), $X_4$ may be C($R_4$), $X_5$ may be C($R_5$), $X_7$ may be N, $X_8$ may be C($R_8$), $X_{11}$ may be C($R_{11}$), $X_{12}$ may be C($R_{12}$), $X_{14}$ may be C($R_{14}$), $X_{15}$ may be C($R_{15}$), $X_{17}$ may be C($R_{17}$), and $X_{18}$ may be C($R_{18}$); or $X_1$ may be C($R_1$), $X_2$ may be C($R_2$), $X_4$ may be C($R_4$), $X_5$ may be C($R_5$), $X_7$ may be C($R_7$), $X_8$ may be N, $X_{11}$ may be C($R_{11}$), $X_{12}$ may be C($R_{12}$), $X_{14}$ may be C($R_{14}$), $X_{15}$ may be C($R_{18}$), $X_{17}$ may be C($R_{17}$), and $X_{18}$ may be C($R_{18}$), but they are not limited thereto.

In some embodiments, $Z_{11}$ to $Z_{14}$ in Formulae 1-11 to 1-25 may be each independently selected from N, C($A_{11}$), and C($A_{12}$); and at least one of $Z_{11}$ to $Z_{14}$ is C($A_{11}$); and $A_{11}$ includes at least one cyano group (CN), and may be a cyano group (CN) or a group represented by one of Formulae 4-1 to 4-90, but they are not limited thereto.

In some embodiments, in Formulae 1-11 to 1-25, $Z_{11}$ may be N, $Z_{12}$ may be C($A_{12}$), $Z_{13}$ may be C($A_{11}$), and $Z_{14}$ may be C($A_{12}$);

$Z_{11}$ may be C($A_{12}$), $Z_{12}$ may be N, $Z_{13}$ may be C($A_{11}$), and $Z_{14}$ may be C($A_{12}$);

$Z_{11}$ may be C($A_{12}$), $Z_{12}$ may be C($A_{12}$), $Z_{13}$ may be C($A_{11}$), and $Z_{14}$ may be N; or $Z_{11}$ may be C($A_{12}$), $Z_{12}$ may be C($A_{12}$), $Z_{13}$ may be C($A_{11}$), and $Z_{14}$ may be C($A_{12}$), but they are not limited thereto.

The condensed cyclic compound represented by Formula 1 may be represented by one of Formulae 1-31 to 1-45, but is not limited thereto:

1-31

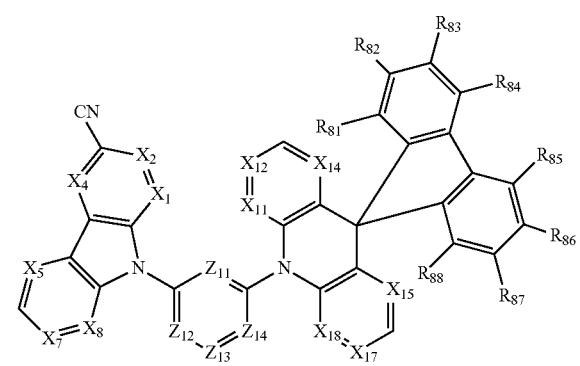

1-32

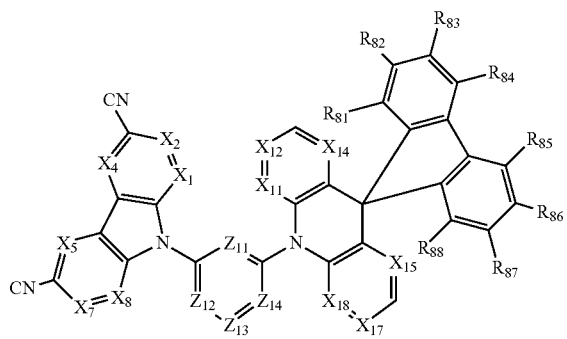

1-33

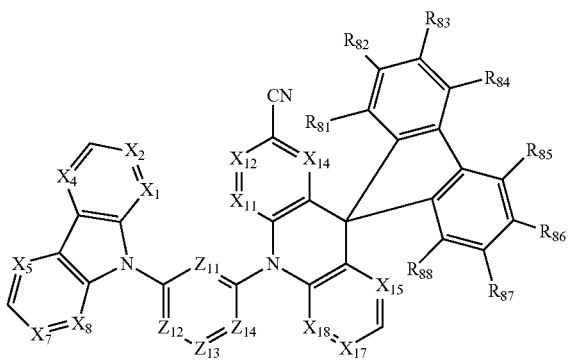

1-34

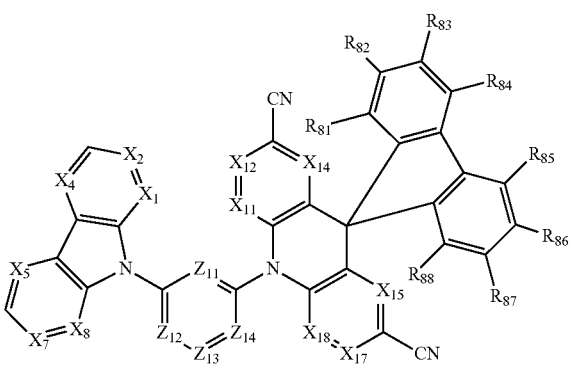

1-35

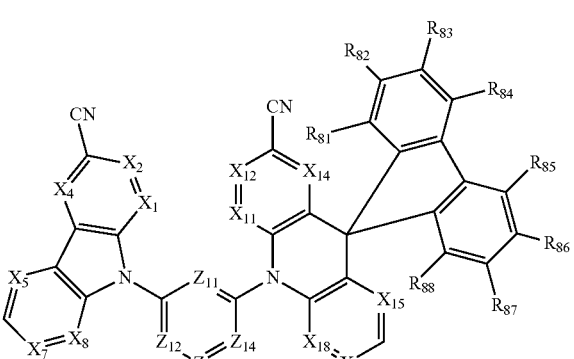

-continued
1-36
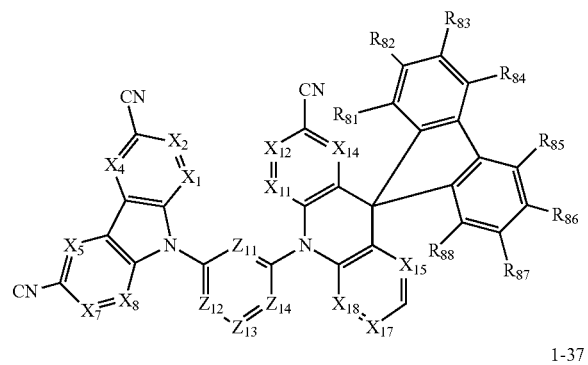
1-37
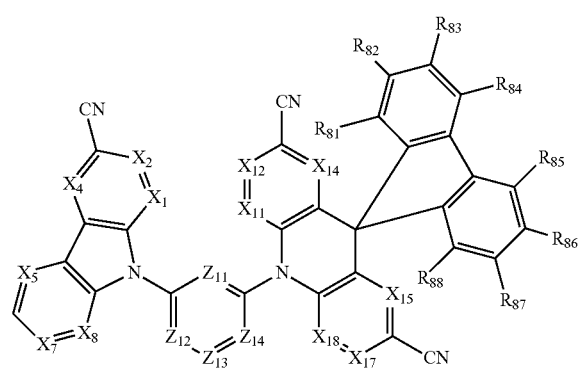
1-38
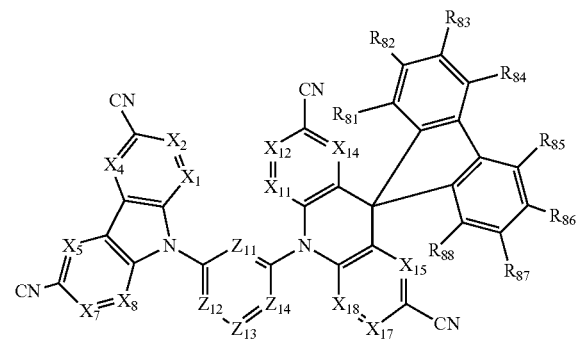
1-39
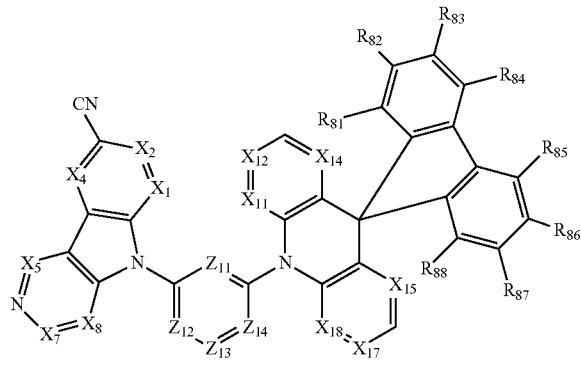
-continued
1-40
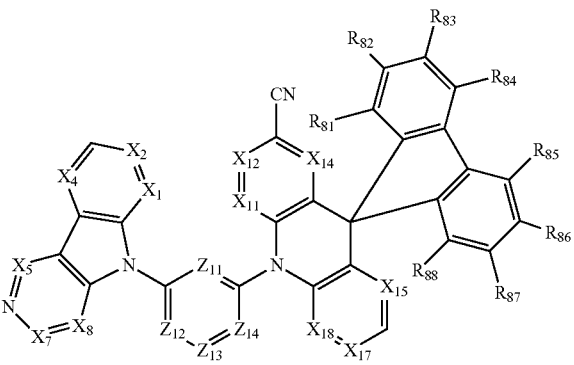
1-41
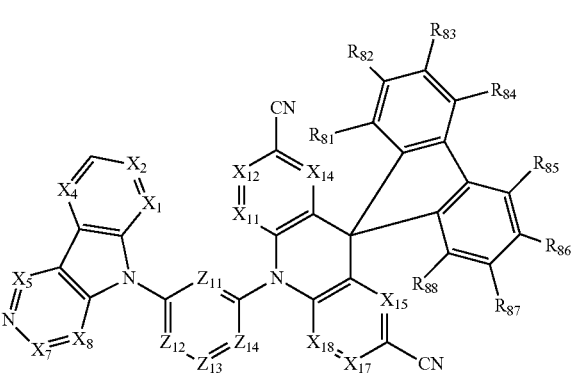
1-42
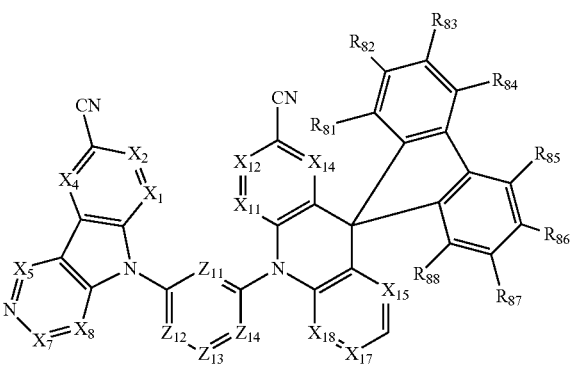
1-43
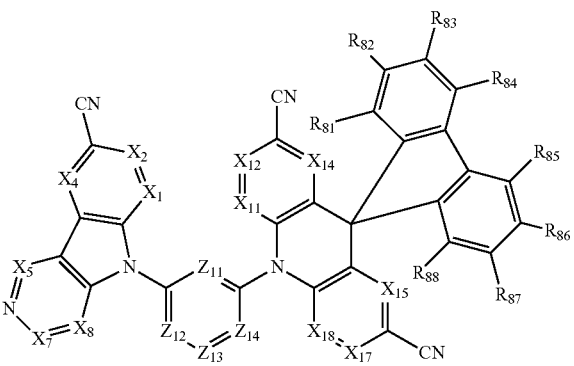

-continued

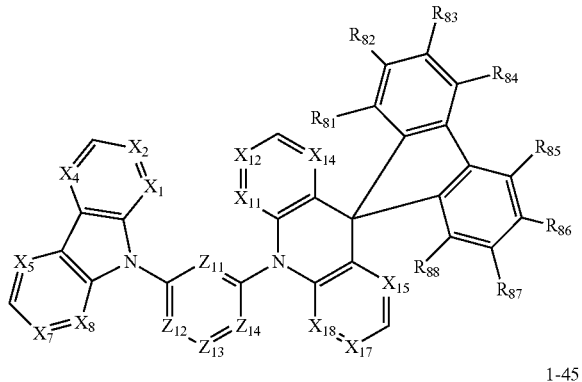

1-44

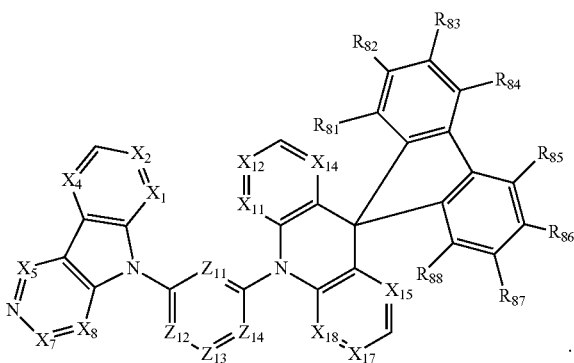

1-45

In Formulae 1-31 to 1-45, $X_1$, $X_2$, $X_4$, $X_5$, $X_7$, $X_8$, $X_{11}$, $X_{12}$, $X_{14}$, $X_{15}$, $X_{17}$, $X_{18}$, and $Z_{11}$ to $Z_{14}$ may be understood by referring to descriptions thereof made in connection with Formula 1; and $R_{81}$ to $R_{88}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

For example, in Formulae 1-31 to 1-45, $X_1$ may be N, $X_2$ may be $C(R_2)$, $X_4$ may be $C(R_4)$, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$;

$X_1$ may be $C(R_1)$, $X_2$ may be N, $X_4$ may be $C(R_4)$, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$;

$X_1$ may be $C(R_1)$, $X_2$ may be $C(R_2)$, $X_4$ may be N, $X_5$ may be $C(R_5)$, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$;

$X_1$ may be $C(R_1)$, $X_2$ may be $C(R_2)$, $X_4$ may be $C(R_4)$, $X_5$ may be N, $X_7$ may be $C(R_7)$, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$;

$X_1$ may be $C(R_1)$, $X_2$ may be $C(R_2)$, $X_4$ may be $C(R_4)$, $X_5$ may be $C(R_5)$, $X_7$ may be N, $X_8$ may be $C(R_8)$, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$; or $X_1$ may be $C(R_1)$, $X_2$ may be $C(R_2)$, $X_4$ may be $C(R_4)$, $X_5$ may be $C(R_5)$, $X_7$ may be $C(R_7)$, $X_8$ may be N, $X_{11}$ may be $C(R_{11})$, $X_{12}$ may be $C(R_{12})$, $X_{14}$ may be $C(R_{14})$, $X_{15}$ may be $C(R_{15})$, $X_{17}$ may be $C(R_{17})$, and $X_{18}$ may be $C(R_{18})$, but they are not limited thereto.

In some embodiments, $Z_{11}$ to $Z_{14}$ in Formulae 1-31 to 1-45 may be each independently selected from N, $C(A_{11})$, and $C(A_{12})$; and at least one of $Z_{11}$ to $Z_{14}$ may be $C(A_{11})$; and $A_{11}$ includes at least one cyano group (CN), and may be a cyano group (CN) or a group represented by one of Formulae 4-1 to 4-110, but $A_{11}$ is not limited thereto.

The condensed cyclic compound represented by Formula 1 may be represented by one of Formulae 1-51 to 1-59 and 1-61 to 1-69, but is not limited thereto:

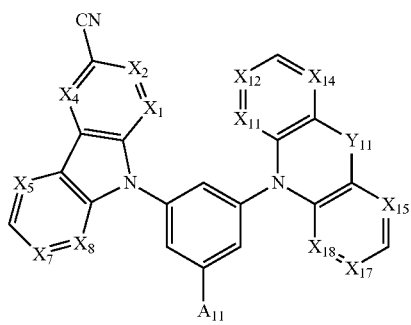

1-51

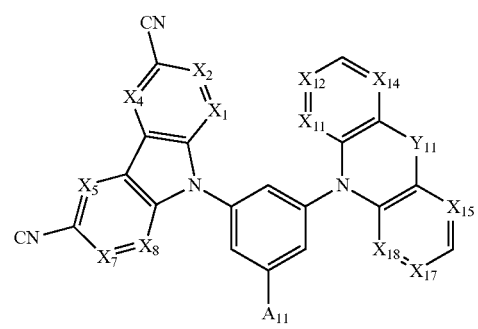

1-52

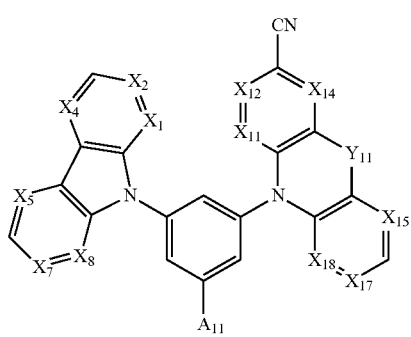

1-53

1-54
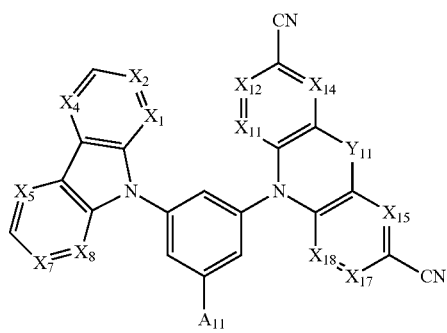
1-55
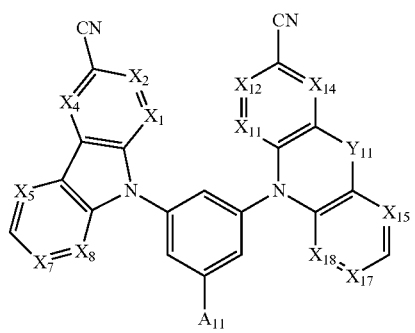
1-56
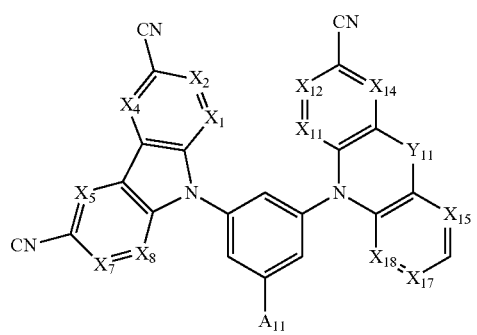
1-57
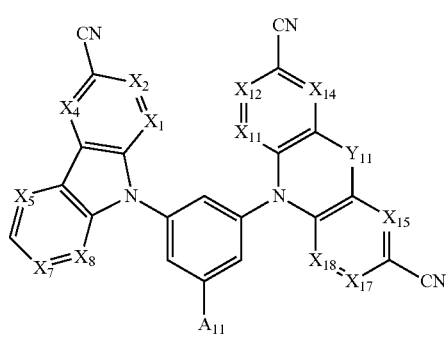
1-58
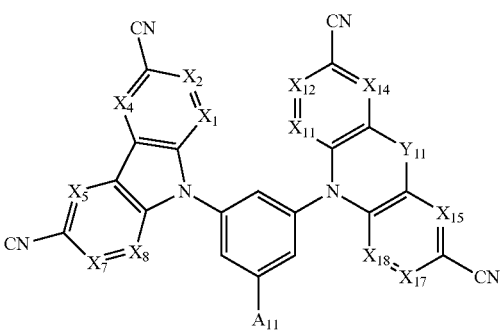
1-59
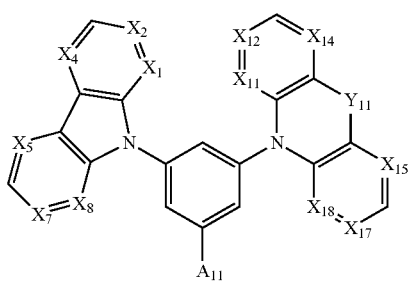
1-61
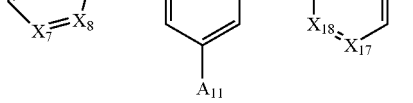
1-62
1-63
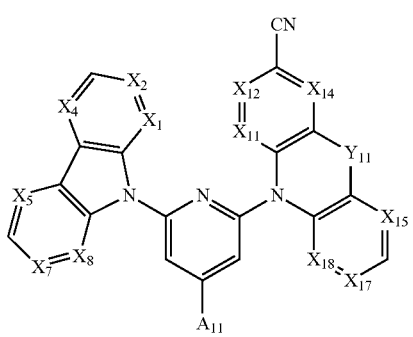

1-64
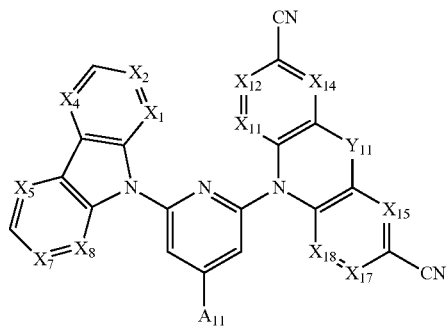
1-65
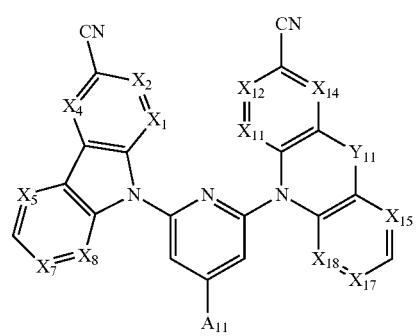
1-66
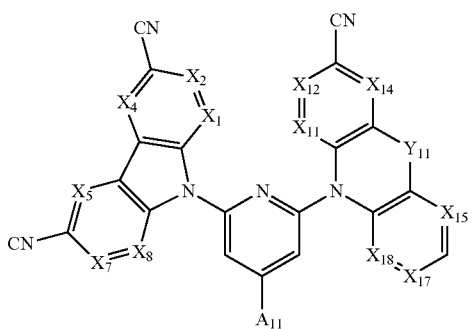
1-67
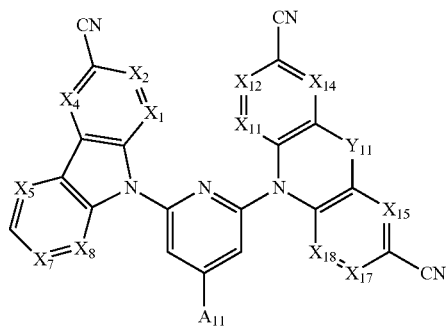
1-68
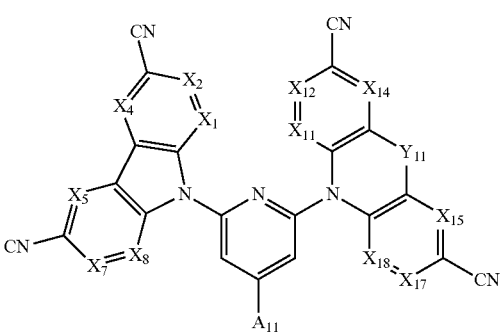
1-69
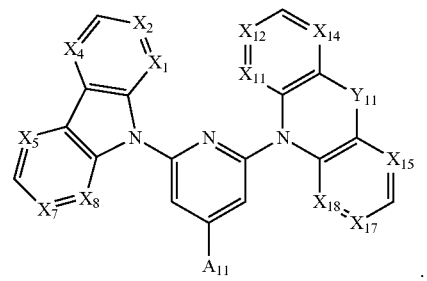
In Formulae 1-51 to 1-59 and 1-61 to 1-69,
$X_1$, $X_2$, $X_4$, $X_5$, $X_7$, $X_8$, $X_{11}$, $X_{12}$, $X_{14}$, $X_{15}$, $X_{17}$, $X_{18}$, $Y_{11}$, and $A_{11}$ may be understood by referring to descriptions thereof made in connection with Formula 1.
The condensed cyclic compound represented by Formula 1 may be represented by one of Formulae 1-71 to 1-79 and 1-81 to 1-89, but is not limited thereto:
1-71
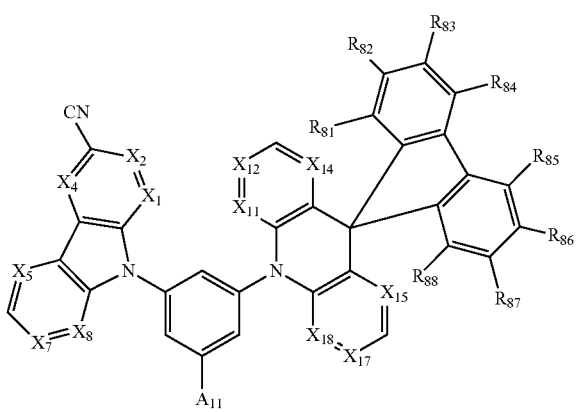

-continued
1-72
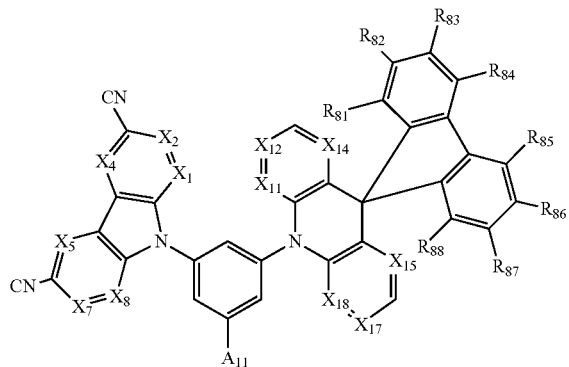
1-73
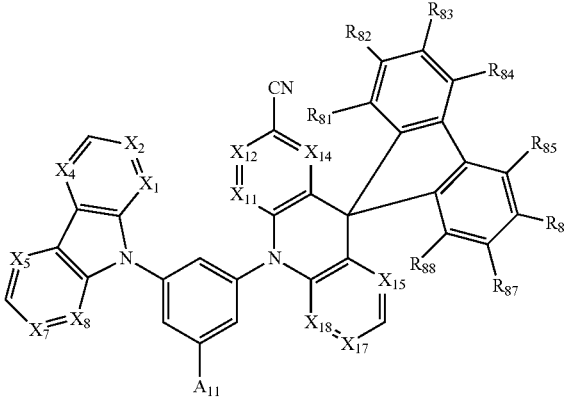
1-74
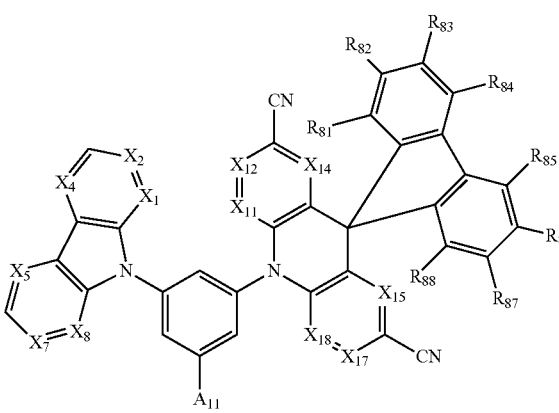
-continued
1-75
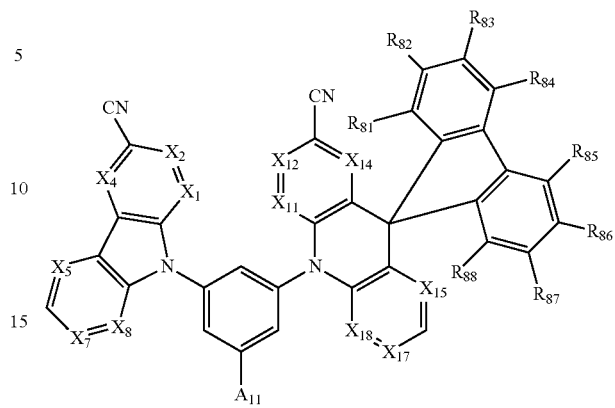
1-76
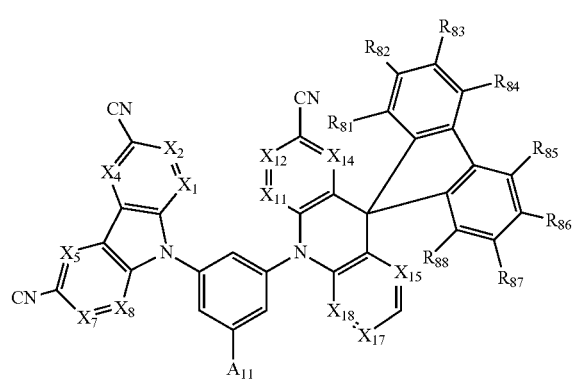
1-77
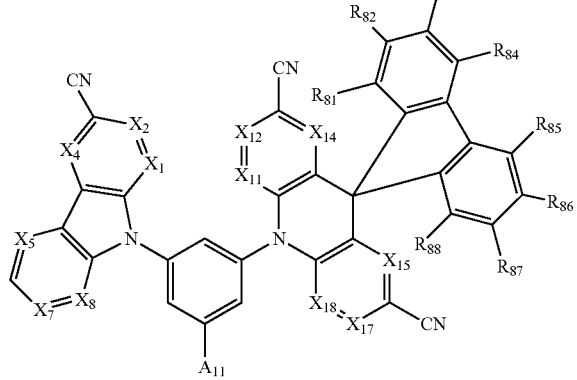
1-78
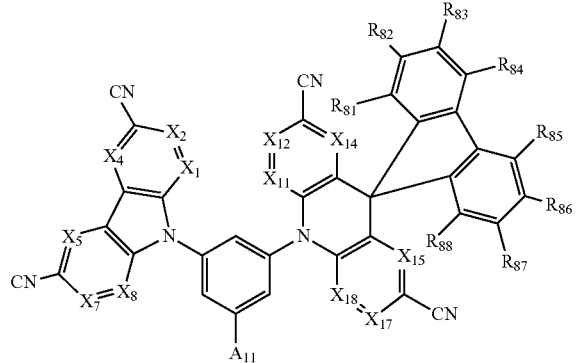

-continued
1-79
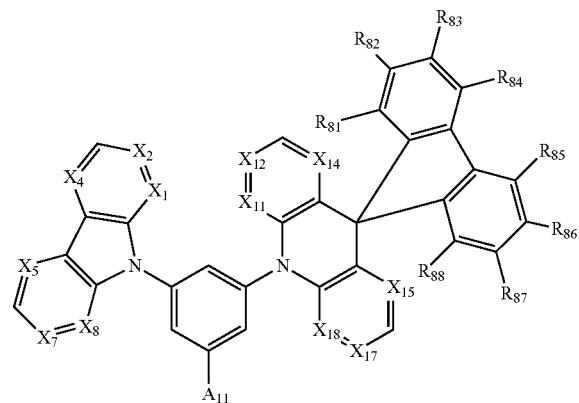
1-83
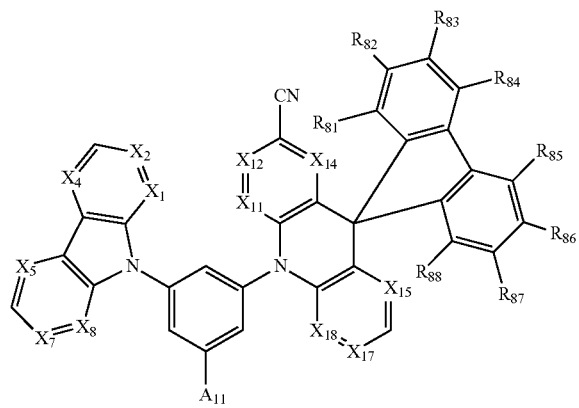
1-81
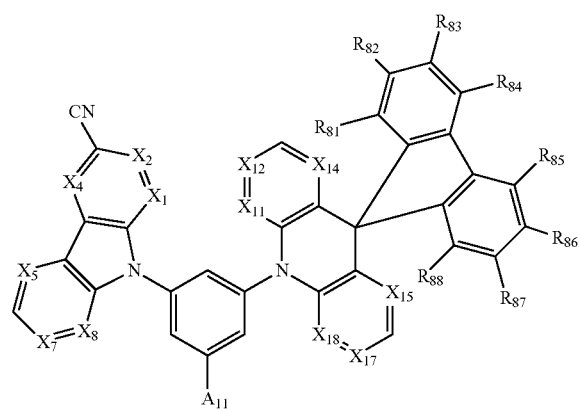
1-84
1-82
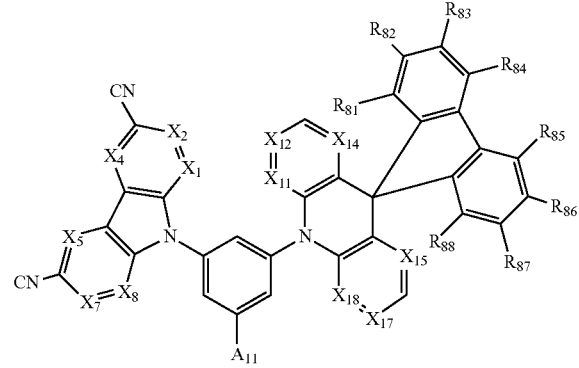
1-85
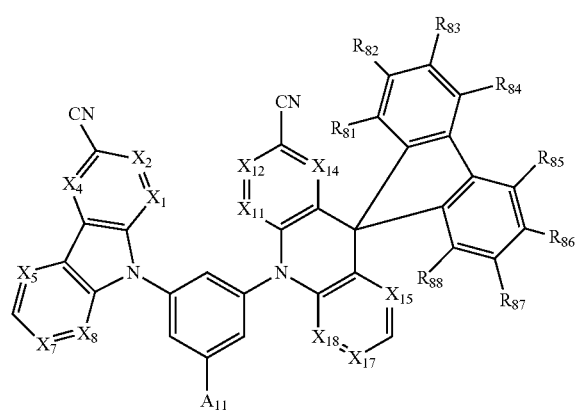

1-86

1-87

1-88

1-89

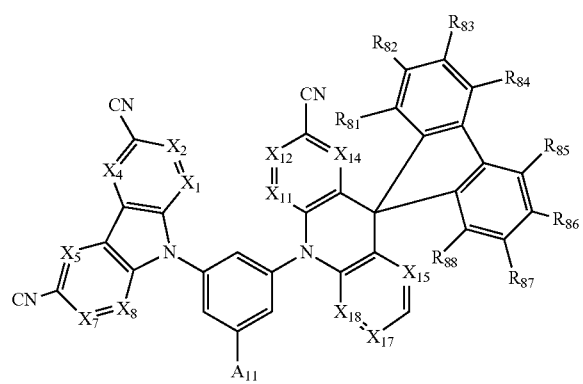
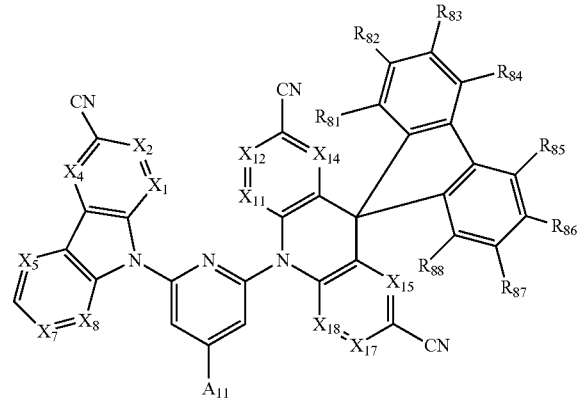

In Formulae 1-71 to 1-79 and 1-81 to 1-89, $X_1, X_2, X_4, X_5, X_7, X_8, X_{11}, X_{12}, X_{14}, X_{15}, X_{17}, X_{18}$, and $A_{11}$ may be understood by referring to descriptions thereof made in connection with Formula 1; and $R_{81}$ to $R_{88}$ may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ may be each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

The condensed cyclic compound represented by Formula 1 may be selected from Compounds 1 to 134, but is not limited thereto:

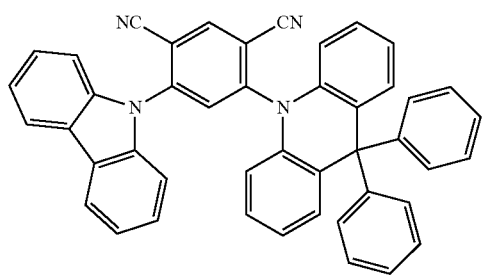
3
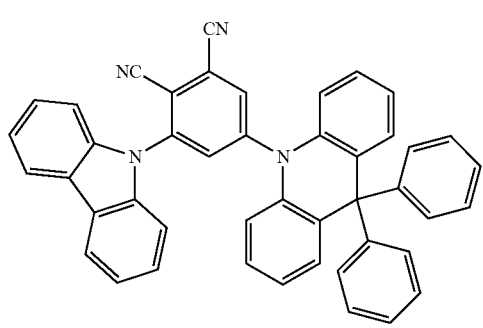
4
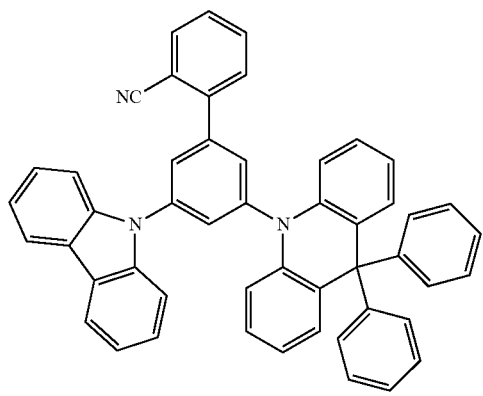
5
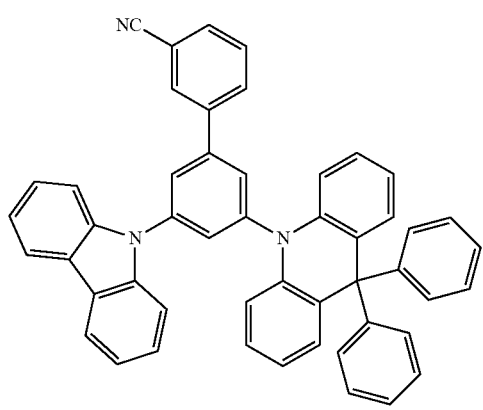
6
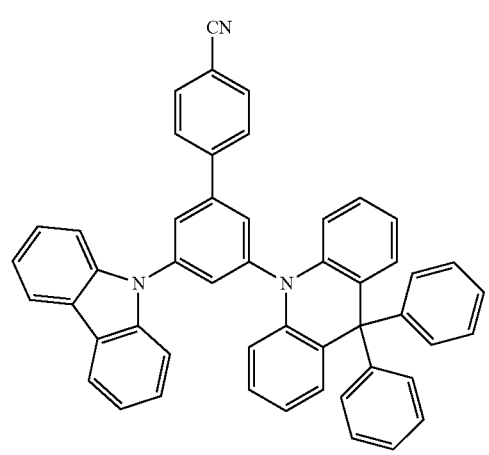
7
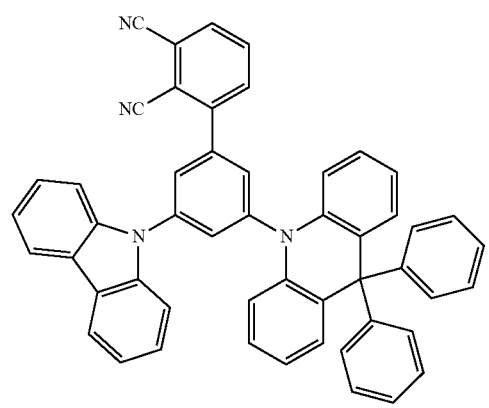
8
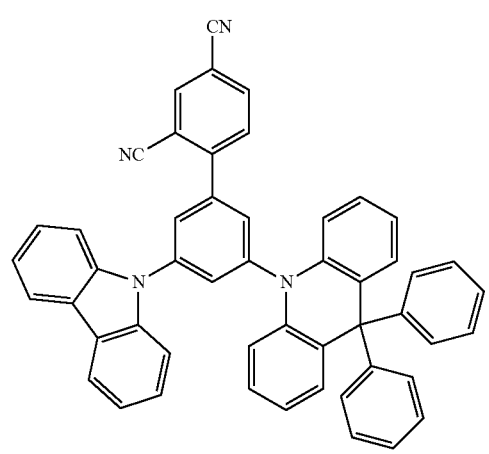
9

10
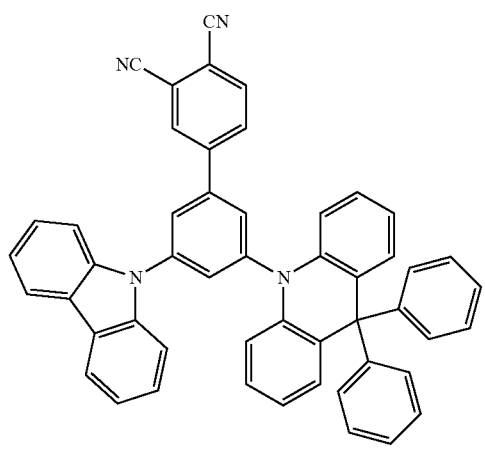
11
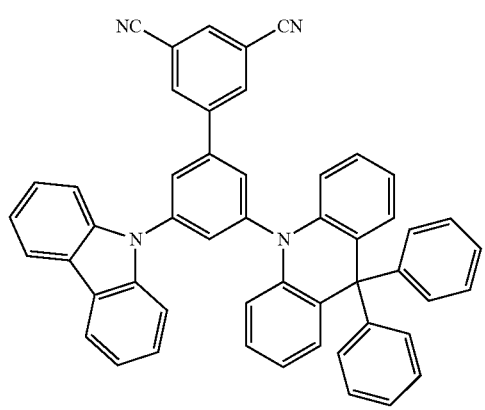
12
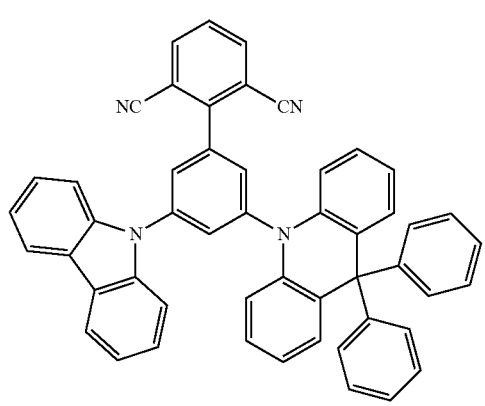
13
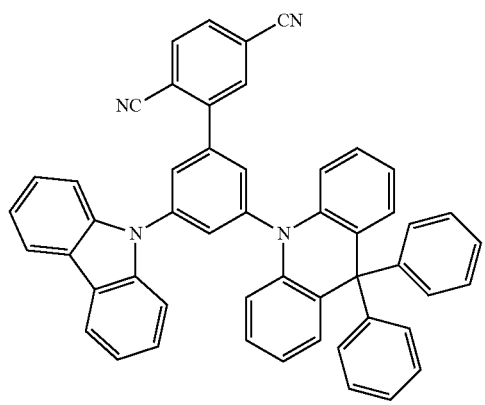
14
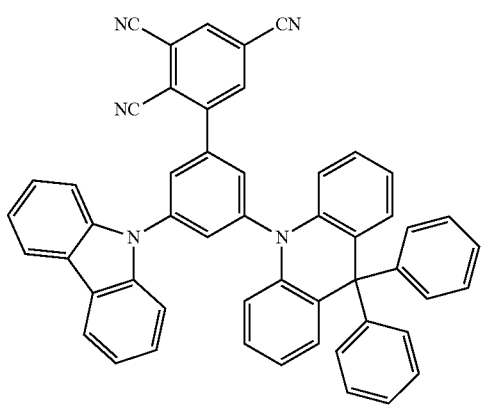
15
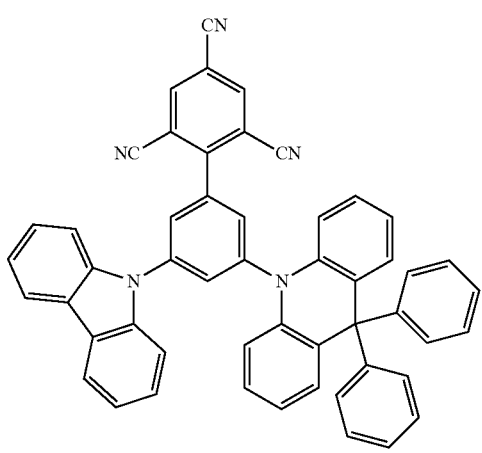
16
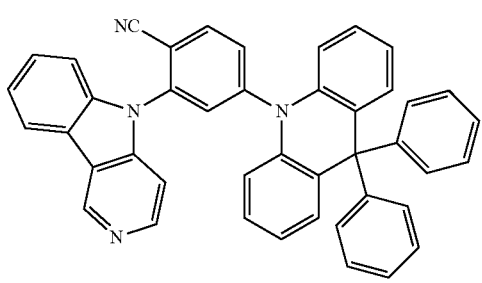
17
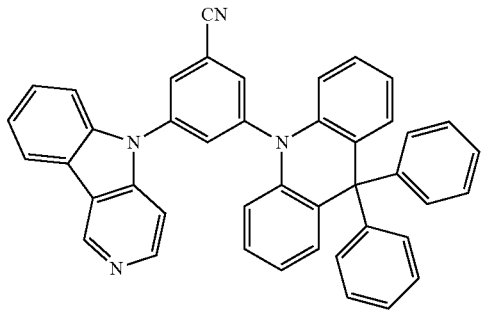

18
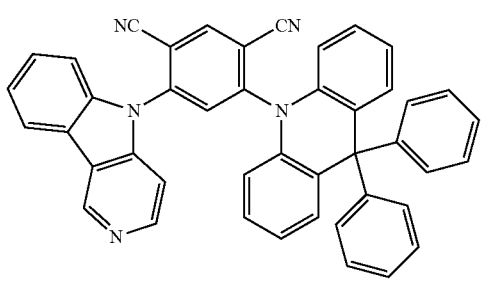
19
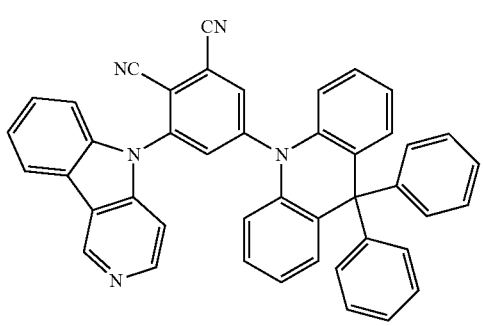
20
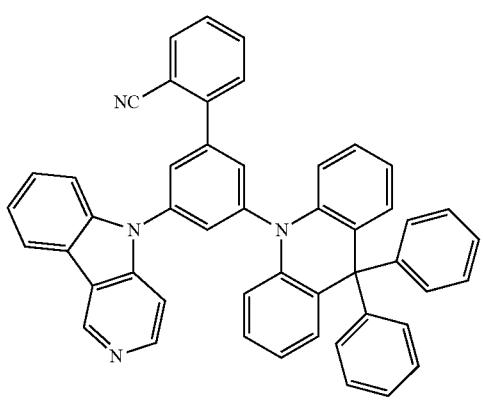
21
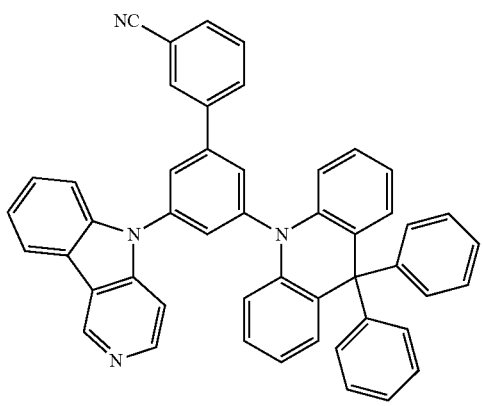
22
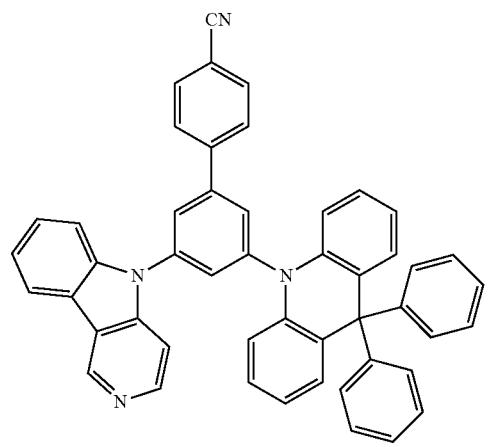
23
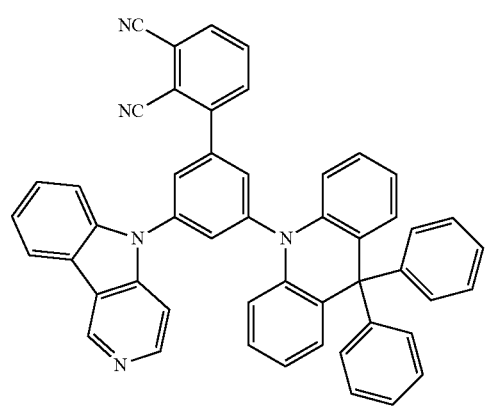
24
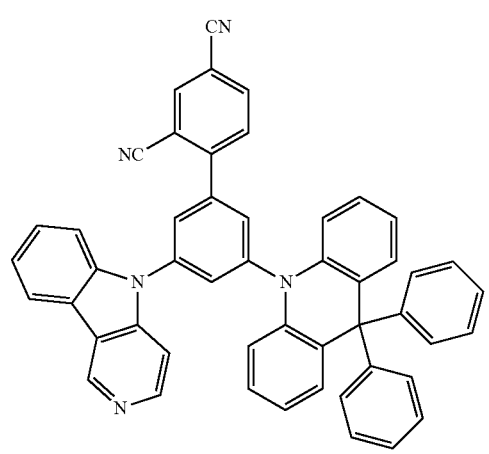

25
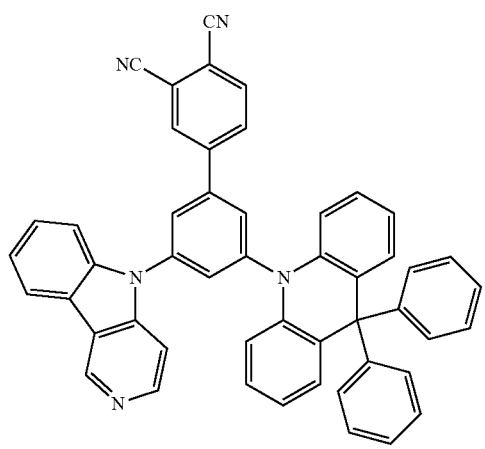
26
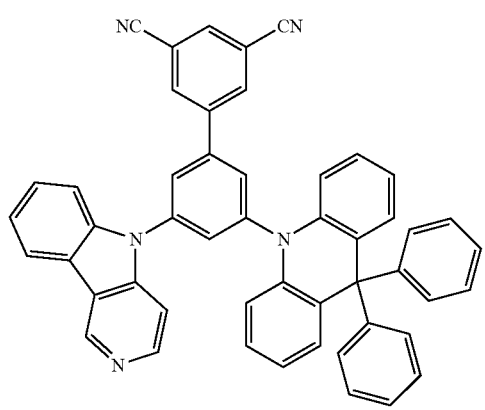
27
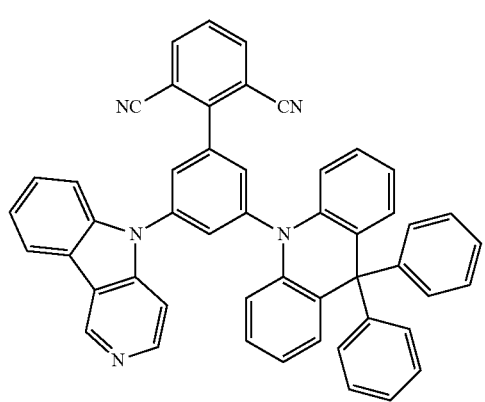
28
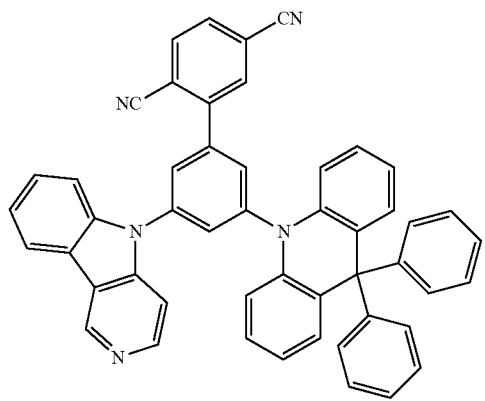
29
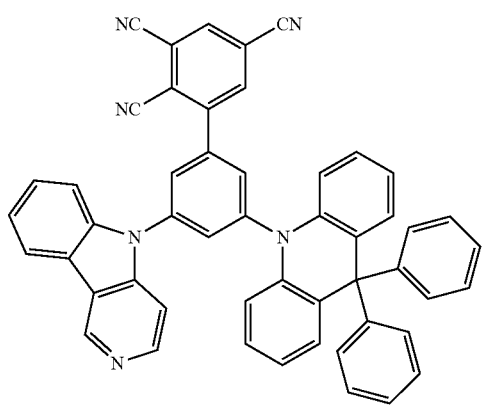
30
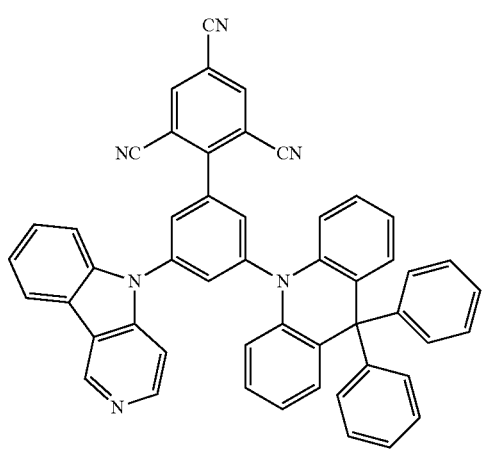
31
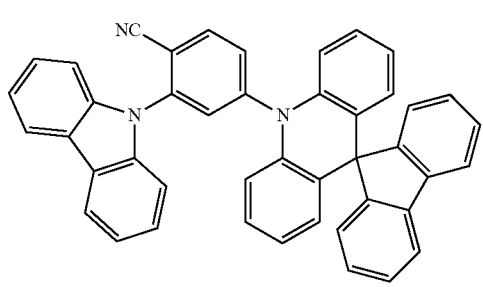
32
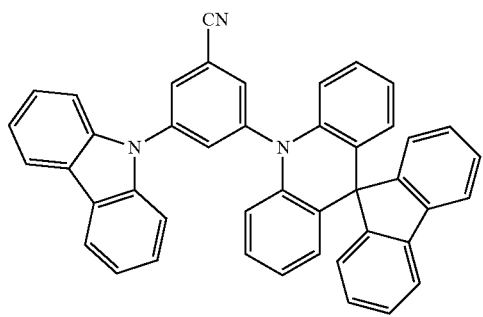

33
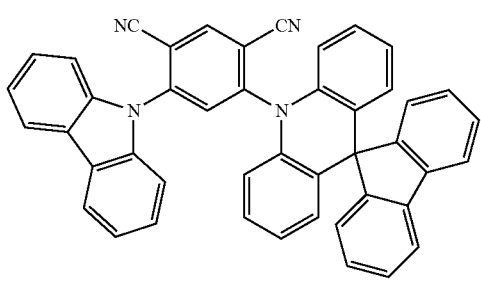
34
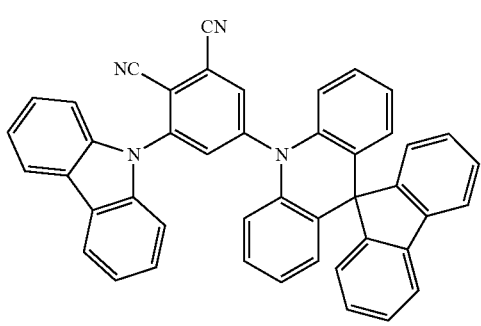
35
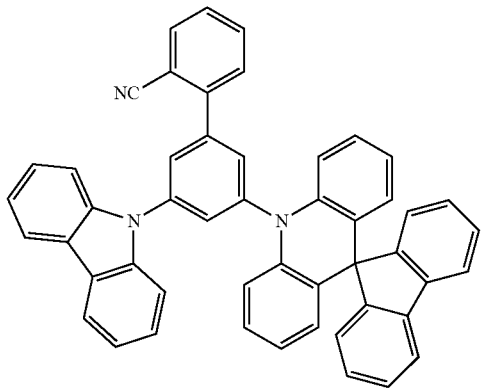
36
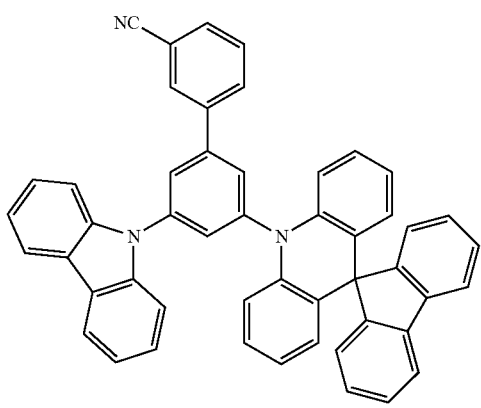
37
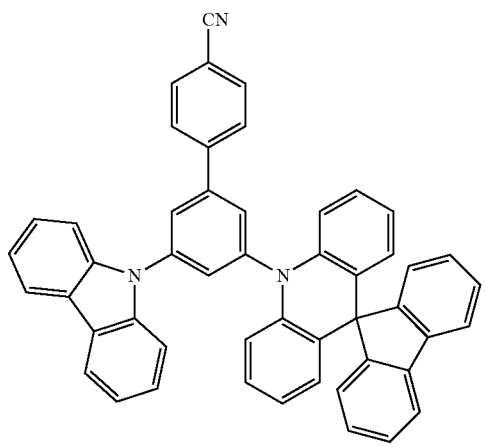
38
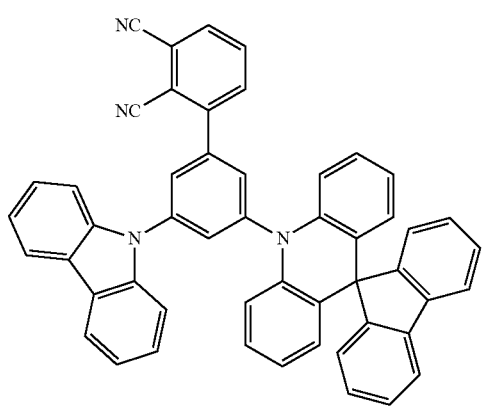
39
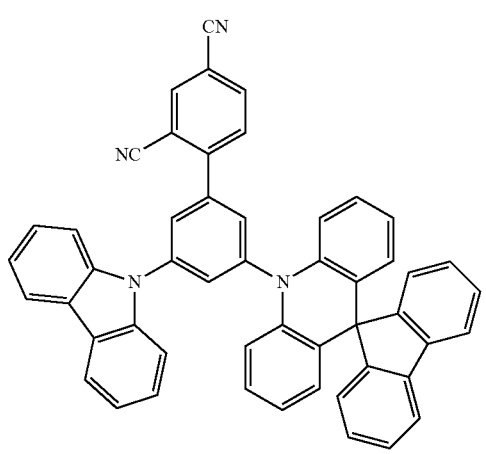

40
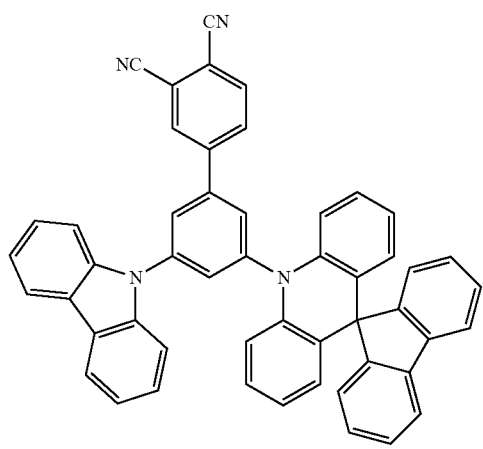
41
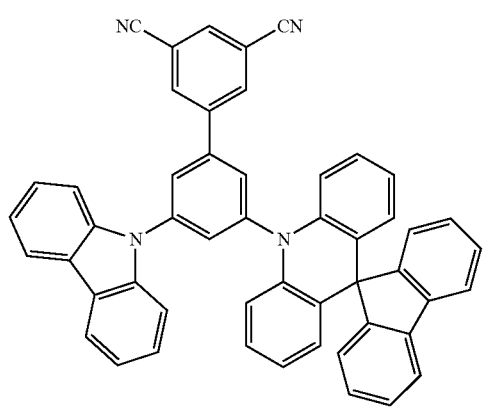
42
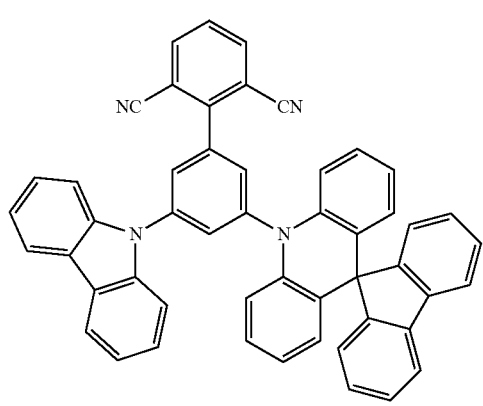
43
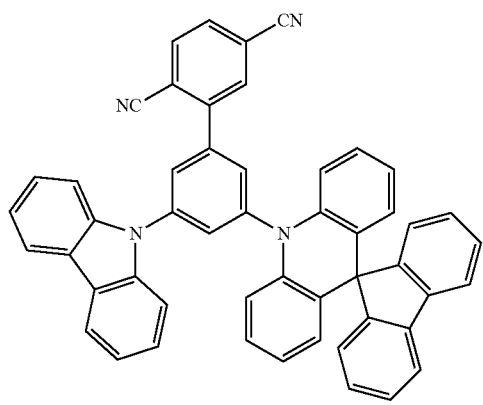
44
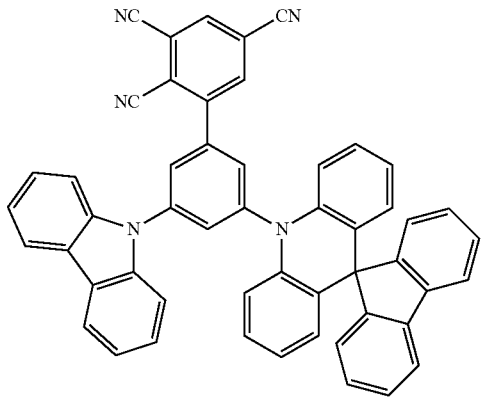
45
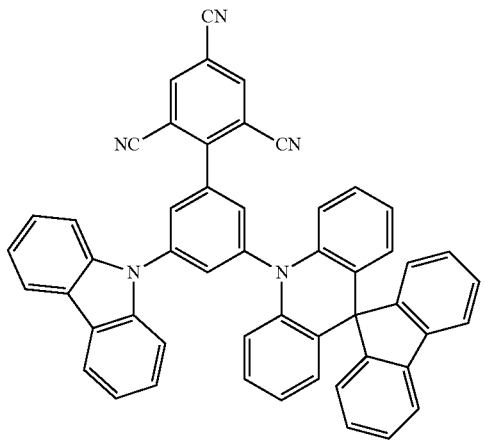
46
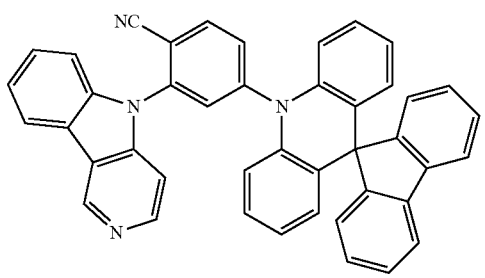
47
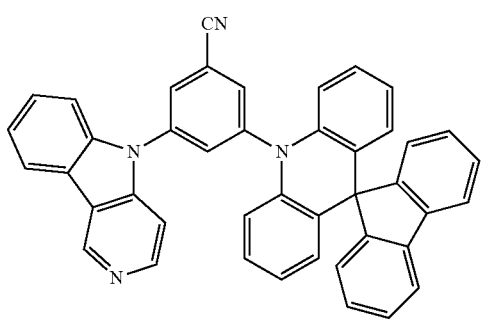

48
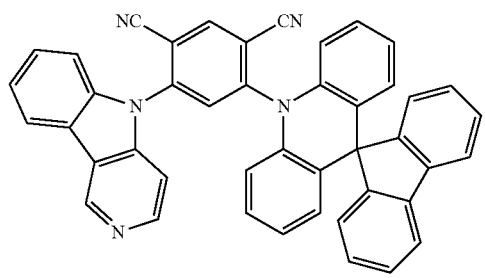
49
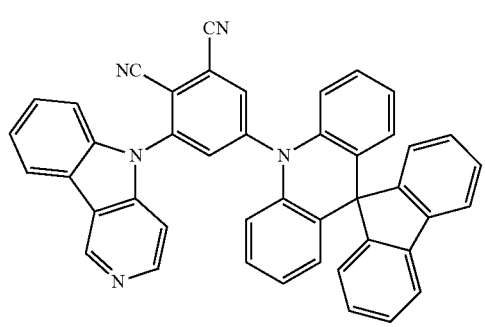
50
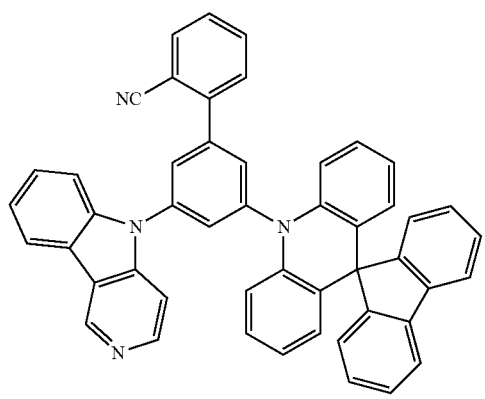
51
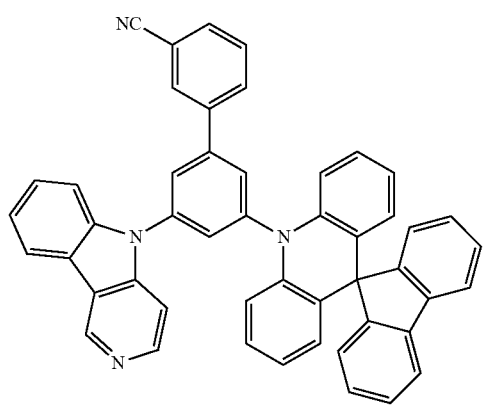
52
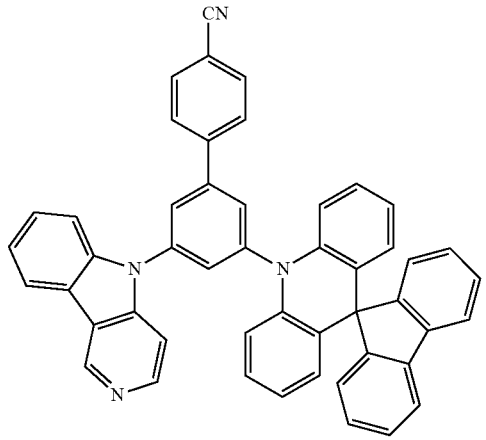
53
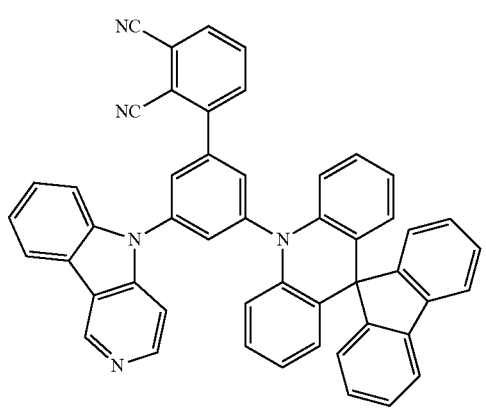
54
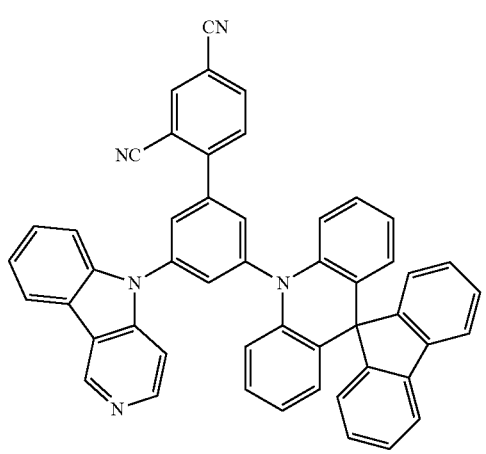

-continued
55
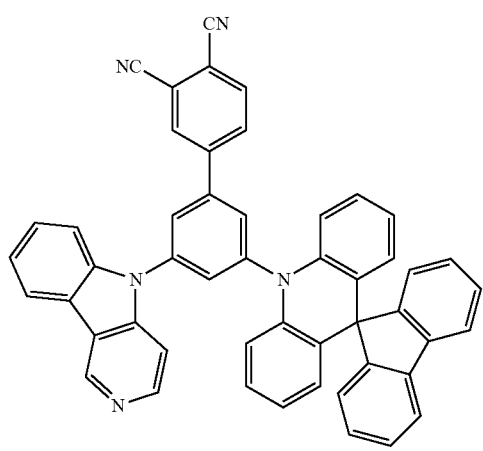
56
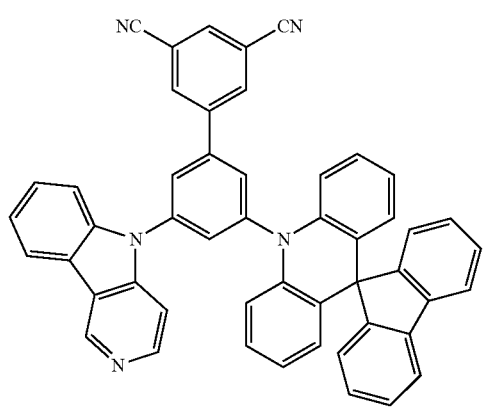
57
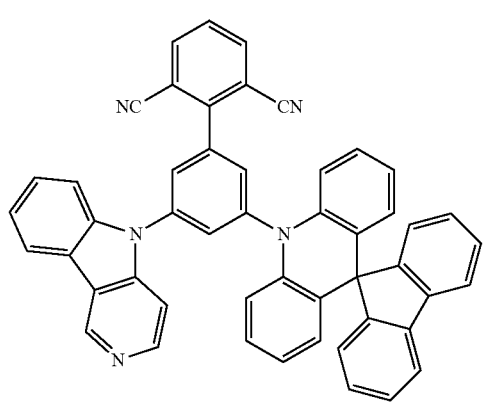
58
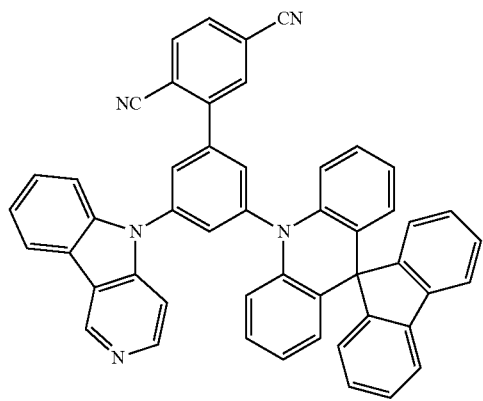
-continued
59
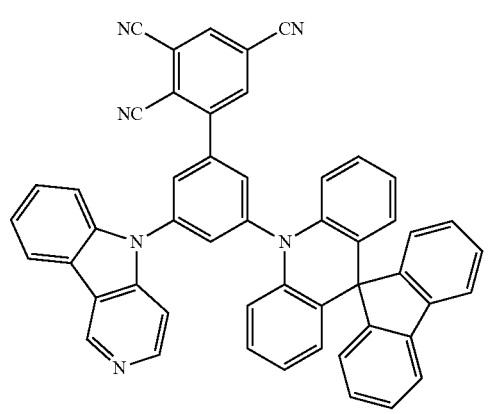
60
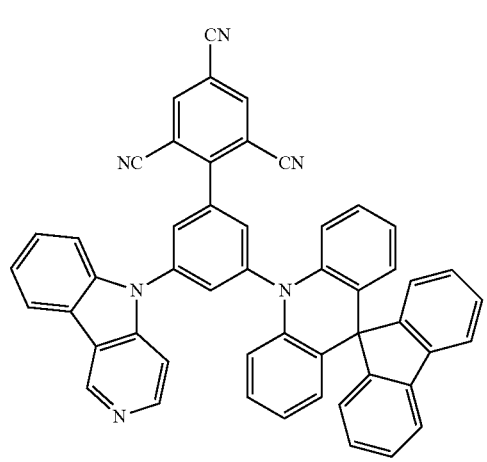
61
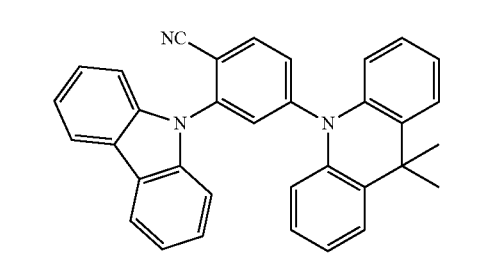
62
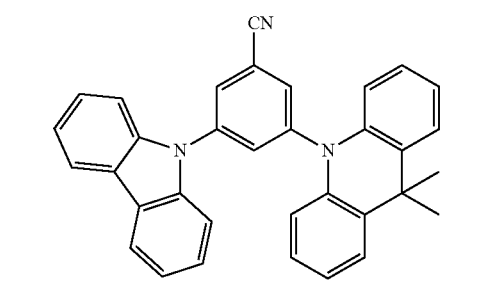
63
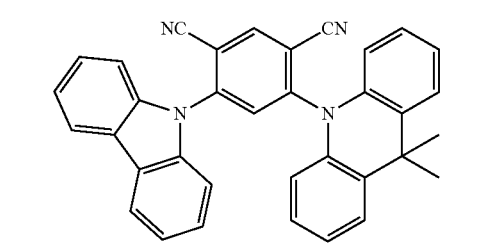

-continued
64
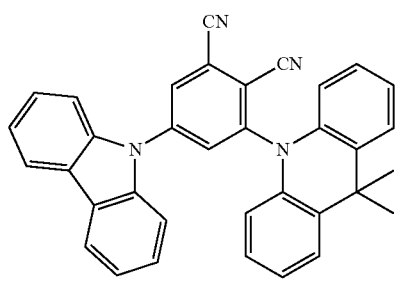
65
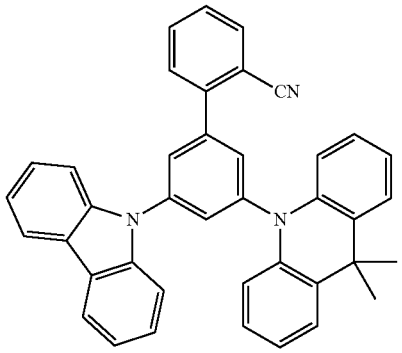
66
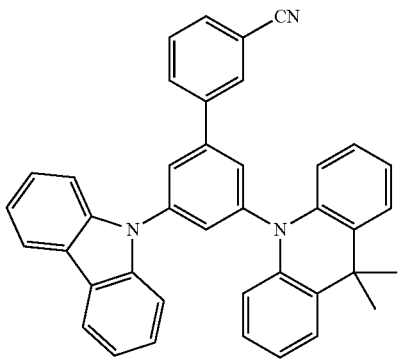
67
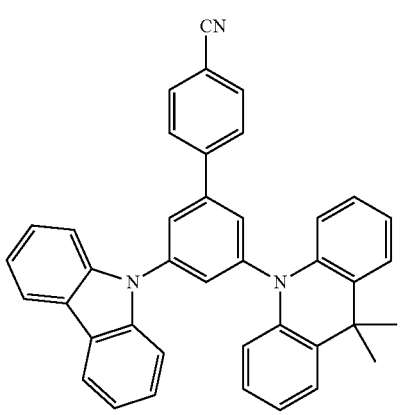
-continued
68
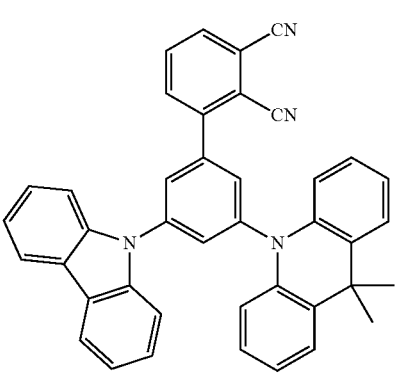
69
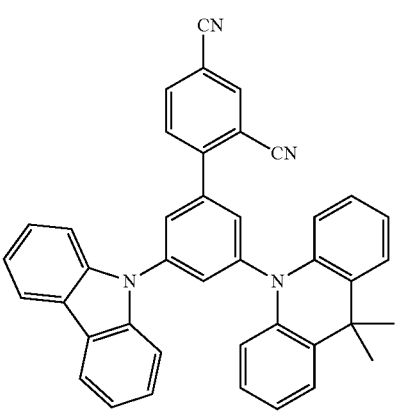
70
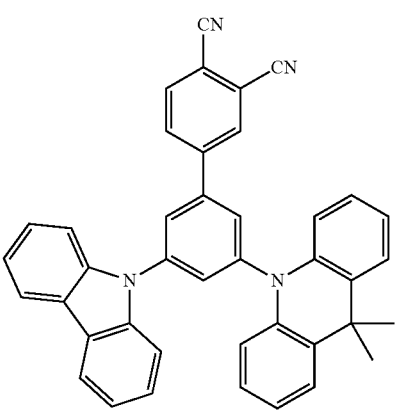
71
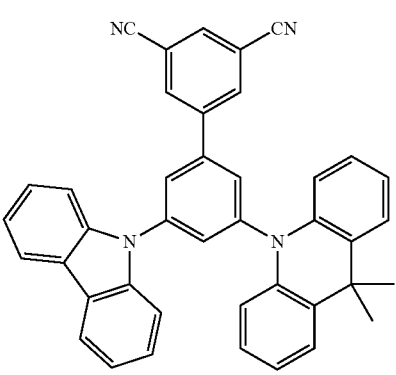

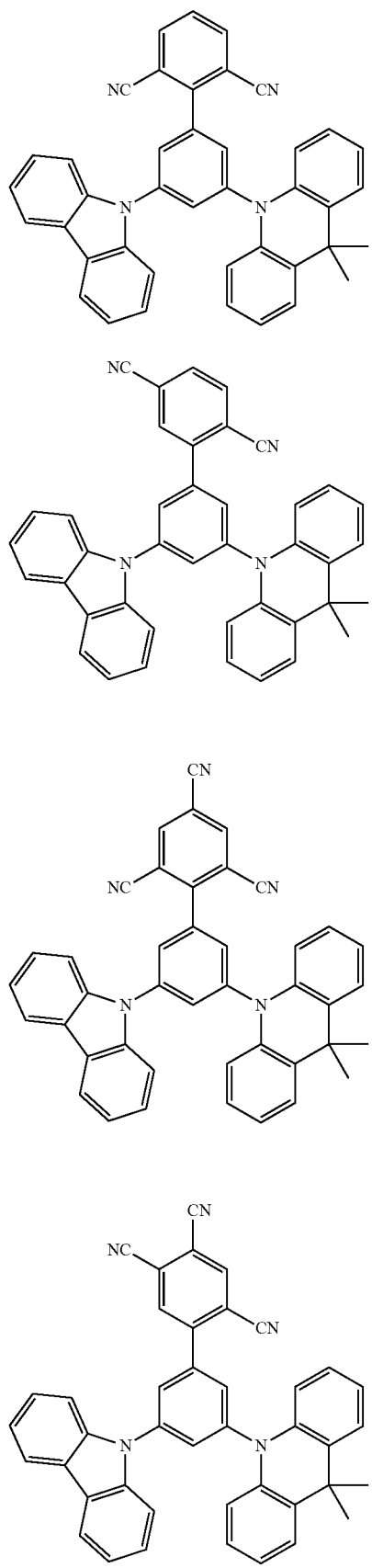
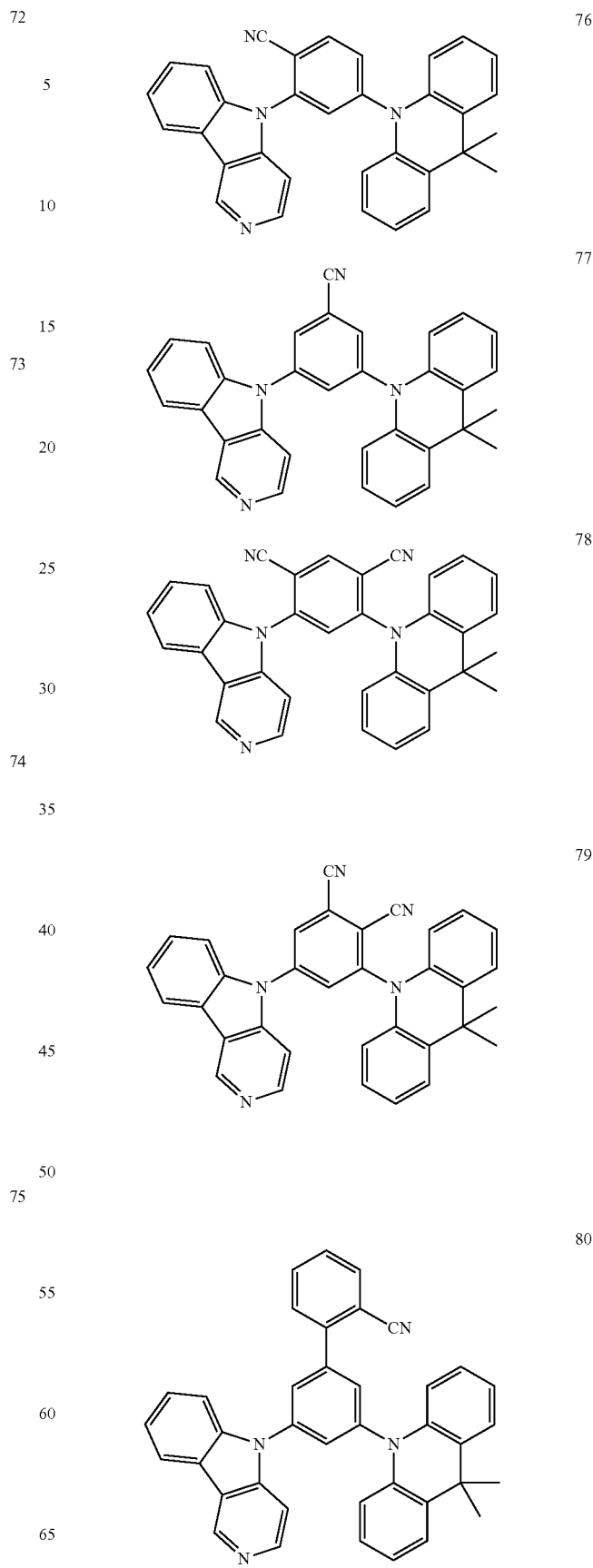

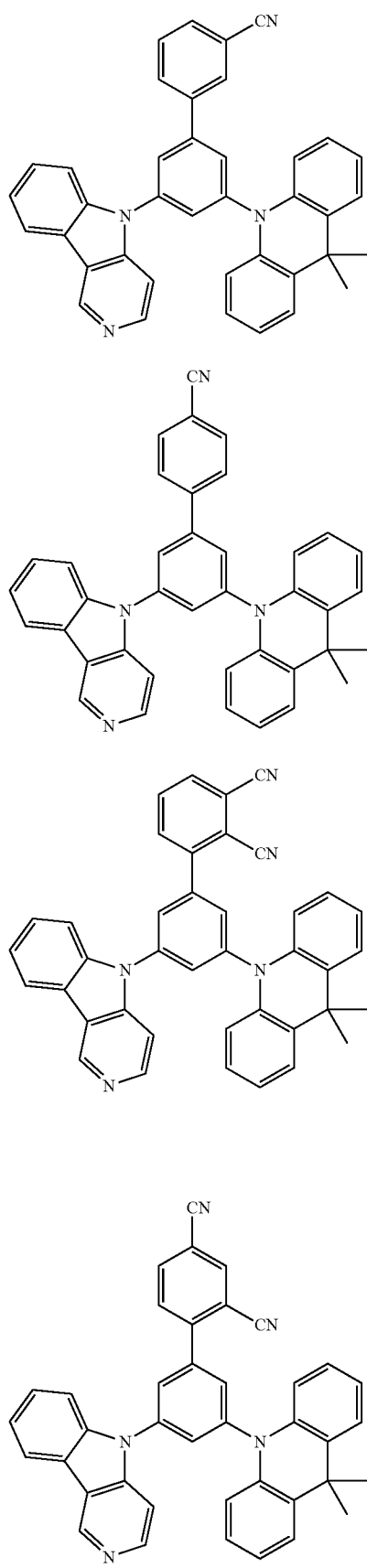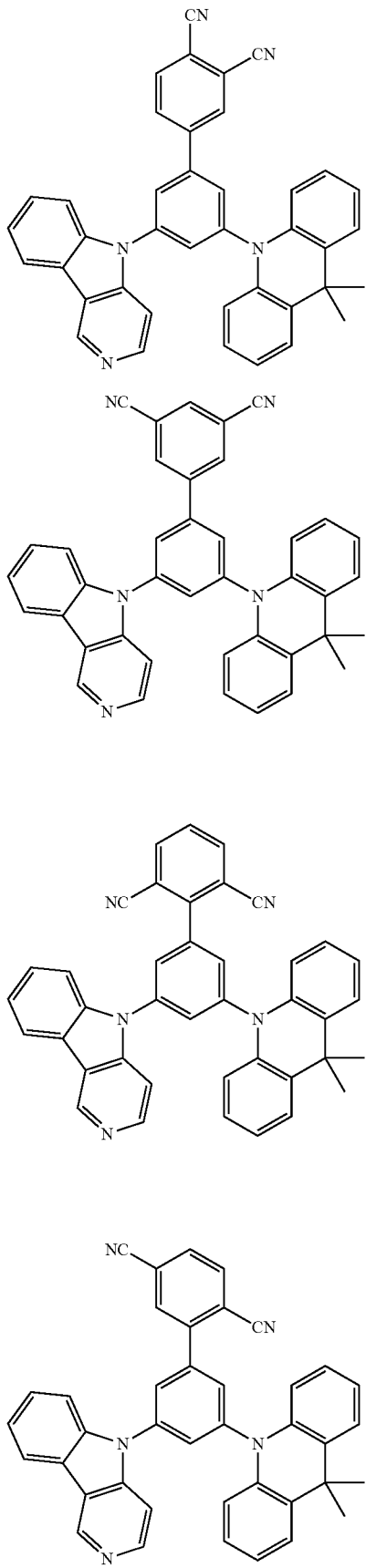

89
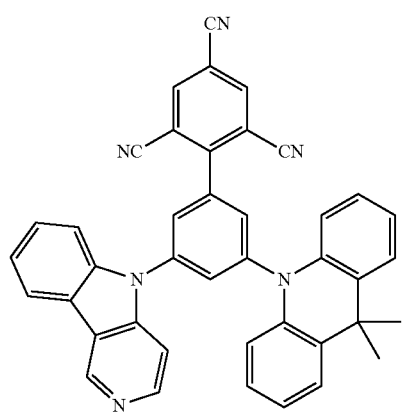
90
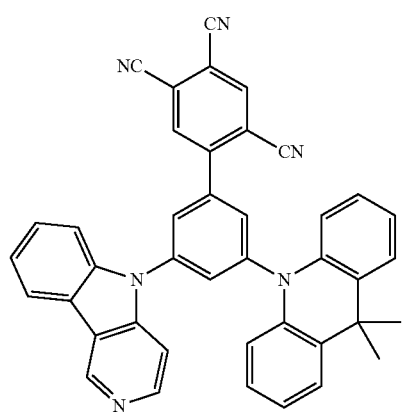
91
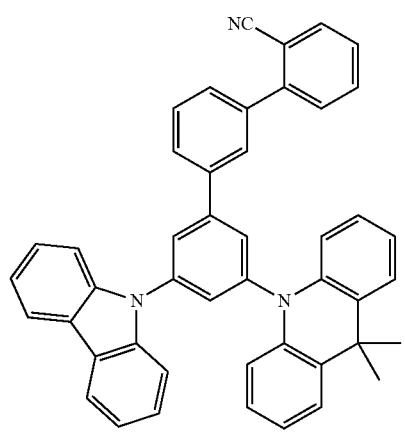
92
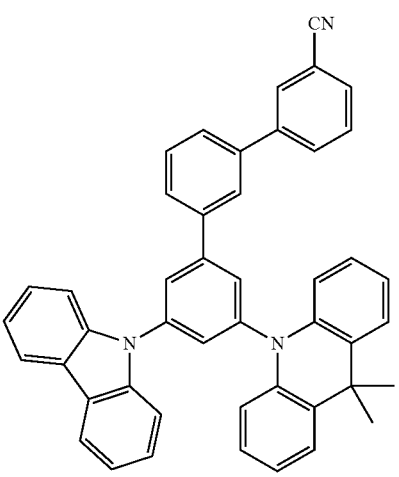
93
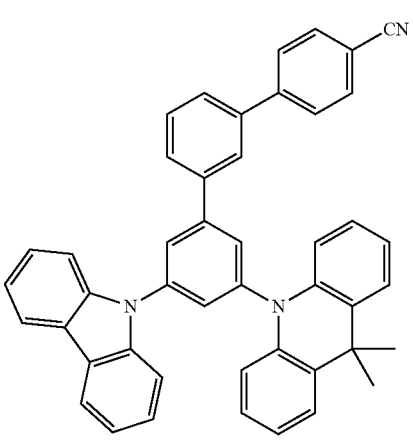
94
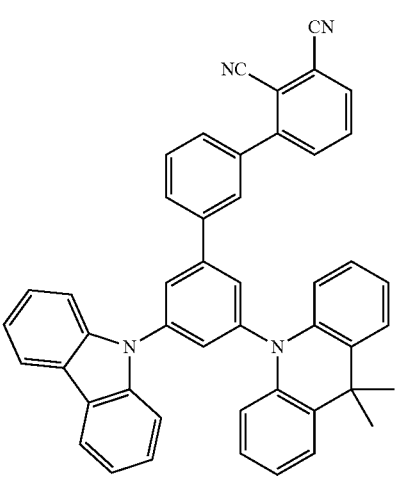

103
-continued
95
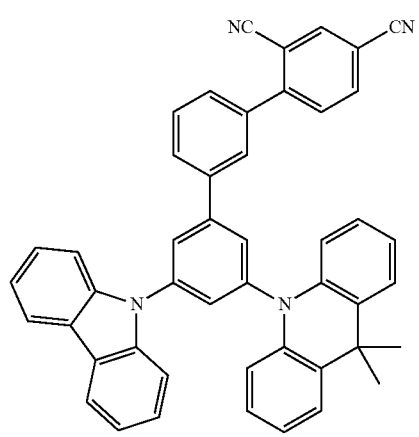
96
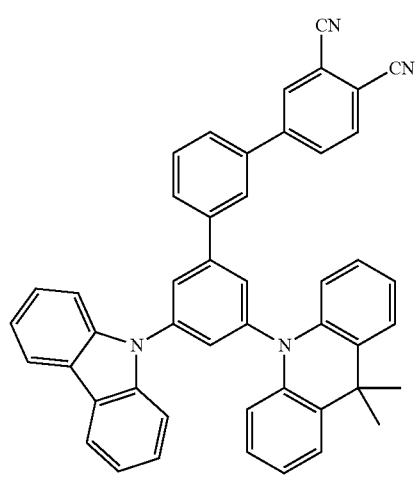
97
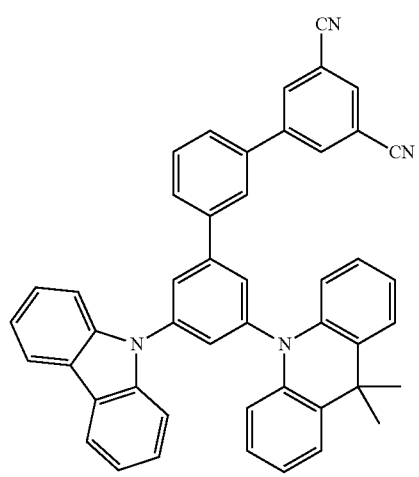
104
-continued
98
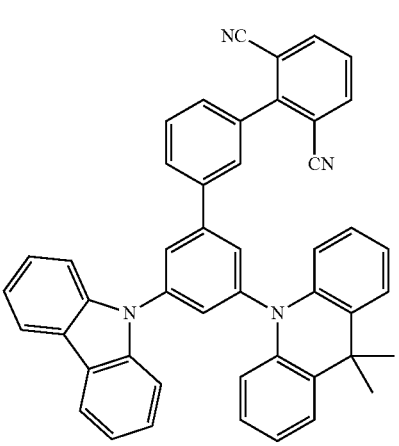
99
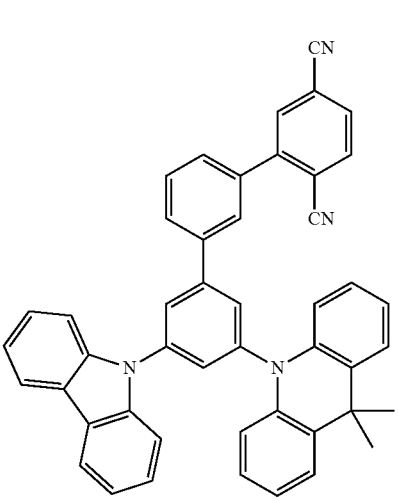
100
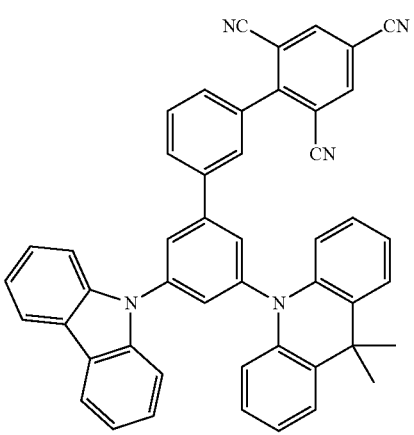

105 -continued
101
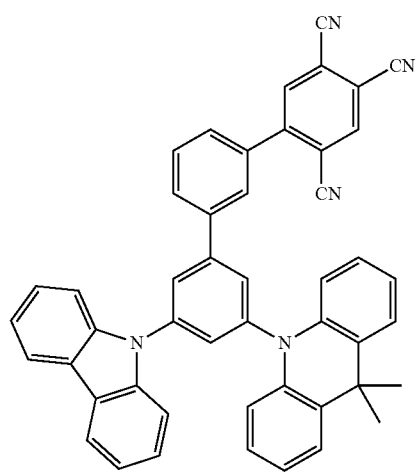
102
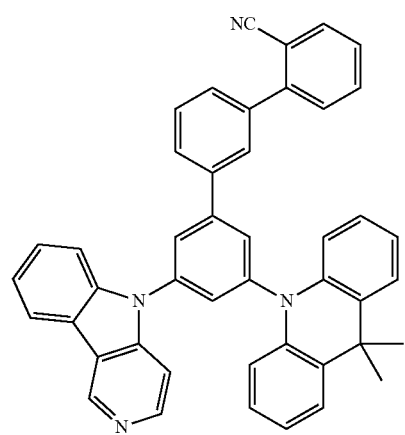
103
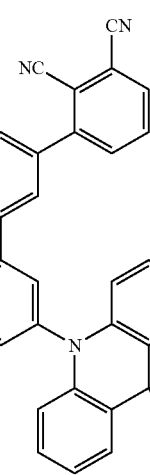
106 -continued
104
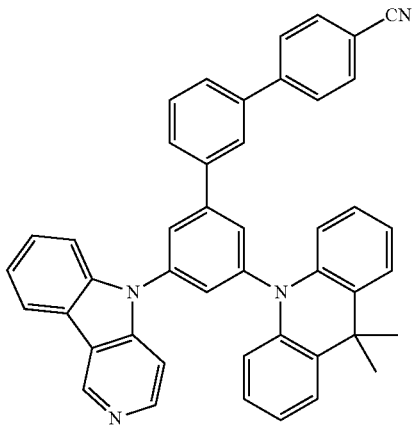
105
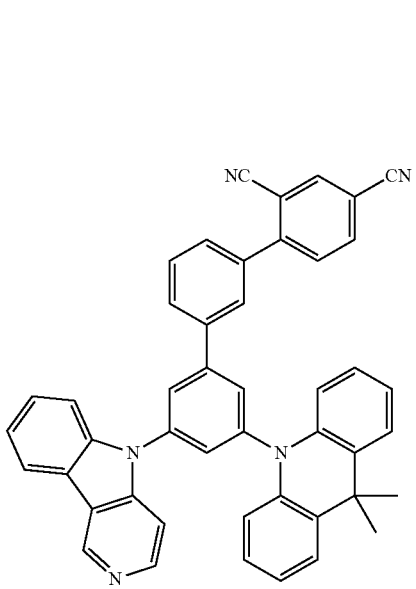
106

-continued
107
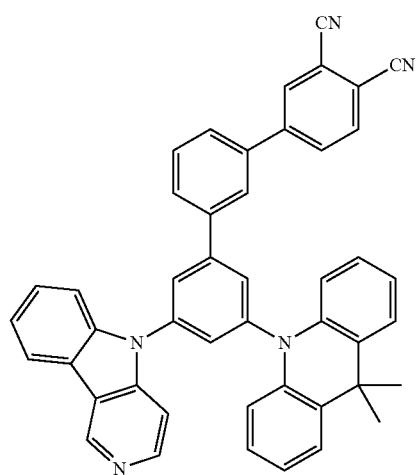
108
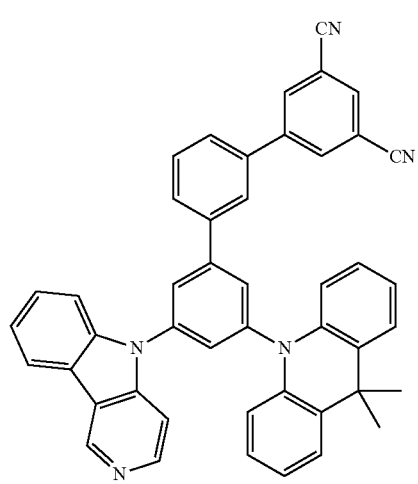
109
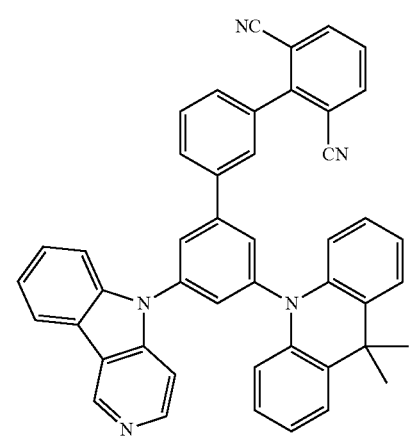
-continued
110
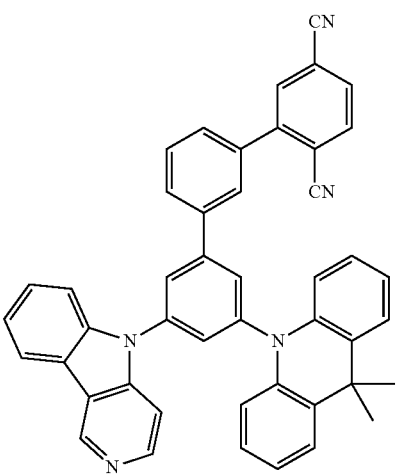
111
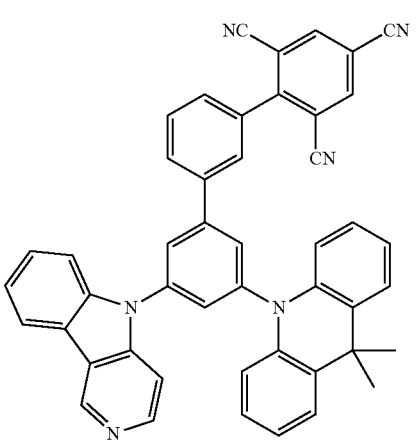
112
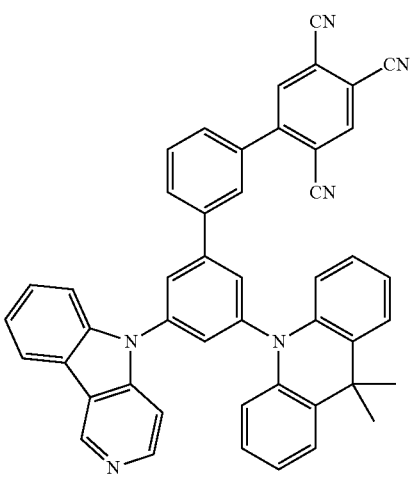

US 10,043,983 B2
109
-continued
113
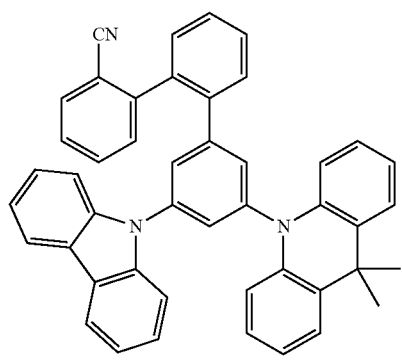
114
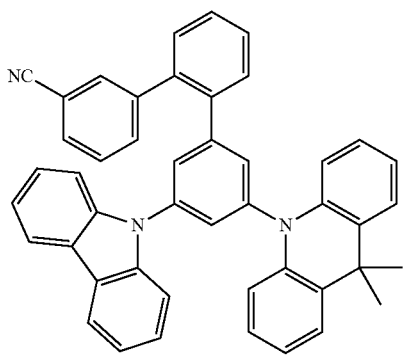
115
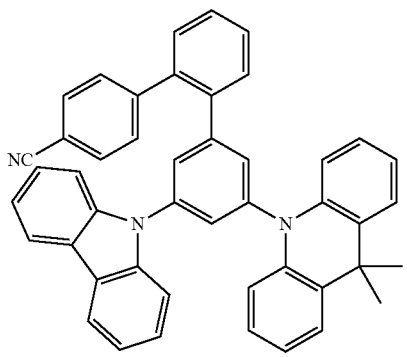
116
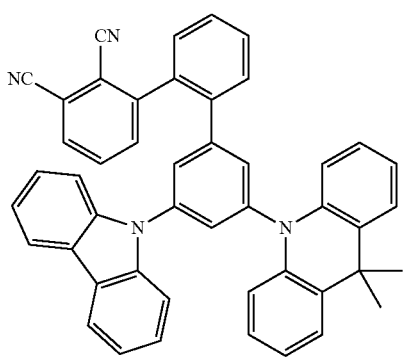
110
-continued
117
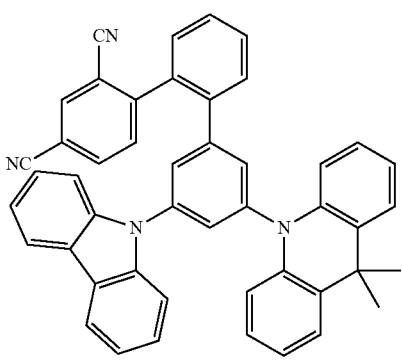
118
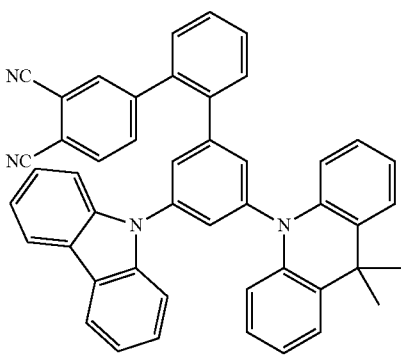
119
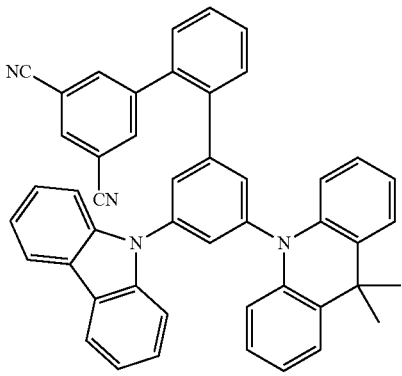
120
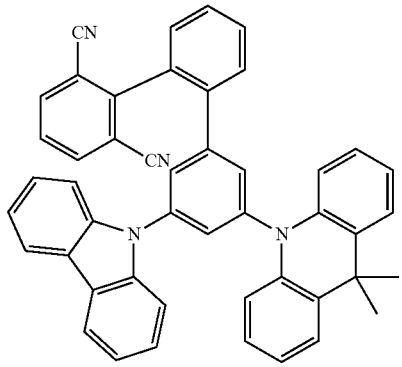

111
-continued
| | |
|---|---|
| 121 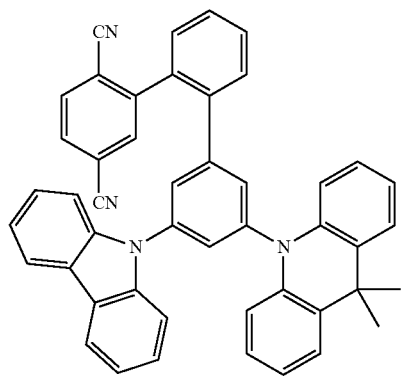 | 125 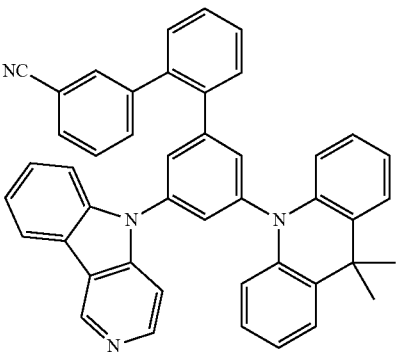 |
| 122 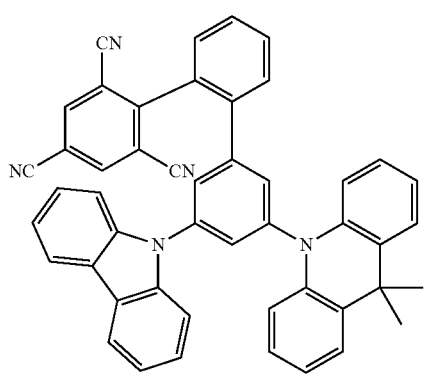 | 126 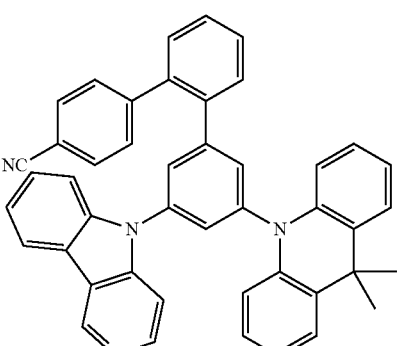 |
| 123 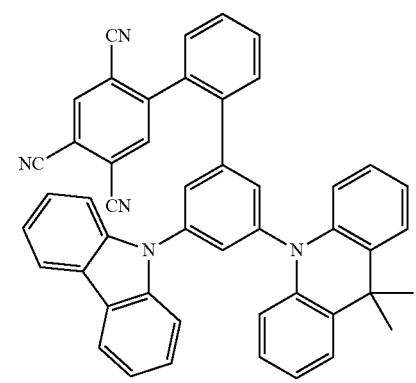 | 127 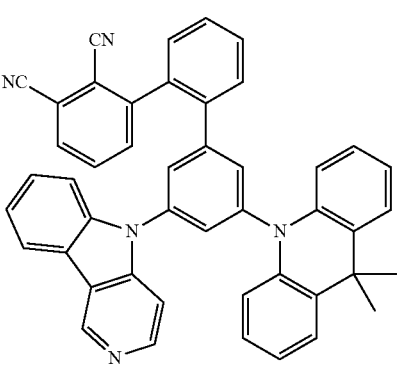 |
| 124 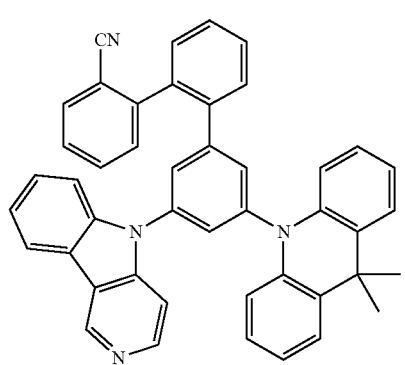 | 128 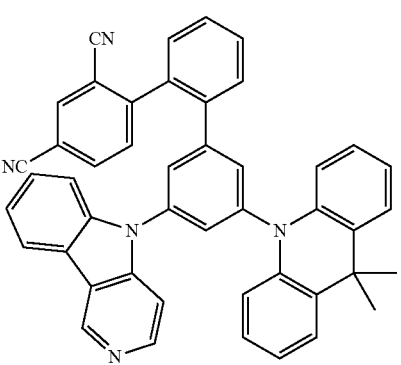 |
112
-continued 129
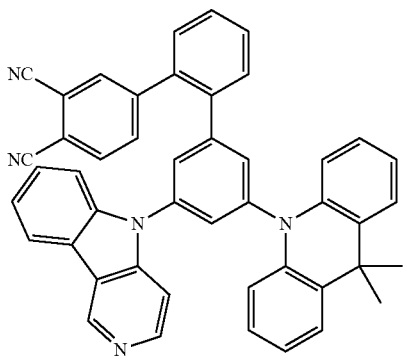

130
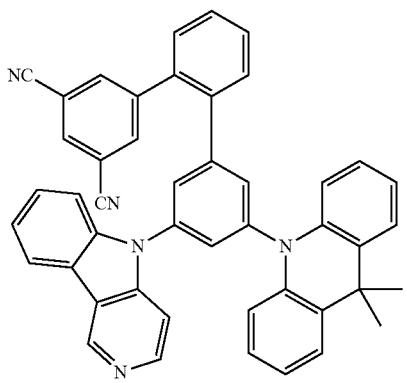

131
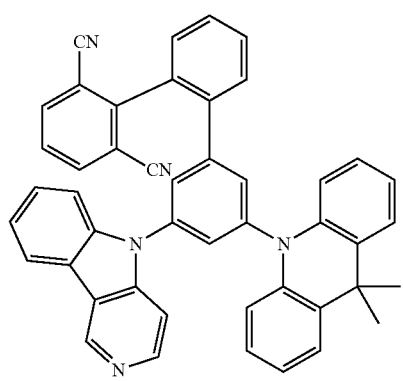

132
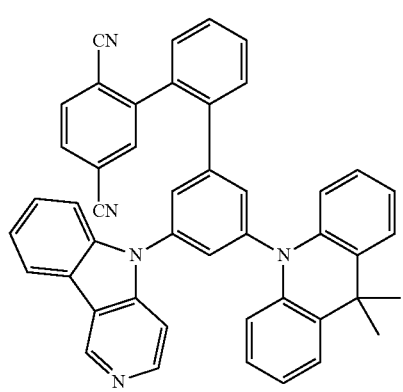

133
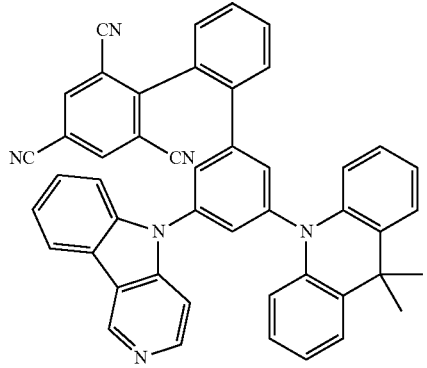

134
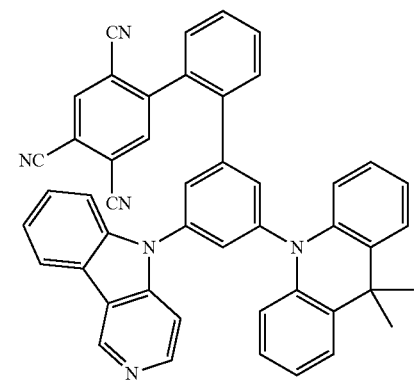

The condensed cyclic compound represented by Formula 1 necessarily includes $A_{11}$ having at least one cyano group, and accordingly, the thermal stability and electric characteristics thereof may be improved. Accordingly, an organic light-emitting device including the condensed cyclic compound represented by Formula 1 may have an improved lifespan and improved efficiency.

A highest occupied molecular orbital (HOMO) energy level and a lowest unoccupied molecular orbital (LUMO) energy level of the condensed cyclic compound represented by Formula 1 may be adjustable by changing the number of cyano groups included therein, and hole or electron mobility of the condensed cyclic compound represented by Formula 1 may be adjustable by changing the number of phenyl groups included in the condensed cyclic compound included therein.

Synthesis methods for the condensed cyclic compound represented by Formula 1 may be recognizable to one of ordinary skill in the art by referring to the following Synthesis Examples.

The condensed cyclic compound represented by Formula 1 is suitable for use in an organic layer of an organic light-emitting device, for example, a host constituting an emission layer included in the organic layer. Accordingly, another aspect provides an organic light-emitting device including:
a first electrode;
a second electrode; and
an organic layer between the first electrode and the second electrode,
wherein the organic layer includes an emission layer and the condensed cyclic compound represented by Formula 1.

The organic light-emitting device may have, due to the inclusion of an organic layer including the condensed cyclic compound represented by Formula 1, low driving voltage, high efficiency, high luminance, high quantum emission efficiency, and a long lifespan.

The condensed cyclic compound of Formula 1 may be used between a pair of electrodes of an organic light-emitting device. For example, the condensed cyclic compound represented by Formula 1 may be included in the emission layer. The condensed cyclic compound may act as a host, and in this case, the emission layer may further include a dopant.

The expression that "(an organic layer) includes a condensed cyclic compound" used herein may include an embodiment in which "(an organic layer) includes identical compounds represented by Formula 1 and an embodiment in which (an organic layer) includes two or more different condensed cyclic compounds represented by Formula 1.

For example, the organic layer may include, as the condensed cyclic compound, only Compound 1. In this regard, Compound 1 may exist in an emission layer of the organic light-emitting device. In some embodiments, the organic layer may include, as the condensed cyclic compound, Compound 1 and Compound 2. In this regard, Compound 1 and Compound 2 may be included in an identical layer (for example, Compound 1 and Compound 2 all may be included in an emission layer).

The first electrode may be an anode, which is a hole injection electrode, and the second electrode may be a cathode, which is an electron injection electrode; or the first electrode may be a cathode, which is an electron injection electrode, or the second electrode may be an anode, which is a hole injection electrode.

For example, the first electrode may be an anode, and the second electrode may be a cathode, and the organic layer may include:

i) a hole transport region that is disposed between the first electrode and the emission layer, wherein the hole transport region may include at least one selected from a hole injection layer, a hole transport layer, and an electron blocking layer, and ii) an electron transport region that is disposed between the emission layer and the second electrode, wherein the electron transport region may include at least one selected from a hole blocking layer, an electron transport layer, and an electron injection layer.

The term "organic layer" as used herein refers to a single layer and/or a plurality of layers between the first electrode and the second electrode of the organic light-emitting device. The "organic layer" may include, in addition to an organic compound, an organometallic complex including metal.

FIG. 1 is a schematic view of an organic light-emitting device 10 according to an embodiment. Hereinafter, the structure of an organic light-emitting device according to an embodiment and a method of manufacturing an organic light-emitting device according to an embodiment will be described in connection with FIG. 1. The organic light-emitting device 10 includes a first electrode 11, an organic layer 15, and a second electrode 19, which are sequentially stacked in this order.

A substrate may be additionally disposed under the first electrode 11 or above the second electrode 19. For use as the substrate, any substrate that is used in general organic light-emitting devices may be used, and the substrate may be a glass substrate or transparent plastic substrate, each with excellent mechanical strength, thermal stability, transparency, surface smoothness, ease of handling, and water-resistance.

The first electrode 11 may be formed by depositing or sputtering a material for forming a first electrode on the substrate. The first electrode 11 may be an anode. The material for the first electrode 11 may be selected from materials with a high work function to facilitate hole injection. The first electrode 11 may be a reflective electrode or a transmissive electrode. The material for the first electrode 11 may be indium tin oxide (ITO), indium zinc oxide (IZO), tin oxide ($SnO_2$), or zinc oxide (ZnO). In some embodiments, the material for the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a three-layered structure of ITO/Ag/ITO, but the structure of the first electrode 11 is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may have a structure of hole injection layer/hole transport layer or hole injection layer/ hole transport layer/electron blocking layer, which are sequentially stacked in this stated order from the first electrode 11.

When the hole transport region includes a hole injection layer, the hole injection layer may be formed on the first electrode 11 by using, for example, one or more methods selected from vacuum deposition, spin coating, casting, and Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100 to about 500° C., a vacuum pressure of about $10^{-8}$ to about $10^{-3}$ torr, and a deposition rate of about 0.01 to about 100 Angstroms per second (Å/sec). However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated NPB, TAPC, HMTPD, 4,4′,4″-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), (polyaniline)/poly(4-styrenesulfonate) (PANI/PSS), a compound represented by Formula 201 below, and a compound represented by Formula 202 below:

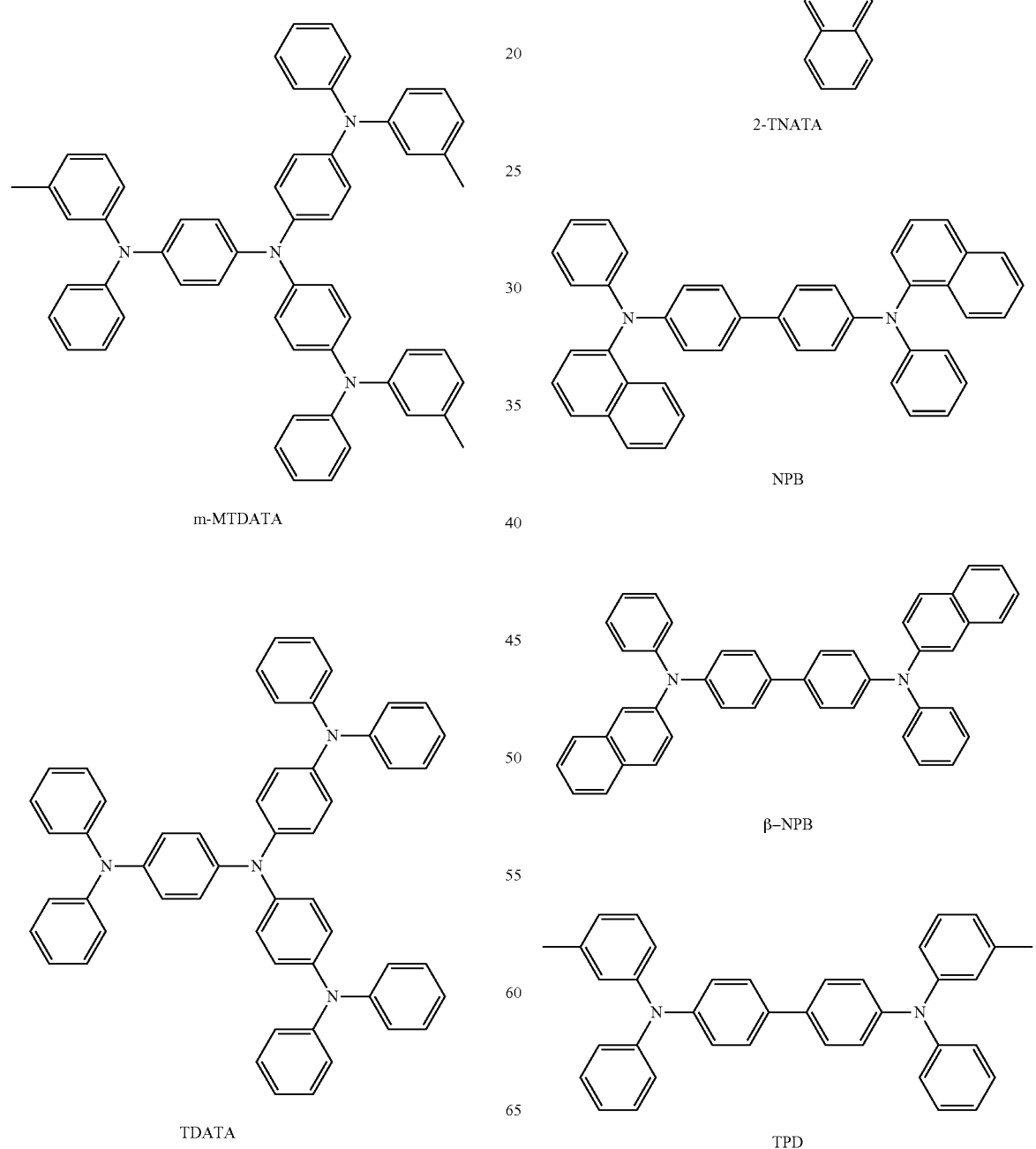

-continued

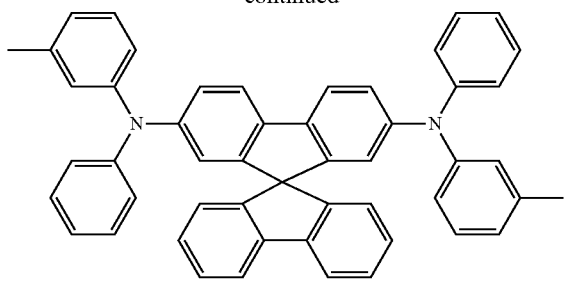

Spiro-TPD

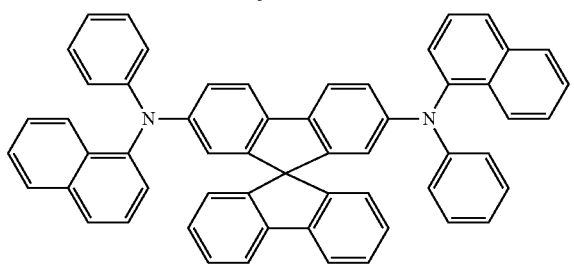

Spiro-NPB

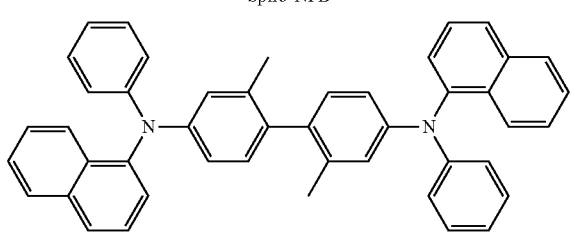

methylated NPB

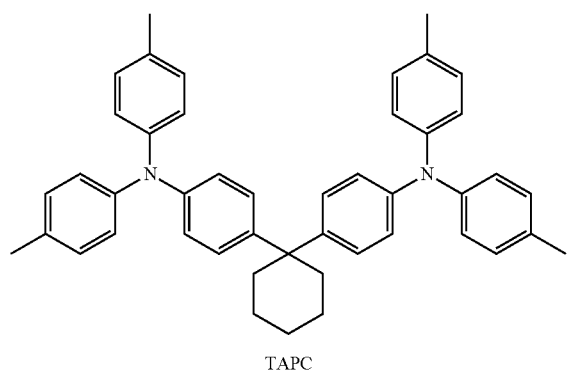

TAPC

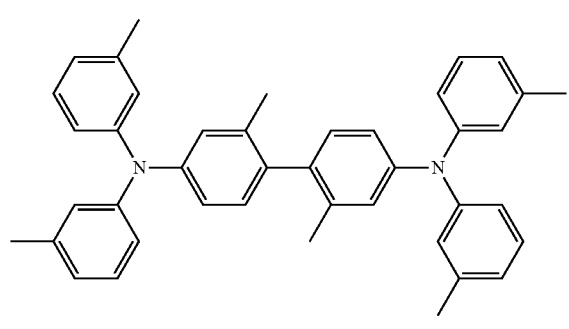

HMTPD

-continued

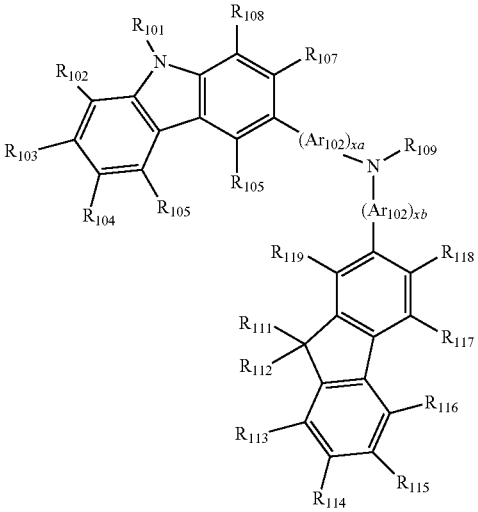

Formula 201

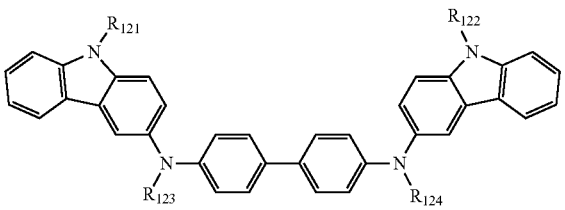

Formula 202

$Ar_{101}$ and $Ar_{102}$ in Formula 201 may be each independently selected from
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and
a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, a hydroxyl group, a cyano group, a nitro group, an amino group, an amid no group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_2$-$C_{10}$ heterocycloalkyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group.

xa and xb in Formula 201 may be each independently an integer of 0 to 5, or 0, 1 or 2. For example, xa may be 1 and xb may be 0, but xa and xb are not limited thereto.

$R_{101}$ to $R_{108}$, $R_{111}$ to $R_{119}$, and $R_{121}$ to $R_{124}$ in Formulae 201 and 202 may be each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, a hexyl group, and so on), or a $C_1$-$C_{10}$ alkoxy group (for example, a methoxy group, an ethoxy group, a propoxy group, a butoxy group, a pentoxy group, and so on);

a $C_1$-$C_{10}$ alkyl group or a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

$R_{109}$ in Formula 201 may be a phenyl group, a naphthyl group, an anthacenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A below, but is not limited thereto:

Formula 201A

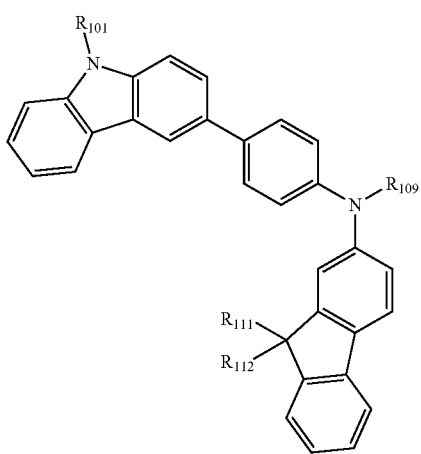

$R_{101}$, $R_{111}$, $R_{112}$, and $R_{109}$ in Formula 201A may be understood by referring to the description provided herein.

For example, the compound represented by Formula 201 and the compound represented by Formula 202 may include compounds HT1 to HT20 illustrated below, but are not limited thereto.

HT1

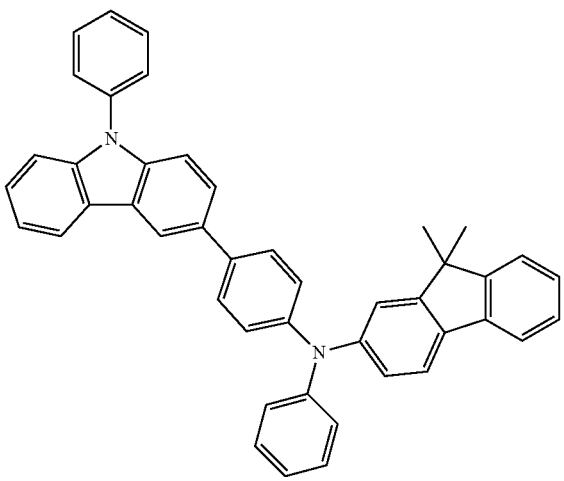

HT2

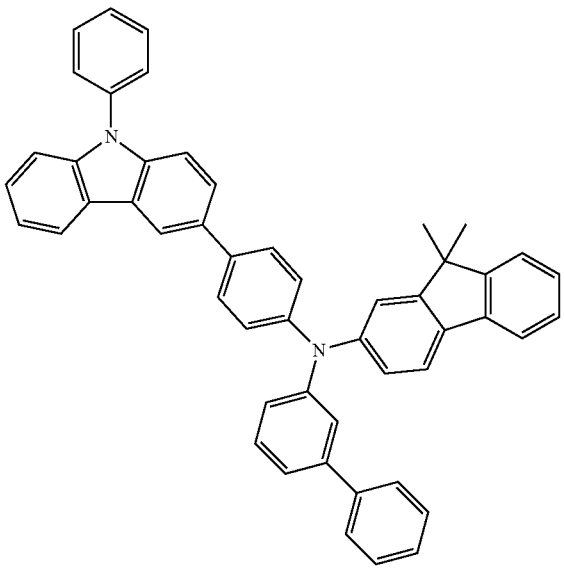

123
-continued
HT3
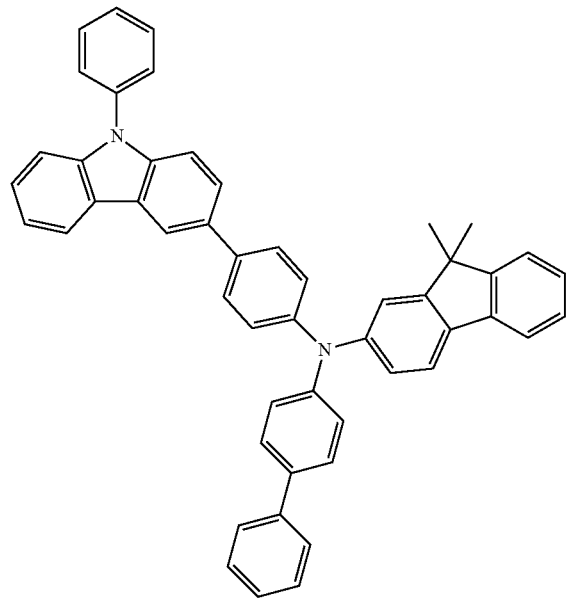
124
-continued
HT5
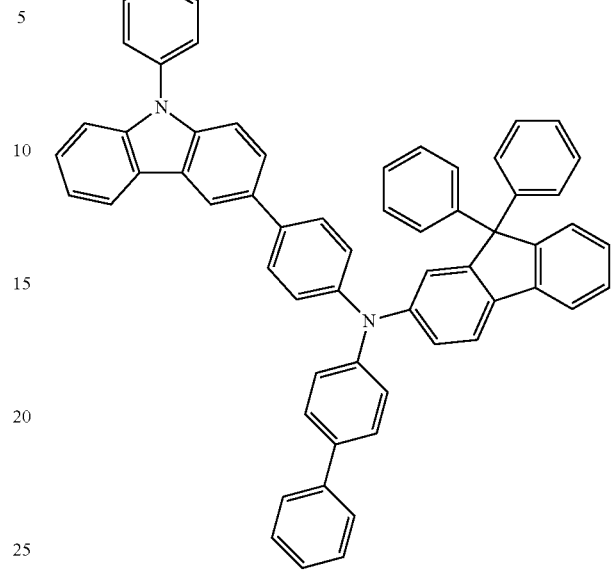
HT4
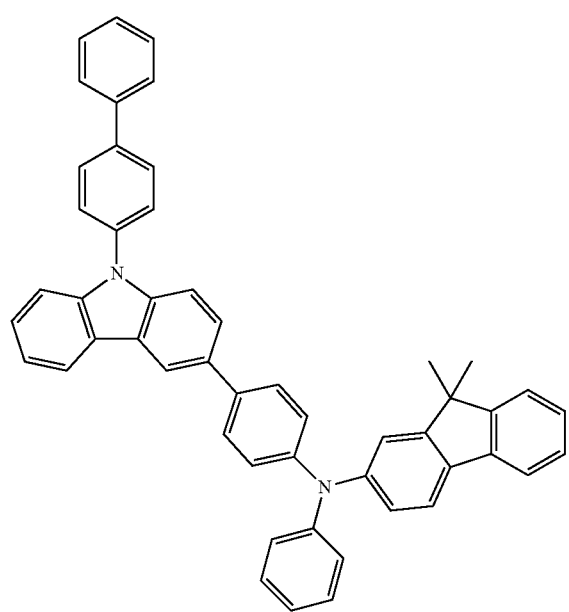
HT6
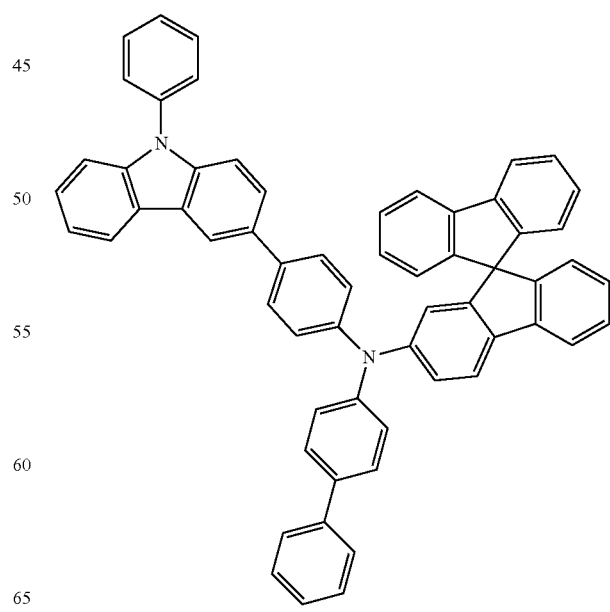

HT7
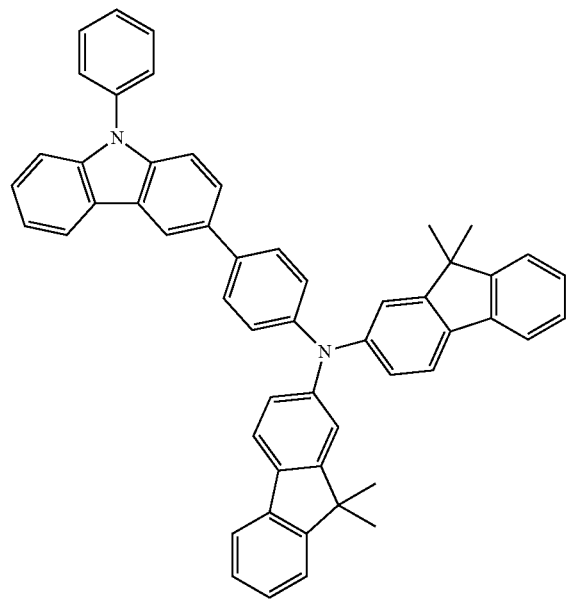
HT10
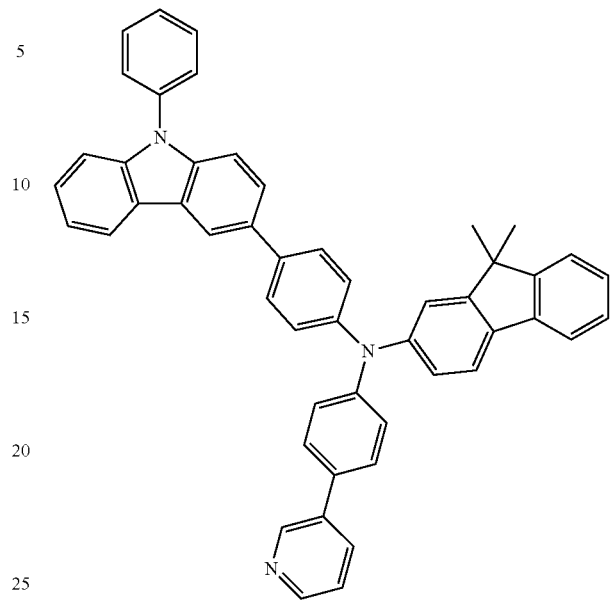
HT8
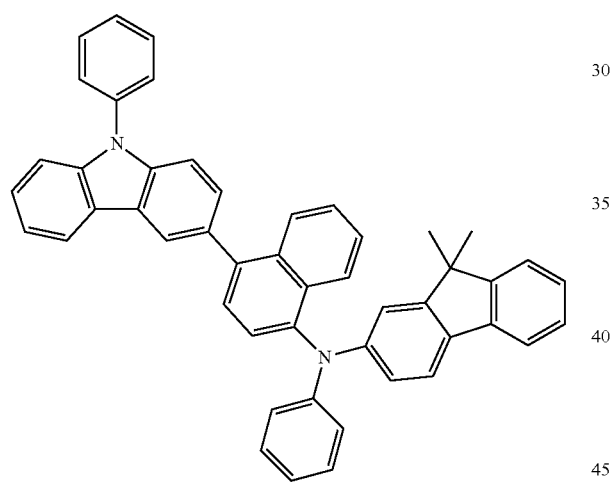
HT9
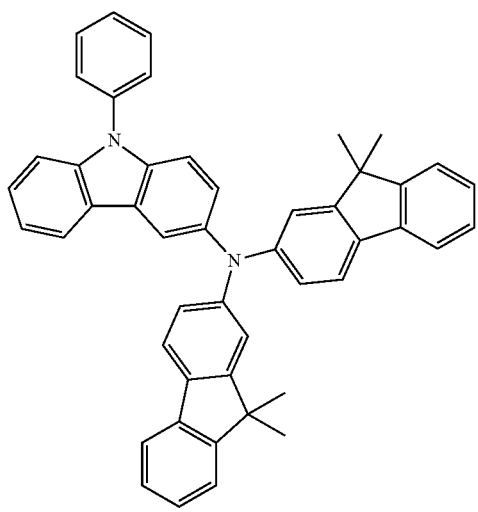
HT11
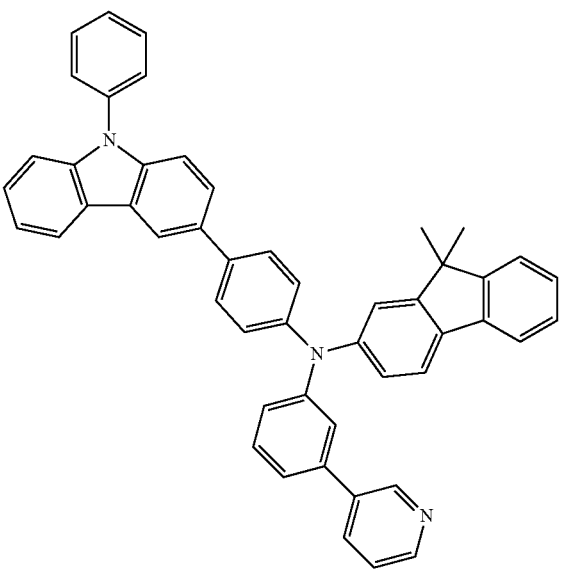

HT12
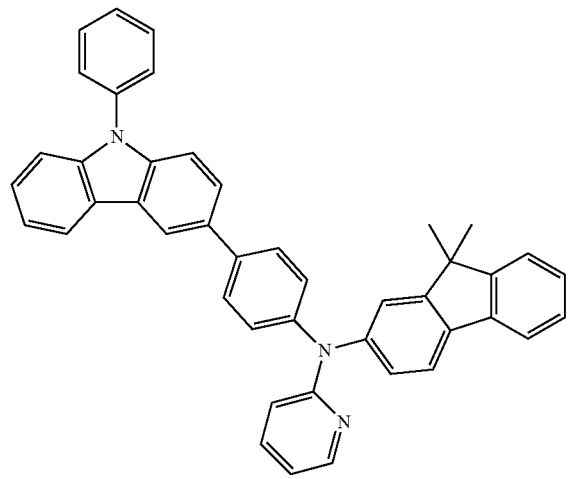
HT13
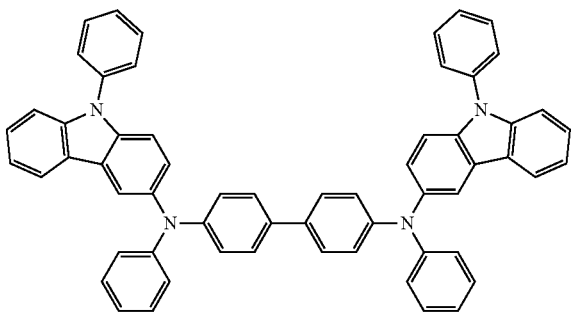
HT14
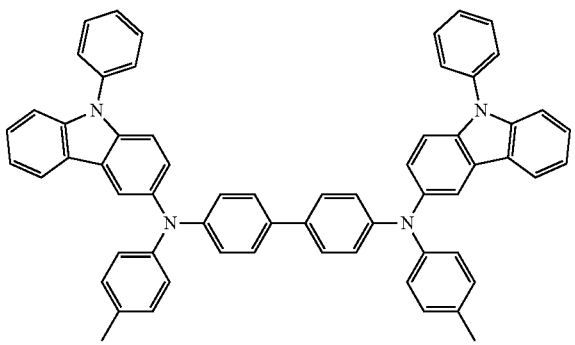
HT15
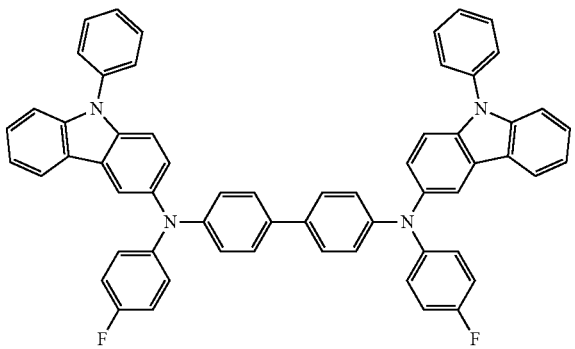
HT16
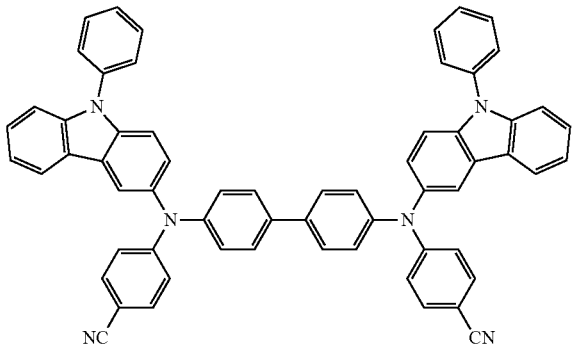
HT17
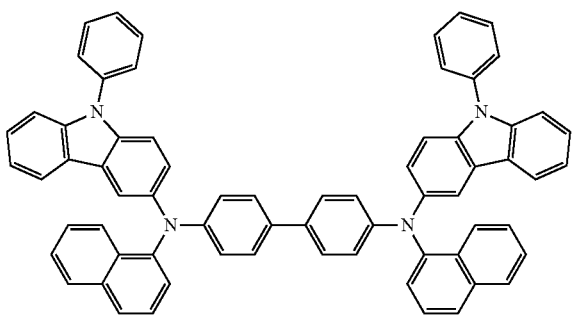
HT18
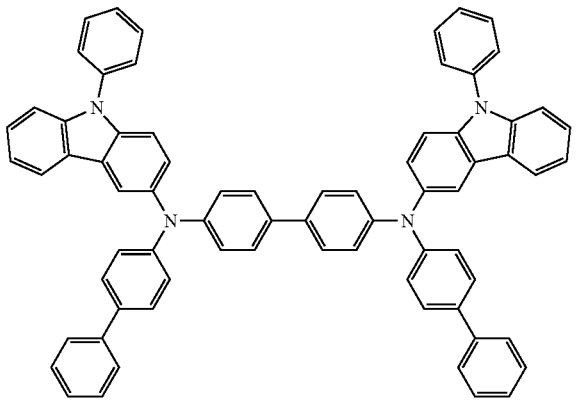
HT19
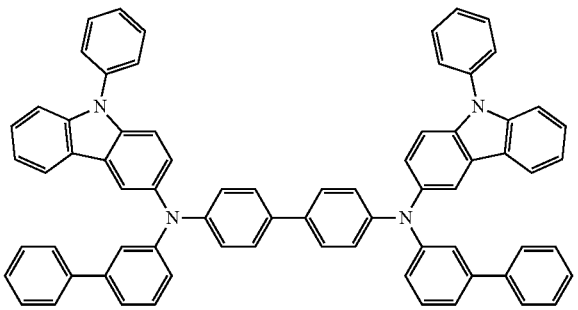

HT20

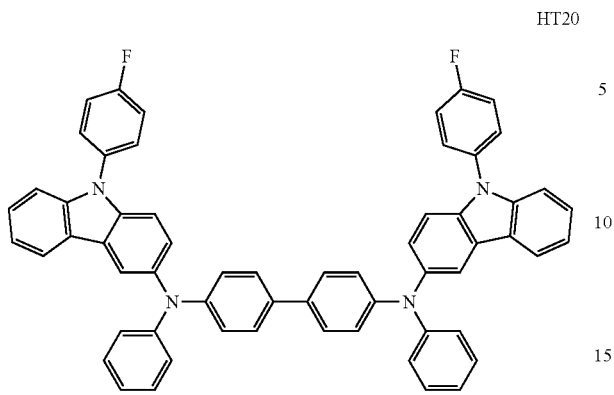

A thickness of the hole transport region may be in a range of about 100 Å to about 10,000 Å, for example, about 100 Å to about 1,000 Å. When the hole transport region includes both a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thickness values of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or Compound HT-D2 below, but are not limited thereto.

Compound HT-D1

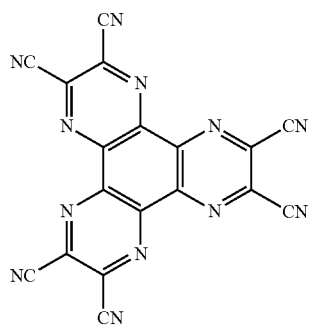

F4-TCNQ

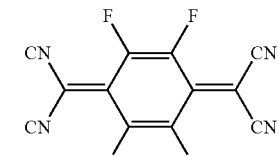

Compound HT-D2

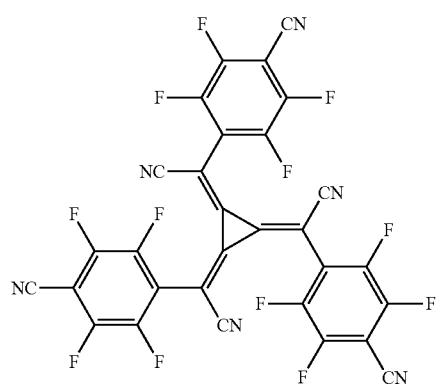

The hole transport region may include a buffer layer.

Also, the buffer layer may compensate for an optical resonance distance depending on a wavelength of light emitted from the emission layer, and thus, the efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied to form the hole injection layer although the deposition or coating conditions may vary according to the material that is used to form the emission layer.

The electron transport region may further include an electron blocking layer. The electron blocking layer may include, for example, mCP, but a material therefor is not limited thereto.

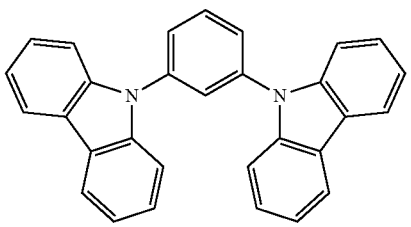

mCP

When the organic light-emitting device is a full color organic light-emitting device, the emission layer may be patterned into a red emission layer, a green emission layer, and a blue emission layer. In some embodiments, due to a stack structure including a red emission layer, a green emission layer, and/or a blue emission layer, the emission layer may emit white light.

The emission layer may include the condensed cyclic compound represented by Formula 1. The emission layer may include a dopant. The dopant may be at least one selected from a phosphorescent dopant and a fluorescent dopant.

For example, a host in the emission layer may include the condensed cyclic compound represented by Formula 1.

A dopant in the emission layer may be a fluorescent dopant that emits light according to a fluorescent emission mechanism or a phosphorescent dopant that emits light according to a phosphorescent emission mechanism.

According to an embodiment, the dopant in the emission layer may be a phosphorescent dopant, and the phosphorescent dopant may include an organometallic compound represented by Formula 81 below:

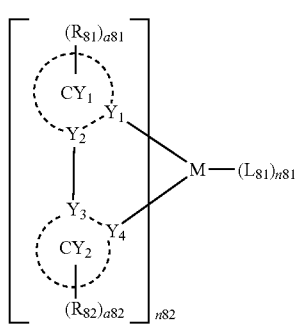

Formula 81

In Formula 81,

M may be selected from iridium (Ir), platinum (Pt), osmium (Os), titanium (Ti), zirconium (Zr), hafnium (Hf), europium (Eu), terbium (Tb), and thulium (Tm);

$Y_1$ to $Y_4$ are each independently carbon (C) or nitrogen (N);

$Y_1$ and $Y_2$ are linked via a single bond or a double bond, and $Y_3$ and $Y_4$ are linked via a single bond or a double bond;

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, an oxadiazole, a triazine, a dibenzofuran, and a dibenzothiophene, and $CY_1$ and $CY_2$ are optionally linked to each other through a single bond or an organic linking group;

$R_{81}$ to $R_{82}$ may be each independently hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), or —B(Q$_5$)(Q$_7$);

a81 and a82 are each independently an integer of 1 to 5;

n81 is an integer of 0 to 4;

n82 is 1, 2, or 3; and $L_{81}$ is a monovalent organic ligand, a divalent organic ligand, or a trivalent organic ligand.

$R_{81}$ and $R_{62}$ may be understood by referring to the description provided herein in connection with $R_{41}$.

The phosphorescent dopant may include at least one selected from Compounds PD1 to PD78 and FIr6 below, but embodiments are not limited thereto;

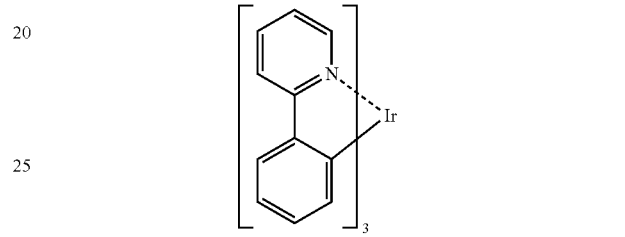
PD1

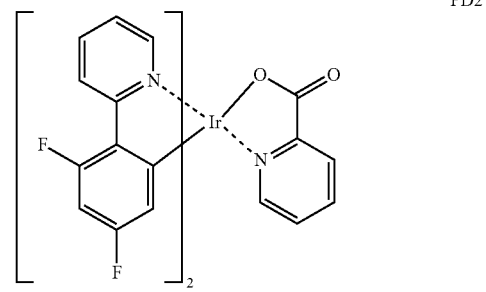
PD2

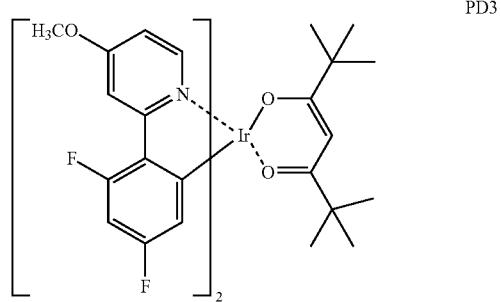
PD3

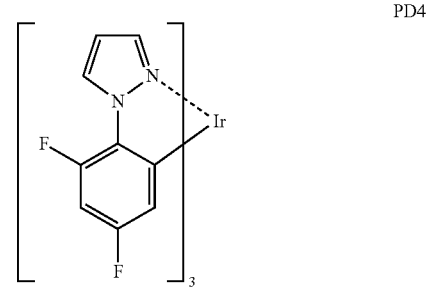
PD4

PD5
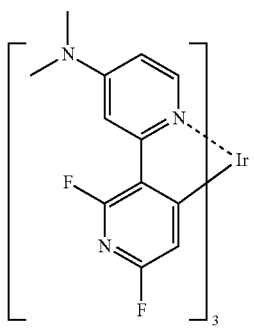
PD6
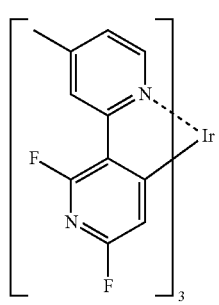
PD7
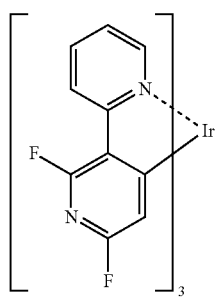
PD8
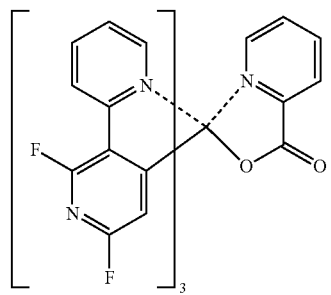
PD9
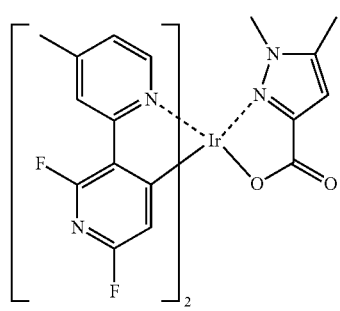
PD10
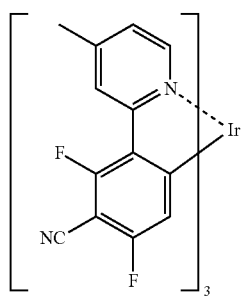
PD11
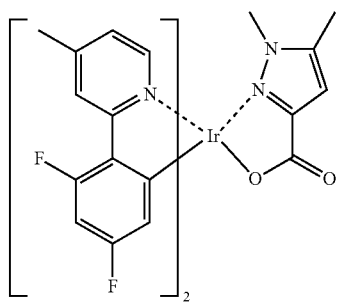
PD12
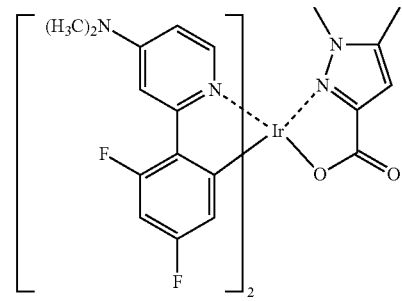
PD13
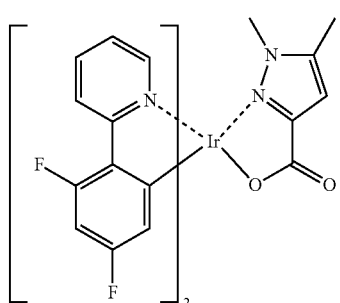
PD14
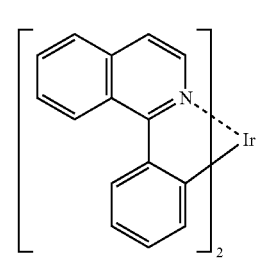

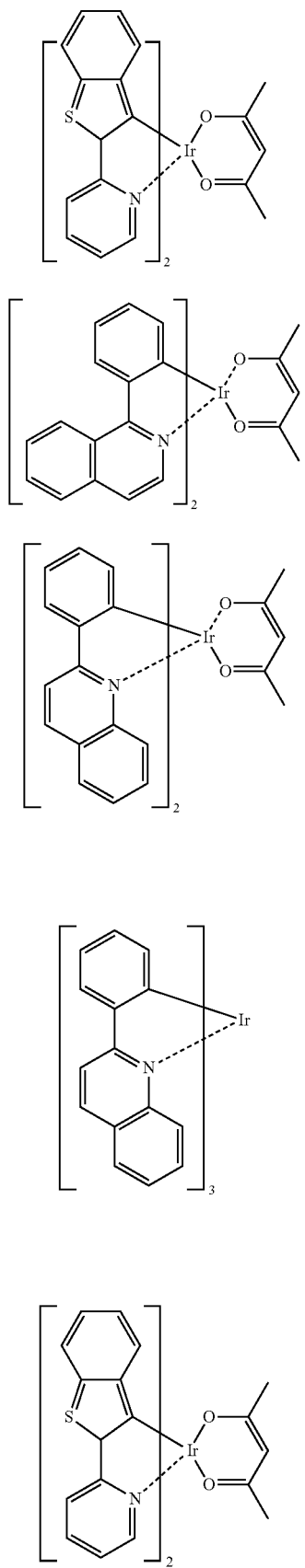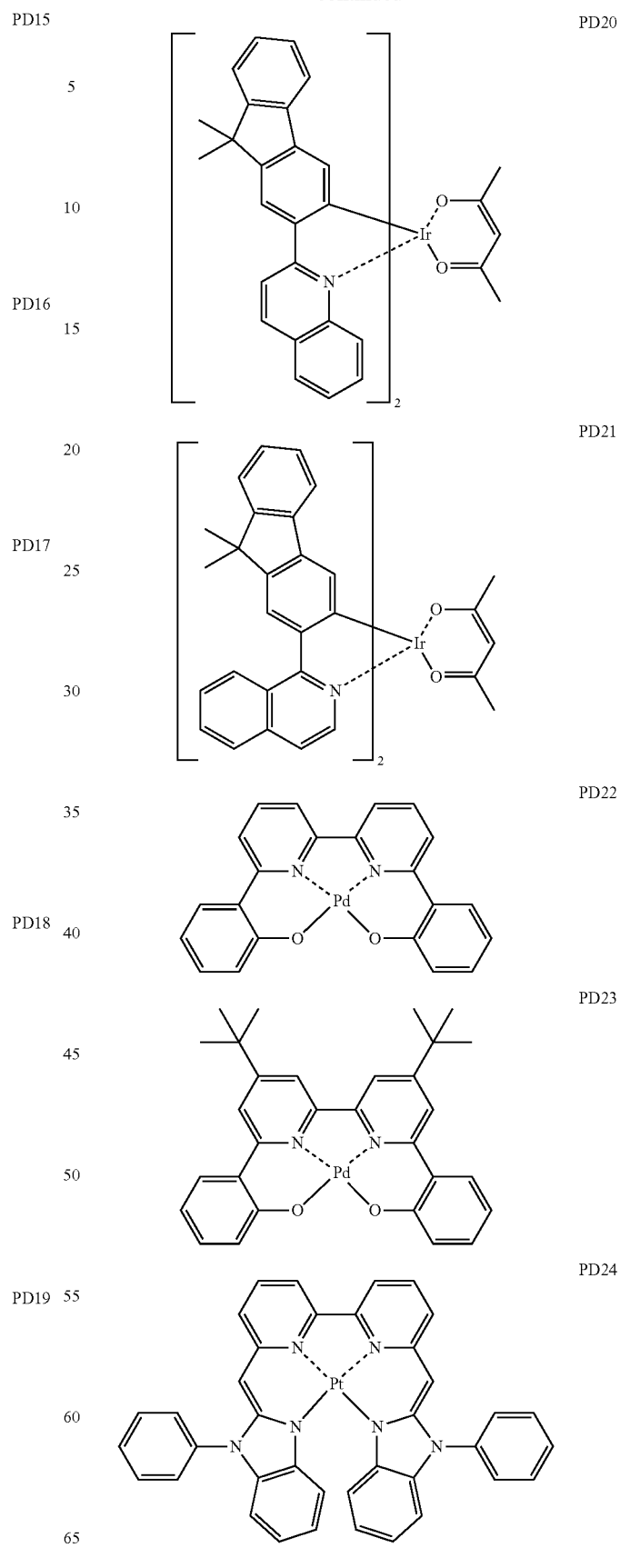

PD25 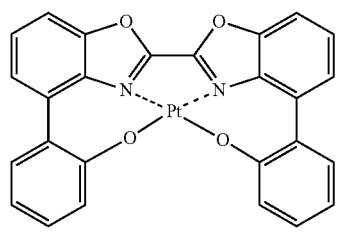
PD26 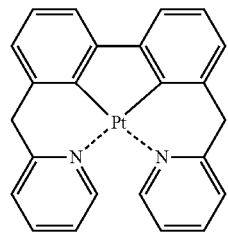
PD27 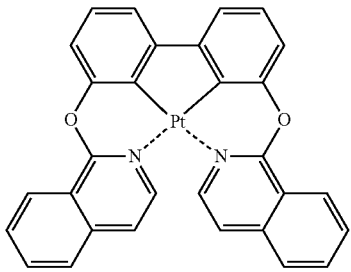
PD28 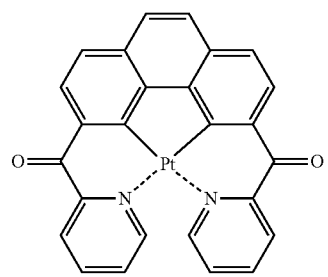
PD29 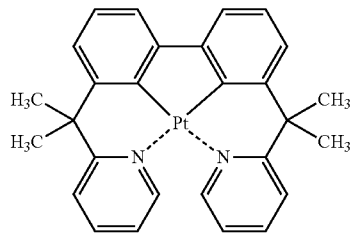
PD30 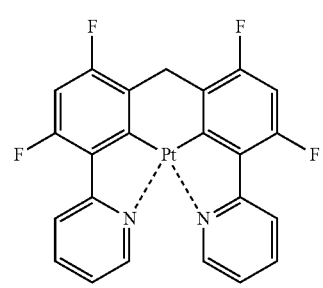
PD31 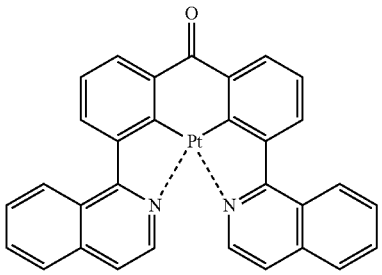
PD32 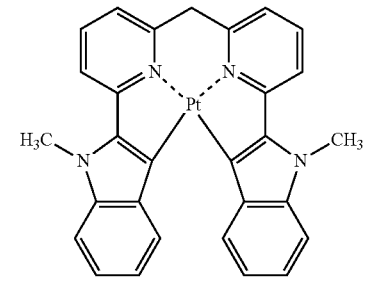
PD33 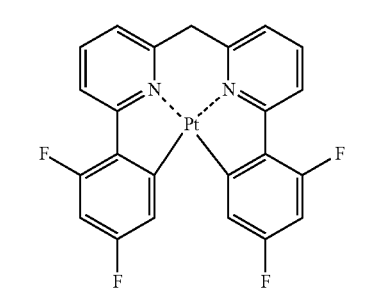
PD34 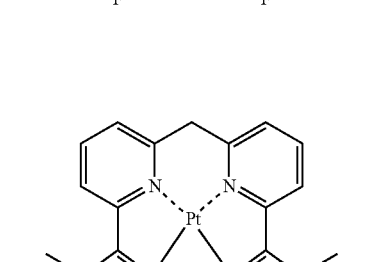
PD35 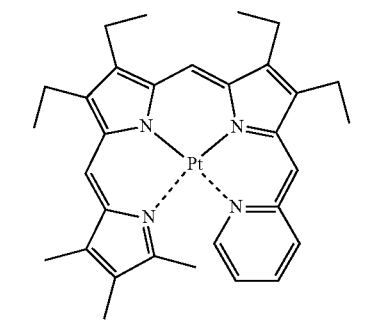

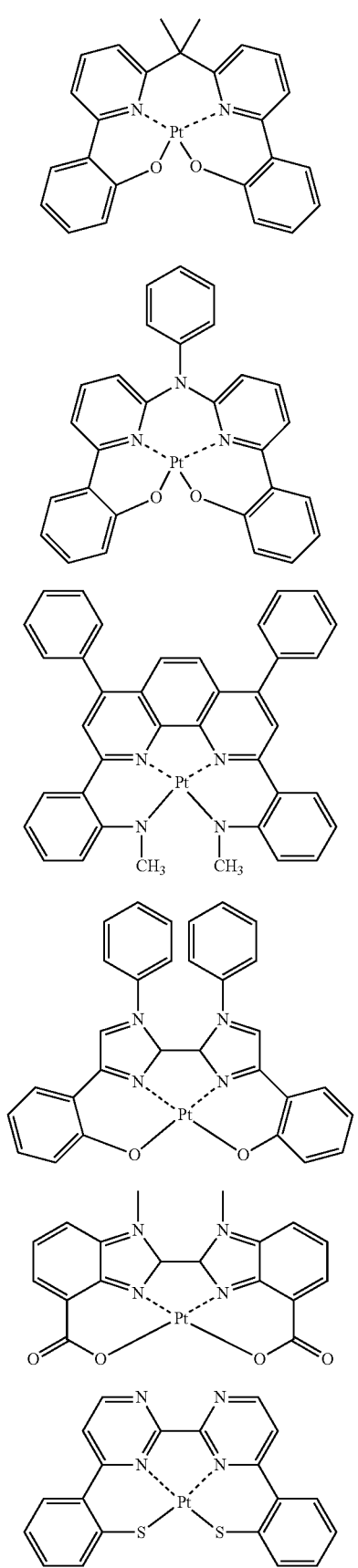

PD47
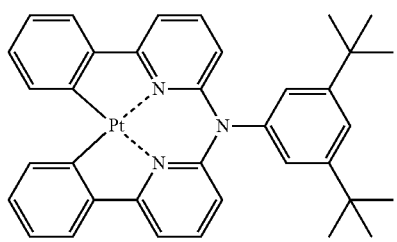
PD48
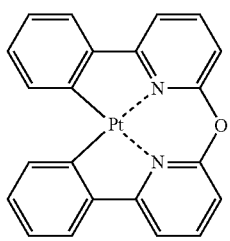
PD49
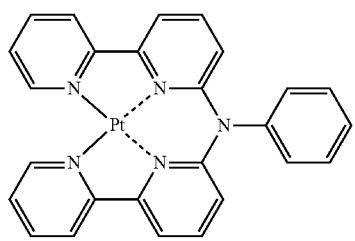
PD50
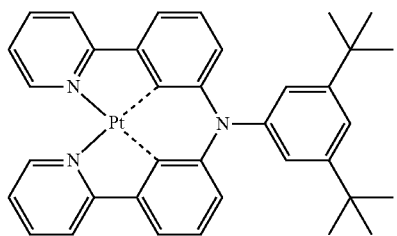
PD51
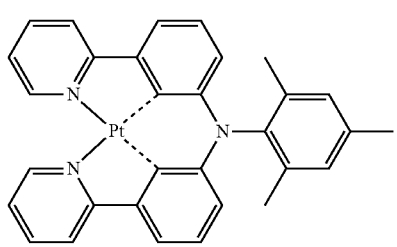
PD52
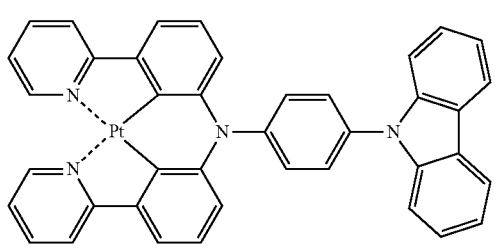
PD53
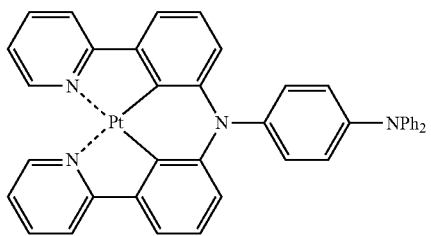
PD54
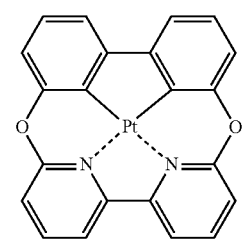
PD55
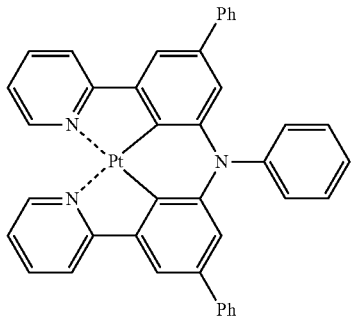
PD56
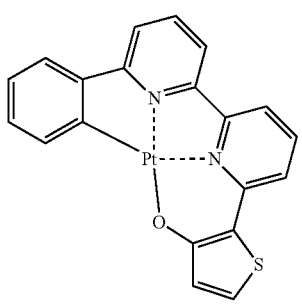
PD57
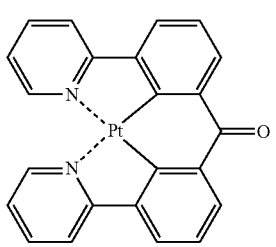

PD58
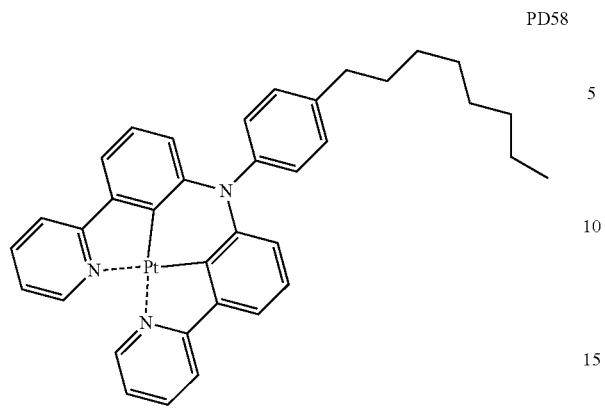
PD59
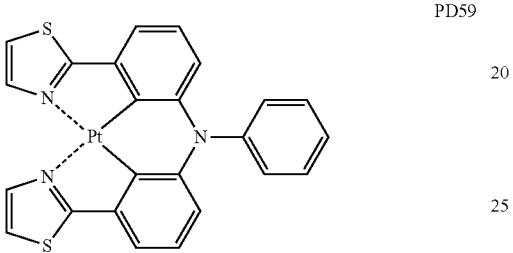
PD60
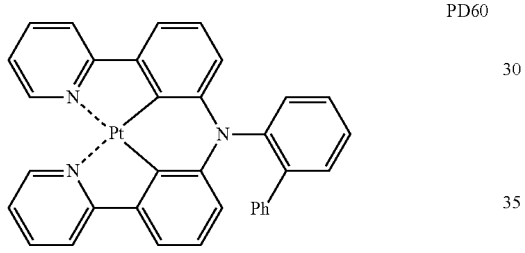
PD61
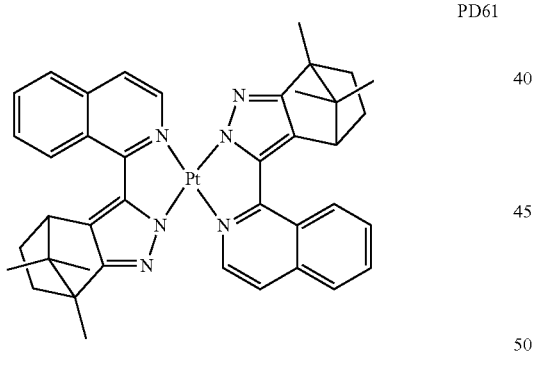
PD62
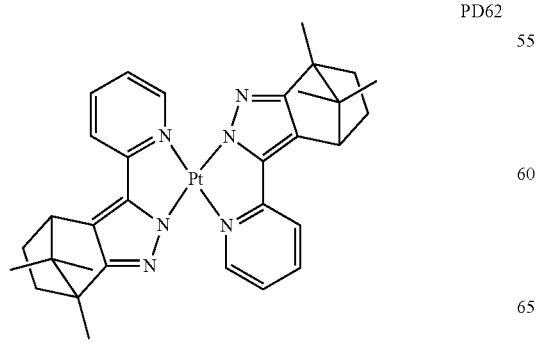
PD63
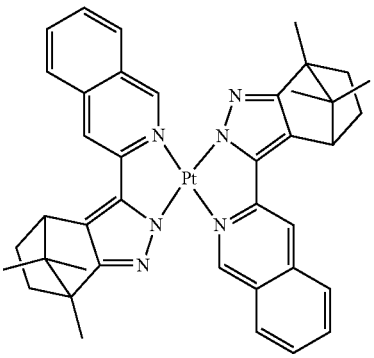
PD64
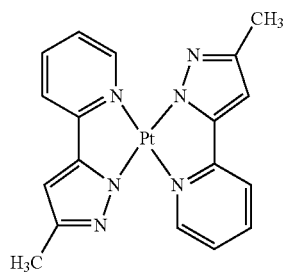
PD65
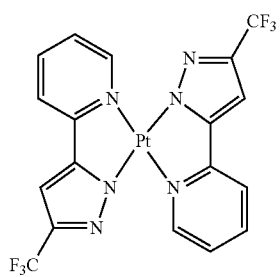
PD66
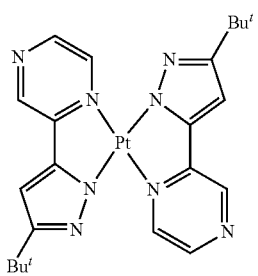
PD67
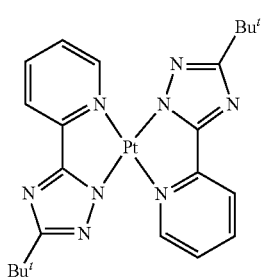

PD68 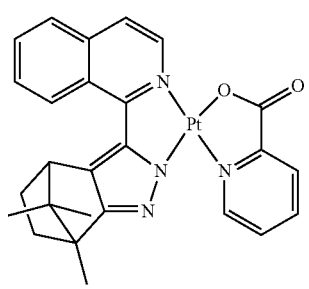
PD69 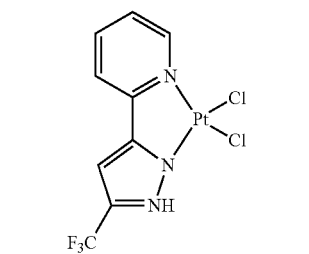
PD70 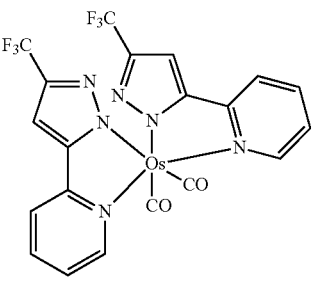
PD71 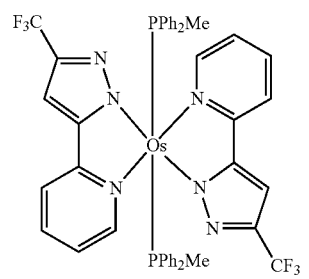
PD72 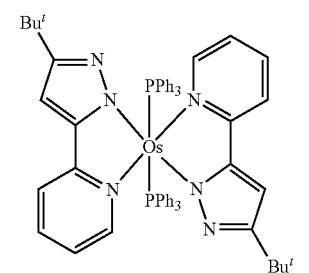
PD73 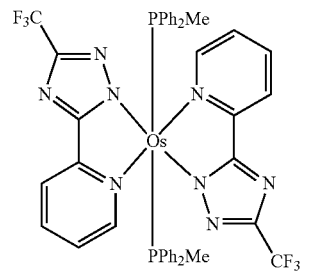
PD74 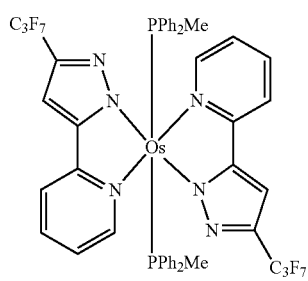
PD75 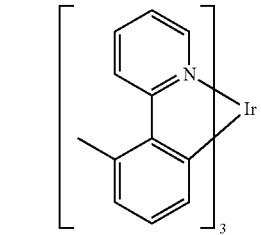
PD76 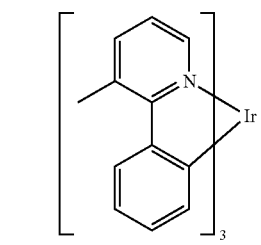
PD77 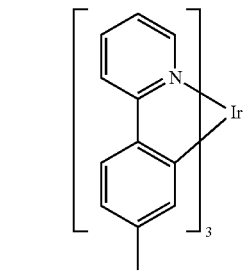
PD78 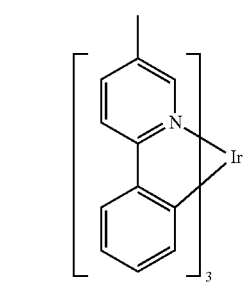
FIr6 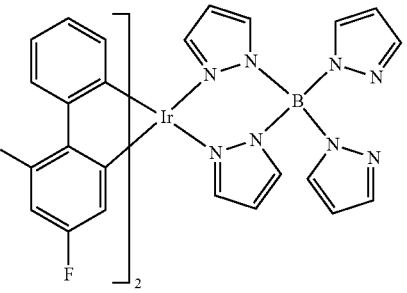

In some embodiments, the phosphorescent dopant may include PtOEP:

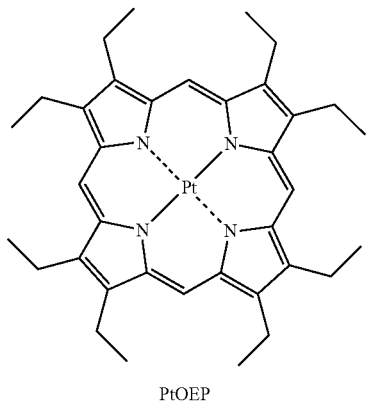

PtOEP

When the emission layer includes a host and a dopant, the amount of the dopant may be in a range of about 0.01 to about 20 parts by weight based on 100 parts by weight of the host, but is not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer, and an electron injection layer.

For example, the electron transport region may have a structure of hole blocking layer/electron transport layer/electron injection layer or a structure of electron transport layer/electron injection layer, but the structure of the electron transport region is not limited thereto. The electron transport layer may have a single-layered structure or a multi-layer structure including two or more different materials.

Conditions for forming the hole blocking layer, the electron transport layer, and the electron injection layer which constitute the electron transport region may be understood by referring to the conditions for forming the hole injection layer.

When the electron transport layer includes a hole blocking layer, the hole blocking layer may include, for example, at least one of BCP and Bphen, but may also include other materials.

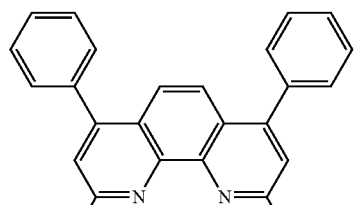

BCP

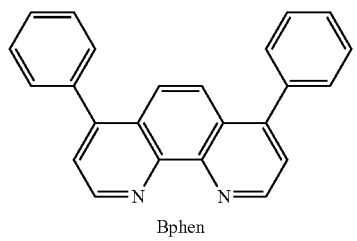

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include, in addition to the organometallic compound represented by Formula 1, at least one selected from BCP, Bphen, Alq$_3$, Balq, TAZ, and NTAZ.

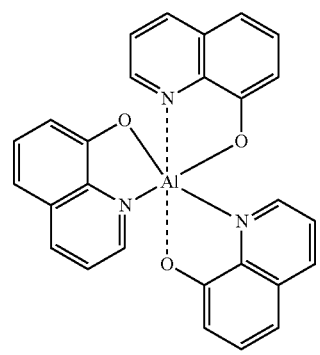

Alq$_3$

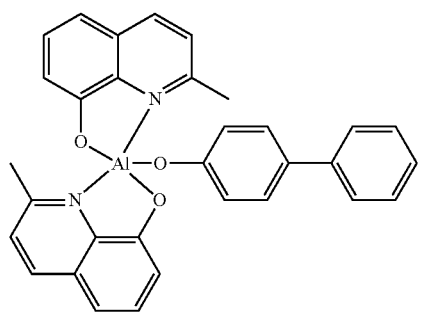

BAlq

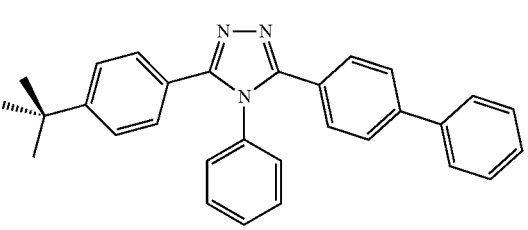

TAZ

-continued
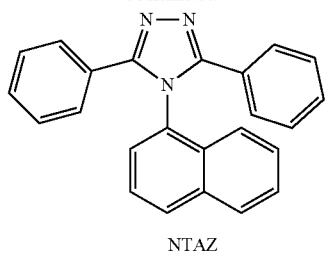
NTAZ
In some embodiments, the electron transport layer may include at least one of ET1 and ET19, but are not limited thereto:
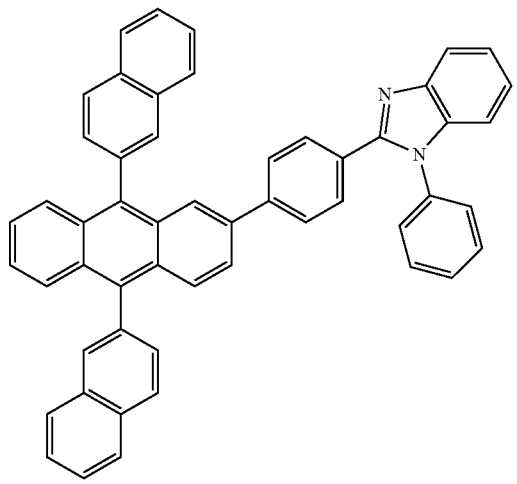
ET1
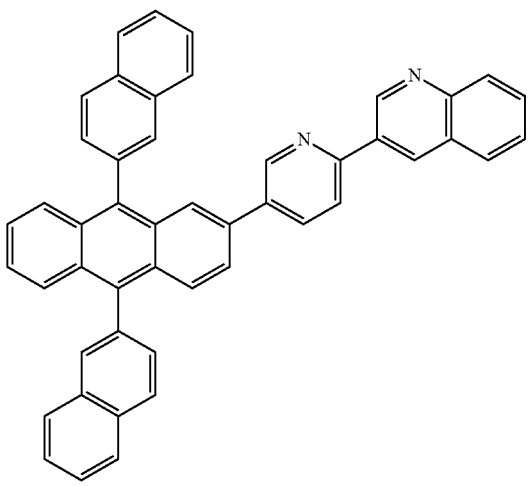
ET2
-continued
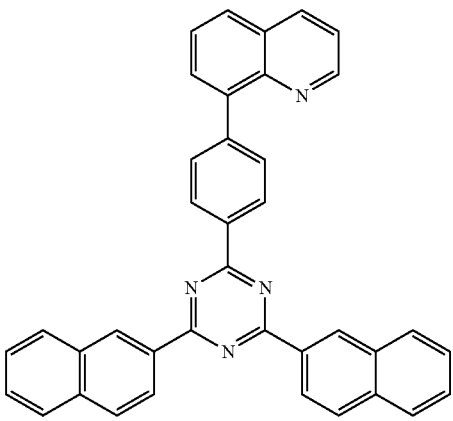
ET3
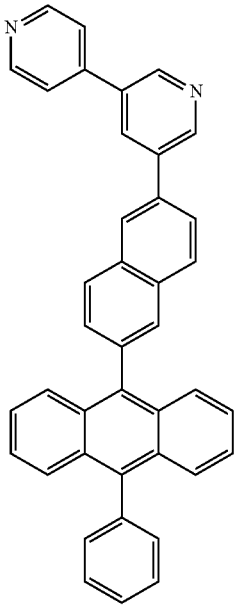
ET4
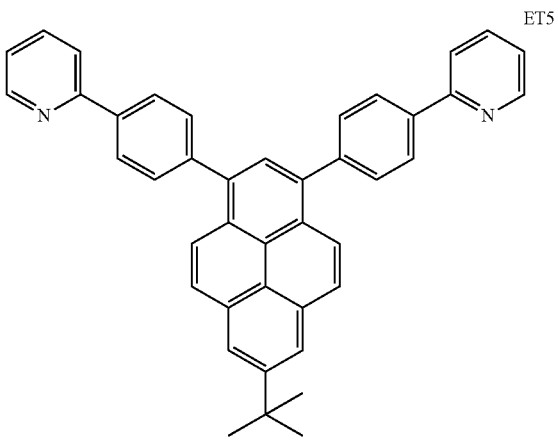
ET5

ET6
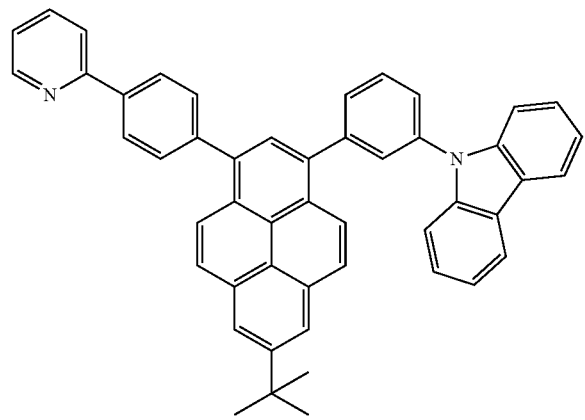
ET9
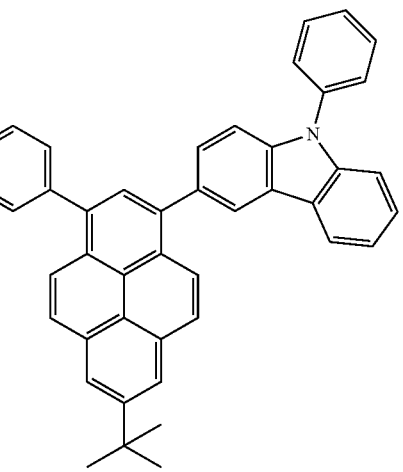
ET7
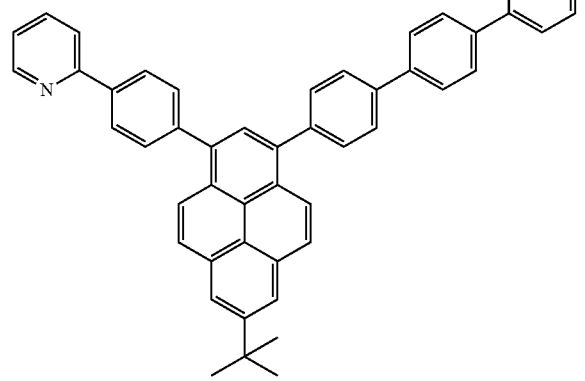
ET10
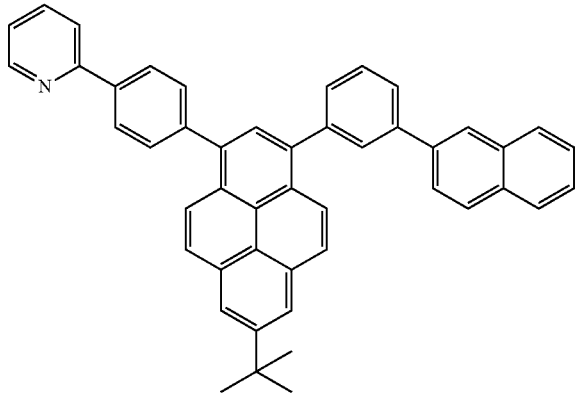
ET8
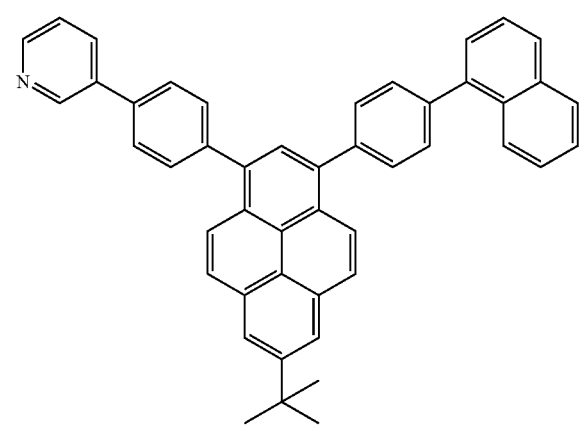
ET11
ET12
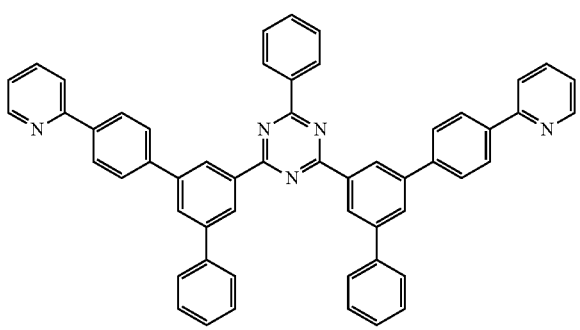

ET13
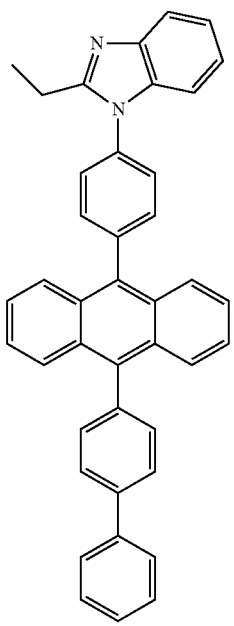
ET14
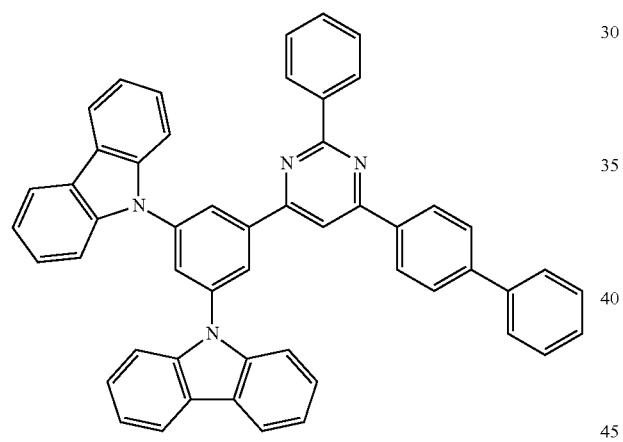
ET15
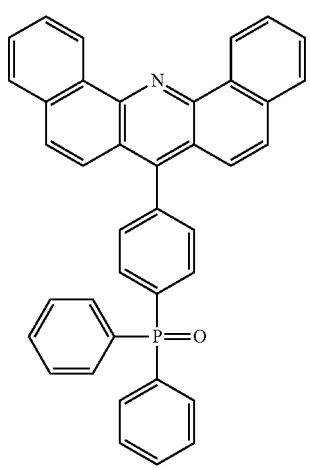
ET16
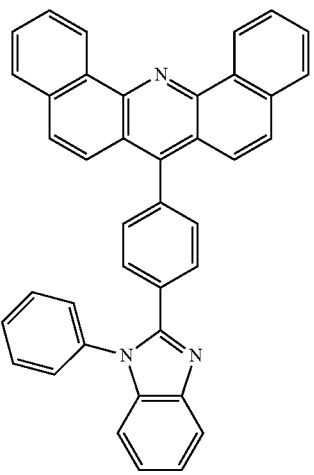
ET17
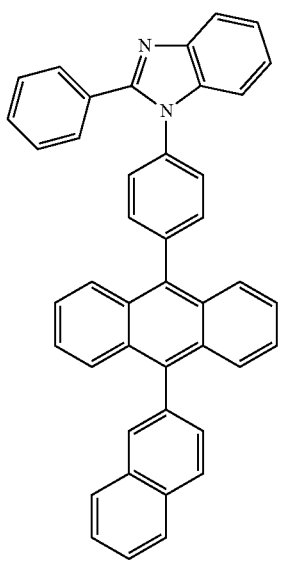
ET18
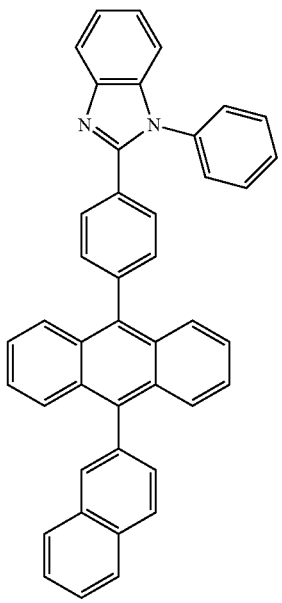

ET19

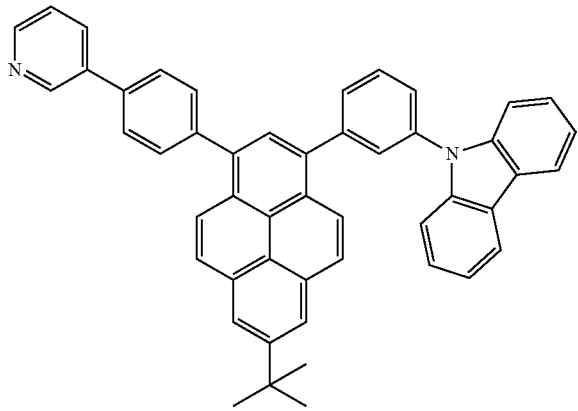

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a Li complex. The Li complex may include, for example, Compound ET-D1 (lithium quinolate, LiQ) or ET-D2.

ET-D1

ET-D2

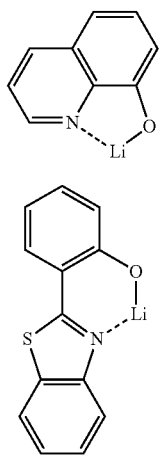

The electron transport layer may include an electron injection layer that promotes flow of electrons from the second electrode 19 thereinto.

The electron injection layer may include at least one selected from, LiF, NaCl, CsF, $Li_2O$, BaO, and LiQ.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top emission-type light-emitting device, a transmissive electrode formed using ITO or IZO may be used as the second electrode 19.

Hereinbefore, the organic light-emitting device has been described with reference to FIG. 1, but is not limited thereto.

A $C_1$-$C_{60}$ alkyl group as used herein refers to a linear or branched aliphatic hydrocarbon monovalent group having 1 to 60 carbon atoms. Detailed examples thereof are a methyl group, an ethyl group, a propyl group, an isobutyl group, a sec-butyl group, a tert-butyl group, a pentyl group, an iso-amyl group, and a hexyl group. A $C_1$-$C_{60}$ alkylene group as used herein refers to a divalent group having the same structure as the $C_1$-$C_{60}$ alkyl group.

A $C_1$-$C_{60}$ alkoxy group as used herein refers to a monovalent group represented by —$OA_{101}$ (wherein $A_{101}$ is the $C_1$-$C_{60}$ alkyl group). Detailed examples thereof are a methoxy group, an ethoxy group, and an isopropyloxy group.

A $C_2$-$C_{60}$ alkenyl group as used herein refers to a hydrocarbon group formed by placing at least one carbon double bond in the middle or at the terminal of the $C_2$-$C_{60}$ alkyl group. Detailed examples thereof are an ethenyl group, a propenyl group, and a butenyl group. A $C_2$-$C_{60}$ alkenylene group as used herein refers to a divalent group having the same structure as the $C_2$-$C_{60}$ alkenyl group.

A $C_2$-$C_{60}$ alkynyl group as used herein refers to a hydrocarbon group having at least one carbon triple bond in the middle or at the terminal of the $C_2$-$C_{60}$ alkyl group. Detailed examples thereof are an ethynyl group and a propynyl group. A $C_2$-$C_{60}$ alkynylene group as used herein refers to a divalent group having the same structure as the $C_2$-$C_{60}$ alkynyl group.

A $C_3$-$C_{10}$ cycloalkyl group as used herein refers to a monovalent hydrocarbon monocyclic group having 3 to 10 carbon atoms. Detailed examples thereof are a cyclopropyl group, a cyclobutyl group, a cyclopentyl group, a cyclohexyl group, and a cycloheptyl group. A $C_3$-$C_{10}$ cycloalkylene group as used herein refers to a divalent group having the same structure as the $C_3$-$C_{10}$ cycloalkyl group.

A $C_1$-$C_{10}$ heterocycloalkyl group as used herein refers to a monovalent monocyclic group having at least one heteroatom selected from N, O, P, and S as a ring-forming atom and 1 to 10 carbon atoms. Detailed examples thereof are a tetrahydrofuranyl group and a tetrahydrothiophenyl group. A $C_1$-$C_{10}$ heterocycloalkylene group as used herein refers to a divalent group having the same structure as the $C_1$-$C_{10}$ heterocycloalkyl group.

A $C_3$-$C_{10}$ cycloalkenyl group as used herein refers to a monovalent monocyclic group that has 3 to 10 carbon atoms and at least one double bond in the ring thereof, and which is not aromatic. Detailed examples thereof are a cyclopentenyl group, a cyclohexenyl group, and a cycloheptenyl group. A $C_3$-$C_{10}$ cycloalkenylene group as used herein refers to a divalent group having the same structure as the $C_3$-$C_{10}$ cycloalkenyl group.

A $C_1$-$C_{10}$ heterocycloalkenyl group as used herein refers to a monovalent monocyclic group that has at least one heteroatom selected from N, O, P, and S as a ring-forming atom, 1 to 10 carbon atoms, and at least one double bond in its ring. Detailed examples of the $C_1$-$C_{10}$ heterocycloalkenyl group are a 2,3-dihydrofuranyl group and a 2,3-dihydrothiophenyl group. A $C_1$-$C_{10}$ heterocycloalkenylene group as used herein refers to a divalent group having the same structure as the $C_1$-$C_{10}$ heterocycloalkenyl group.

A $C_6$-$C_{60}$ aryl group as used herein refers to a monovalent group having a carbocyclic aromatic system having 6 to 60 carbon atoms, and a $C_6$-$C_{60}$ arylene group as used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group as used herein refers to a monovalent group having a carbocyclic aromatic system that has at least one heteroatom selected from N, O, P, and S as a ring-forming atom, and 1 to 60 carbon atoms. A $C_1$-$C_{60}$ heteroarylene group as used herein refers to a divalent group having a carbocyclic aromatic system that has at least one heteroatom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group as used herein indicates —$OA_{102}$ (wherein $A_{102}$ is the $C_6$-$C_{60}$ aryl group), and a $C_6$-$C_{60}$ arylthio group indicates —$SA_{103}$ (wherein $A_{103}$ is the $C_6$-$C_{60}$ aryl group).

A monovalent non-aromatic condensed polycyclic group as used herein refers to a monovalent group that has two or more rings condensed to each other, only carbon atoms (for example, the number of carbon atoms may be in a range of 8 to 60) as a ring-forming atom, and which is non-aromatic in the entire molecular structure. An example of the monovalent non-aromatic condensed polycyclic group is a fluorenyl group. A divalent non-aromatic condensed polycyclic group as used herein refers to a divalent group having the same structure as the monovalent non-aromatic condensed polycyclic group.

A monovalent non-aromatic condensed heteropolycyclic group as used herein refers to a monovalent group that has two or more rings condensed to each other, has a heteroatom selected from N, O, P, and S other than carbon atoms (for example, the number of carbon atoms may be in a range of 1 to 60), as a ring-forming atom, and which is non-aromatic in the entire molecular structure. An example of the monovalent non-aromatic condensed heteropolycyclic group is a carbazolyl group. A divalent non-aromatic condensed heteropolycyclic group as used herein refers to a divalent group having the same structure as the monovalent non-aromatic condensed heteropolycyclic group.

At least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group as used herein is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_5$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{31})(Q_{32})(Q_{33})$, wherein $Q_{31}$ to $Q_{33}$ may be each independently selected from hydrogen, a $C_1$-$C_{60}$ alkyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The "biphenyl group" as used herein refers to "a phenyl group substituted with a phenyl group."

Hereinafter, a compound and an organic light-emitting device according to embodiments are described in detail with reference to Synthesis Example and Examples. However, the organic light-emitting device is not limited thereto. The wording "B was used instead of A" used in describing Synthesis Examples means that an amount of A used was identical to an amount of B used, in terms of a molar equivalent.

EXAMPLE

Synthesis Example 1: Synthesis of Compound 5

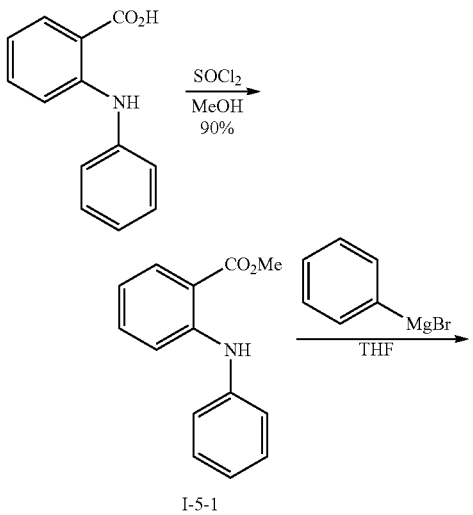

-continued

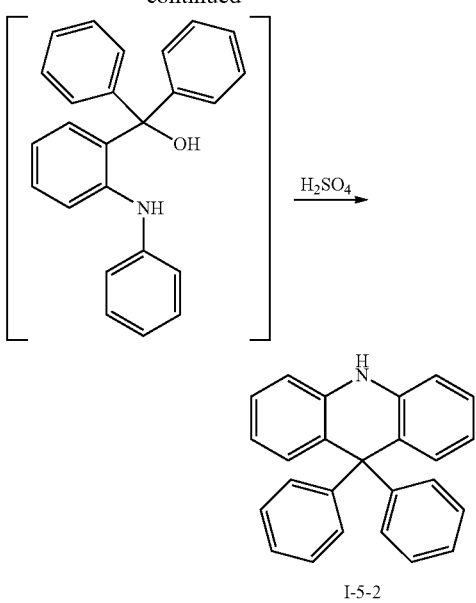

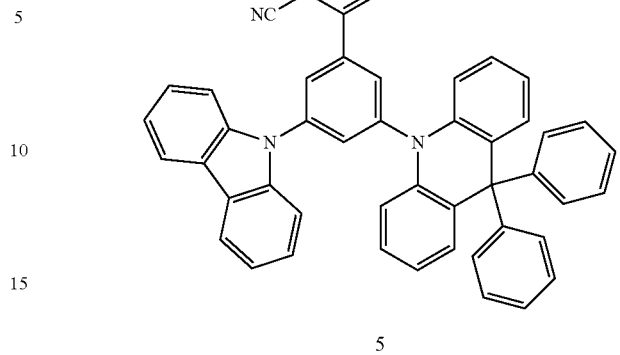

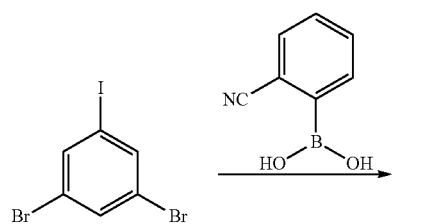

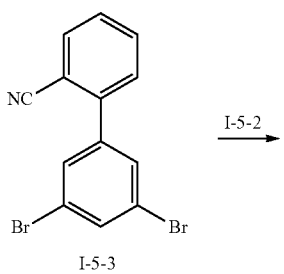

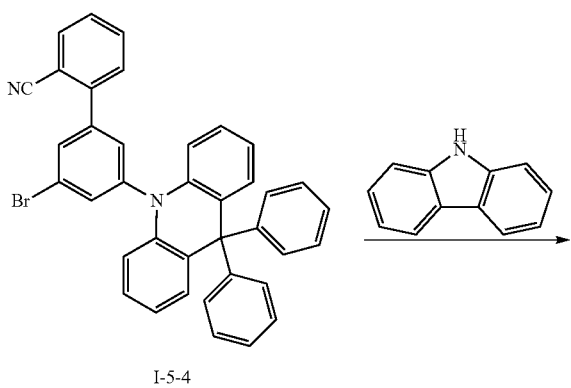

1) Synthesis of Intermediate I-5-1

2-(phenylamino)benzoic acid (2.5 grams (g), 0.12 moles (mol)), thionyl chloride (1.39 g, 0.13 mol), and 50 milliliters (mL) of methanol were added to a flask, and the mixture was allowed to react for 5 hours. Once the reaction was completed, the reaction mixture was filtered, and the remaining solid was washed with water to obtain Intermediate I-3-1 (2.4 g, 90%).

2) Synthesis of Intermediate I-5-2

A Grignard reaction was performed by using Intermediate I-3-1 (2 g, 0.009 mol) and phenyl magnesium bromide (2.07 g, 0.012 mol) to obtain diphenyl(2-(phenylamino)phenyl)methanol. Without separating diphenyl(2-(phenylamino)phenyl)methanol, 30 mL of sulfuric acid was added thereto to obtain Intermediate I-5-2 (1.6 g, 56%).

3) Synthesis of Intermediate I-5-3

1,3-dibromo-5-iodobenzene (20 g, 55.28 millimoles (mmol)), (2-cyanophenyl)boronic acid (9.74 g, 66.33 mmol), potassium carbonate (15.28 g, 110.56 mmol), and 0.05 mole percent (mol %) of Pd catalyst were added to a reaction vessel, and a mixture of tetrahydrofuran and distilled water (110 mL, 1:1 volume to volume (v/v)) were added thereto. The reaction mixture was allowed to react for 12 hours. Once the reaction was complete, methanol was added thereto to form a precipitate, which was then filtered. The precipitate was purified by column chromatography to obtain Intermediate I-5-3 (9.1 g, 48%).

4) Synthesis of Intermediate I-5-4

Intermediate I-5-3 (8.5 g, 25.19 mmol), Intermediate I-5-2 (7 g, 21 mmol), copper iodide (0.2 g, 1.05 mmol), sodium-tert-butoxide (4.035 g, 42 mmol), trans-1,2-diamino cyclohexane (0.48 g, 4.2 mmol), and 50 mL of dimethylformamide were reacted at a temperature of 150° C. for 12 hours. The reaction mixture was cooled to room temperature, and methanol was added thereto to form a precipitate, which was then filtered. The precipitate was purified by column chromatography to obtain Intermediate I-5-4 (6.6 g, 45%).

5) Synthesis of Compound 5

9H-carbazole (1 g, 5.98 mmol), Intermediate I-5-4 (4.23 g, 7.18 mmol), copper iodide (0.57 g, 2.99 mmol), potassium carbonate (6.362 g, 46 mmol), 1,10-phenanthroline (1.08 g, 5.98 mmol), and 30 mL of dimethylformamide were reacted for 24 hours. The obtained crude product was purified by column chromatography using dichloromethane and n-hexane. The obtained purification product was re-crystallized from ethyl acetate and ethanol to obtain Compound 5 (1.1 g, 98%). Compound 5 was identified by LC-Mass.

LC-Mass (calc.: 675.83 g/mol, found: M+H=676 g/mol).

Comparative Synthesis Example 1: Synthesis of Compound A

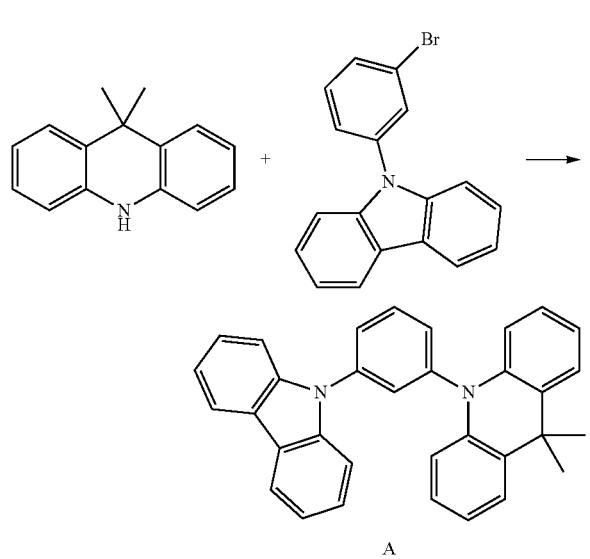

A

Acridine (10 g, 47.78 mmol), 9-(3-bromophenyl)-9H-carbazole (18.4 g, 57.34 mmol), potassium-tert-butoxide (8 g, 71.67 mmol), palladium acetate (0.536 g, 2.39 mmol), tri-tert-butylphosphine (50 wt % toluene) (0.774 mL, 1.91 mmol), and 60 mL of toluene were reacted at a temperature of 110° C. for 24 hours. Once the reaction was completed, filtering was performed thereon to obtain a crude product. The obtained crude product was re-crystallized twice by using toluene and methanol to obtain Compound A (14.6 g, 68%). Compound A was identified by LC-Mass.

LC-Mass (calc.: 450.59 g/mol, found: M+H=451 g/mol).

Comparative Synthesis Example 2: Synthesis of Compound B

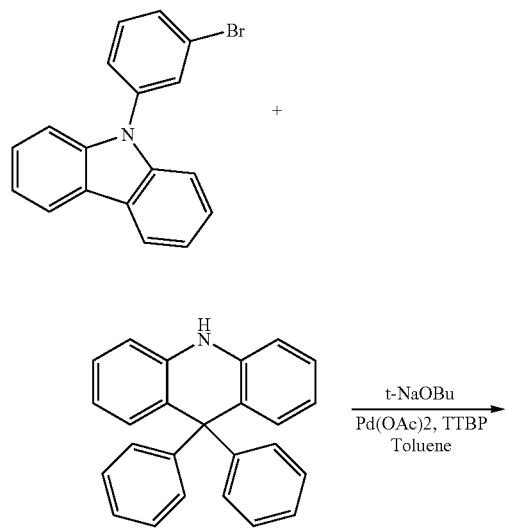

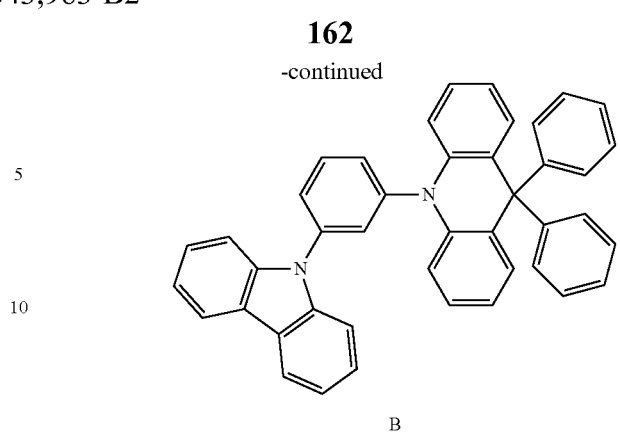

B 9,9-diphenyl-9,10-dihydroacridine (10 g, 30 mmol), 9-(3-bromophenyl)-9H-carbazole (11.6 g, 36 mmol), sodium-tert-butoxide (4.324 g, 45 mmol), palladium acetate (0.337 g, 1.5 mmol), tri-tert-butylphosphine (0.6 mL, 1.5 mmol), and 60 mL of toluene were reacted at a temperature of 110° C. for 24 hours. Once the reaction was completed, filtering was performed thereon to obtain a crude product. The obtained crude product was re-crystallized twice by using dichloromethane and n-hexane to obtain Compound B (4.44 g, 26%). Compound B was identified by LC-Mass.

LC-Mass (calc.: 574.73 g/mol, found: M+H=575 g/mol).

Comparative Synthesis Example 3: Synthesis of Compound C

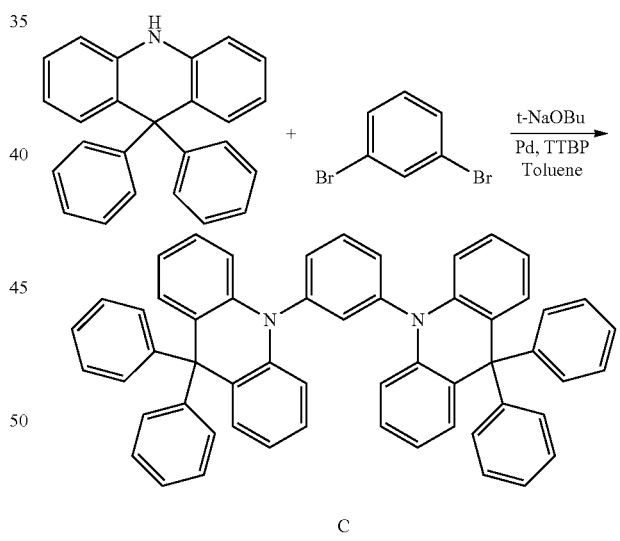

C 9,9-diphenyl-9,10-dihydroacridine (10 g, 30 mmol), 1,3-dibromobenzene (15.4 g, 66 mmol), sodium-tert-butoxide (4.324 g, 45 mmol), palladium acetate (0.337 g, 1.5 mmol), tri-tert-butylphosphine (1.2 mL, 3 mmol), and 60 mL of toluene were reacted at a temperature of 110° C. for 24 hours. Once the reaction was completed, filtering was performed thereon to obtain a crude product. The obtained crude product was purified by column chromatography to obtain Compound C (11.5 g, 52%). Compound C was identified by LC-Mass.

LC-Mass (calc.: 740.95 g/mol, found: M+H=742 g/mol).

Comparative Synthesis Example 4: Synthesis of Compound D

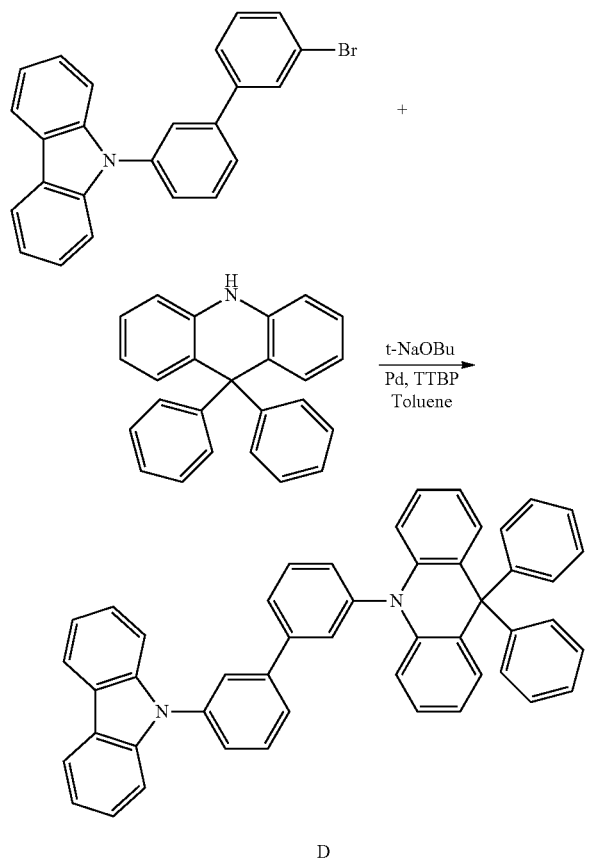

D 9,9-diphenyl-9,10-dihydroacridine (10 g, 30 mmol), 9-(3'-bromo-[1,1'-biphenyl]-3-yl)-9H-carbazole (14.3 g, 36 mmol), sodium-tert-butoxide (4.324 g, 45 mmol), palladium acetate (0.337 g, 1.5 mmol), tri-tert-butylphosphine (0.6 mL, 1.5 mmol), and 60 mL of toluene were reacted at a temperature of 110° C. for 24 hours. Once the reaction was completed, filtering was performed thereon to obtain a crude product. The obtained crude product was purified by column chromatography to obtain Compound D (16 g, 84%). Compound D was identified by LC-Mass.

LC-Mass (calc.: 650.83 g/mol, found: M+H=652 g/mol).

Evaluation Example 1: Evaluation on HOMO, LUMO, and Triplet ($T_1$) Energy Levels HOMO, LUMO and $T_1$ energy levels of Compounds 5 and A to D were evaluated according to the method shown in Table 1. Results thereof are shown in Table 2.

TABLE 1

| | |
|---|---|
| HOMO energy level evaluation method | A potential (volts, V)-current (amperes, A) graph of each compound was obtained by using cyclic voltammetry (CV) (electrolyte: 0.1 molar (M) $Bu_4NClO_4$/solvent: $CH_2Cl_2$/electrode: 3 electrode system (working electrode: GC, reference electrode: Ag/AgCl, auxiliary electrode: Pt)). From reduction onset of the graph, a HOMO energy level of the compound was calculated. |

TABLE 1-continued

| | |
|---|---|
| LUMO energy level evaluation method | Each compound was diluted at a concentration of $1 \times 10^{-5}$ M in $CHCl_3$, and an UV absorption spectrum thereof was measured at room temperature by using a Shimadzu UV-350 spectrometer, and a LUMO energy level thereof was calculated by using an optical band gap (Eg) from an edge of the absorption spectrum. |
| T1 energy level evaluation method | A mixture (each compound was dissolved in an amount of 1 milligram (mg) in 3 cubic centimeters (cc) of toluene and, each compound was loaded into a quartz cell. The resultant quartz cell was loaded into liquid nitrogen (77 Kelvin (K)) and a photoluminescence spectrum thereof was measured by using a device for measuring photoluminescence. The obtained spectrum was compared with a photoluminescence spectrum measured at room temperature, and peaks observed only at low temperature were analyzed to calculate $T_1$ energy levels. |

TABLE 2

| Compound No. | HOMO (eV) | LUMO (eV) | $T_1$ (eV) |
|---|---|---|---|
| Compound 5 | −5.57 | −1.98 | 3.02 |
| Compound A | −5.39 | −1.80 | 3.02 |
| Compound B | −5.47 | −1.89 | 3.01 |
| Compound C | −5.42 | −1.91 | 3.07 |
| Compound D | −5.46 | −1.91 | 3.04 |

From Table 2, it is seen that Compound 5 above has electric characteristics that are suitable for use as a material for forming an organic light-emitting device.

Evaluation Example 2: Thermal Characteristics Evaluation

Thermal analysis ($N_2$ atmosphere, temperature range: from room temperature to 800° C. (10° C./min)-TGA, from room temperature to 400° C.-DSC, Pan Type: Pt Pan in disposable Al Pan(TGA), and disposable Al pan(DSC)) was performed on Compounds 5, and A to C by using thermo gravimetric analysis (TGA) and differential scanning calorimetry (DSC), and results thereof are shown in Table 3. As shown in Table 3, it is seen that Compound 5 has excellent thermal stability.

TABLE 3

| | Tg (° C.) | Td (° C., 0.1%) |
|---|---|---|
| Compound 5 | 163 | 375 |
| Compound A | — | 282 |
| Compound B | 108 | 297 |
| Compound C | 133 | 301 |
| Compound D | 127 | 245 |

Example 1

A glass substrate with a 1,500 Å-thick ITO (Indium tin oxide) electrode (first electrode, anode) formed thereon was washed with distilled water and ultrasonic waves. When the washing with distilled water was completed, sonification washing was performed using a solvent, such as isopropyl alcohol, acetone, or methanol. The result was dried and then transferred to a plasma washer, and the resultant substrate was washed with oxygen plasma for 5 minutes and then, transferred to a vacuum depositing device.

Compound HT3 and Compound HP-D2 were co-deposited on the ITO electrode on the glass substrate to form a hole injection layer having a thickness of 100 Angstroms (Å). Then, Compound HT3 was deposited on the hole injection layer to form a hole transport layer having a thickness of 1,300 Å, and mCP was deposited on the hole transport layer to form an electron blocking layer having a thickness of 150 Å, thereby completing the manufacture of a hole transport region.

On the hole transport region, Compound 5 (host) and Flr6 (dopant, 10 percent by weight (wt %)) were co-deposited to form an emission layer having a thickness of 300 Å.

BCP was vacuum-deposited on the emission layer to form a hole blocking layer having a thickness of 100 Å. Compound ET3 and Liq were vacuum deposited together on the hole blocking layer to form an electron transport layer having a thickness of 250 Å. Liq was deposited on the electron transport layer to form an electron injection layer having a thickness of 5 Å, and an Al second electrode (cathode) having a thickness of 1,000 Å was formed on the electron injection layer to complete manufacturing of an organic light-emitting device.

Comparative Examples 1 to 4

Organic light-emitting devices were manufactured in the same manner as in Example 1, except that in forming an emission layer, for use as a host, corresponding compounds shown in Table 4 were used instead of Compound 5.

Figure 2:
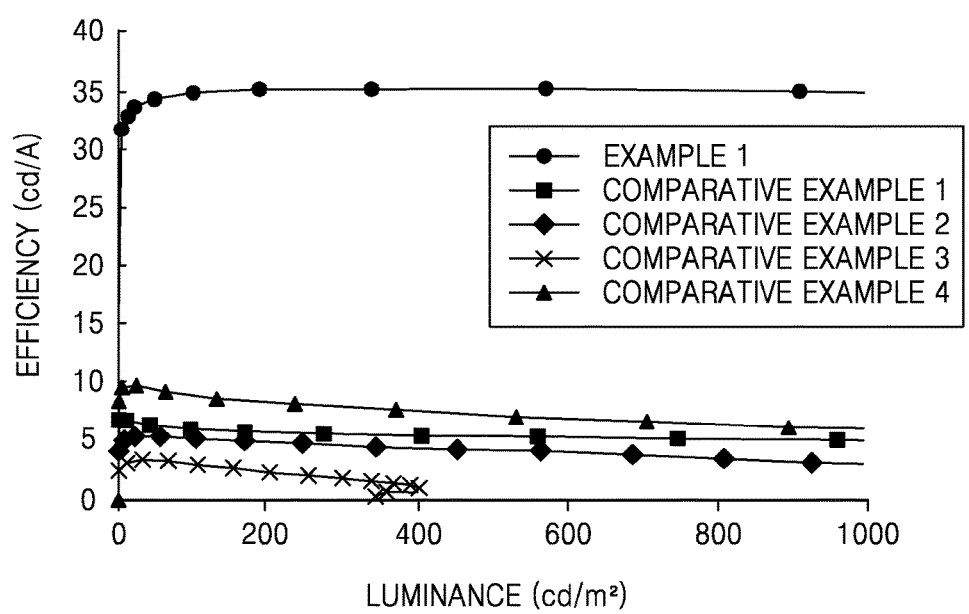
FIG. 2 is a graph of efficiency (candelas per ampere (cd/A) versus luminance (candelas per square meter), which is luminance-efficiency graph of organic light-emitting devices manufactured according to Example 1 and Comparative Examples 1 to 4.
Figure 3:
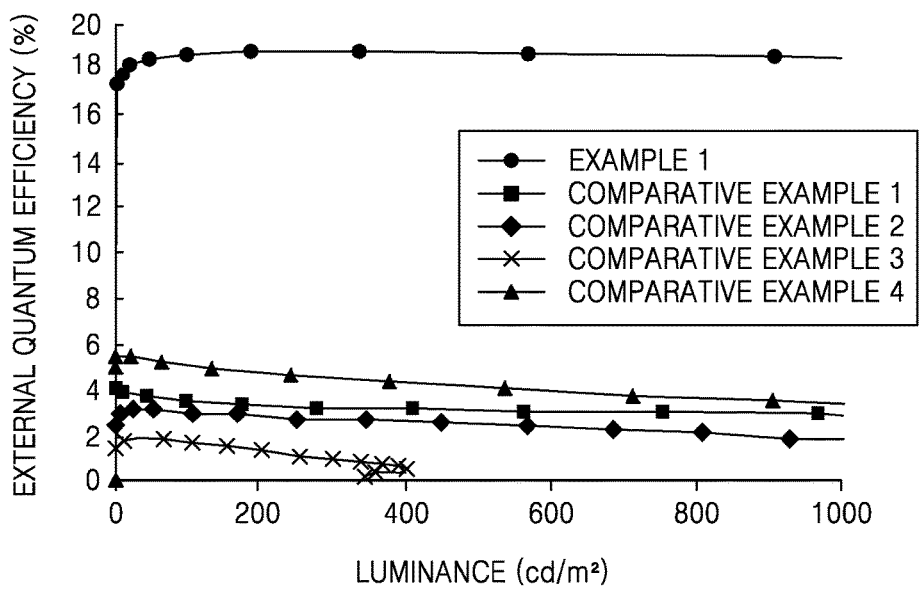
FIG. 3 is a graph of external quantum efficiency (percent, %) versus luminance (candelas per square meter), which is a luminance-external quantum efficiency graph of the organic light-emitting devices manufactured according to Example 1 and Comparative Examples 1 to 4.
Figure 4:
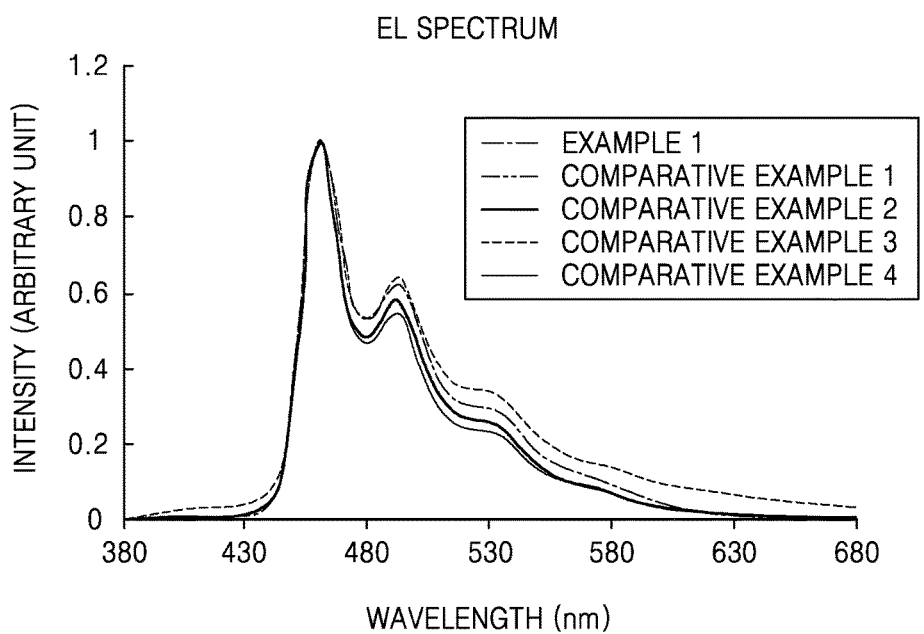
FIG. 4 is a graph of intensity (arbitrary unit) versus wavelength (nanometer, nm) showing electroluminescent (EL) spectra of the organic light-emitting devices manufactured according to Example 1 and Comparative Examples 1 to 4.

Evaluation Example 4: Evaluation on Characteristics of Organic Light-Emitting Devices The driving voltage, current density, efficiency, power efficiency, quantum efficiency, and lifespan of the organic light-emitting devices of Example 1 and Comparative Examples 1 to 4 were measured by using a current-voltage meter (Keithley 2400) and a luminance meter (Minolta Cs-1000A). The results thereof are shown in Table 4. FIG. 2 is a luminance-efficiency graph of organic light-emitting devices manufactured according to Example 1 and Comparative Examples 1 to 4. FIG. 3 is a luminance-external quantum efficiency graph of the organic light-emitting devices. FIG. 4 shows electroluminescent (EL) spectra of the organic light-emitting devices.

TABLE 4

| Host | Driving voltage (relative value) | Current efficiency (relative value) | Quantum efficiency (relative value) | Emission color |
|---|---|---|---|---|
| Example 1 | Compound 5 | 109 | 637 | 587 | blue |
| Comparative Example 1 | Compound A | 100 | 100 | 100 | blue |
| Comparative Example 2 | Compound B | 112 | 79 | 81 | blue |
| Comparative Example 3 | Compound C | 96 | 58 | 56 | blue |
| Comparative Example 4 | Compound D | 114 | 134 | 100 | blue |

From Table 4 and FIGS. 2 to 4 it is seen that the organic light-emitting device according to Example 1 has lower driving voltage and higher efficiency than the organic light-emitting devices of Comparative Examples 1 to 4.

The condensed cyclic based compounds according to embodiments have excellent electric characteristics and thermal stability. Accordingly, an organic light-emitting device including the condensed cyclic based compounds may have a low driving voltage, high efficiency, high power, high quantum efficiency, and a long lifespan.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A condensed cyclic compound represented by Formula 1:

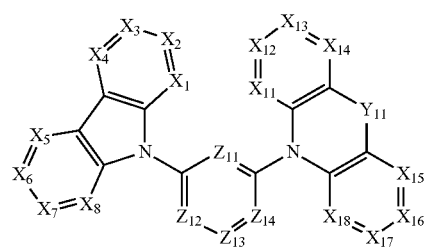

Formula 1 wherein, in Formula 1, $X_1$ is N or $C(R_1)$, $X_2$ is N or $C(R_2)$, $X_3$ is N or $C(R_3)$, $X_4$ is N or $C(R_4)$, $X_5$ is N or $C(R_5)$, $X_6$ is N or $C(R_6)$, $X_7$ is N or $C(R_7)$, $X_8$ is N or $C(R_8)$, $X_{11}$ is N or $C(R_{11})$, $X_{12}$ is N or $C(R_{12})$, $X_{13}$ is N or $C(R_{13})$, $X_{14}$ is N or $C(R_{14})$, $X_{15}$ is N or $C(R_{15})$, $X_{16}$ is N or $C(R_{16})$, $X_{17}$ is N or $C(R_{17})$, and $X_{18}$ is N or $C(R_{18})$;

$Y_{11}$ is O, S, $C(R_{101})(R_{102})$, or $Si(R_{101})(R_{102})$;

$Z_{11}$ to $Z_{14}$ are each independently selected from N, $C(A_{11})$, and $C(A_{12})$;

at least one of $Z_{11}$ to $Z_{14}$ is $C(A_{11})$;

$A_{11}$ comprises at least one cyano group (CN); and is a cyano group (CN) or a group represented by one of Formulae 2-1 to 2-10;

$A_{12}$ is hydrogen, deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group and —Si($Q_{21}$)($Q_{22}$)($Q_{23}$); and —Si($Q_{31}$)($Q_{32}$)($Q_{33}$);

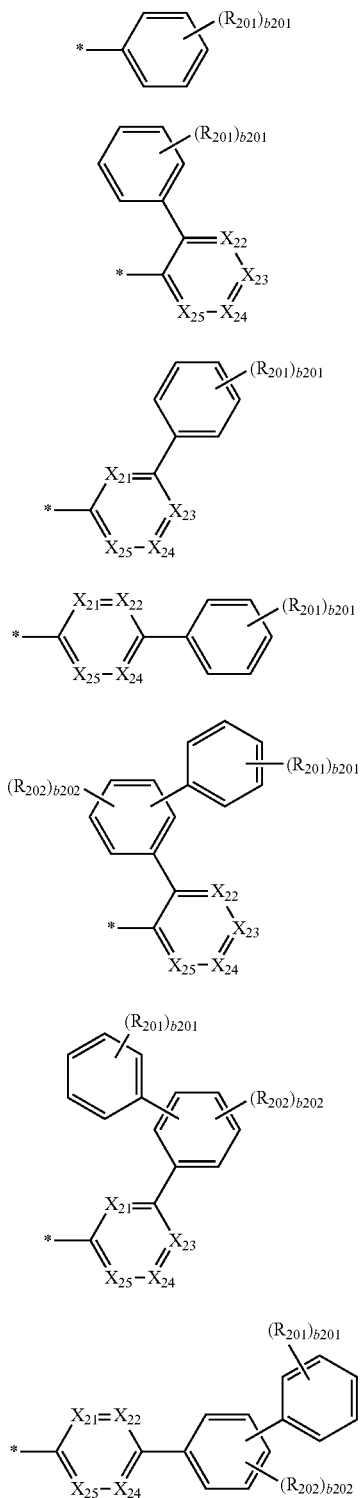

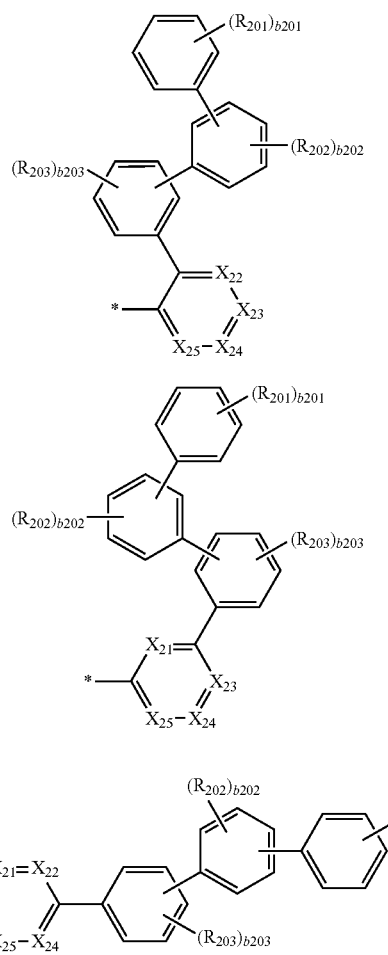

wherein, in Formulae 2-1 to 2-10, $X_{21}$ is N or C($R_{21}$), $X_{22}$ is N or C($R_{22}$), $X_{23}$ is N or C($R_{23}$), $X_{24}$ is N or C($R_{24}$), $X_{25}$ is N or C($R_{25}$), $R_1$ to $R_8$, $R_{11}$ to $R_{18}$, $R_{101}$, $R_{102}$, $R_{21}$ to $R_{25}$, and $R_{201}$ to $R_{203}$ are each independently selected from hydrogen, deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a pyridinyl group, a fluorenyl group, a dibenzofuranyl group, and a dibenzothiophenyl group;

a phenyl group, a pyridinyl group, a fluorenyl group, a dibenzofuranyl group, and a dibenzothiophenyl group, each substituted with at least one selected from a deuterium, —F, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pyridinyl group, a fluorenyl group, a dibenzofuranyl group, a dibenzothiophenyl group, and —Si($Q_1$)($Q_2$)($Q_3$); and —Si($Q_{11}$)($Q_{12}$)($Q_{13}$), $R_{101}$ and $R_{102}$ are optionally linked to each other to form a saturated ring or an unsaturated ring;

b201 is selected from 1, 2, 3, 4, and 5;

b202 and b203 are each independently selected from 1, 2, 3, and 4; and

* indicates a carbon atom in Formula 1, wherein $Q_1$ to $Q_3$, $Q_{11}$ to $Q_{13}$, $Q_{21}$ to $Q_{23}$ and $Q_{31}$ to $Q_{33}$ are each independently selected from hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

2. The condensed cyclic compound of claim 1, wherein $X_1$ is N, $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$);

$X_1$ is C($R_1$), $X_2$ is N, $X_3$ is C($R_3$), $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$);

$X_1$ is C($R_1$), $X_2$ is C($R_2$), $X_3$ is N, $X_4$ is C($R_4$), $X_5$ is C($R_5$), $X_6$ is C($R_5$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$);

$X_1$ is C($R_1$), $X_2$ is C($R_2$), $X_3$ is C($R_3$), $X_4$ is N, $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is O($R_{15}$);

$X_1$ is C($R_1$), $X_2$ is C($R_2$), $X_3$ is C($R_3$), $X_4$ is C($R_4$), $X_5$ is N, $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$);

$X_1$ is C($R_1$), $X_2$ is C($R_2$), $X_3$ is C($R_3$), $X_4$ is C($R_4$), $X_5$ is C($R_5$), $X_6$ is N, $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$);

$X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is N, $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$);

$X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is N, $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$); or $X_1$ is C($R_1$), $X_2$ is C($R_2$), $X_3$ is C($R_3$), $X_4$ is C($R_4$), $X_5$ is C($R_5$), $X_6$ is C($R_6$), $X_7$ is C($R_7$), $X_8$ is C($R_8$), $X_{11}$ is C($R_{11}$), $X_{12}$ is C($R_{12}$), $X_{13}$ is C($R_{13}$), $X_{14}$ is C($R_{14}$), $X_{15}$ is C($R_{15}$), $X_{16}$ is C($R_{16}$), $X_{17}$ is C($R_{17}$), and $X_{18}$ is C($R_{18}$).

3. The condensed cyclic compound of claim 1, wherein $A_{11}$ is a cyano group (CN) or a group represented by one of Formulae 2-1 to 2-7.

4. The condensed cyclic compound of claim 1, wherein $A_{11}$ is a cyano group (CN) or a group represented by one of Formulae 3-1 to 3-110:

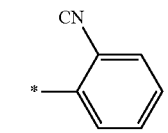
3-1

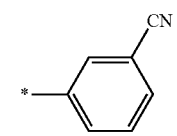
3-2

3-3

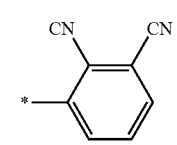
3-4

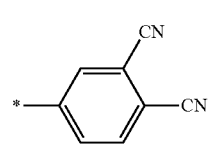
3-5

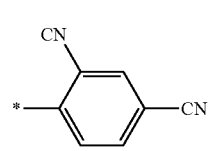
3-6

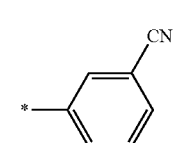
3-7

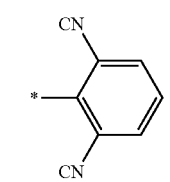
3-8

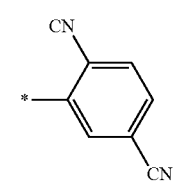
3-9

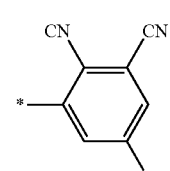
3-10

3-11 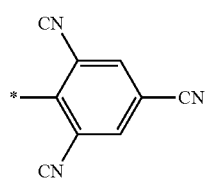
3-12 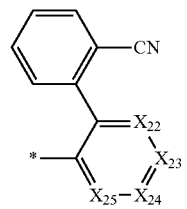
3-13 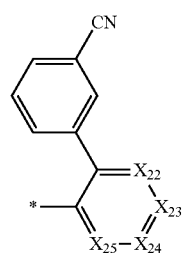
3-14 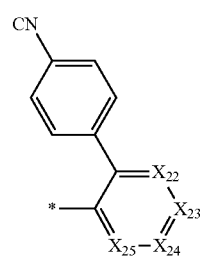
3-15 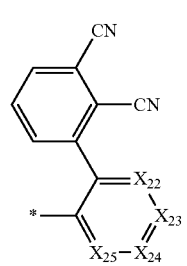
3-16 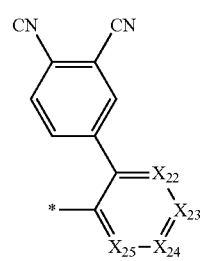
3-17 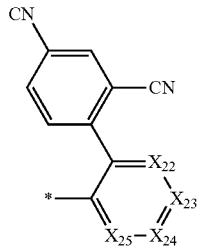
3-18 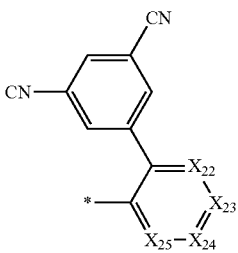
3-19 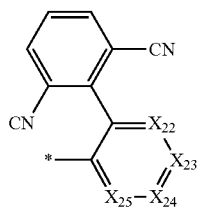
3-20 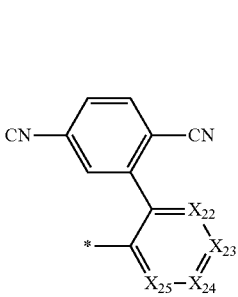
3-21 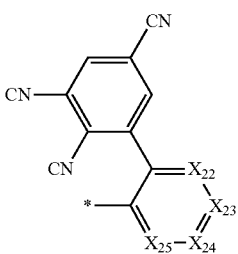
3-22 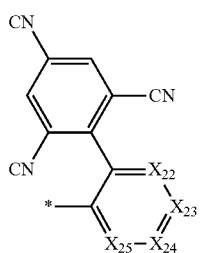

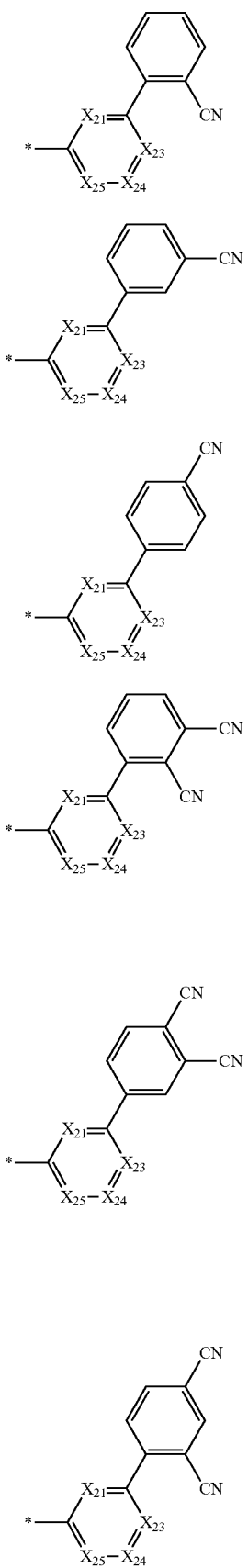
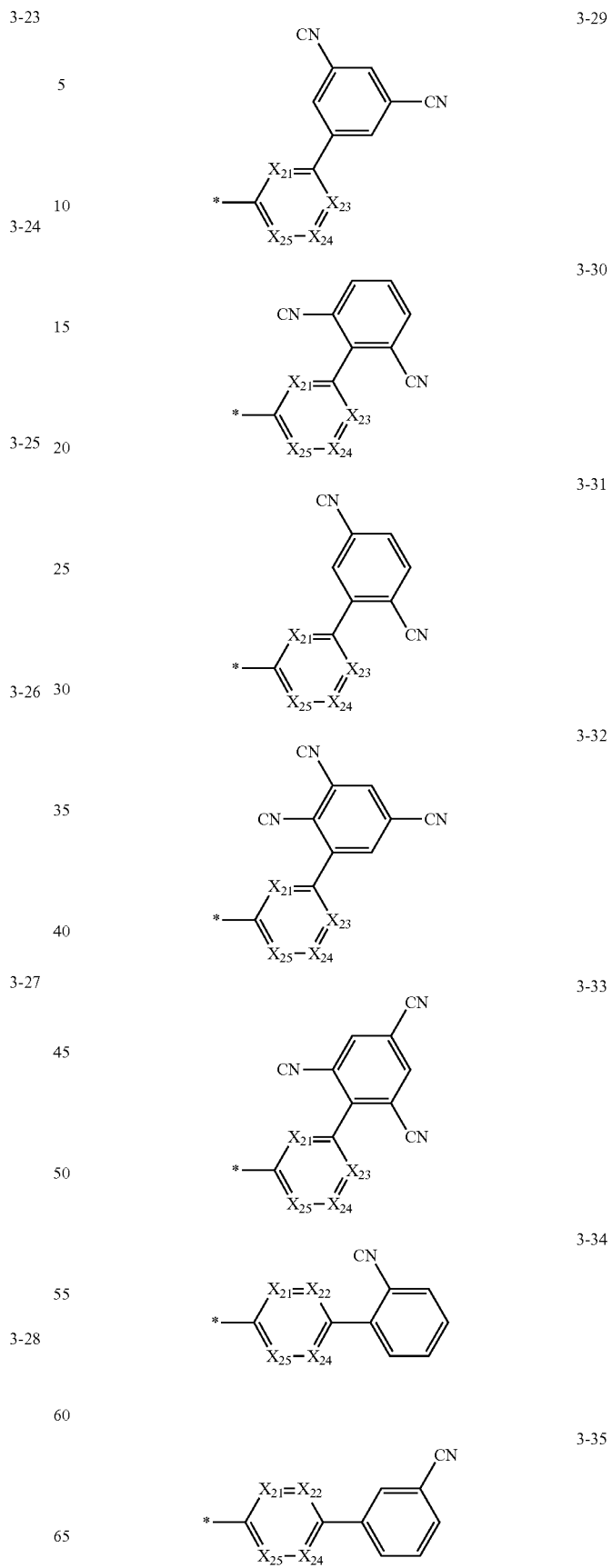

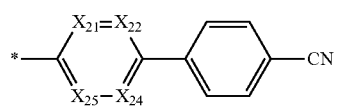 3-36
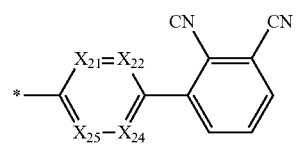 3-37
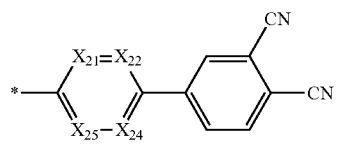 3-38
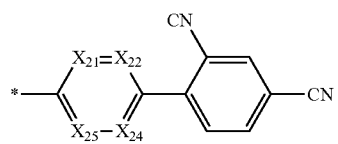 3-39
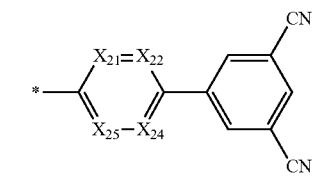 3-40
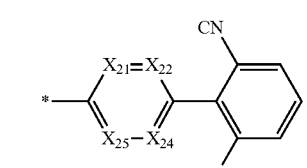 3-41
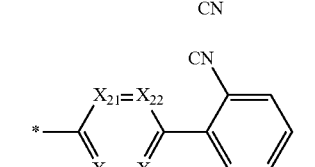 3-42
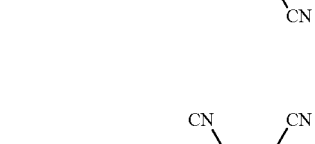 3-43
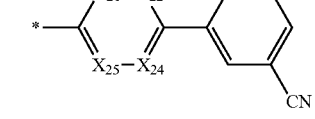 3-44
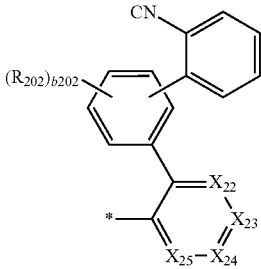 3-45
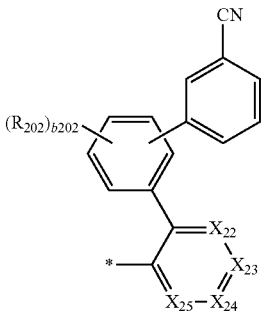 3-46
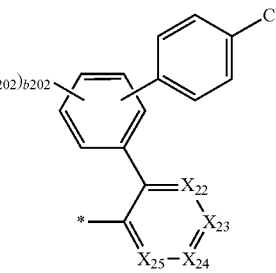 3-47
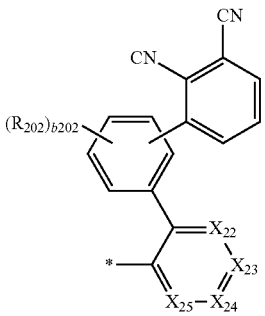 3-48
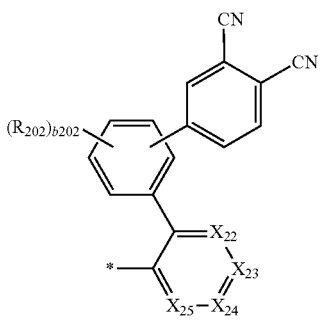 3-49

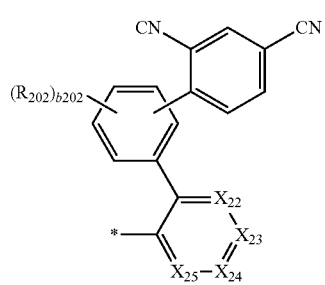 3-50
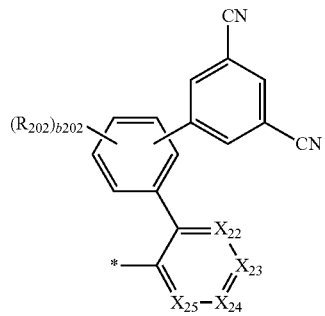 3-51
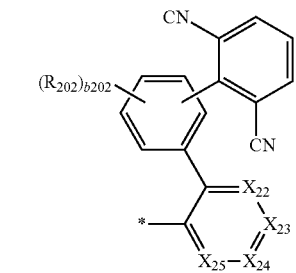 3-52
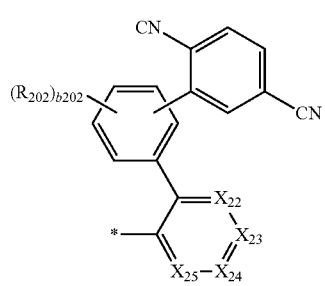 3-53
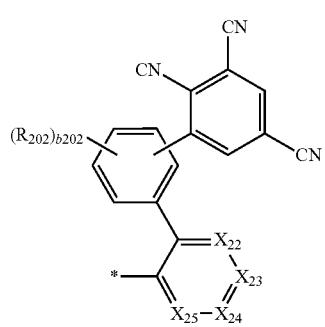 3-54
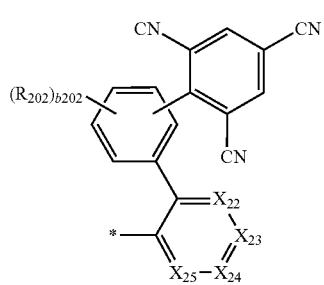 3-55
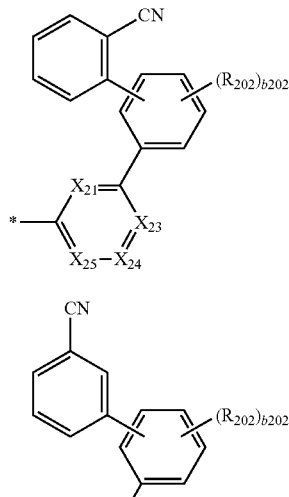 3-56
3-57
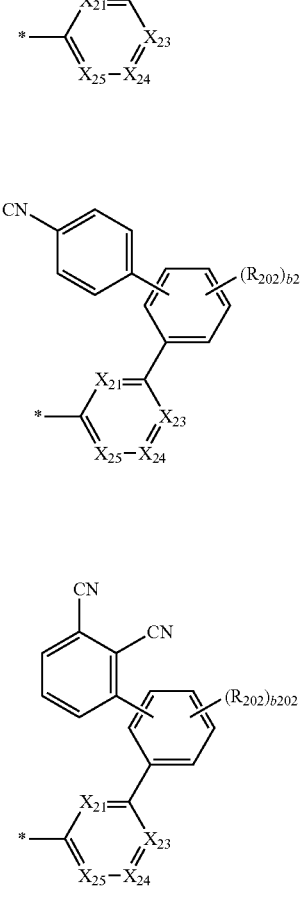 3-58
3-59

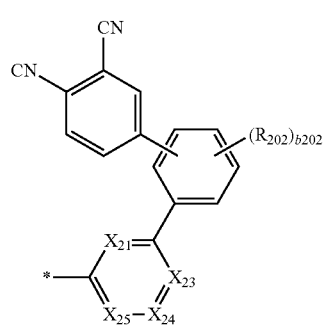 3-60
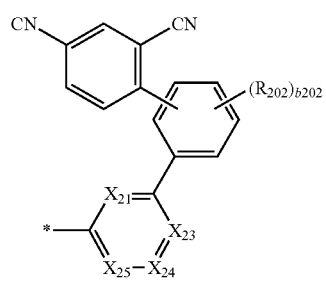 3-61
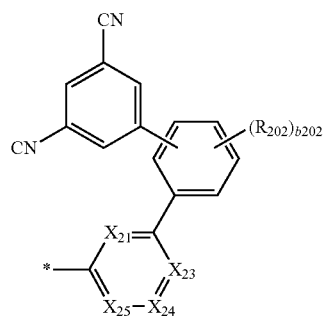 3-62
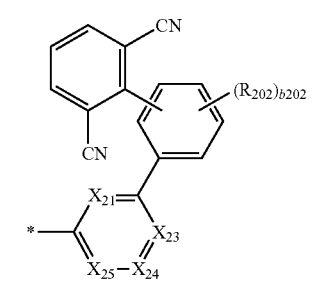 3-63
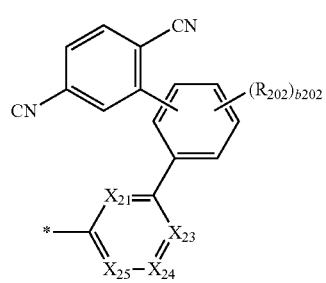 3-64
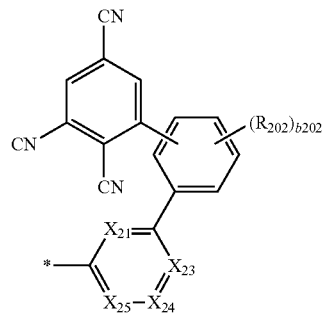 3-65
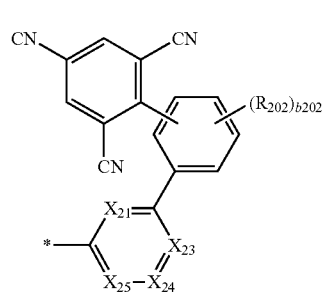 3-66
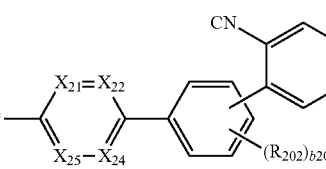 3-67
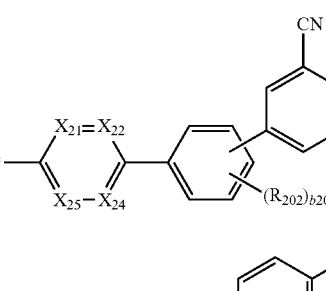 3-68
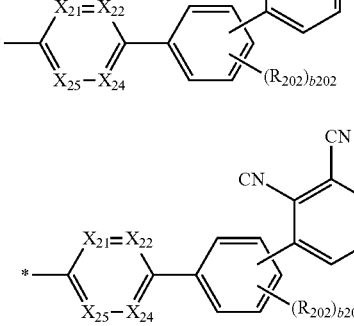 3-69
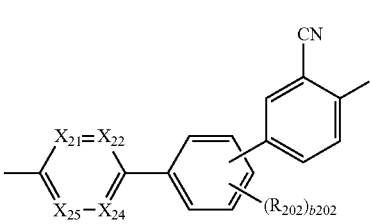 3-70
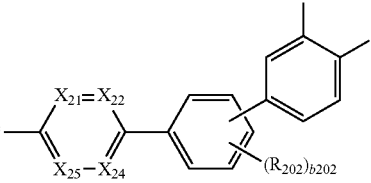 3-71

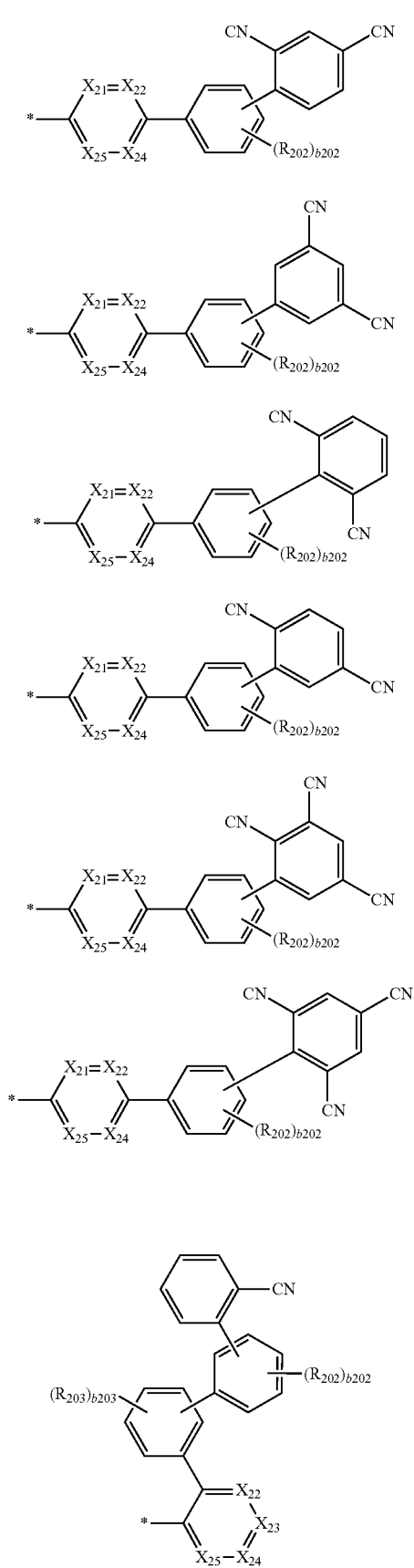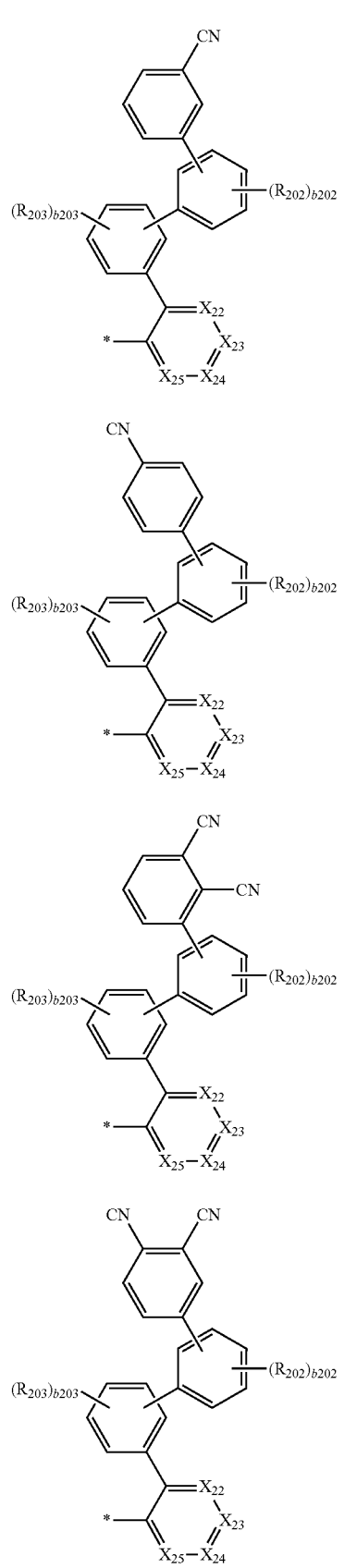

-continued
3-83
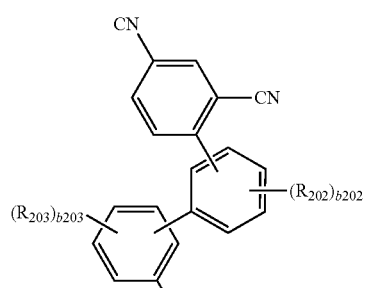
3-84
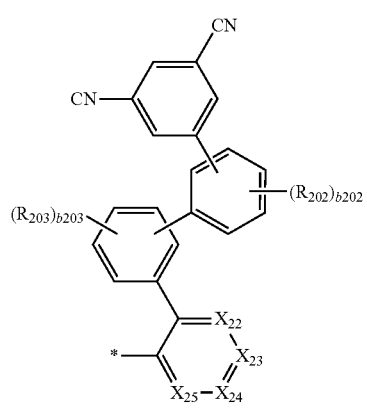
3-85
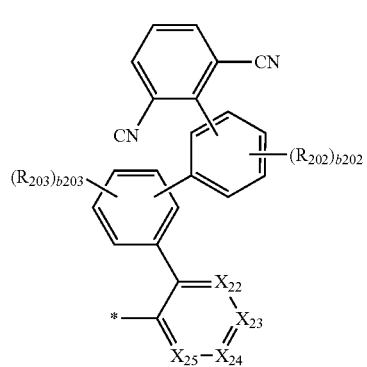
3-86
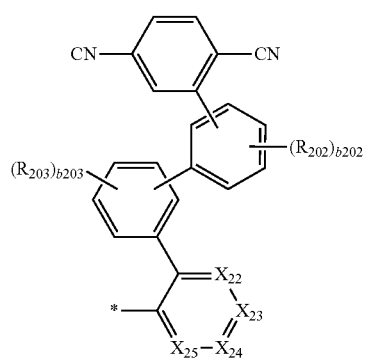
3-87
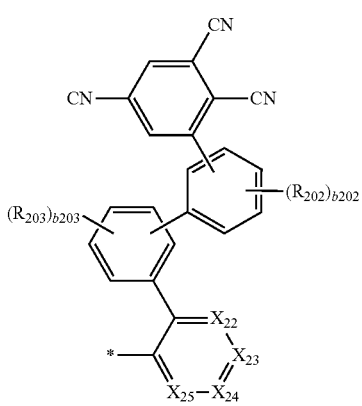
3-88
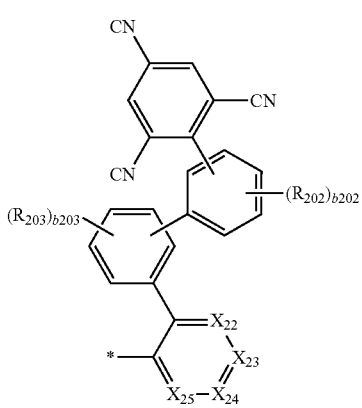
3-89
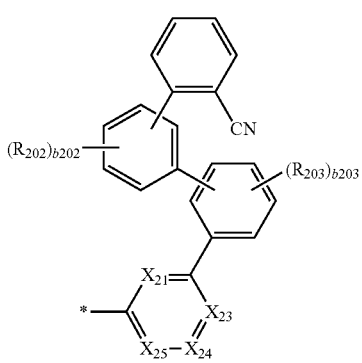
3-90
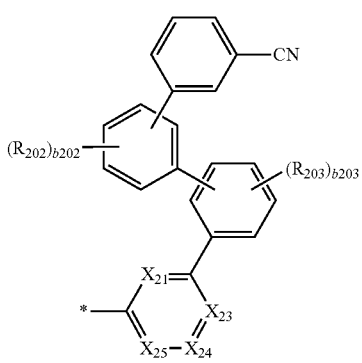

3-91 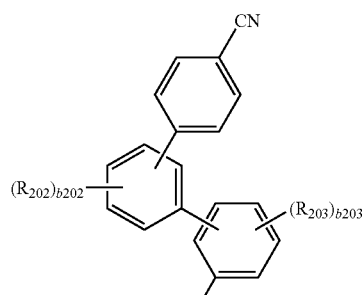
3-92 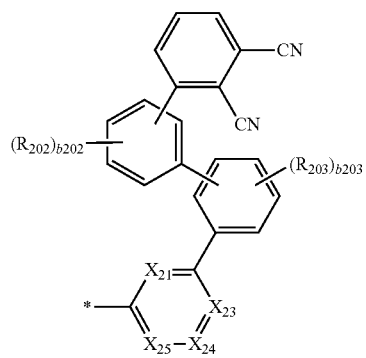
3-93 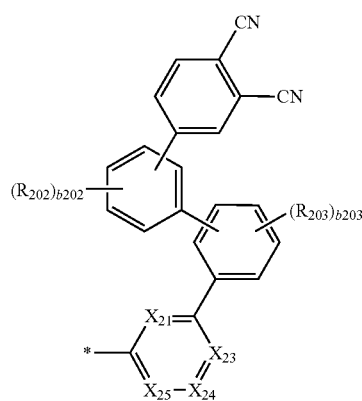
3-94 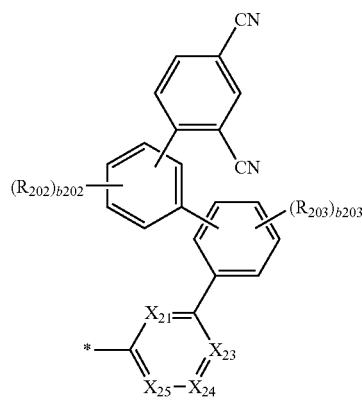
3-95 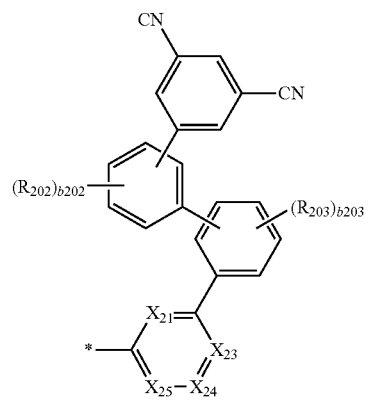
3-96 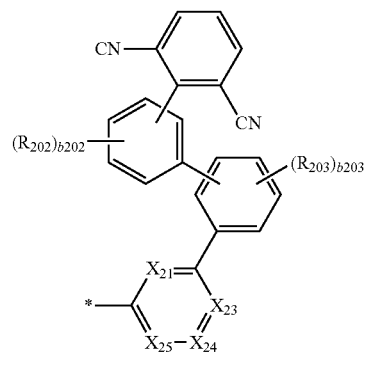
3-97 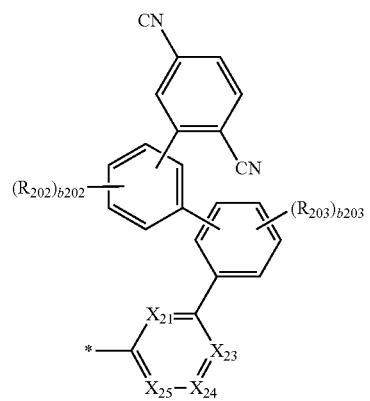
3-98 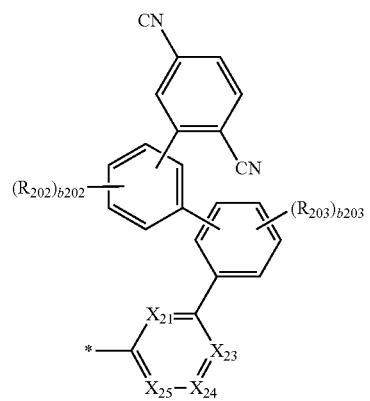

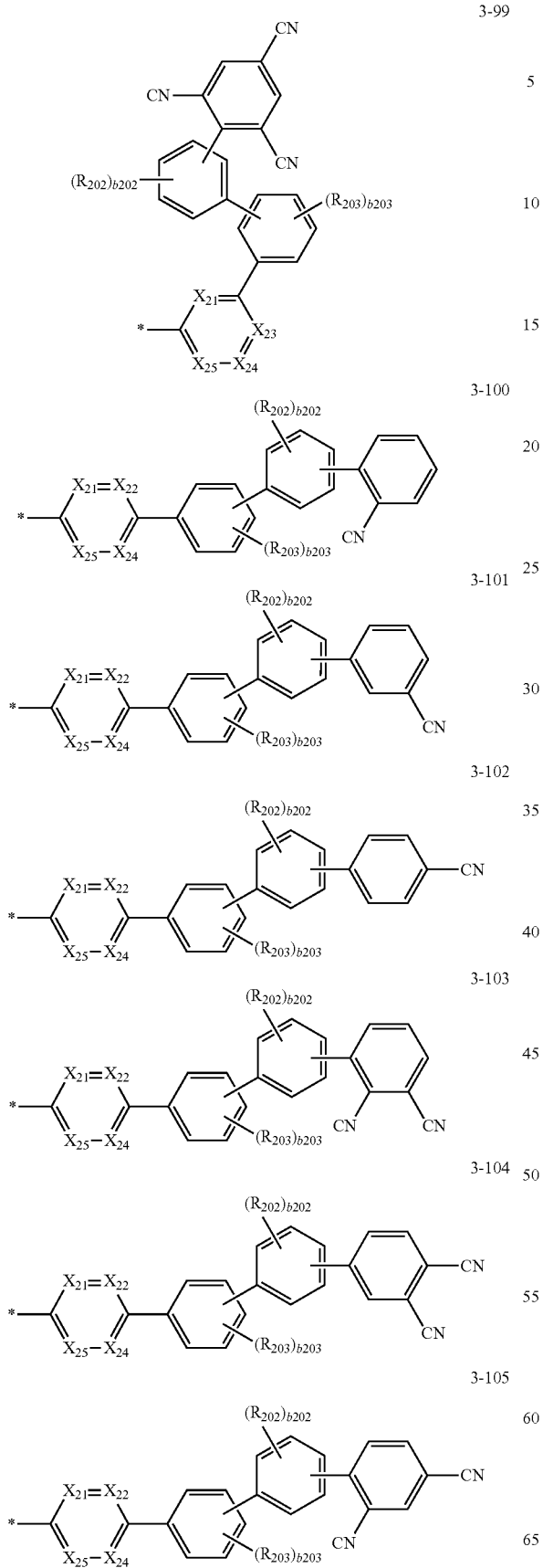
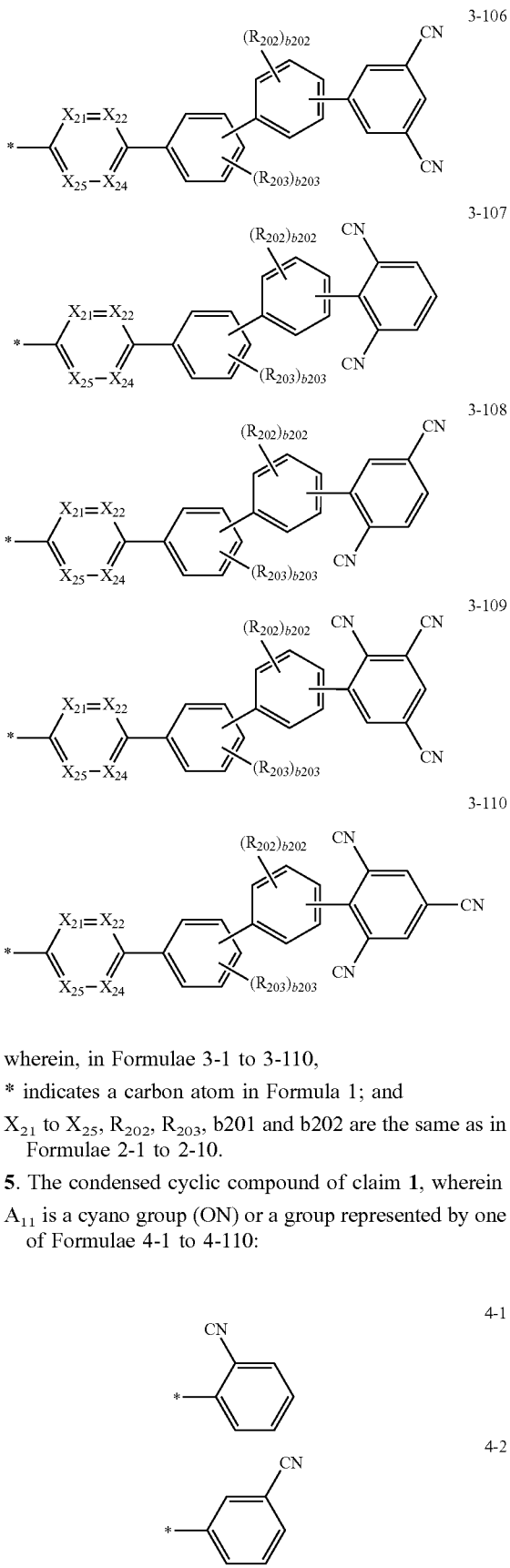
wherein, in Formulae 3-1 to 3-110,
* indicates a carbon atom in Formula 1; and
$X_{21}$ to $X_{25}$, $R_{202}$, $R_{203}$, b201 and b202 are the same as in Formulae 2-1 to 2-10.
5. The condensed cyclic compound of claim 1, wherein $A_{11}$ is a cyano group (ON) or a group represented by one of Formulae 4-1 to 4-110:

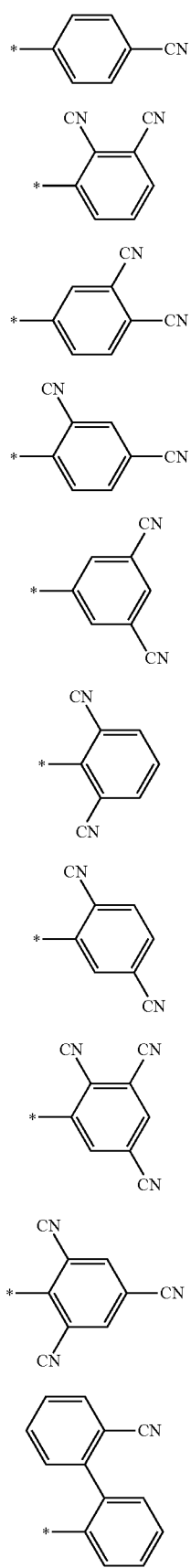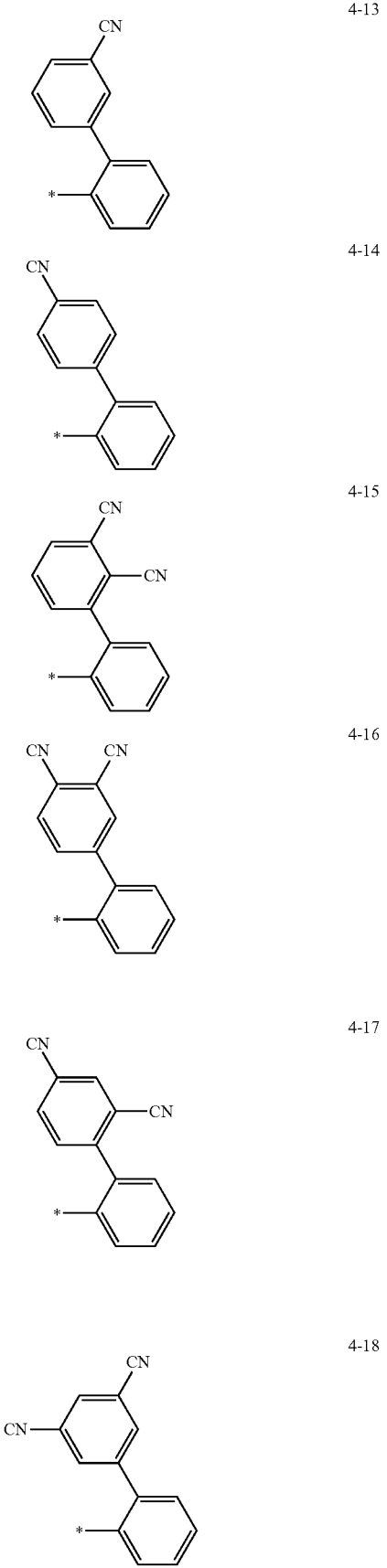

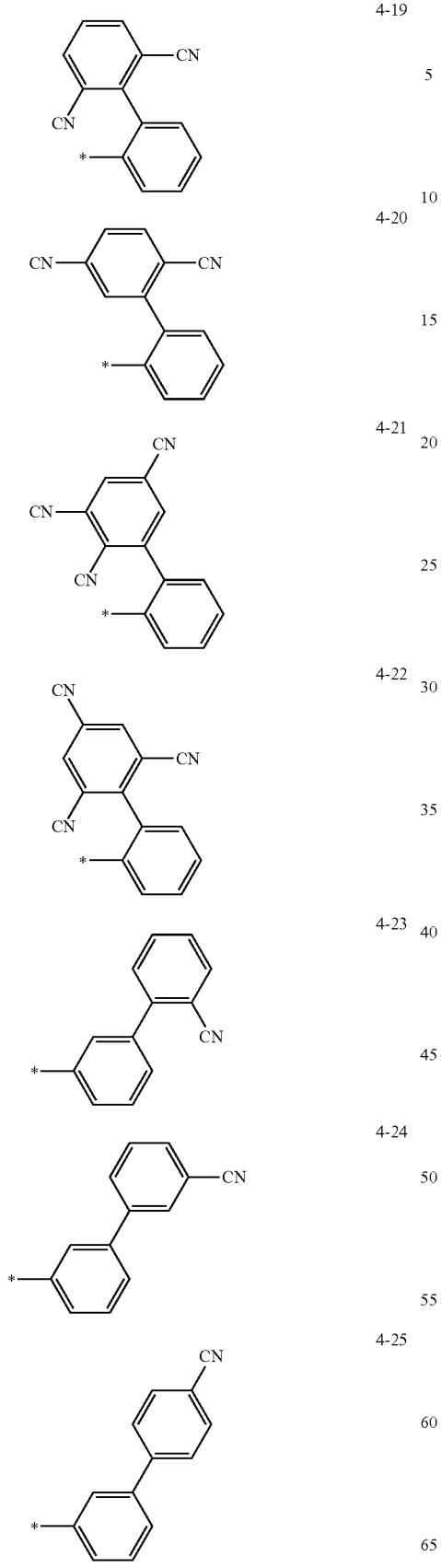
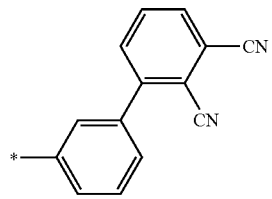
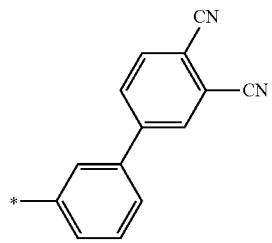
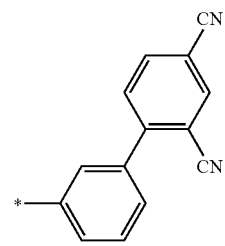
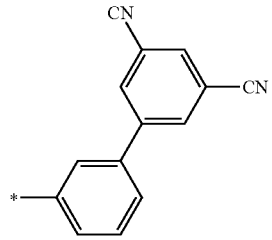
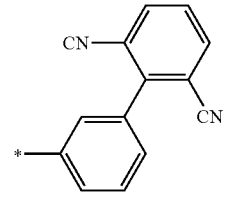
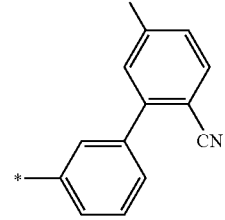
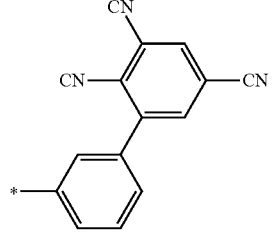

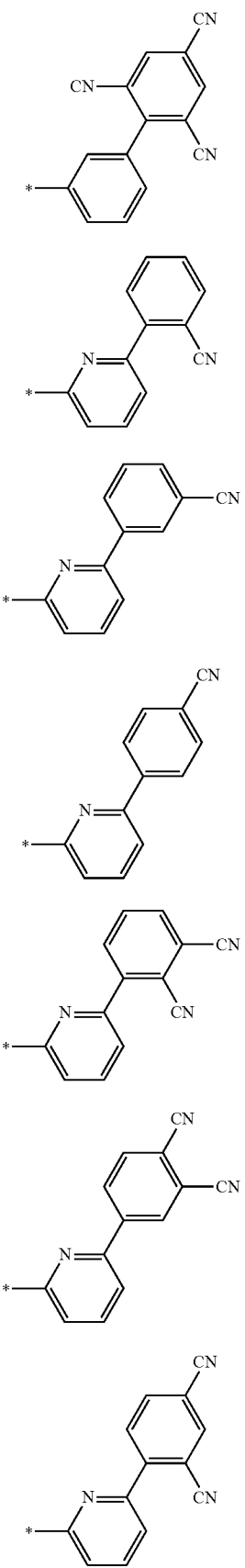
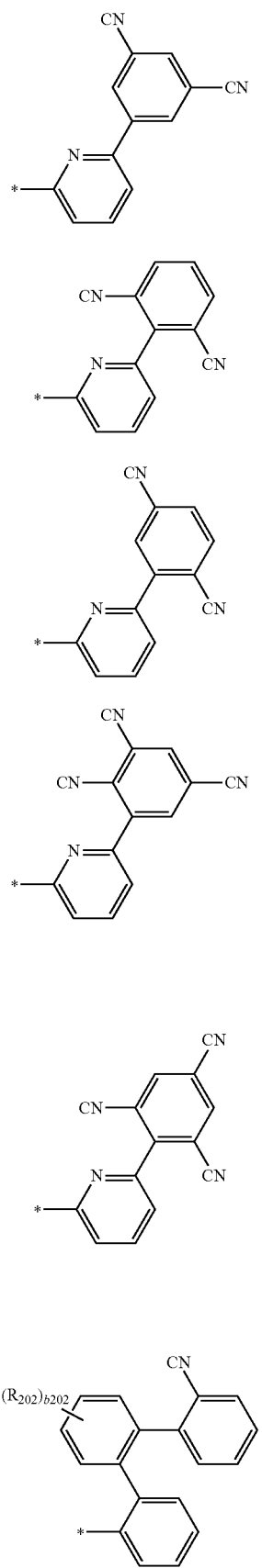

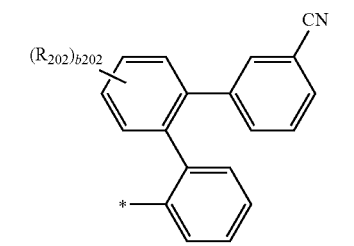
4-46
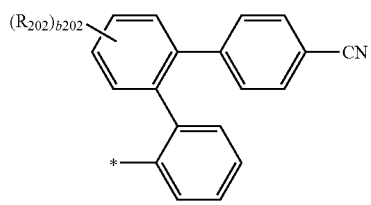
4-47
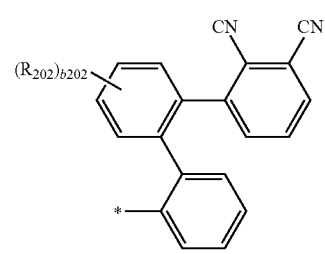
4-48
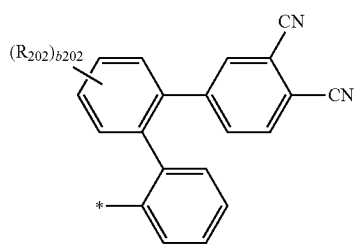
4-49
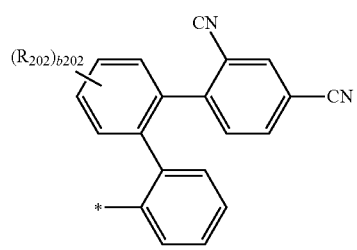
4-50
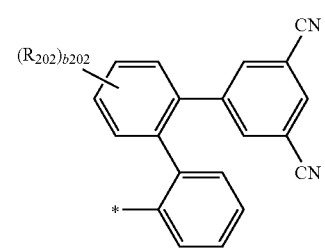
4-51
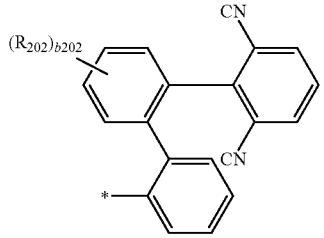
4-52
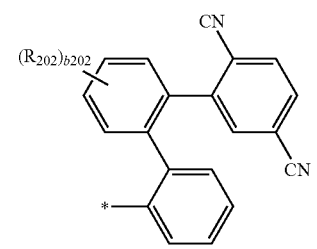
4-53
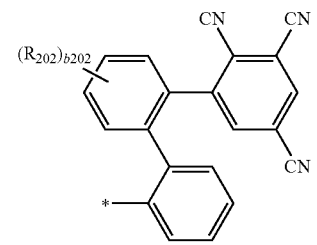
4-54
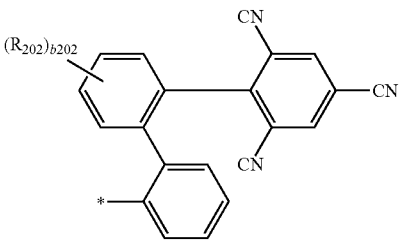
4-55
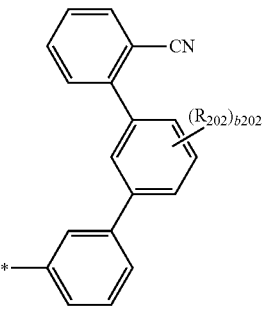
4-56
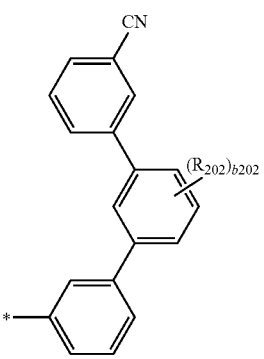
4-57

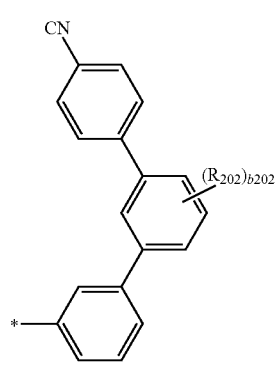 4-58
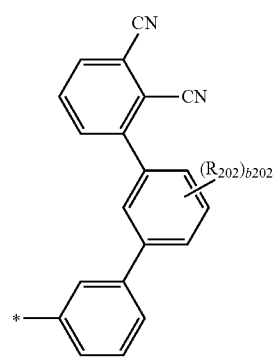 4-59
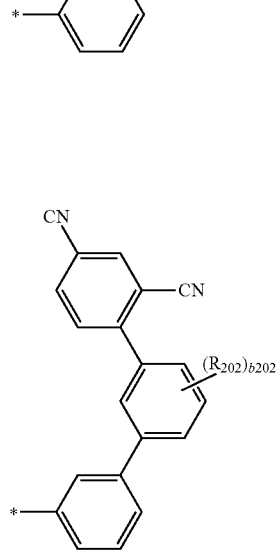 4-60
4-61
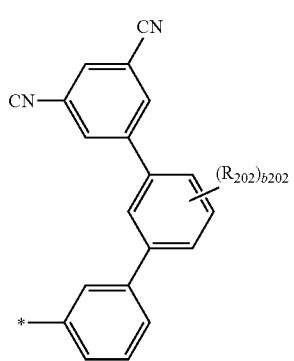 4-62
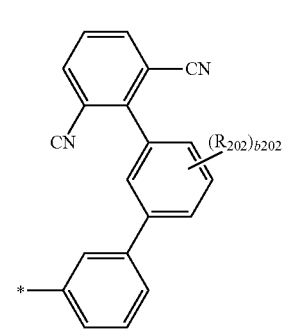 4-63
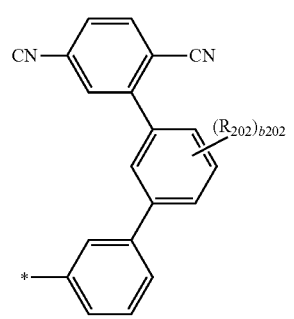 4-64
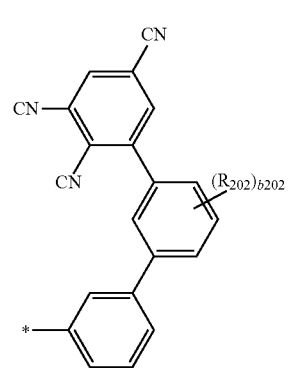 4-65

-continued
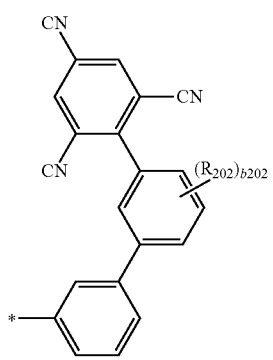
4-66
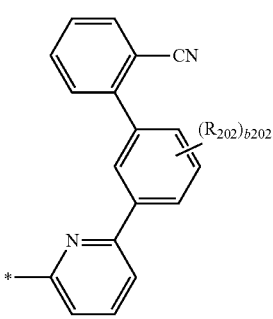
4-67
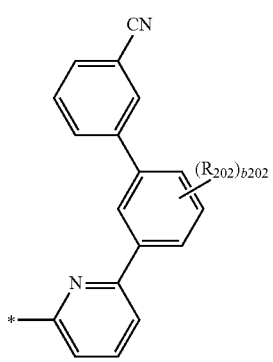
4-68
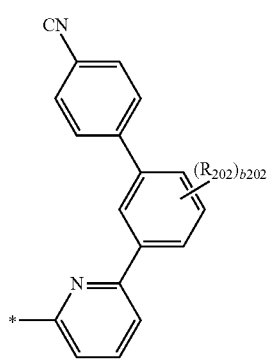
4-69
-continued
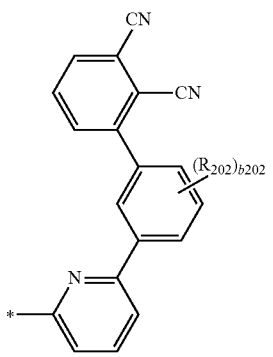
4-70
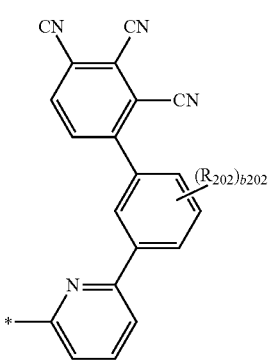
4-71
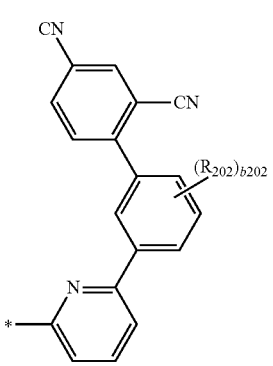
4-72
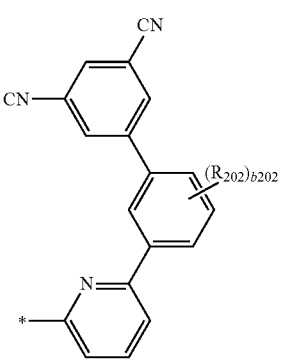
4-73

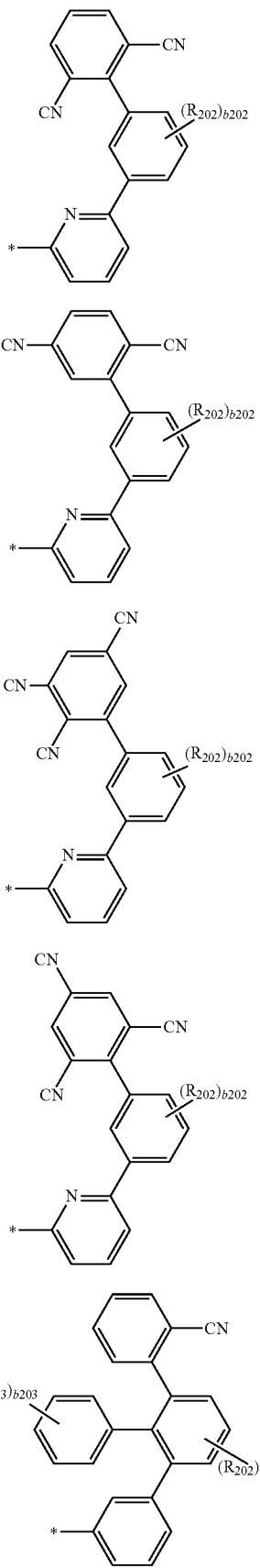
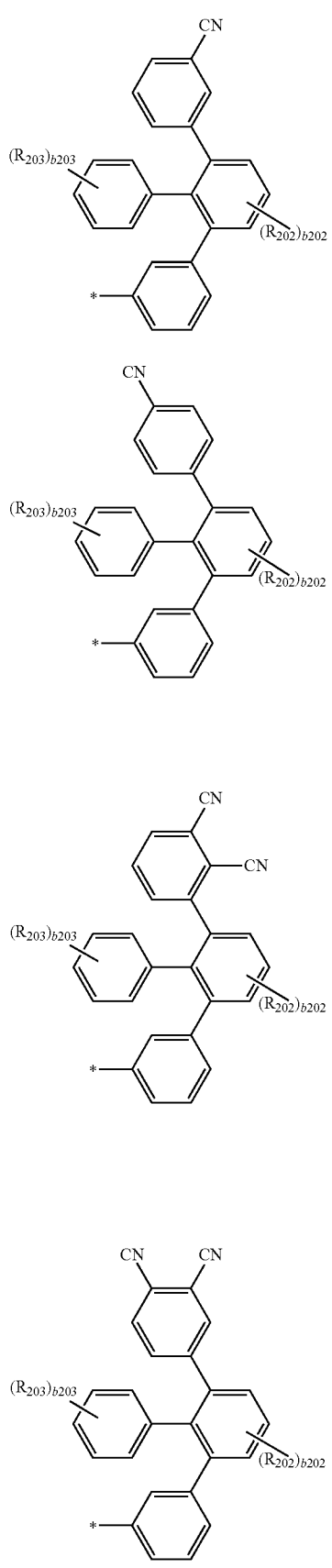

-continued
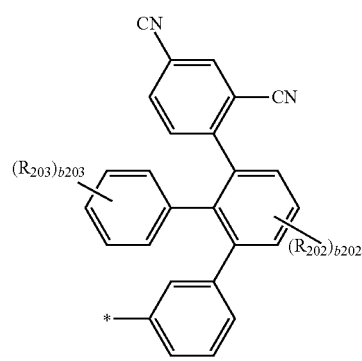
4-83
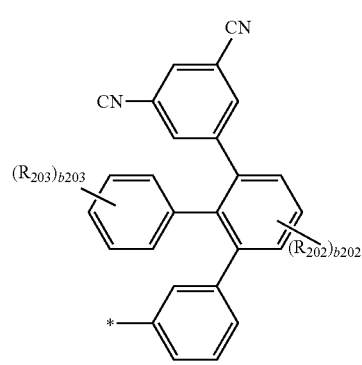
4-84
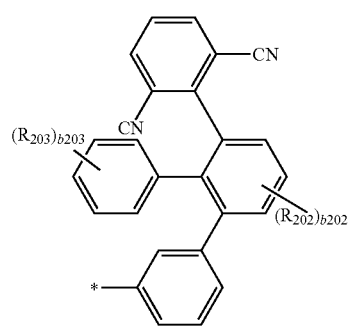
4-85
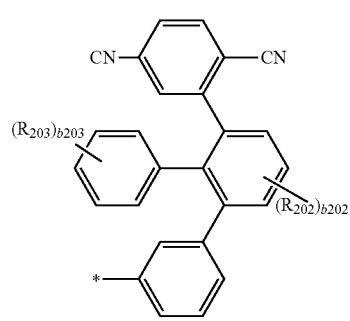
4-86
-continued
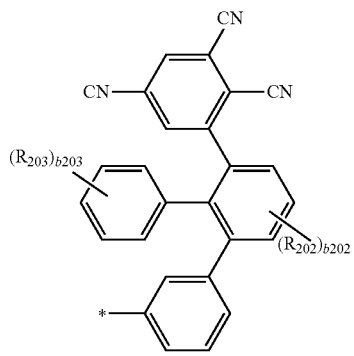
4-87
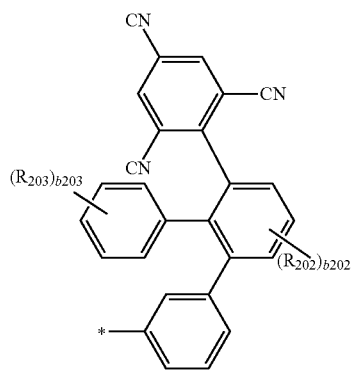
4-88
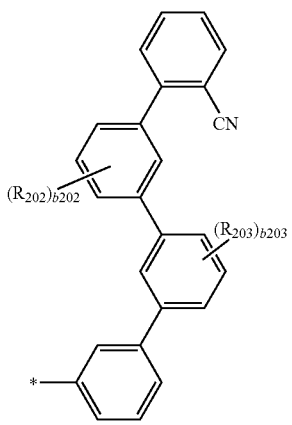
4-89
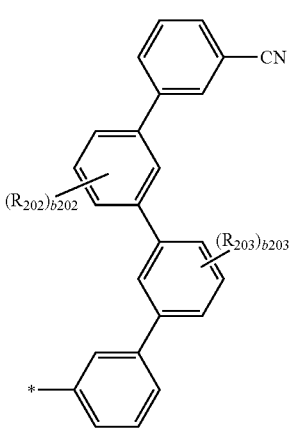
4-90

4-91
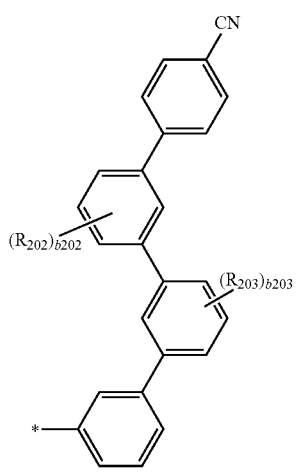
4-92
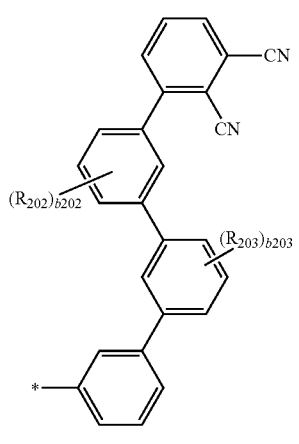
4-93
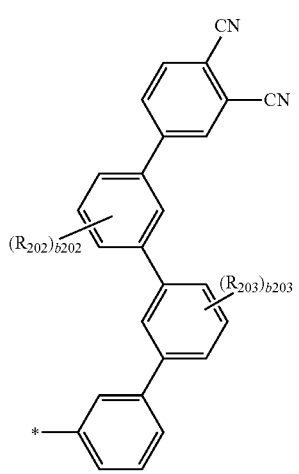
4-94
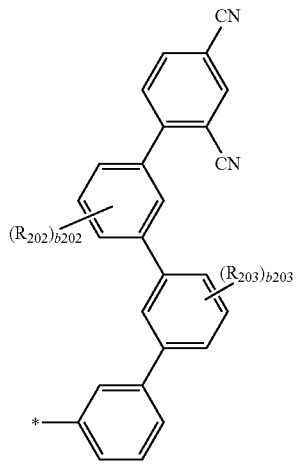
4-95
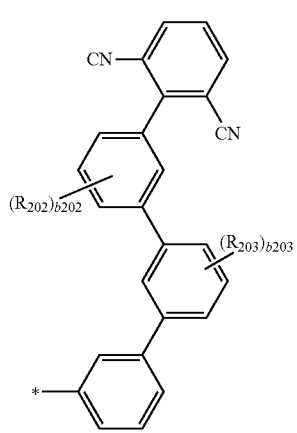
4-96

4-97
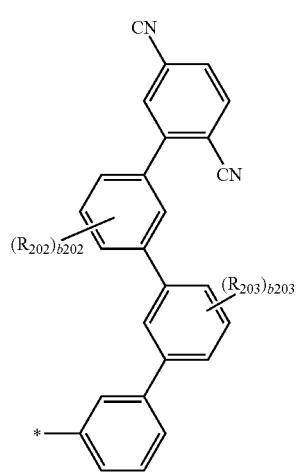
4-98
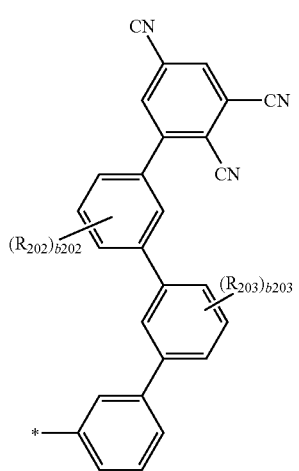
4-99
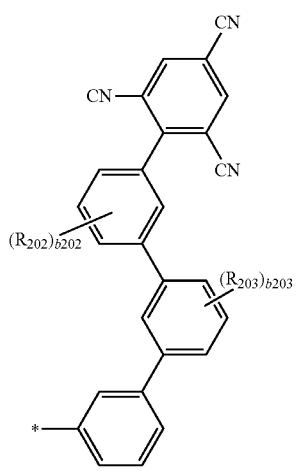
4-100
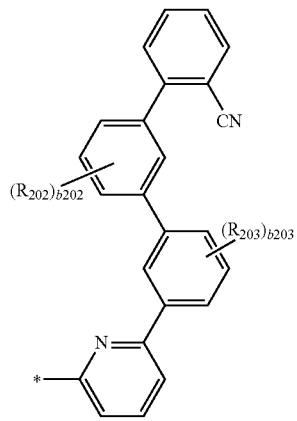
4-101
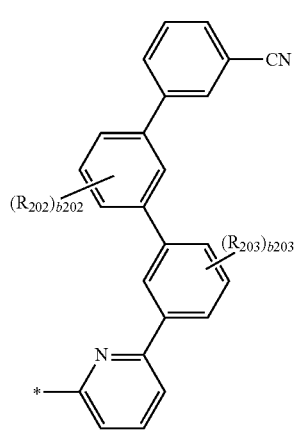
4-102
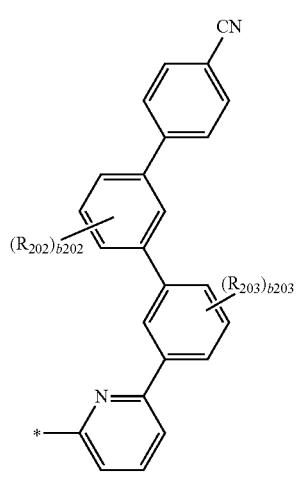

4-103
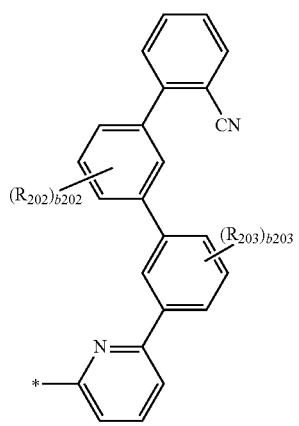
4-104
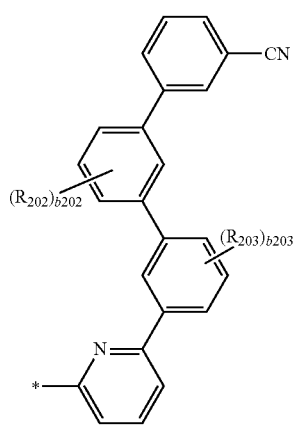
4-105
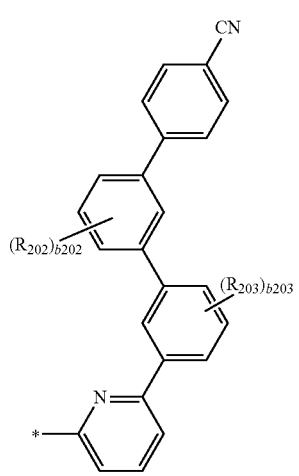
4-106
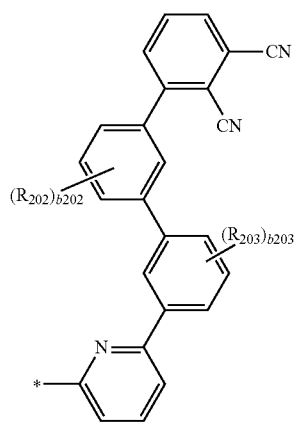
4-107
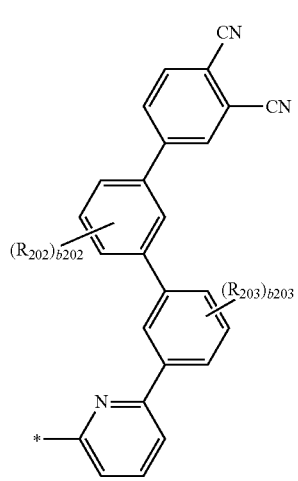
4-108
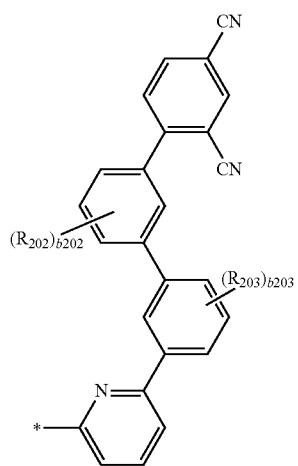

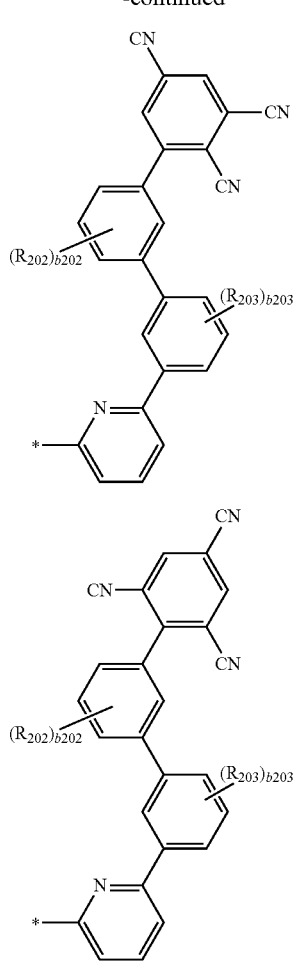

4-109

4-110 wherein, in Formulae 4-1 to 4-110;
* indicates a carbon atom in Formula 1; and
$R_{202}$, $R_{203}$, b201 and b202 are the same as in Formulae 2-1 to 2-10.

6. The condensed cyclic compound of claim 1, wherein $A_{12}$ is hydrogen, deuterium, —F, a hydroxyl group, a cyano group (CN), a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;
a phenyl group, a pyridinyl group, a fluorenyl group, a dibenzofuranyl group, and a dibenzothiophenyl group; and
—Si($Q_{31}$)($Q_{32}$)($Q_{33}$),
wherein $Q_{31}$ to $Q_{33}$ are each independently selected from a $C_1$-$C_{10}$ alkyl group, a $C_1$-$C_{10}$ alkoxy group, a phenyl group, a naphthyl group, and a pyridinyl group.

7. The condensed cyclic compound of claim 1, wherein $R_1$ to $R_8$, $R_{11}$ to $R_{18}$, $R_{101}$, $R_{102}$, $R_{21}$ to $R_{25}$, and $R_{201}$ to $R_{203}$ are each independently selected from
hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group;
a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decyl group, an isodecyl group, a sec-decyl group, a tert-decyl group, a methoxy group, an ethoxy group, a propoxy group, a butoxy group, a pentoxy group, a phenyl group, a pyridinyl group, a fluorenyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; and —Si($Q_{11}$)($Q_{12}$)($Q_{13}$), wherein $Q_{11}$ to $Q_{13}$ are each independently selected from hydrogen, a $C_1$-$C_{20}$ alkyl group, a $C_1$-$C_{20}$ alkoxy group, a phenyl group, a naphthyl group, a pyridinyl group, a fluorenyl group, a dibenzofuranyl group, and a dibenzothiophenyl group.

8. The condensed cyclic compound of claim 1, wherein $R_1$ to $R_8$, $R_{11}$ to $R_{18}$, $R_{21}$ to $R_{25}$, and $R_{201}$ to $R_{203}$ are each independently selected from hydrogen, deuterium, a cyano group, a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, and —Si($Q_{11}$)($Q_{12}$)($Q_{13}$), wherein $Q_{11}$ to $Q_{13}$ are each independently selected from hydrogen, a $C_1$-$C_{20}$ alkyl group, a $C_1$-$C_{20}$ alkoxy group, and a phenyl group.

9. The condensed cyclic compound of claim 1, wherein $R_{101}$ and $R_{102}$ are linked to each other to from a structure represented by Formula 8:

Formula 8

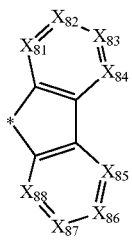

wherein, in Formula 8,
* indicates a carbon atom belonging to $Y_{11}$ in Formula 1,
$X_{81}$ is N or $C(R_{81})$, $X_{82}$ is N or $C(R_{82})$, $X_{83}$ is N or $C(R_{83})$, $X_{84}$ is N or $C(R_{84})$, $X_{85}$ is N or $C(R_{85})$, $X_{86}$ is N or $C(R_{86})$, $X_{87}$ is N or $C(R_{87})$, and $X_{88}$ is N or $C(R_{88})$, and $R_{81}$ to $R_{88}$ are each independently selected from hydrogen, deuterium, —F, —Cl, —Br, —I, hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si$(Q_{31})(Q_{32})(Q_{33})$,
wherein $Q_{31}$ to $Q_{33}$ are each independently hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

10. The condensed cyclic compound of claim 1, wherein at least one of $X_3$, $X_6$, $X_{13}$, and $X_{16}$ is C(CN).

11. The condensed cyclic compound of claim 1, wherein the condensed cyclic compound represented by Formula 1 is represented by one of Formulae 1-1 and 1-2:

1-1

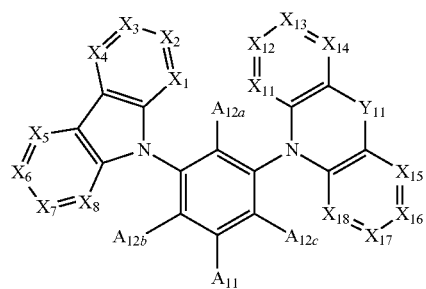

1-2

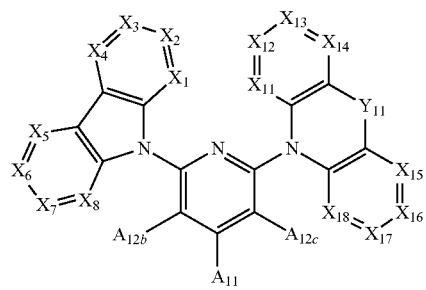

wherein, in Formulae 1-1 and 1-2,
descriptions of $X_1$ to $X_8$, $X_{11}$ to $X_{18}$, $Y_{11}$, and $A_{11}$ are the same as provided in connection with Formula 1; and descriptions of $A_{12a}$, $A_{12b}$, and $A_{12c}$ are the same as provided in connection with $A_{12}$ in Formula 1.

12. The condensed cyclic compound of claim 1, wherein the condensed cyclic compound represented by Formula 1 is represented by one of Formulae 1-3 to 1-6:

1-3

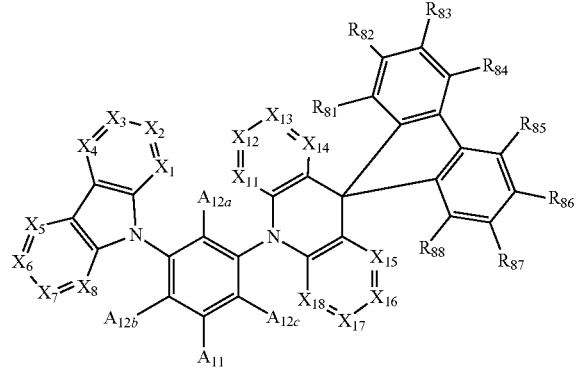

1-4

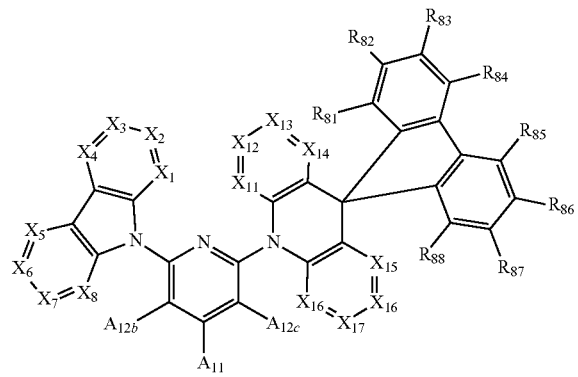

1-5

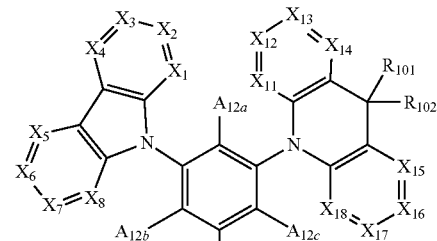

1-6

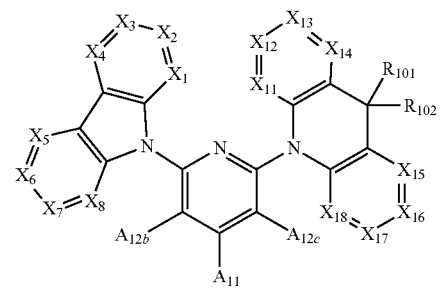

wherein, in Formulae 1-3 to 1-6,
descriptions of $X_1$ to $X_8$, $X_{11}$ to $X_{18}$, $Y_{11}$, $R_{101}$, $R_{102}$, and $A_{11}$ are the same as provided in connection with Formula 1;

$A_{12a}$, $A_{12b}$, and $A_{12c}$ are the same as provided in connection with $A_{12}$ in Formula 1; and $R_{81}$ to $R_{88}$ are each independently selected from hydrogen, deuterium, —F, —Cl, —Br, —I, hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$), wherein $Q_{31}$ to $Q_{33}$ are each independently hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

13. The condensed cyclic compound of claim 1, wherein the condensed cyclic compound represented by Formula 1 is represented by one of Formulae 1-11 to 1-25:

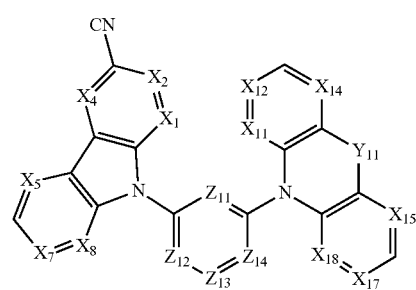

1-11

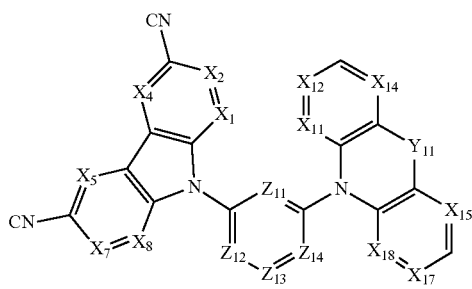

1-12

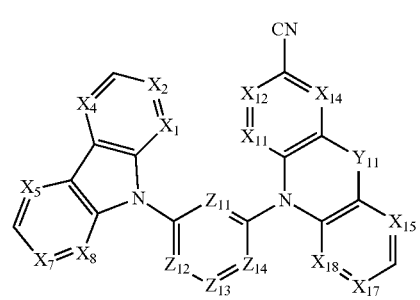

1-13

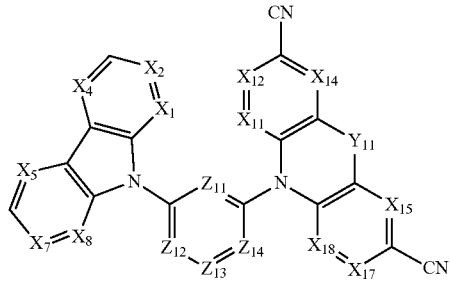

1-14

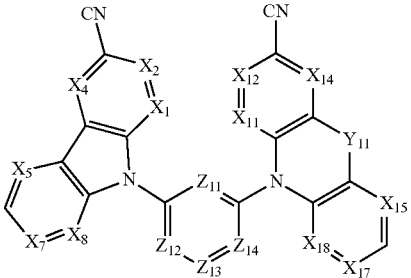

1-15

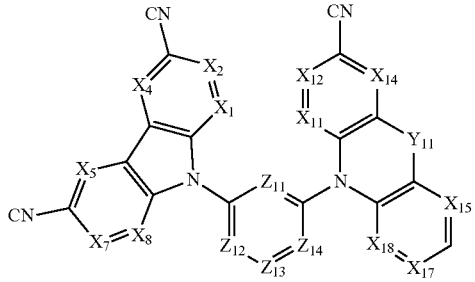

1-16

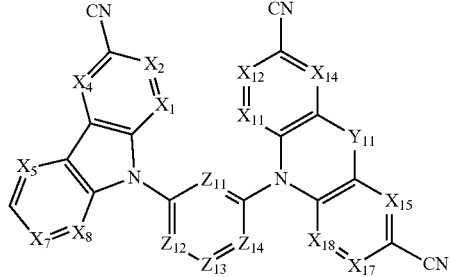

1-17

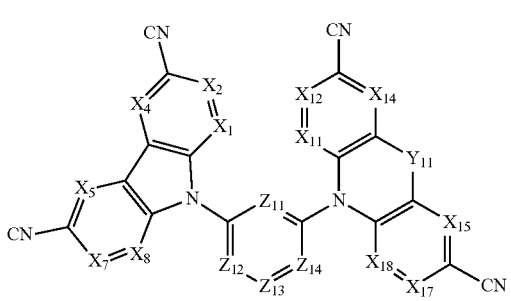

1-18 wherein, in Formulae 1-11 to 1-25,
$X_1, X_2, X_4, X_5, X_7, X_8, X_{11}, X_{12}, X_{14}, X_{15}, X_{17}, X_{18}, Y_{11},$ and $Z_{11}$ to $Z_{14}$ are the same as in Formula 1.

14. The condensed cyclic compound of claim 13, wherein the condensed cyclic compound represented by Formula 1 is represented by one of Formulae 1-11 to 1-25; and $X_1$ is N, $X_2$ is $C(R_2)$, $X_4$ is $C(R_4)$, $X_5$ is $C(R_5)$, $X_7$ is $C(R_7)$, $X_8$ is $C(R_8)$, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$;

$X_1$ is $C(R_1)$, $X_2$ is N, $X_4$ is $C(R_4)$, $X_5$ is $C(R_5)$, $X_7$ is $C(R_7)$, $X_8$ is $C(R_8)$, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$;

$X_1$ is $C(R_1)$, $X_2$ is $C(R_2)$, $X_4$ is N, $X_5$ is $C(R_5)$, $X_7$ is $C(R_7)$, $X_8$ is $C(R_8)$, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$;

$X_1$ is $C(R_1)$, $X_2$ is $C(R_2)$, $X_4$ is $C(R_4)$, $X_5$ is N, $X_7$ is $C(R_7)$, $X_8$ is $C(R_8)$, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$;

$X_1$ is $C(R_1)$, $X_2$ is $C(R_2)$, $X_4$ is $C(R_4)$, $X_5$ is $C(R_5)$, $X_7$ is N, $X_8$ is $C(R_8)$, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$; or $X_1$ is $C(R_1)$, $X_2$ is $C(R_2)$, $X_4$ is $C(R_4)$, $X_5$ is $C(R_5)$, $X_7$ is $C(R_7)$, $X_8$ is N, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$.

15. The condensed cyclic compound of claim 1, wherein the condensed cyclic compound represented by Formula 1 is represented by one of Formulae 1-31 to 1-45:

1-32
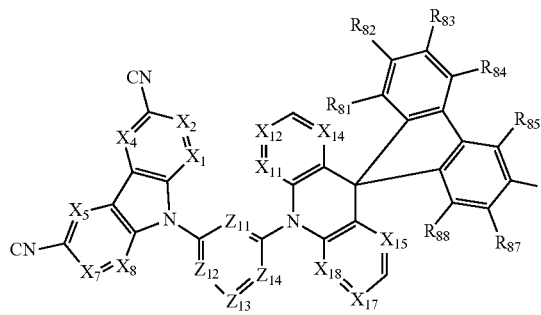
1-33
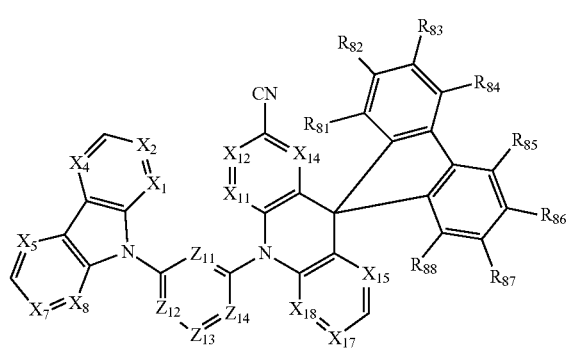
1-34
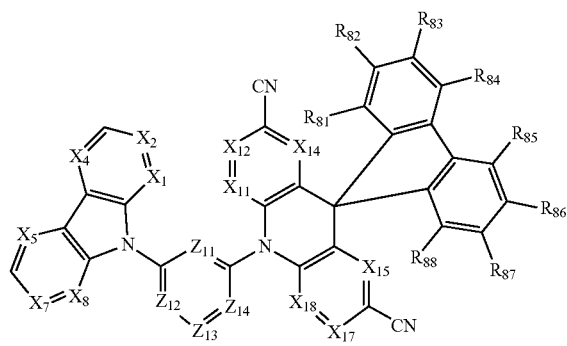
1-35
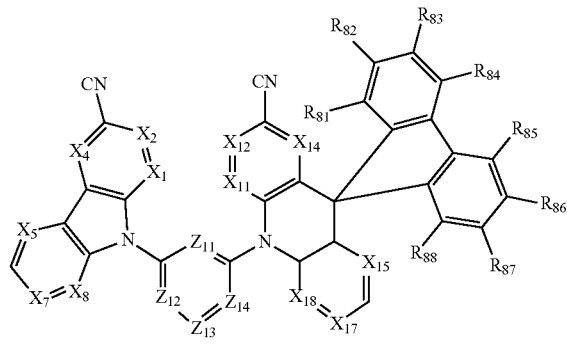
1-36
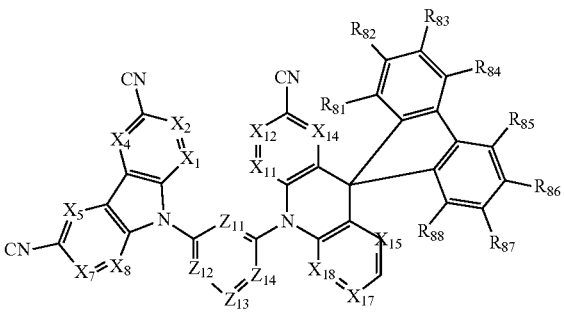
1-37
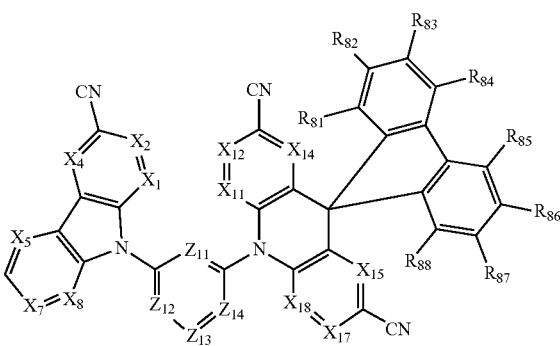
1-38
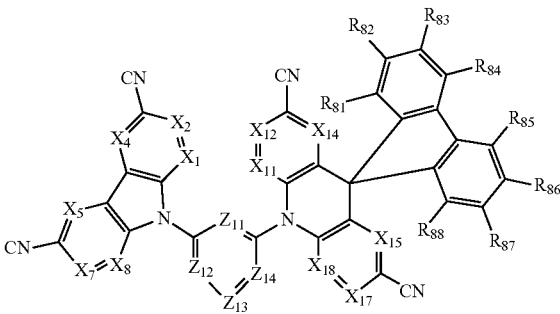
1-39
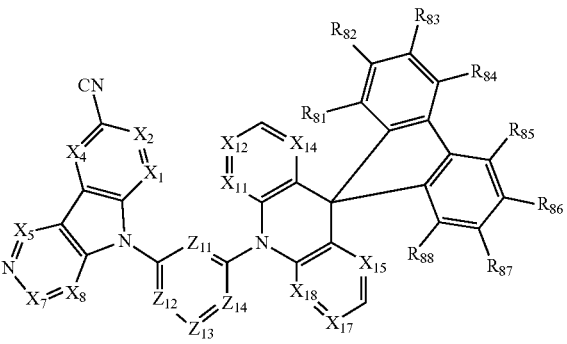

1-40

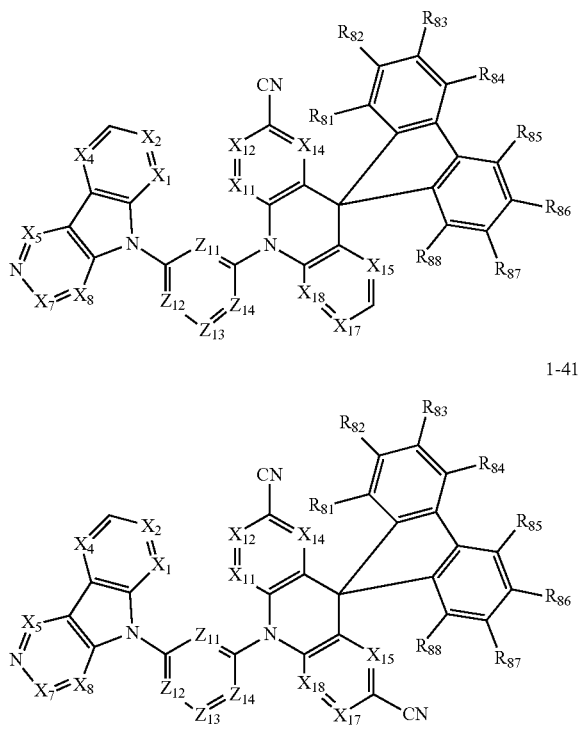

1-41

1-42

1-43

1-44

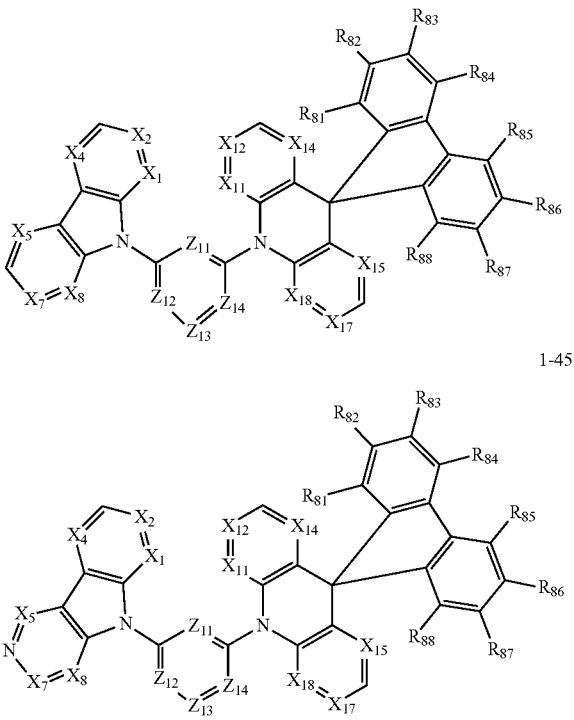

1-45 wherein, in Formulae 1-31 to 1-45,
$X_1$, $X_2$, $X_4$, $X_5$, $X_7$, $X_8$, $X_{11}$, $X_{12}$, $X_{14}$, $X_{15}$, $X_{17}$, $X_{18}$, and $Z_{11}$ to $Z_{14}$ are the same as in Formula 1; and
$R_{81}$ to $R_{88}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, a triazinyl group, and —Si($Q_{31}$)($Q_{32}$)($Q_{33}$),
wherein $Q_{31}$ to $Q_{33}$ are each independently selected from hydrogen, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group.

16. The condensed cyclic compound of claim 15, wherein the condensed cyclic compound represented by Formula 1 is represented by one of Formulae 1-31 to 1-45; and
$X_1$ is N, $X_2$ is C($R_2$), $X_4$ is C($R_4$), $X_5$ is C($R_5$), $X_7$ is C($R_7$), $X_8$ is C($R_8$), $X_{11}$ is C($R_{11}$), $X_{12}$ is C($R_{12}$), $X_{14}$ is C($R_{14}$), $X_{15}$ is C($R_{15}$), $X_{17}$ is C($R_{17}$), and $X_{18}$ is C($R_{18}$);
$X_1$ is C($R_1$), $X_2$ is N, $X_4$ is C($R_4$), $X_5$ is C($R_5$), $X_7$ is C($R_7$), $X_8$ is C($R_8$), $X_{11}$ is C($R_{11}$), $X_{12}$ is C($R_{12}$), $X_{14}$ is C($R_{14}$), $X_{15}$ is C($R_{15}$), $X_{17}$ is C($R_{17}$), and $X_{18}$ is C($R_{18}$);
$X_1$ is C($R_1$), $X_2$ is C($R_2$), $X_4$ is N, $X_5$ is C($R_5$), $X_7$ is C($R_7$), $X_8$ is C($R_8$), $X_{11}$ is C($R_{11}$), $X_{12}$ is C($R_{12}$), $X_{14}$ is C($R_{14}$), $X_{15}$ is C($R_{15}$), $X_{17}$ is C($R_{17}$), and $X_{18}$ is C($R_{18}$);
$X_1$ is C($R_1$), $X_2$ is C($R_2$), $X_4$ is C($R_4$), $X_5$ is N, $X_7$ is C($R_7$), $X_8$ is C($R_8$), $X_{11}$ is C($R_{11}$), $X_{12}$ is C($R_{12}$), $X_{14}$ is C($R_{14}$), $X_{15}$ is C($R_{15}$), $X_{17}$ is C($R_{17}$), and $X_{18}$ is C($R_{18}$);
$X_1$ is C($R_1$), $X_2$ is C($R_2$), $X_4$ is C($R_4$), $X_5$ is C($R_5$), $X_7$ is N, $X_8$ is C($R_8$), $X_{11}$ is C($R_{11}$), $X_{12}$ is C($R_{12}$), $X_{14}$ is C($R_{14}$), $X_{15}$ is C($R_{15}$), $X_{17}$ is C($R_{17}$), and $X_{18}$ is C($R_{18}$);
or

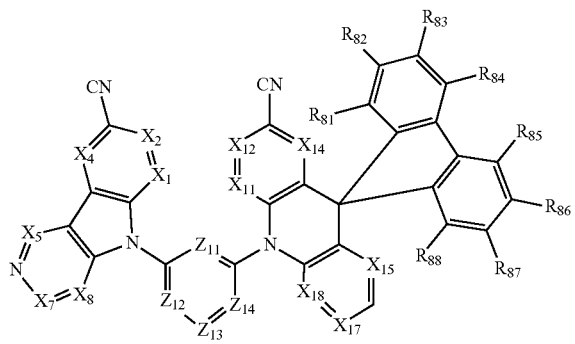

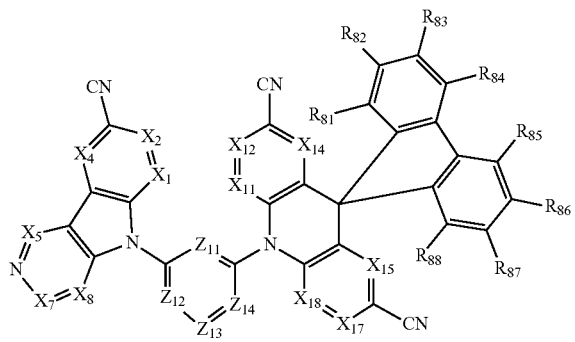

$X_1$ is $C(R_1)$, $X_2$ is $C(R_2)$, $X_4$ is $C(R_4)$, $X_5$ is $C(R_5)$, $X_7$ is $C(R_7)$, $X_8$ is N, $X_{11}$ is $C(R_{11})$, $X_{12}$ is $C(R_{12})$, $X_{14}$ is $C(R_{14})$, $X_{15}$ is $C(R_{15})$, $X_{17}$ is $C(R_{17})$, and $X_{18}$ is $C(R_{18})$.
17. The condensed cyclic compound of claim 1, wherein the condensed cyclic compound represented by Formula 1 is selected from Compounds 1 to 134:
1
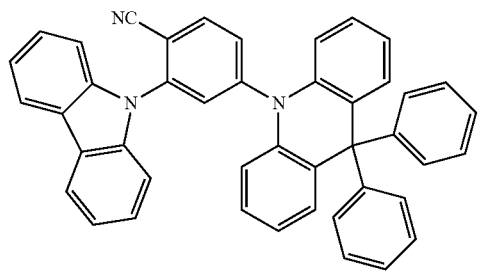
2
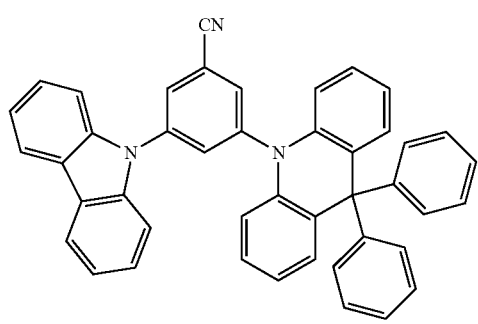
3
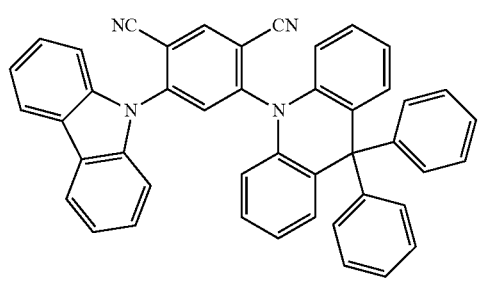
4
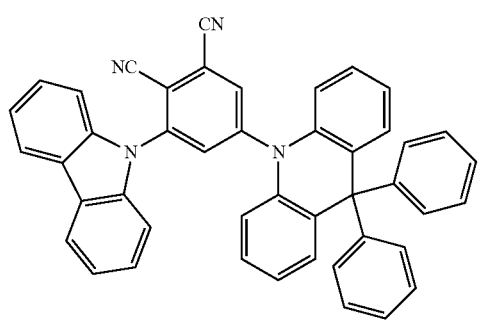
-continued
5
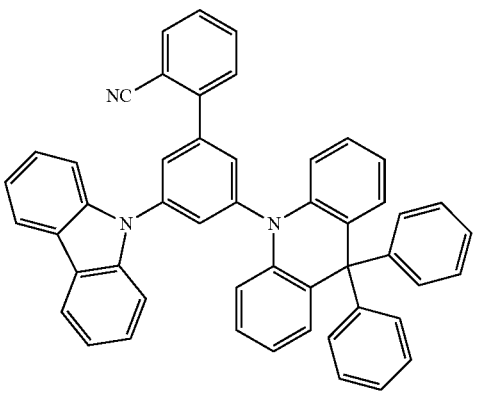
6
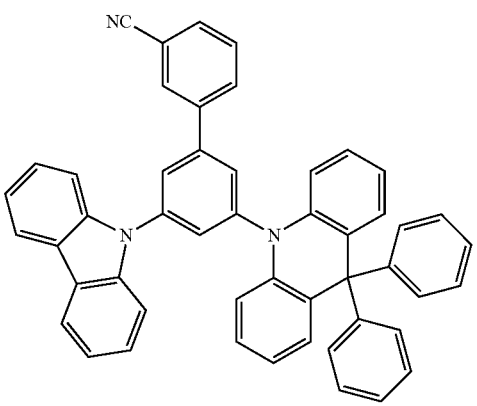
7
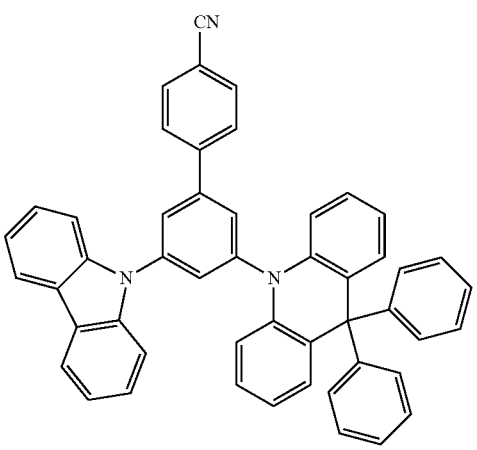
8
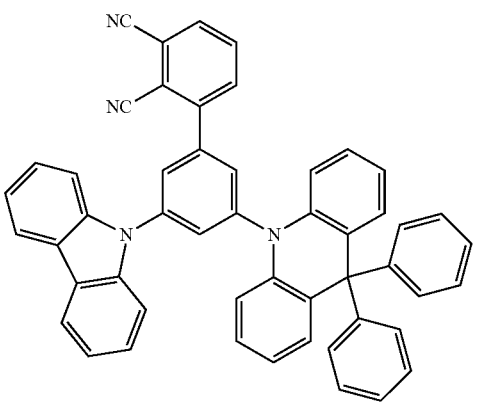

-continued
9
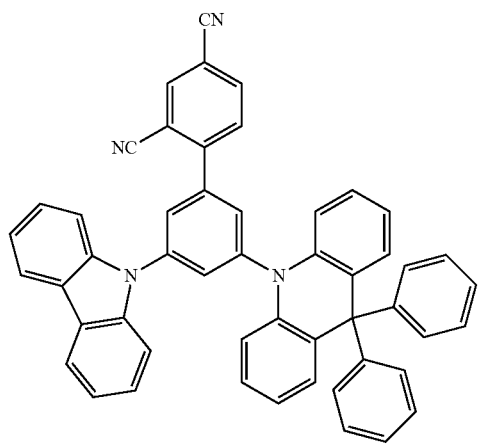
10
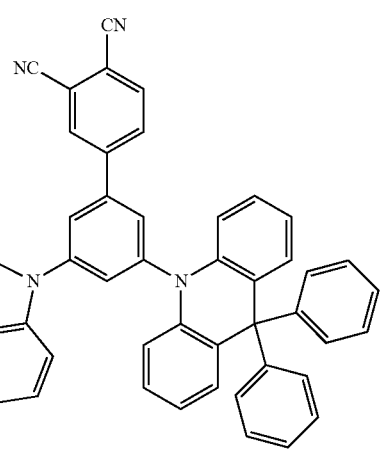
11
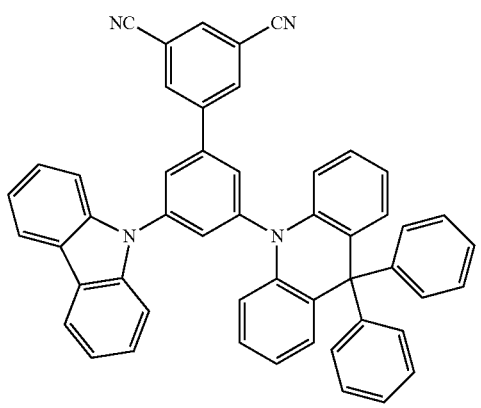
-continued
12
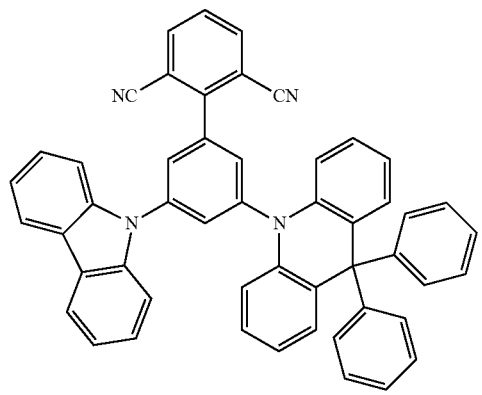
13
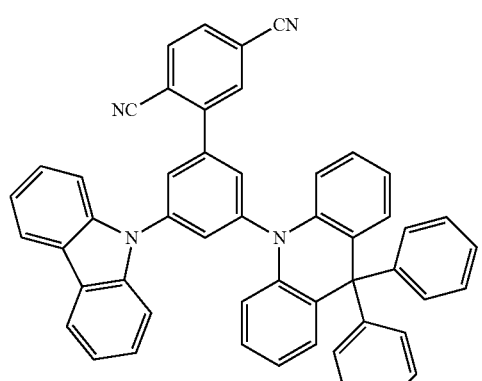
14
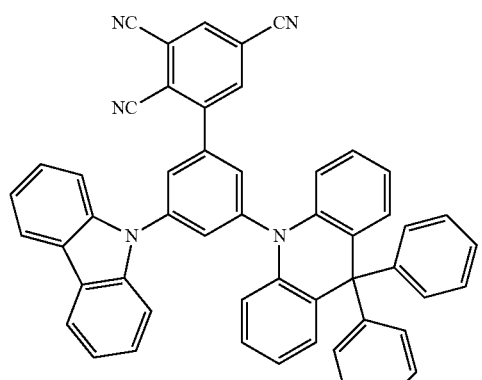
15
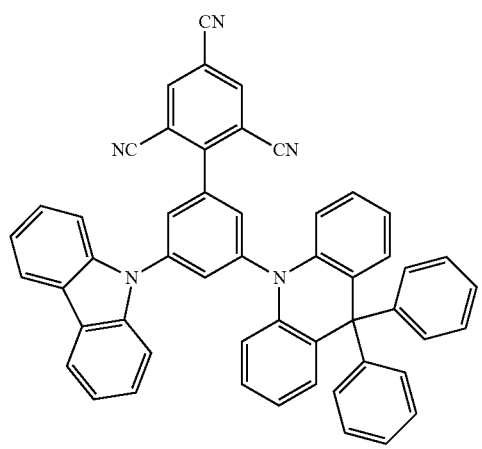

16
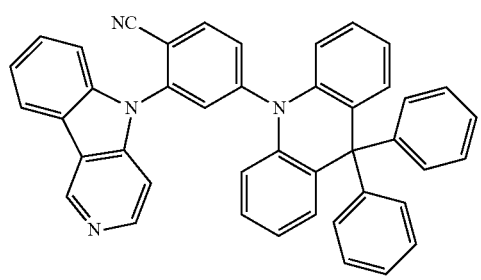
17
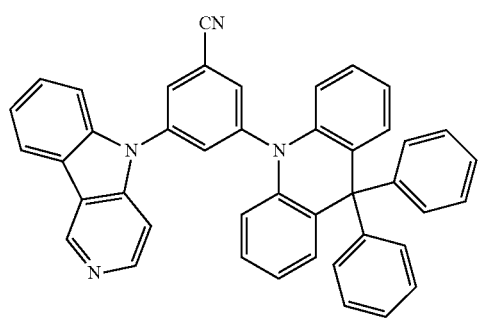
18
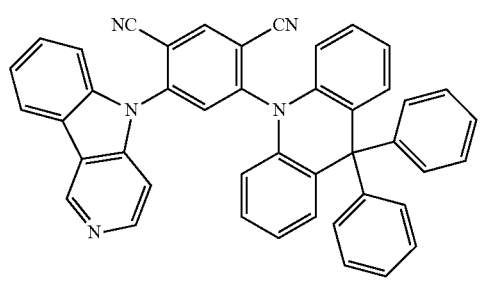
19
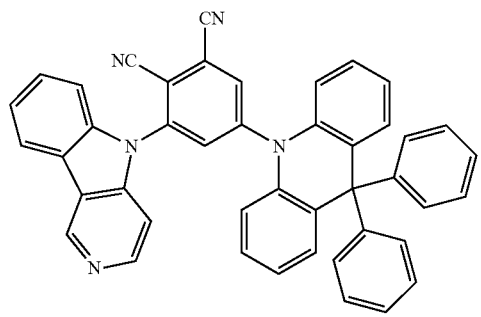
20
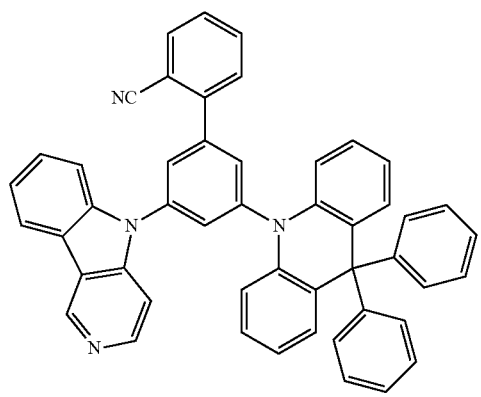
21
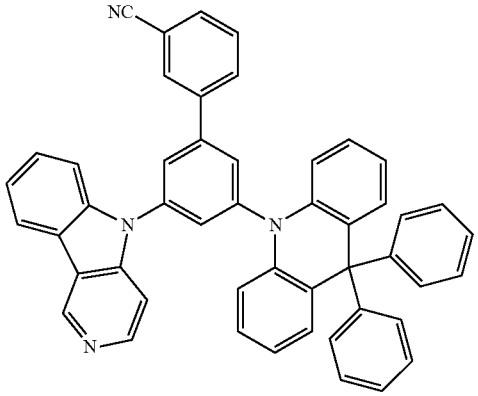
22
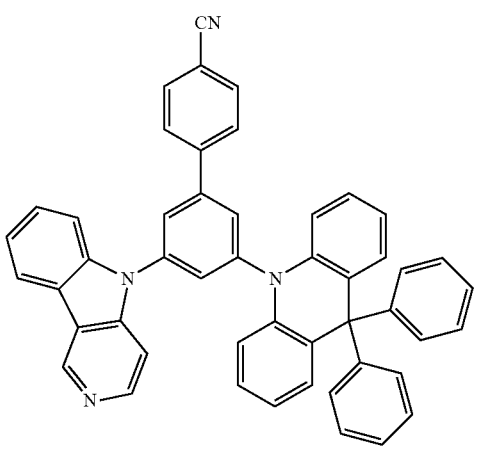
23
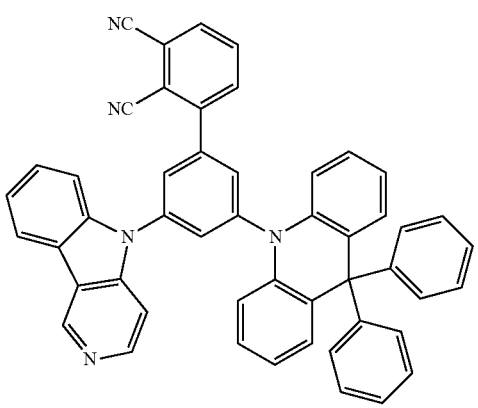

-continued
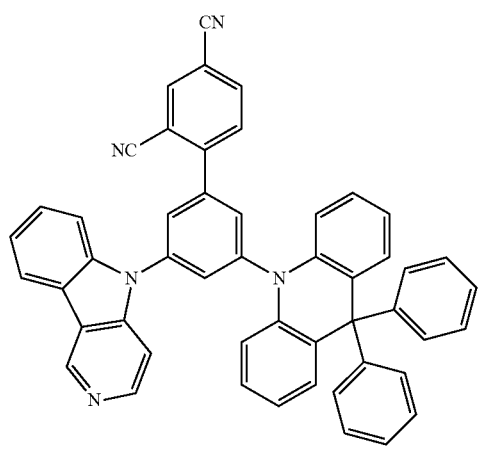
24
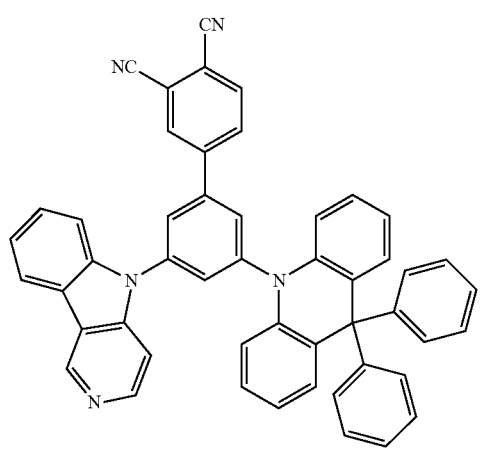
25
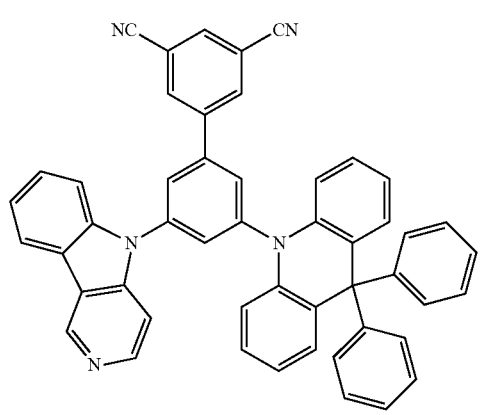
26
-continued
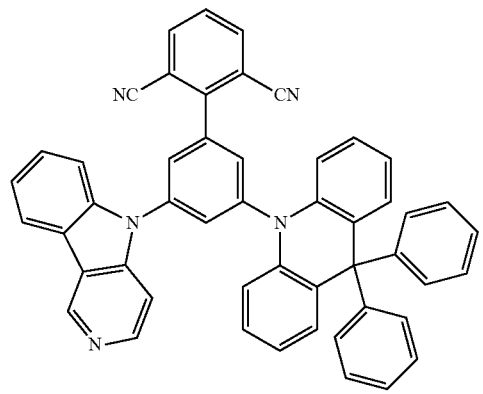
27
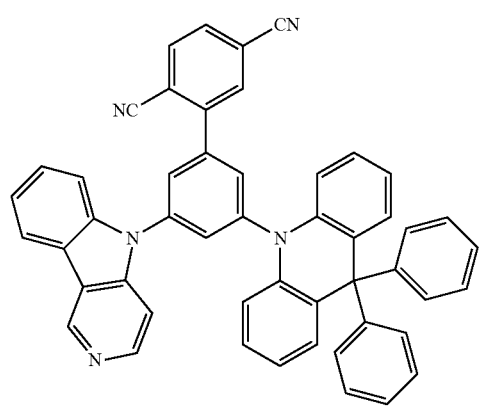
28
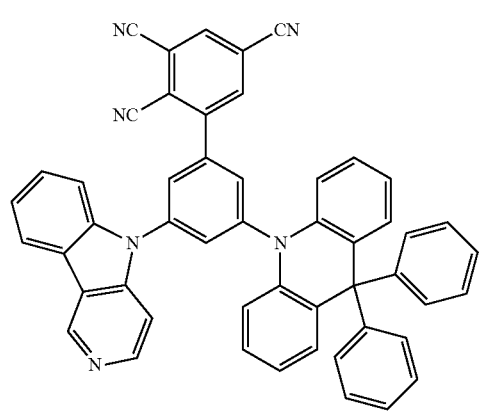
29
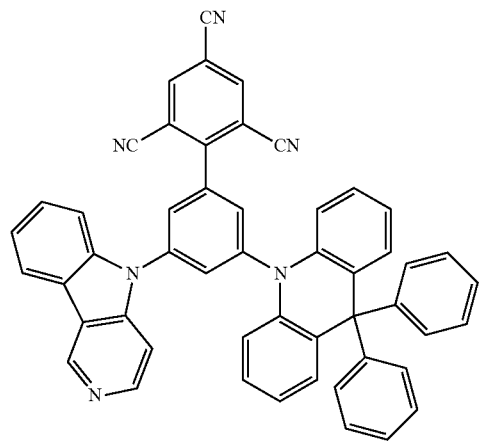
30

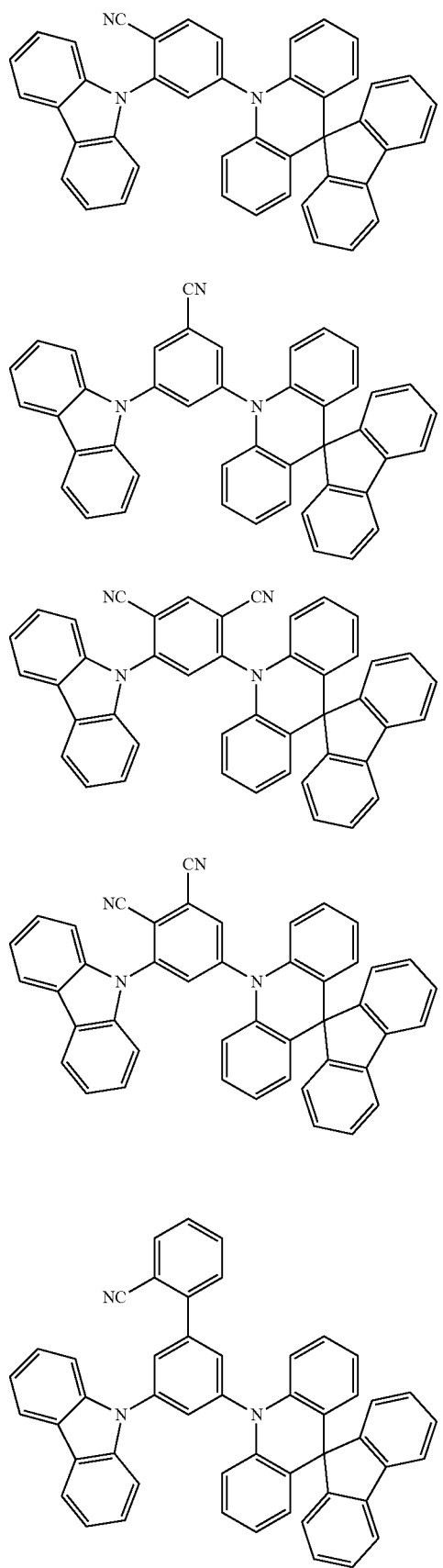
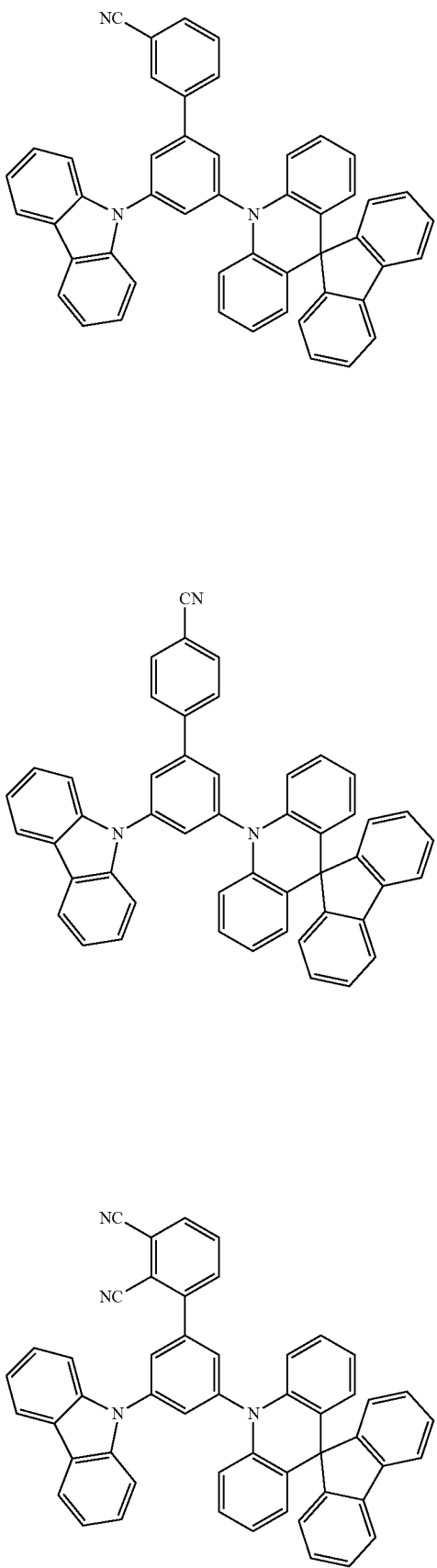

233
-continued
39
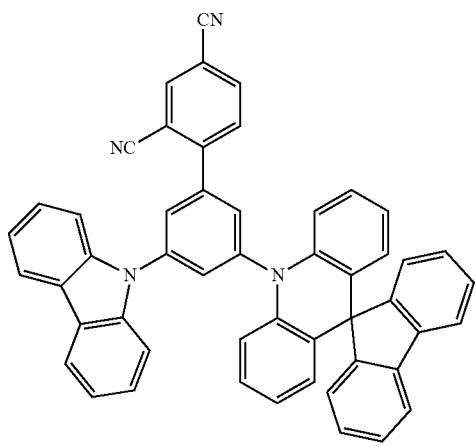
40
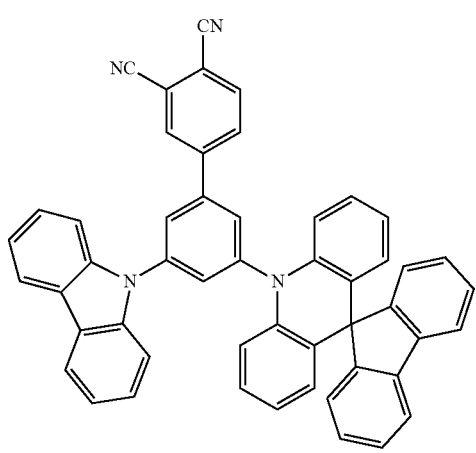
41
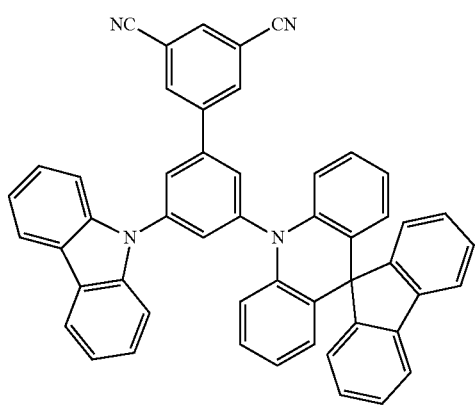
234
-continued
42
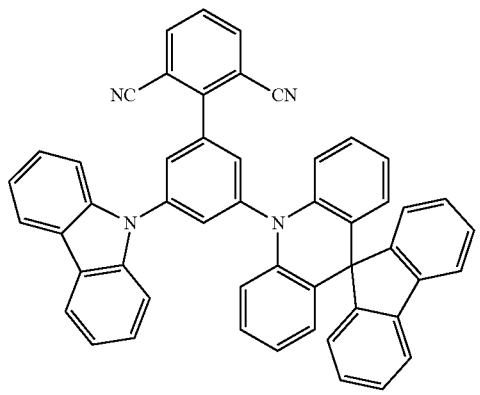
43
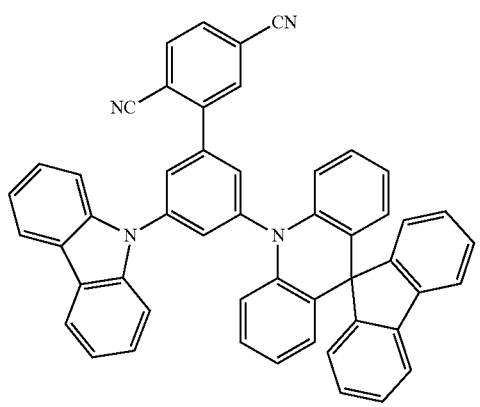
44
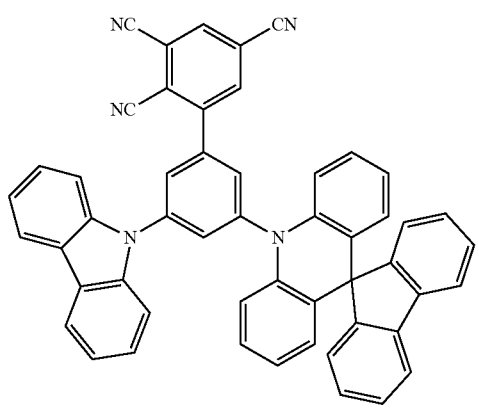

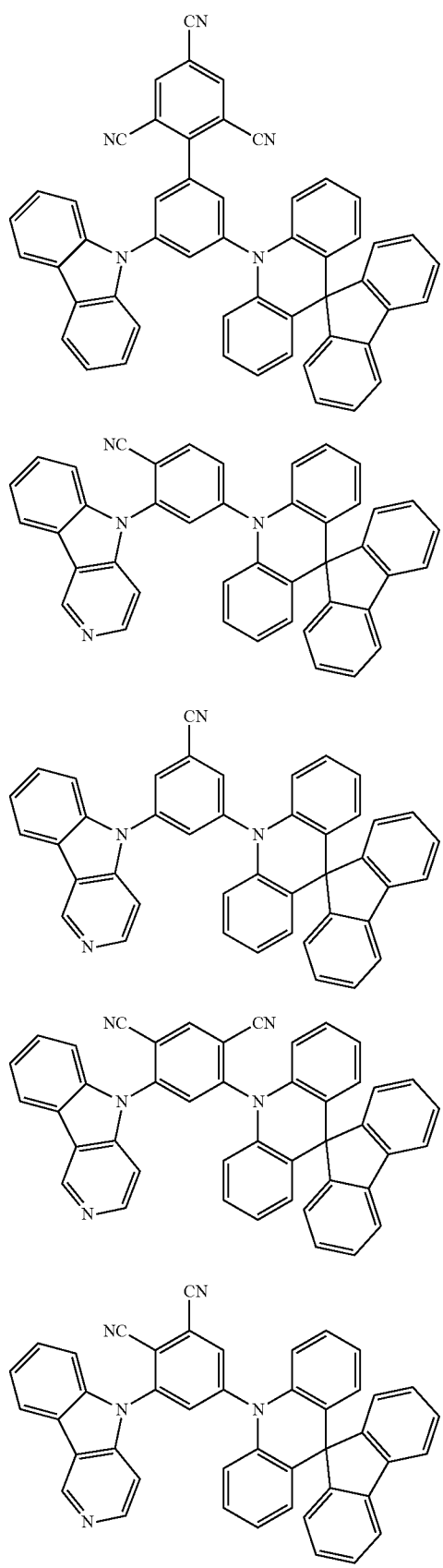
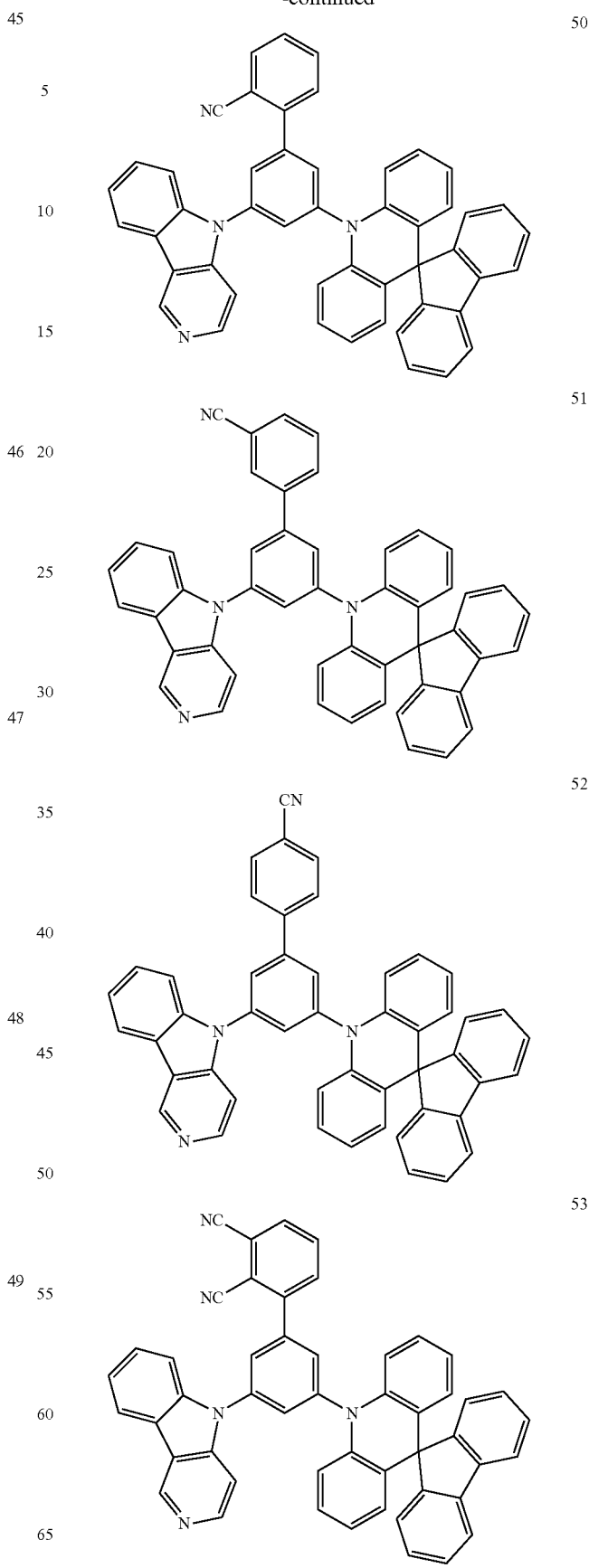

54
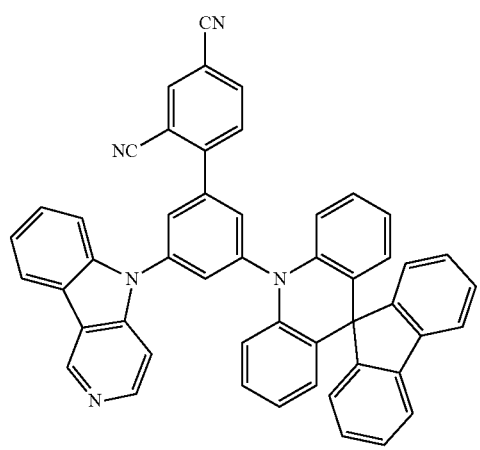
55
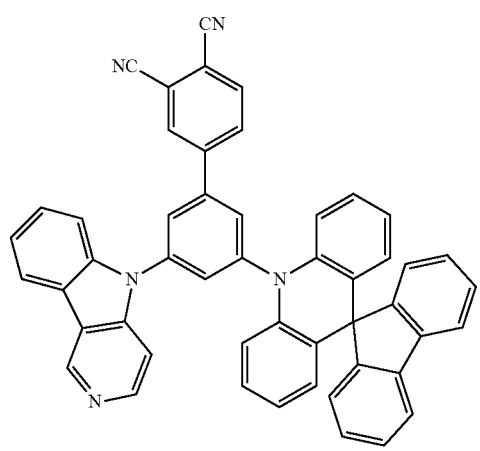
56
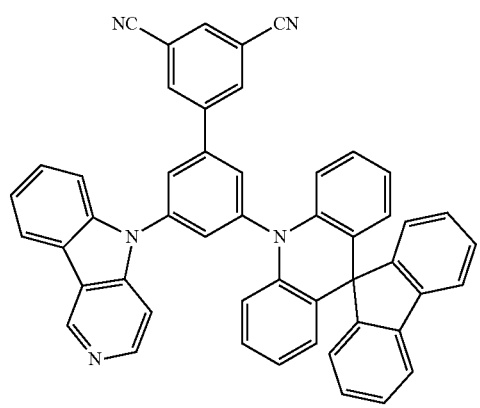
57
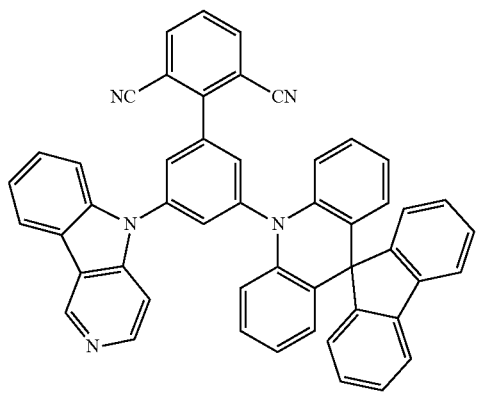
58
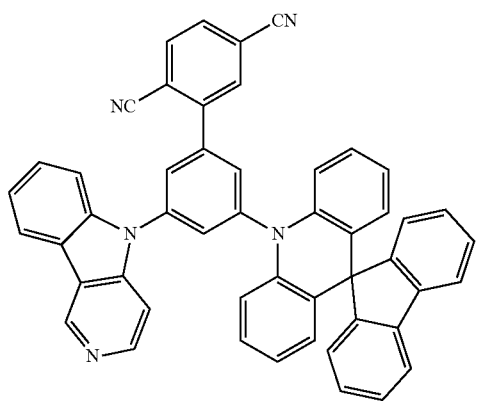
59
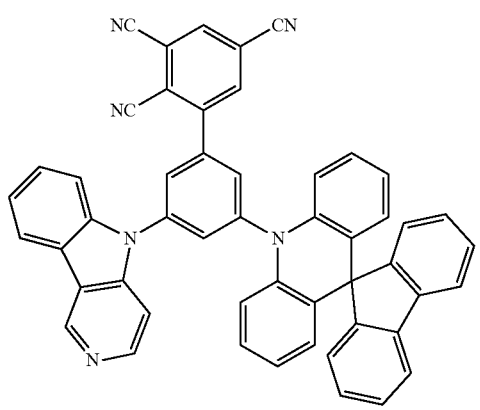
60
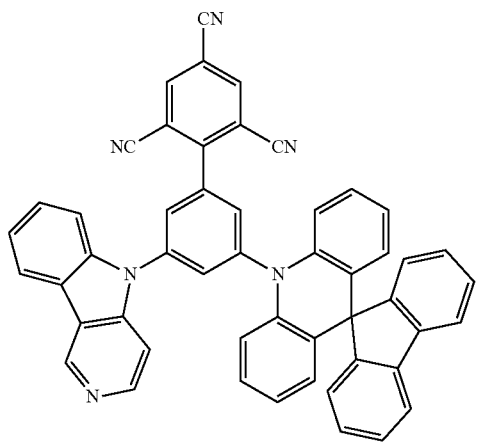

61
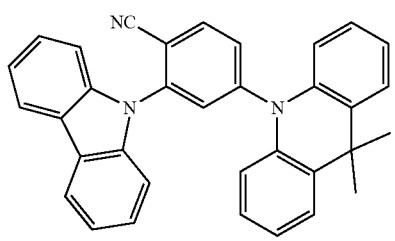
62
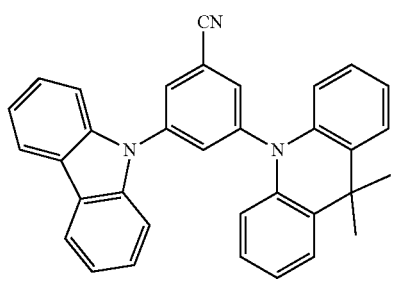
63
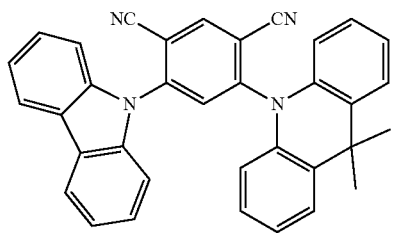
64
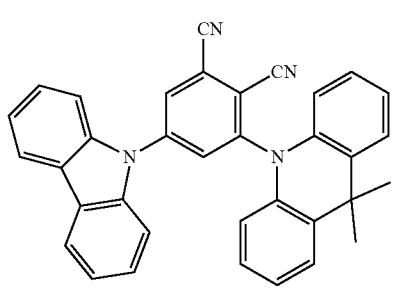
65
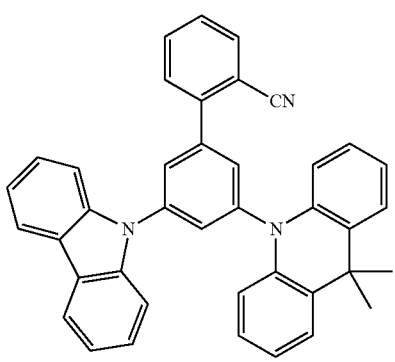
66
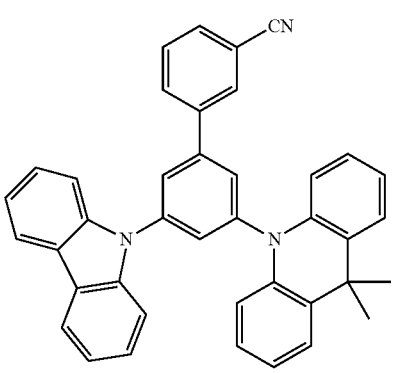
67
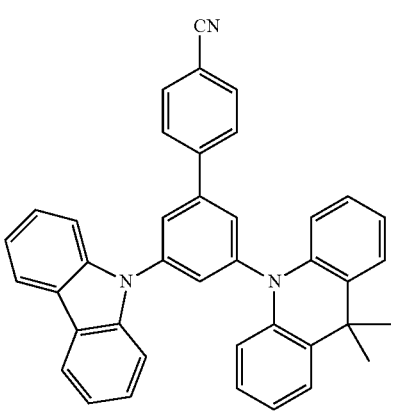
68
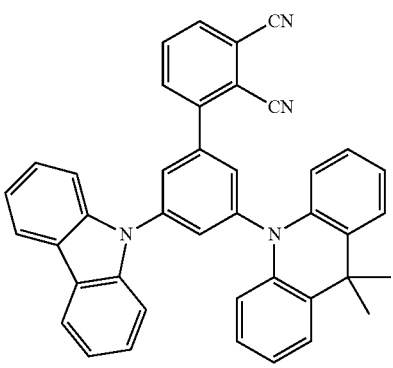
69
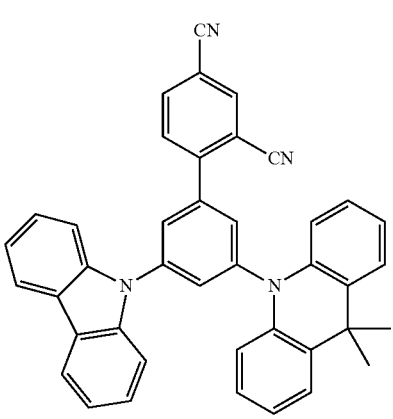

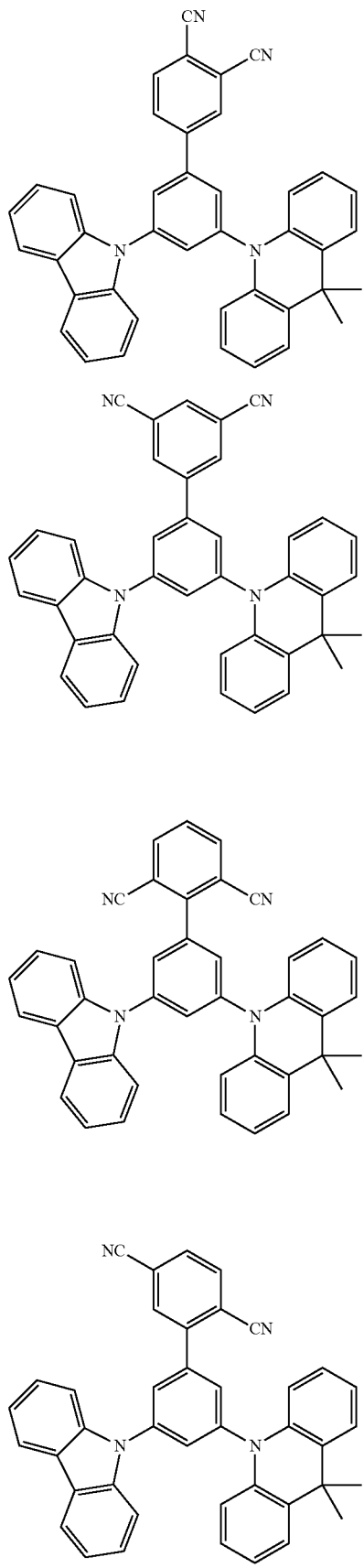
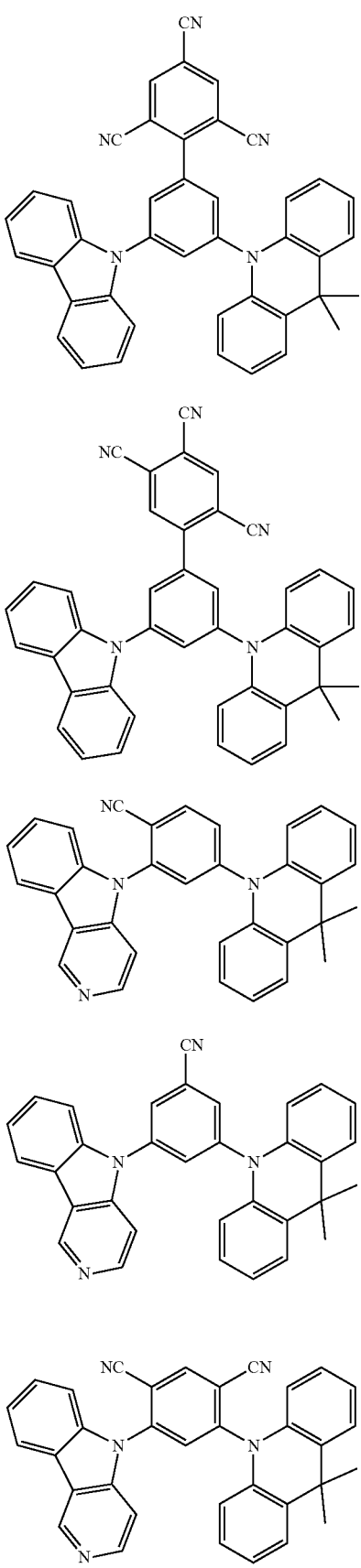

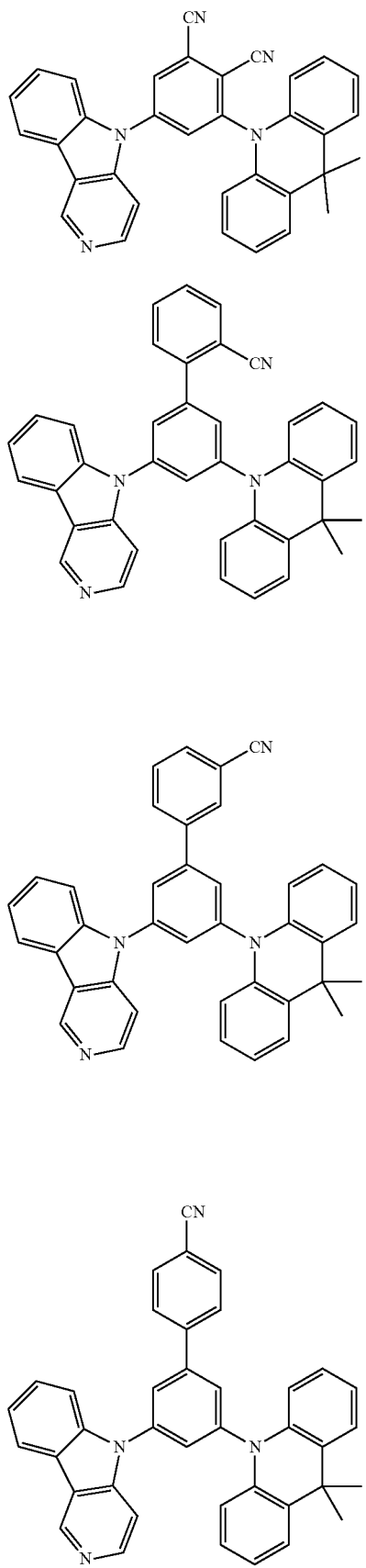
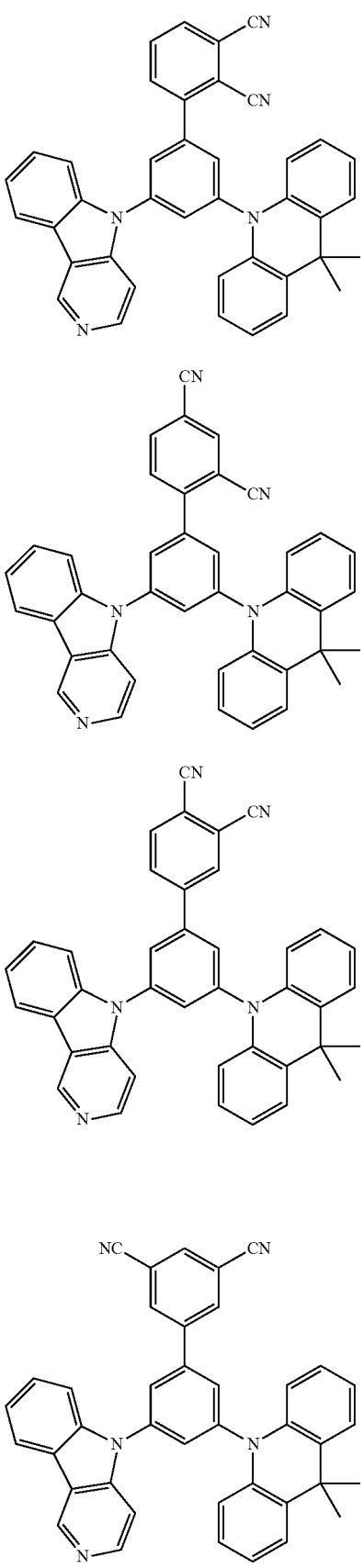

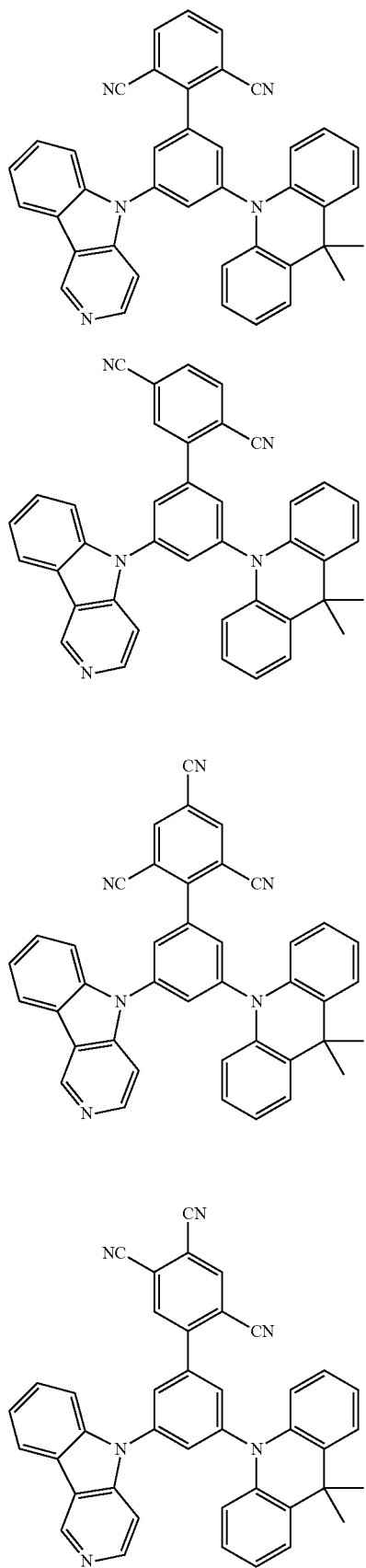
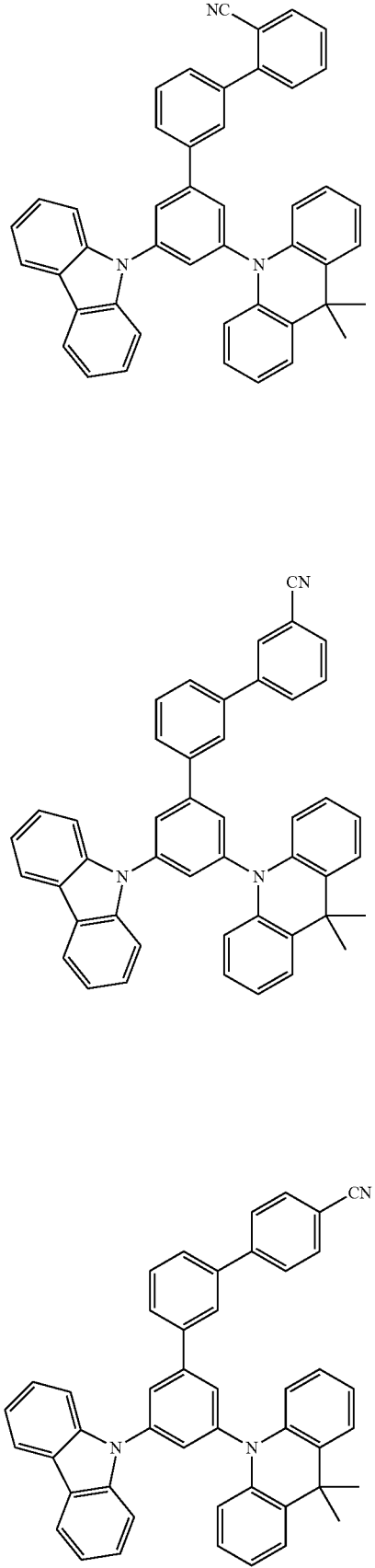

-continued
94
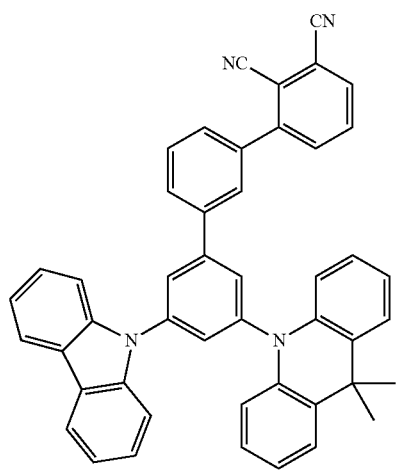
95
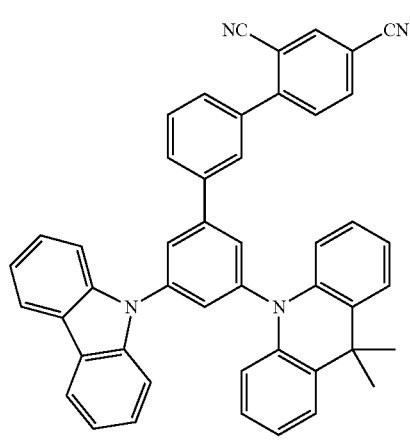
96
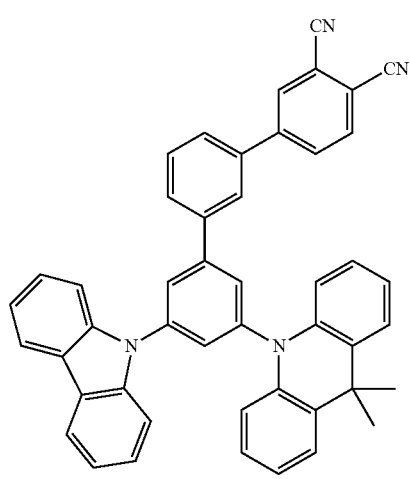
-continued
97
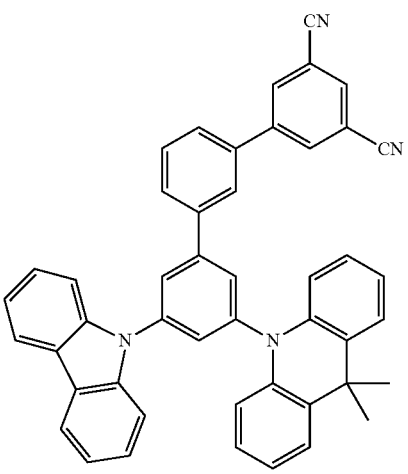
98
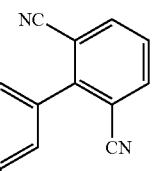
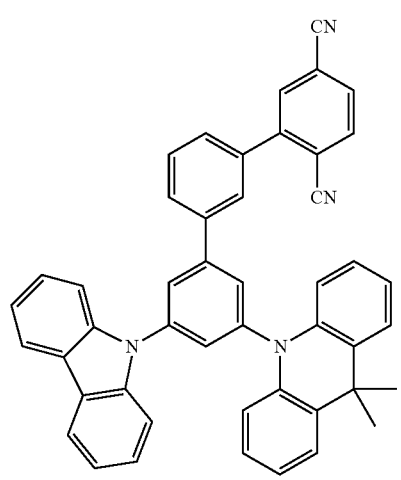
99

-continued
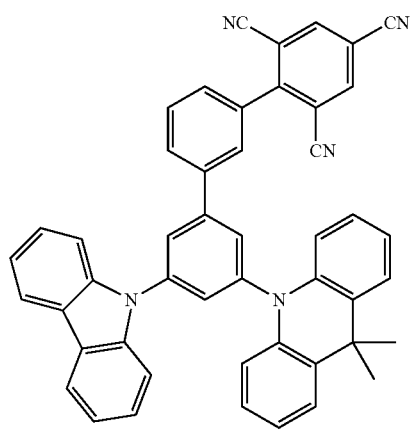
100
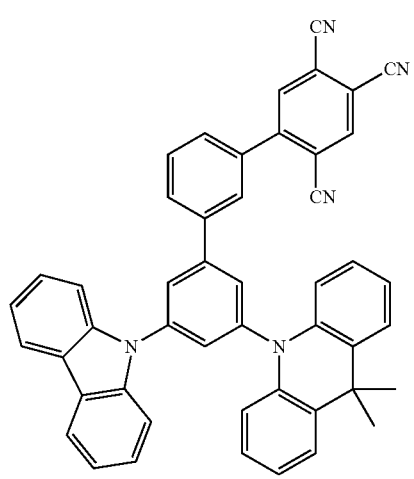
101
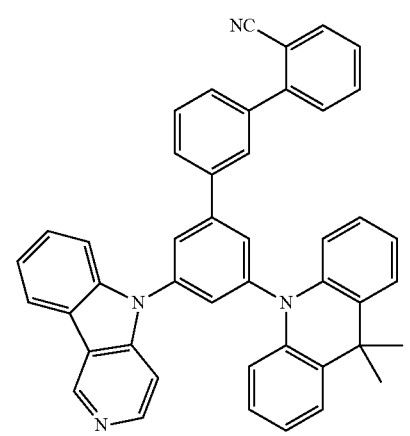
102
-continued
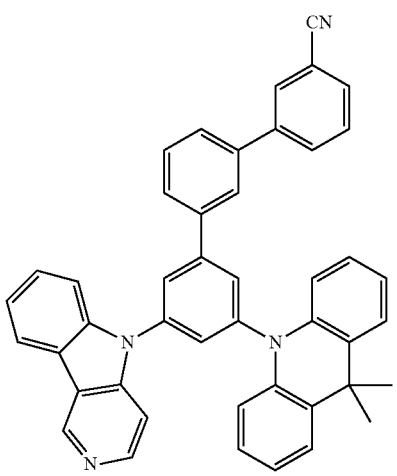
103
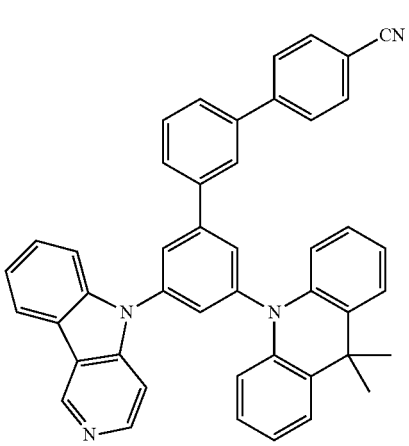
104
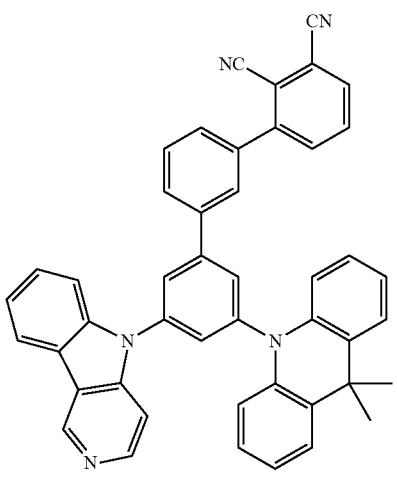
105

251
-continued
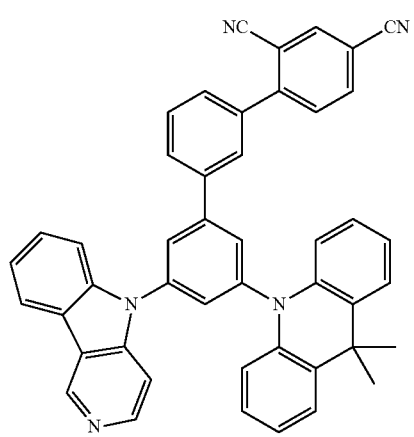
106
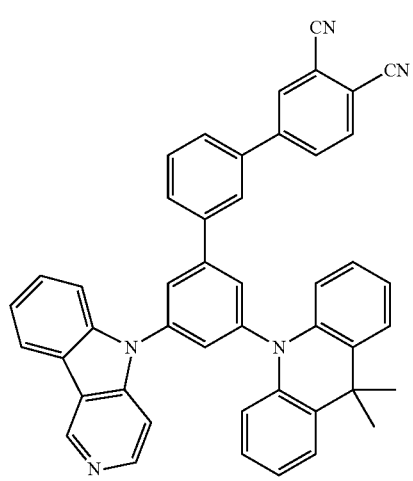
107
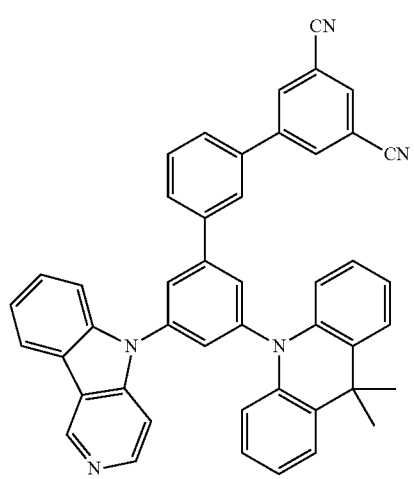
108
252
-continued
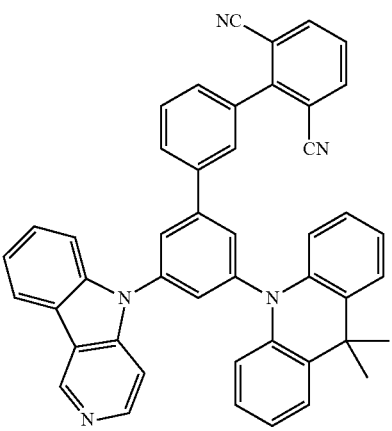
109
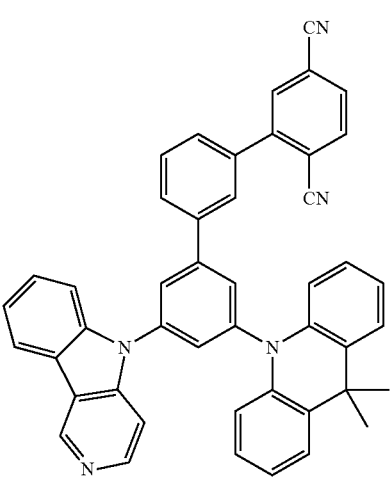
110
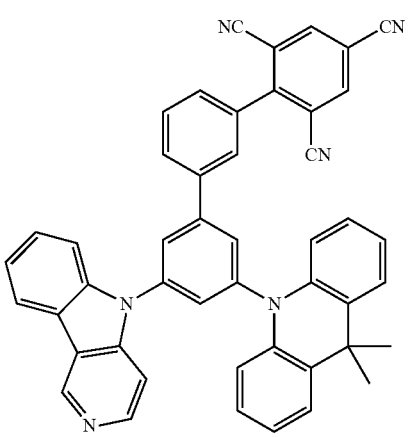
111

-continued
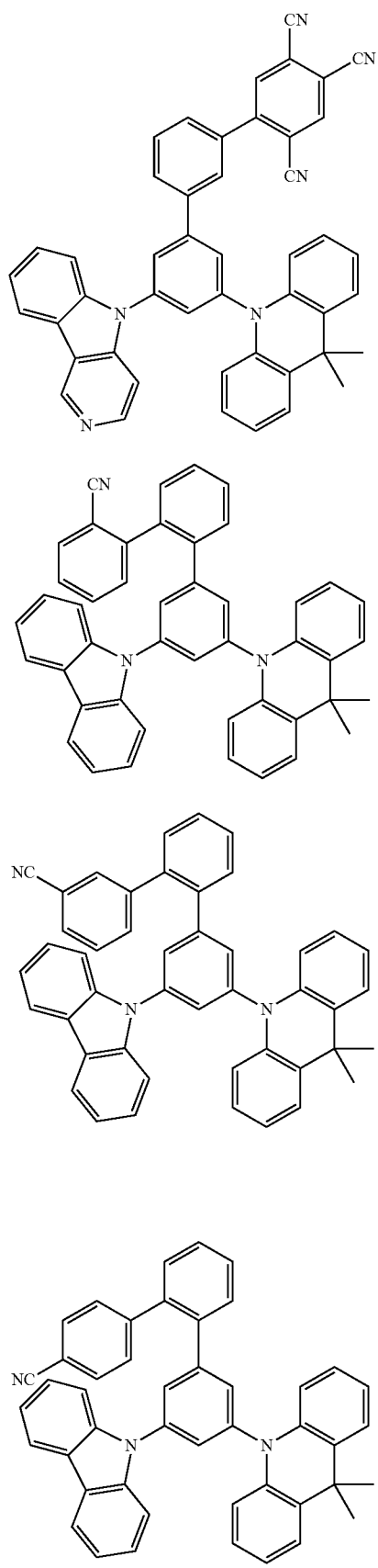
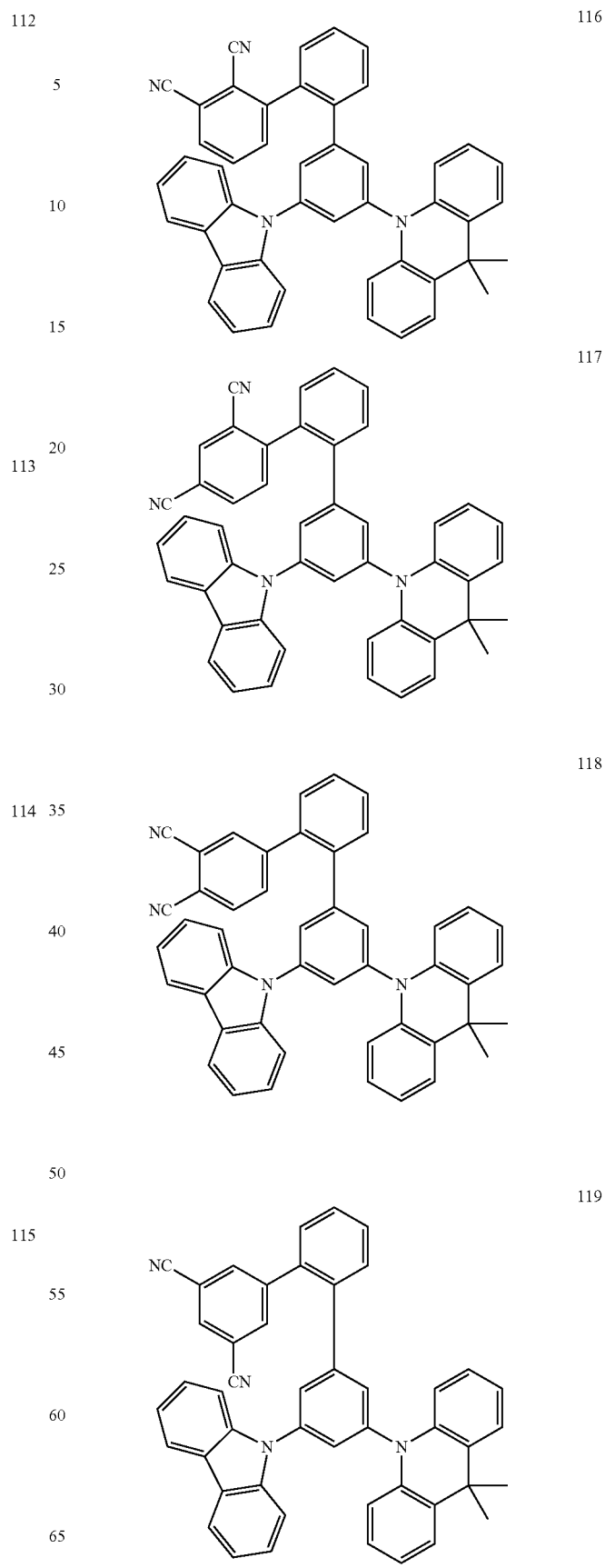

255
-continued
120
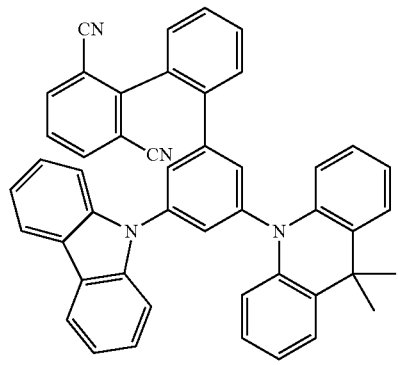
121
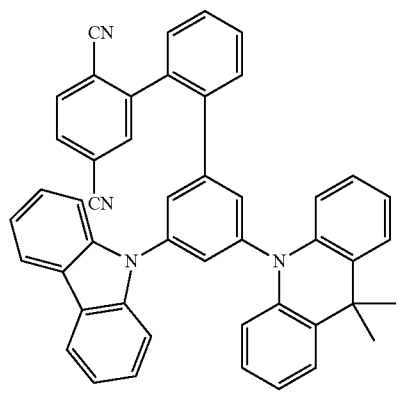
122
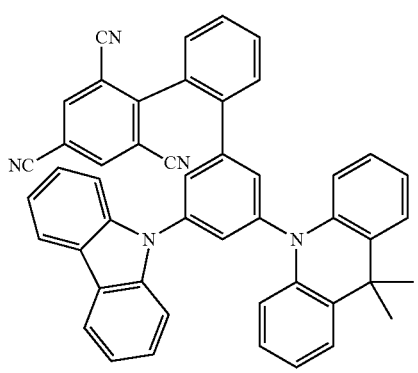
123
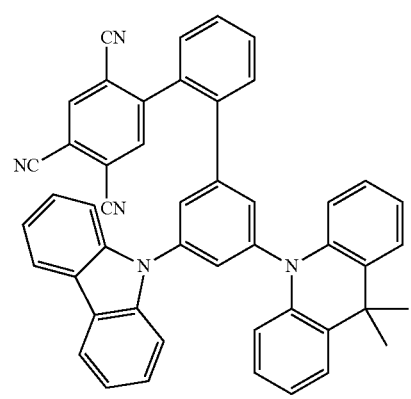
256
-continued
124
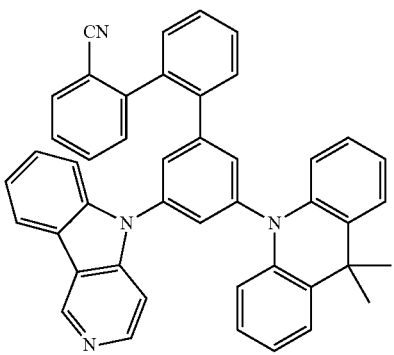
125
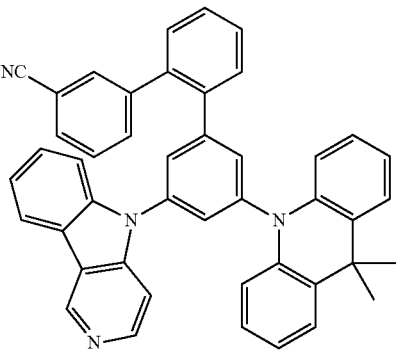
126
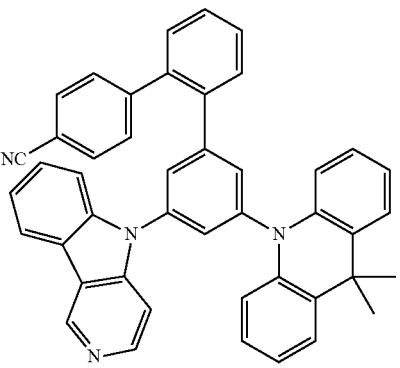
127
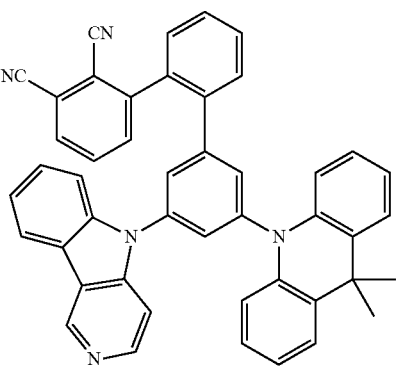

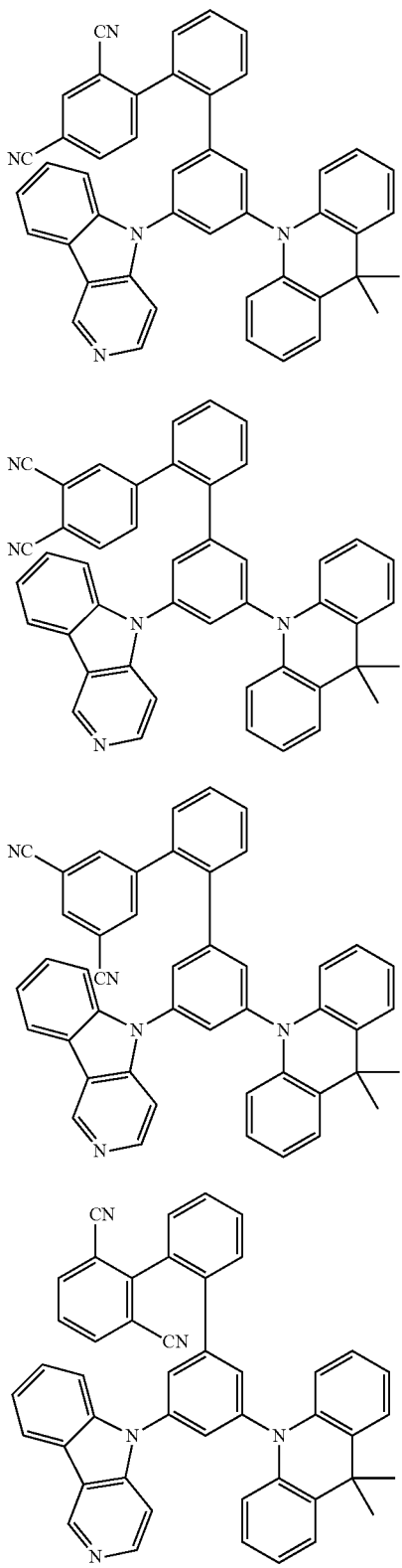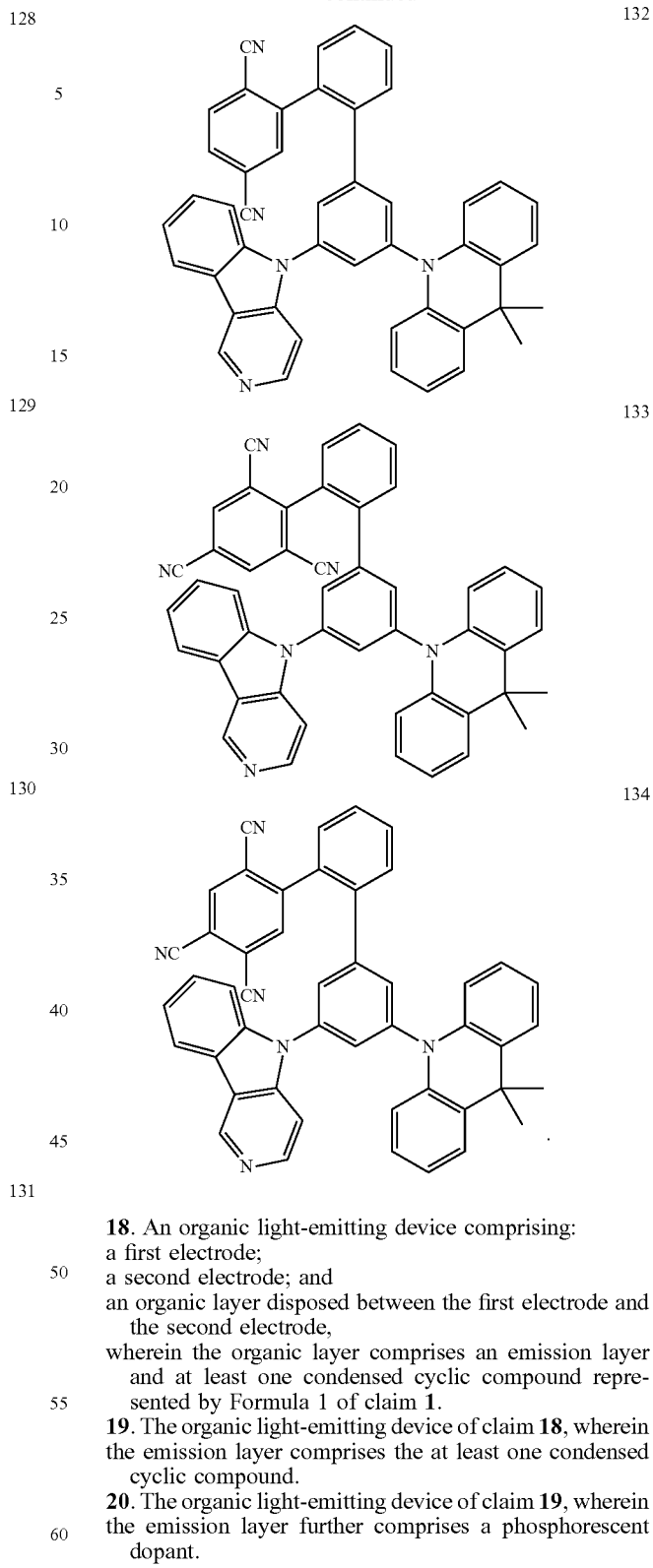

18. An organic light-emitting device comprising:
   a first electrode;
   a second electrode; and
   an organic layer disposed between the first electrode and the second electrode,
   wherein the organic layer comprises an emission layer and at least one condensed cyclic compound represented by Formula 1 of claim 1.
19. The organic light-emitting device of claim 18, wherein the emission layer comprises the at least one condensed cyclic compound.
20. The organic light-emitting device of claim 19, wherein the emission layer further comprises a phosphorescent dopant.

* * * * *